(12) United States Patent
Simmen et al.

(10) Patent No.: US 8,741,926 B2
(45) Date of Patent: *Jun. 3, 2014

(54) MACROCYCLIC INHIBITORS OF HEPATITIS C VIRUS

(71) Applicants: Tibotec Pharmaceuticals Ltd., County Cork (IE); Medivir AB, Huddinge (SE)

(72) Inventors: Kenneth Alan Simmen, Tervuren (BE); Herman Augustinus De Kock, Arendonk (BE); Pierre Jean-Marie Bernard Raboisson, Sterrebeek (BE); Lili Hu, Mechelen (BE); Abdellah Tahri, Anderlecht (BE); Dominique Louis Nestor Ghislain Surleraux, Braine-le-chateau (BE); Karl Magnus Nilsson, Göteborg (SE); Bengt Bertil Samuelsson, Skärholmen (SE); Åsa Annica Kristina Rosenquist, Huddinge (SE); Vladimir Ivanov, Moscow (RU); Mikael Pelcman, Älvsjö (SE); Anna Karin Gertrud Linnea Belfrage, Uppsala (SE); Per-Ola Mikael Johansson, Huddinge (SE); Sandrine Marie Helene Vendeville, Etterbeek (BE)

(73) Assignees: Janssen R&D Ireland, Little Island, County Cork (IE); Medivir AB, Huddinge (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/687,037

(22) Filed: Nov. 28, 2012

(65) Prior Publication Data

US 2013/0089520 A1 Apr. 11, 2013

Related U.S. Application Data

(60) Continuation of application No. 13/412,997, filed on Mar. 6, 2012, now Pat. No. 8,349,869, which is a division of application No. 13/197,226, filed on Aug. 3, 2011, now Pat. No. 8,153,800, which is a division of application No. 11/632,102, filed as application No. PCT/EP2006/064820 on Jul. 28, 2006, now Pat. No. 8,148,399.

(30) Foreign Application Priority Data

Jul. 29, 2005 (EP) .................................. 05107074
Aug. 11, 2005 (EP) .................................. 05107417
Feb. 3, 2006 (EP) .................................. 06101280

(51) Int. Cl.
*C07D 487/04* (2006.01)
*A61K 31/33* (2006.01)
*A61P 31/14* (2006.01)

(52) U.S. Cl.
USPC ......................................... 514/314; 540/460

(58) Field of Classification Search
USPC .......................................... 540/460; 514/314
See application file for complete search history.

(56) References Cited

U.S. PATENT DOCUMENTS

| | | | |
|---|---|---|---|
| 5,484,801 A | 1/1996 | Al-Razzak et al. |
| 5,807,876 A | 9/1998 | Armistead et al. |
| 5,948,436 A | 9/1999 | Al Razzak et al. |
| 6,038,157 A | 3/2000 | Mortimer et al. |
| 6,054,472 A | 4/2000 | Armistead et al. |
| 6,265,380 B1 | 7/2001 | Tung et al. |
| 6,344,465 B1 | 2/2002 | Armistead et al. |
| 6,498,178 B2 | 12/2002 | Stamos et al. |
| 6,608,027 B1 | 8/2003 | Tsantrizos et al. |
| 6,867,185 B2 | 3/2005 | Campbell et al. |
| 7,102,047 B2 | 9/2006 | Grubbs et al. |
| 7,125,845 B2 | 10/2006 | Wu et al. |
| 7,375,218 B2 | 5/2008 | Gallou |
| 7,608,590 B2 | 10/2009 | Rosenquist et al. |
| 7,671,032 B2 | 3/2010 | Rosenquist et al. |
| 7,989,471 B2 | 8/2011 | Simmen et al. |
| 8,012,939 B2 | 9/2011 | Simmen et al. |
| 8,148,399 B2 | 4/2012 | Simmen et al. |
| 8,153,800 B2 | 4/2012 | Simmen et al. |
| 2003/0186895 A1 | 10/2003 | Llinas-Brunet et al. |
| 2004/0048802 A1 | 3/2004 | Ripka et al. |
| 2007/0203072 A1 | 8/2007 | Rosenquist et al. |
| 2008/0200503 A1 | 8/2008 | Simmen et al. |
| 2008/0262058 A1 | 10/2008 | Simmen et al. |
| 2009/0023758 A1 | 1/2009 | Wahling et al. |
| 2009/0062311 A1 | 3/2009 | Simmen et al. |
| 2009/0105302 A1 | 4/2009 | Simmen et al. |
| 2009/0118312 A1 | 5/2009 | Simmen et al. |
| 2009/0247512 A1 | 10/2009 | DeKock et al. |
| 2010/0120855 A1 | 5/2010 | Simmen et al. |

FOREIGN PATENT DOCUMENTS

| | | |
|---|---|---|
| EP | 0126587 | 11/1984 |
| EP | 0443132 | 8/1991 |
| EP | 1090997 | 12/1999 |
| EP | 1043399 | 3/2000 |
| EP | 1408031 | 4/2004 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/47561 | 8/2000 |
| WO | WO 00/59929 | 10/2000 |
| WO | WO 01/74768 | 10/2001 |
| WO | WO 02/08198 | 1/2002 |
| WO | WO 02/060926 | 8/2002 |
| WO | WO 03/035060 | 5/2003 |
| WO | WO 03/053349 | 7/2003 |
| WO | WO 03/062228 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/087092 | 10/2003 |
| WO | WO 03/099274 | 12/2003 |
| WO | WO 03/099316 | 12/2003 |
| WO | WO 2004/009121 | 1/2004 |
| WO | WO 2004/002896 | 4/2004 |
| WO | WO 2004/026896 | 4/2004 |
| WO | WO 2004/032827 | 4/2004 |
| WO | WO 2004/039833 | 5/2004 |
| WO | WO 2004/039970 | 5/2004 |
| WO | WO 2004/043339 | 5/2004 |
| WO | WO 2004/093915 | 5/2004 |
| WO | WO 2004/037855 | 6/2004 |

| | | |
|---|---|---|
| WO | WO 2004/072243 | 8/2004 |
| WO | WO 2004/092161 | 10/2004 |
| WO | WO 2004/092203 | 10/2004 |
| WO | WO 2004/093798 | 11/2004 |
| WO | WO 2004/094452 | 11/2004 |
| WO | WO 2004/101602 | 11/2004 |
| WO | WO 2004/103996 | 12/2004 |
| WO | WO 2004/113365 | 12/2004 |
| WO | WO 2005/010029 | 2/2005 |
| WO | WO 2005/073195 | 8/2005 |
| WO | WO 2005/073216 | 8/2005 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014927 | 2/2007 |
| WO | WO 2007/017144 | 2/2007 |

OTHER PUBLICATIONS

U.S. Appl. No. 10/572,394: Non-Final Rejection dated Nov. 24, 2008, 18 pages.

Zanotti et al., "Synthesis of analogues of amaninamide, an amatoxin from the white Amanita virosa mushroom," Int. J. Peptide Protein Res., 1987, 450-459.

Zanotti et al., "Synthesis of the Ile3-Amaninamide and its Diastereoisomeric(s)-Sulfoxide form the Analogues of Amanin," Int. J. Peptide Protein Res., 1981, 18:162-168.

European Patent Application No. 08708575.9: Communication pursuant to Article 94(3) EPC dated Jul. 25, 2012, 3 pages.

European Patent Application No. 08708575.9: Communication pursuant to Article 94(3) EPC dated Feb. 21, 2013, 4 pages.

European Patent Application No. 08708575.9: Response to the communication pursuant to A94(3) EPC dated Feb. 21, 2013, Response dated Aug. 28, 2013, 17 pages.

European Patent Application No. 08708575.9: Response to the communication pursuant to A94(3) EPC dated Jul. 25, 2012, Response dated Nov. 16, 2012, 2 pages.

European Patent Application No. 10706539.3: Communication pursuant to Rules 161(1) and 162 EPC dated Oct. 17, 2011, 2 pages.

European Patent Application No. 10706539.3: Communication pursuant to Article 94(3) EPC dated Dec. 18, 2012, 5 pages.

European Patent Application No. 10706539.3: Response to the communication pursuant to Article 94(3) EPC dated Dec. 18, 2012, Response dated Jun. 28, 2013, 13 pages.

European Patent Application No. 10706539.3: Response to the communication pursuant to Rules 161(1) and 162 EPC dated Oct. 17, 2011, Response dated Apr. 27, 2012, 6 pages.

International Patent Application No. PCT/EP2010/001197: International Preliminary Report on Patentability dated Aug. 30, 2011, 6 pages.

Raboisson et al., "Structure-activity relationship study on a novel series of cyclopentane-containing macrocyclic inhibitors of the hepatitis C virus NS3/4A protease leading to the discovery of TMC435350", Bioorganic & Medicinal Chemistry Letters, 2008, 18, 4853-4858.

*Primary Examiner* — Bruck Kifle

(74) *Attorney, Agent, or Firm* — Baker & Hostetler LLP

(57) ABSTRACT

Inhibitors of HCV replication of formula (I)

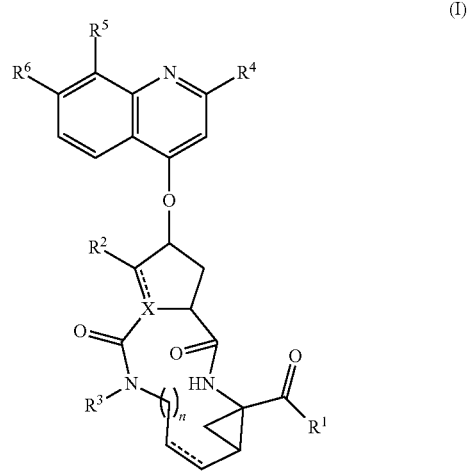

(I)

and the N-oxides, salts, and stereoisomers, wherein
each dashed line represents an optional double bond;
X is N, CH and where X bears a double bond it is C;
$R^1$ is —$OR^7$, —NH—$SO_2R^8$;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, $C_{3-7}$cycloalkyl;
$R^4$ is aryl or Het; n is 3, 4, 5, or 6;
$R^5$ is halo, $C_{1-6}$alkyl, hydroxy, $C_{1-6}$alkoxy, phenyl, or Het;
$R^6$ is $C_{1-6}$alkoxy, or dimethylamino;
$R^7$ is hydrogen; aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
$R^8$ is aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
aryl is phenyl optionally substituted with one, two or three substituents;
Het is a 5 or 6 membered saturated, partially unsaturated or completely unsaturated heterocyclic ring containing 1 to 4 heteroatoms selected from nitrogen, oxygen and sulfur, and being optionally substituted with one, two or three substituents;
pharmaceutical compositions containing compounds (I) and processes for preparing compounds (I). Bioavailable combinations of the inhibitors of HCV of formula (I) with ritonavir are also provided.

19 Claims, No Drawings

MACROCYCLIC INHIBITORS OF HEPATITIS C VIRUS

CROSS-REFERENCE TO RELATED APPLICATIONS

This application is a continuation of U.S. application Ser. No. 13/412,997, filed Mar. 6, 2012, which is a divisional of U.S. application Ser. No. 13/197,226, filed Aug. 3, 2011, now U.S. Pat. No. 8,153,800, which is a divisional of U.S. application Ser. No. 11/632,102, now U.S. Pat. No. 8,148,399, filed Jan. 10, 2007, which is the National Stage Entry of International Application No. PCT/EP2006/064820, filed Jul. 28, 2006, which claims the benefit of European Application Nos. 06101280.3, filed Feb. 3, 2006, 05107417.7, filed Aug. 11, 2005, and 05107074.6, filed Jul. 29, 2005, the entireties of which are incorporated herein by reference.

The present invention is concerned with macrocylic compounds having inhibitory activity on the replication of the hepatitis C virus (HCV). It further concerns compositions comprising these compounds as active ingredients as well as processes for preparing these compounds and compositions.

Hepatitis C virus is the leading cause of chronic liver disease worldwide and has become a focus of considerable medical research. HCV is a member of the Flaviviridae family of viruses in the hepacivirus genus, and is closely related to the flavivirus genus, which includes a number of viruses implicated in human disease, such as dengue virus and yellow fever virus, and to the animal pestivirus family, which includes bovine viral diarrhea virus (BVDV). HCV is a positive-sense, single-stranded RNA virus, with a genome of around 9,600 bases. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are differently distributed geographically. HCV type 1 is the predominant genotype in Europe and the US. The extensive genetic heterogeneity of HCV has important diagnostic and clinical implications, perhaps explaining difficulties in vaccine development and the lack of response to therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better tolerated treatments.

Recently, two peptidomimetic HCV protease inhibitors have gained attention as clinical candidates, namely BILN-2061 disclosed in WO00/59929 and VX-950 disclosed in WO03/87092. A number of similar HCV protease inhibitors have also been disclosed in the academic and patent literature. It has already become apparent that the sustained administration of BILN-2061 or VX-950 selects HCV mutants which are resistant to the respective drug, so called drug escape mutants. These drug escape mutants have characteristic mutations in the HCV protease genome, notably D168V, D168A and/or A156S. Accordingly, additional drugs with different resistance patterns are required to provide failing patients with treatment options, and combination therapy with multiple drugs is likely to be the norm in the future, even for first line treatment.

Experience with HIV drugs, and HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design. The strong peptidomimetic nature of prior art HCV protease inhibitors, with multiple peptide bonds poses pharmacokinetic hurdles to effective dosage regimes.

There is a need for HCV inhibitors which may overcome the disadvantages of current HCV therapy such as side effects, limited efficacy, the emerging of resistance, and compliance failures.

The present invention concerns HCV inhibitors which are superior in one or more of the following pharmacological related properties, i.e. potency, decreased cytotoxicity, improved pharmacokinetics, improved resistance profile, acceptable dosage and pill burden.

In addition, the compounds of the present invention have relatively low molecular weight and are easy to synthesize, starting from starting materials that are commercially available or readily available through art-known synthesis procedures.

WO05/010029 discloses aza-peptide macrocyclic Hepatitis C serine protease inhibitors, pharmaceutical compositions comprising the aforementioned compounds for administration to a subject suffering from HCV infection, and methods of treating an HCV infection in a subject by administering a pharmaceutical composition comprising the said compounds.

The present invention concerns inhibitors of HCV replication, which can be represented by formula (I):

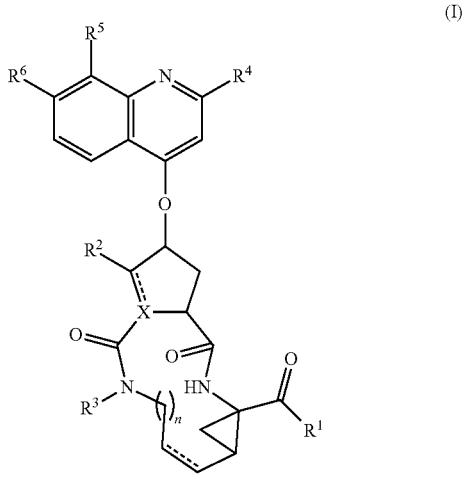

and the N-oxides, salts, and stereoisomers thereof, wherein
each dashed line (represented by - - - - -) represents an optional double bond;
X is N, CH and where X bears a double bond it is C;
$R^1$ is —$OR^7$, —NH—$SO_2R^8$;
$R^2$ is hydrogen, and where X is C or CH, $R^2$ may also be $C_{1-6}$alkyl;
$R^3$ is hydrogen, $C_{1-6}$alkyl, $C_{1-6}$alkoxy$C_{1-6}$alkyl, $C_{3-7}$cycloalkyl;
$R^4$ is aryl or Het;
n is 3, 4, 5, or 6;
$R^5$ represents halo, $C_{1-6}$alkyl, hydroxy, $C_{1-6}$alkoxy, polyhalo$C_{1-6}$alkyl, phenyl, or Het;
$R^6$ represents $C_{1-6}$alkoxy, mono- or di$C_{1-6}$alkylamino;
$R^7$ is hydrogen; aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
$R^8$ is aryl; Het; $C_{3-7}$cycloalkyl optionally substituted with $C_{1-6}$alkyl; or $C_{1-6}$alkyl optionally substituted with $C_{3-7}$cycloalkyl, aryl or with Het;
aryl as a group or part of a group is phenyl optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di-$C_{1-6}$alkyl-amino, azido, mercapto, polyhalo$C_{1-6}$alkyl, polyhalo$C_{1-6}$alkoxy, $C_{3-7}$cycloalkyl, pyrrolidinyl, piperidinyl, piperazinyl, 4-$C_{1-6}$alkyl-piperazinyl, 4-$C_{1-6}$alkylcarbonyl-piperazinyl, and morpholinyl; wherein the morpholinyl and piperidinyl groups may be optionally substituted with one or with two $C_{1-6}$alkyl radicals;
Het as a group or part of a group is a 5 or 6 membered saturated, partially unsaturated or completely unsaturated heterocyclic ring containing 1 to 4 heteroatoms each independently selected from nitrogen, oxygen and sulfur, said heterocyclic ring being optionally condended with a benzene ring; and Het as a whole being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di-$C_{1-6}$alkylamino, azido, mercapto, polyhalo$C_{1-6}$alkyl, polyhalo$C_{1-6}$alkoxy, $C_{3-7}$cycloalkyl, pyrrolidinyl, piperidinyl, piperazinyl, 4-$C_{1-6}$alkylpiperazinyl, 4-$C_{1-6}$alkylcarbonylpiperazinyl, and morpholinyl; wherein the morpholinyl and piperidinyl groups may be optionally substituted with one or with two $C_{1-6}$alkyl radicals.

The invention further relates to methods for the preparation of the compounds of formula (I), the N-oxides, addition salts, quaternary amines, metal complexes, and stereochemically isomeric forms thereof, their intermediates, and the use of the intermediates in the preparation of the compounds of formula (I).

The invention relates to the compounds of formula (I) per se, the N-oxides, addition salts, quaternary amines, metal complexes, and stereochemically isomeric forms thereof, for use as a medicament. The invention further relates to pharmaceutical compositions comprising a carrier and an antivirally effective amount of a compound of formula (I) as specified herein. The pharmaceutical compositions may comprise combinations of the aforementioned compounds with other anti-HCV agents. The invention further relates to the aforementioned pharmaceutical compositions for administration to a subject suffering from HCV infection.

The invention also relates to the use of a compound of formula (I), or a N-oxide, addition salt, quaternary amine, metal complex, or stereochemically isomeric forms thereof, for the manufacture of a medicament for inhibiting HCV replication. Or the invention relates to a method of inhibiting HCV replication in a warm-blooded animal said method comprising the administration of an effective amount of a compound of formula (I), or a prodrug, N-oxide, addition salt, quaternary amine, metal complex, or stereochemically isomeric forms thereof.

As used in the foregoing and hereinafter, the following definitions apply unless otherwise noted.

The term halo is generic to fluoro, chloro, bromo and iodo.

The term "polyhalo$C_{1-6}$alkyl" as a group or part of a group, e.g. in polyhalo$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoro-ethyl. Preferred is trifluoromethyl. Also included are perfluoro$C_{1-6}$ alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-pentynyl, 3-pentynyl, 2-hexynyl, 3-hexynyl and the like. Of interest amongst $C_{2-6}$alkynyl is $C_{2-4}$alkynyl.

$C_{3-7}$cycloalkyl is generic to cyclopropyl, cyclobutyl, cyclopentyl, cyclohexyl and cycloheptyl.

$C_{1-6}$alkanediyl defines bivalent straight and branched chain saturated hydrocarbon radicals having from 1 to 6 carbon atoms such as, for example, methylene, ethylene, 1,3-propanediyl, 1,4-butanediyl, 1,2-propanediyl, 2,3-butanediyl, 1,5-pentanediyl, 1,6-hexanediyl and the like. Of interest amongst $C_{1-6}$alkanediyl is $C_{1-4}$alkanediyl.

$C_{1-6}$alkoxy means $C_{1-6}$alkyloxy wherein $C_{1-6}$alkyl is as defined above.

As used herein before, the term (=O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a staturated carbon.

The radical Het is a heterocycle as specified in this specification and claims. Preferred amongst the Het radicals are those that are monocyclic.

Examples of Het comprise, for example, pyrrolidinyl, piperidinyl, morpholinyl, thiomorpholinyl, piperazinyl, pyrrolyl, pyrazolyl, imidazolyl, oxazolyl, isoxazolyl, thiazinolyl, isothiazinolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, triazinyl, and the like. Of interest amongst the Het radicals are those which are non-saturated, in particular those having an aromatic character. Of further interest are those Het radicals having one or two nitrogens.

Each of the Het radicals mentioned in this and the following paragraph may be optionally substituted with the number and kind of substituents mentioned in the definitions of the compounds of formula (I) or any of the subgroups of compounds of formula (I). Some of the Het radicals mentioned in this and the following paragraph may be substituted with one, two or three hydroxy substituents. Such hydroxy substituted rings may occur as their tautomeric forms bearing keto groups. For example a 3-hydroxypyridazine moiety can occur in its tautomeric form 2H-pyridazin-3-one. Where Het is piperazinyl, it preferably is substituted in its 4-position by a substituent linked to the 4-nitrogen with a carbon atom, e.g. 4-$C_{1-6}$alkyl, 4-polyhalo$C_{1-6}$alkyl, $C_{1-6}$alkoxy$C_{1-6}$alkyl, $C_{1-6}$alkylcarbonyl, $C_{3-7}$cycloalkyl.

Interesting Het radicals comprise, for example pyrrolidinyl, piperidinyl, morpholinyl, thiomorpholinyl, piperazinyl, pyrrolyl, pyrazolyl, imidazolyl, oxazolyl, isoxazolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, pyrazolyl, triazinyl, or any of such heterocycles condensed with a benzene ring, such as indolyl, indazolyl (in particular 1H-indazolyl), indolinyl, quinolinyl, tetrahydroquinolinyl (in particular 1,2,3,4-tetrahydroquinolinyl), isoquinolinyl, tetrahydroisoquinolinyl (in particular 1,2,3,4-tetrahydroisoquinolinyl), quinazolinyl, phthalazinyl, benzimidazolyl, benzoxazolyl, benzisoxazolyl, benzothiazolyl, benzoxadiazolyl, benzothiadiazolyl, benzofuranyl, benzothienyl.

The Het radicals pyrrolidinyl, piperidinyl, morpholinyl, thiomorpholinyl, piperazinyl, 4-substituted piperazinyl preferably are linked via their nitrogen atom (i.e. 1-pyrrolidinyl, 1-piperidinyl, 4-thiomorpholinyl, 4-morpholinyl, 1-piperazinyl, 4-substituted 1-piperazinyl).

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar terms, it is meant to include the compounds of formula (I), their prodrugs, N-oxides, addition salts, quaternary amines, metal complexes, and stereochemically isomeric forms. One embodiment comprises the compounds of formula (I) or any subgroup of compounds of formula (I) specified herein, as well as the N-oxides, salts, as the possible stereoisomeric forms thereof. Another embodiment comprises the compounds of formula (I) or any subgroup of compounds of formula (I) specified herein, as well as the salts as the possible stereoisomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes, and the intermediates used in the preparation thereof, the absolute stereochemical configuration was not experimentally determined A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxy-methyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

As mentioned above, the compounds of formula (I) have several asymmetric centers. In order to more efficiently refer to each of these asymmetric centers, the numbering system as indicated in the following structural formula will be used.

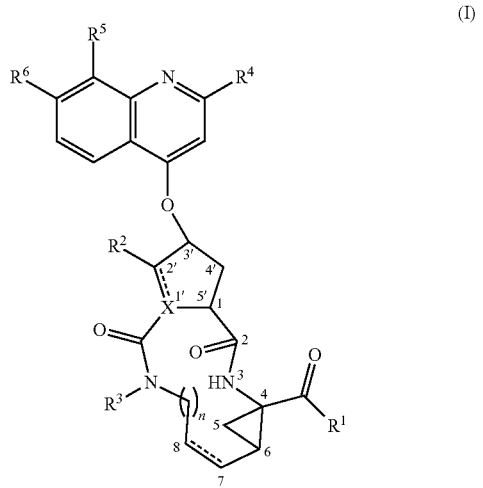

Asymmetric centers are present at positions 1, 4 and 6 of the macrocycle as well as at the carbon atom 3' in the 5-membered ring, carbon atom 2' when the $R^2$ substituent is $C_{1-6}$alkyl, and at carbon atom 1' when X is CH. Each of these asymmetric centers can occur in their R or S configuration.

The stereochemistry at position 1 preferably corresponds to that of an L-amino acid configuration, i.e. that of L-proline.

When X is CH, the 2 carbonyl groups substituted at positions 1' and 5' of the cyclopentane ring preferably are in a trans configuration. The carbonyl substituent at position 5' preferably is in that configuration that corresponds to an L-proline configuration. The carbonyl groups substituted at positions 1' and 5' preferably are as depicted below in the structure of the following formula

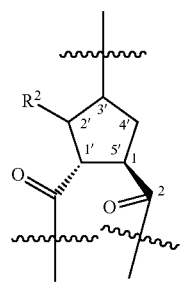

The compounds of formula (I) include a cyclopropyl group as represented in the structural fragment below:

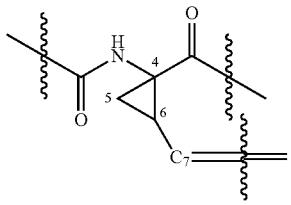

wherein $C_7$ represents the carbon at position 7 and carbons at position 4 and 6 are asymmetric carbon atoms of the cyclopropane ring.

Notwithstanding other possible asymmetric centers at other segments of the compounds of formula (I), the presence of these two asymmetric centers means that the compounds can exist as mixtures of diastereomers, such as the diastereomers of compounds of formula (I) wherein the carbon at position 7 is configured either syn to the carbonyl or syn to the amide as shown below.

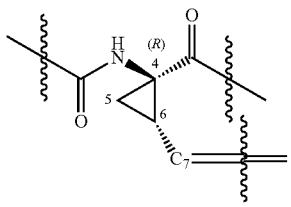

C7 syn to carbonyl

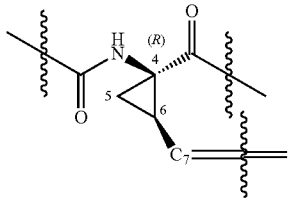

C7 syn to amide

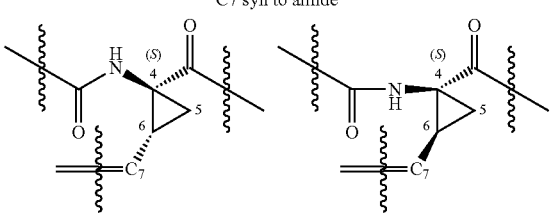

C7 syn to carbonyl          C7 syn to amide1

One embodiment concerns compounds of formula (I) wherein the carbon at position 7 is configured syn to the carbonyl. Another embodiment concerns compounds of formula (I) wherein the configuration at the carbon at position 4 is R. A specific subgroup of compounds of formula (I) are those wherein the carbon at position 7 is configured syn to the carbonyl and wherein the configuration at the carbon at position 4 is R.

The compounds of formula (I) may include as well a proline residue (when X is N) or a cyclopentyl or cyclopentenyl residue (when X is CH or C). Preferred are the compounds of formula (I) wherein the substituent at the 1 (or 5') position and the substituent at position 3' are in a trans configuration. Of particular interest are the compounds of formula (I) wherein position 1 has the configuration corresponding to L-proline and the substituent at position 3' is in a trans configuration in respect of position 1. Preferably the compounds of formula (I) have the stereochemistry as indicated in the structures of formulae (I-a) and (I-b) below:

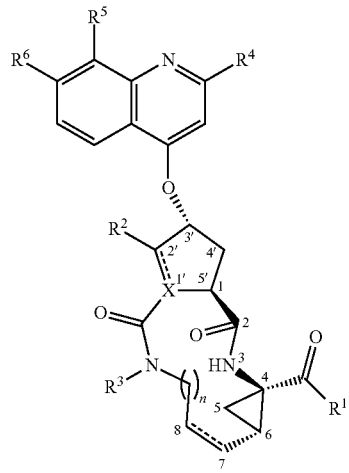

(I-a)

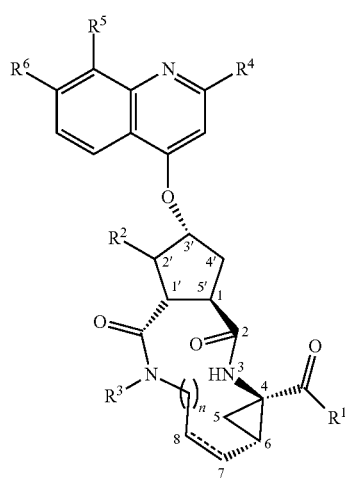

(I-b)

One embodiment of the present invention concerns compounds of formula (I) or of formula (I-a) or of any subgroup of compounds of formula (I), wherein one or more of the following conditions apply:
(a) $R^2$ is hydrogen;
(b) X is nitrogen;
(c) a double bond is present between carbon atoms 7 and 8.

One embodiment of the present invention concerns compounds of formula (I) or of formulae (I-a), (I-b), or of any subgroup of compounds of formula (I), wherein one or more of the following conditions apply:
(a) $R^2$ is hydrogen;
(b) X is CH;
(c) a double bond is present between carbon atoms 7 and 8.

Particular subgroups of compounds of formula (I) are those represented by the following structural formulae:

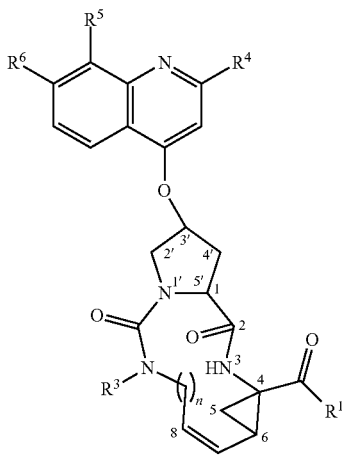

(I-c)

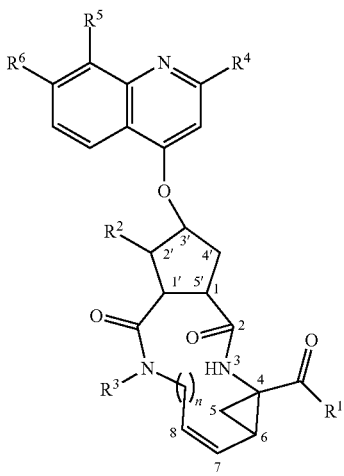

(I-d)

Amongst the compounds of formula (I-c) and (I-d), those having the stereochemical configuration of the compounds of formulae (I-a), and (I-b), respectively, are of particular interest.

The double bond between carbon atoms 7 and 8 in the compounds of formula (I), or in any subgroup of compounds of formula (I), may be in a cis or in a trans configuration. Preferably the double bond between carbon atoms 7 and 8 is in a cis configuration, as depicted in formulae (I-c) and (I-d).

A double bond between carbon atoms 1' and 2' may be present in the compounds of formula (I), or in any subgroup of compounds of formula (I), as depicted in formula (I-e) below.

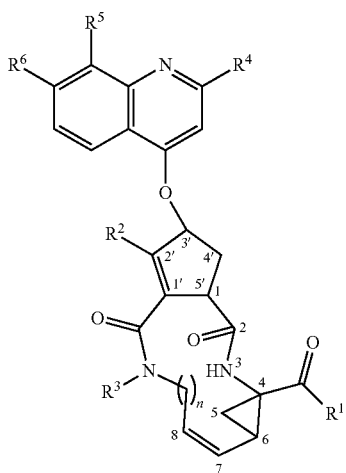

(I-e)

Yet another particular subgroup of compounds of formula (I) are those represented by the following structural formulae:

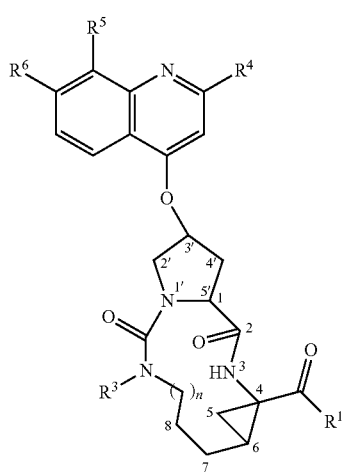

(I-f)

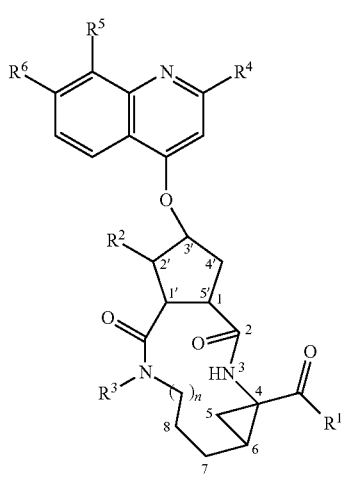

(I-g)

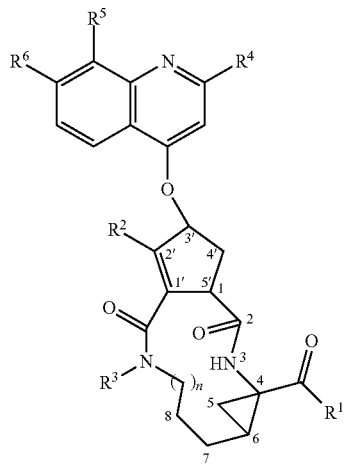

(I-h)

Amongst the compounds of formulae (I-f), (I-g) or (I-h), those having the stereochemical configuration of the compounds of formulae (I-a) and (I-b) are of particular interest.

In (I-a), (I-b), (I-c), (I-d), (I-e), (I-f), (I-g) and (I-h), where applicable, X, n, $R^1$, $R^2$, $R^3$, $R^4$, $R^5$, and $R^6$ are as specified in the definitions of the compounds of formula (I) or in any of the subgroups of compounds of formula (I) specified herein.

It is to be understood that the above defined subgroups of compounds of formulae (I-a), (I-b), (I-c), (I-d), (I-e), (I-f), (I-g) or (I-h), as well as any other subgroup defined herein, are meant to also comprise any N-oxides, addition salts, quaternary amines, metal complexes and stereochemically isomeric forms of such compounds.

When n is 2, the moiety —$CH_2$— bracketed by "n" corresponds to ethanediyl in the compounds of formula (I) or in any subgroup of compounds of formula (I). When n is 3, the moiety —$CH_2$— bracketed by "n" corresponds to propanediyl in the compounds of formula (I) or in any subgroup of compounds of formula (I). When n is 4, the moiety —$CH_2$— bracketed by "n" corresponds to butanediyl in the compounds of formula (I) or in any subgroup of compounds of formula (I). When n is 5, the moiety —$CH_2$-bracketed by "n" corresponds to pentanediyl in the compounds of formula (I) or in any subgroup of compounds of formula (I). When n is 6, the moiety —$CH_2$— bracketed by "n" corresponds to hexanediyl in the compounds of formula (I) or in any subgroup of compounds of formula (I). Particular subgroups of the compounds of formula (I) are those compounds wherein n is 4 or 5.

Embodiments of the invention are compounds of formula (I) or any of the subgroups of compounds of formula (I) wherein (a) $R^1$ is —$OR^7$, in particular wherein $R^7$ is $C_{1-6}$alkyl, such as methyl, ethyl, or tert-butyl (or t.butyl) and most preferably where $R^7$ is hydrogen;

(b) $R^1$ is —$NHS(=O)_2R^8$, in particular wherein $R^8$ is $C_{1-6}$alkyl, $C_3$-$C_7$cycloalkyl, or aryl, e.g. wherein $R^8$ is methyl, cyclopropyl, or phenyl; or (c) $R^1$ is —$NHS(=O)_2R^8$, in particular wherein $R^8$ is $C_{3-7}$cycloalkyl substituted with $C_{1-6}$alkyl, preferably wherein $R^8$ is cyclopropyl, cyclobutyl, cyclopentyl, or cyclohexyl, any of which is substituted with $C_{1-4}$alkyl, i.e. with methyl, ethyl, propyl, isopropyl, butyl, tert-butyl, or isobutyl.

Further embodiments of the invention are compounds of formula (I) or any of the subgroups of compounds of formula (I) wherein $R^1$ is —NHS(=O)$_2$R$^8$, in particular wherein $R^8$ is cyclopropyl substituted with $C_{1-4}$alkyl, i.e. with methyl, ethyl, propyl, or isopropyl.

Further embodiments of the invention are compounds of formula (I) or any of the subgroups of compounds of formula (I) wherein $R^1$ is —NHS(=O)$_2$R$^8$, in particular wherein $R^8$ is 1-methylcyclopropyl.

Further embodiments of the invention are compounds of formula (I) or any of the subgroups of compounds of formula (I) wherein
(a) $R^2$ is hydrogen;
(b) $R^2$ is $C_{1-6}$alkyl, preferably methyl.

Embodiments of the invention are compounds of formula (I) or any of the subgroups of compounds of formula (I) wherein
(a) X is N, C (X being linked via a double bond) or CH (X being linked via a single bond) and $R^2$ is hydrogen;
(b) X is C (X being linked via a double bond) and $R^2$ is $C_{1-6}$alkyl, preferably methyl.

Further embodiments of the invention are compounds of formula (I) or any of the subgroups of compounds of formula (I) wherein
(a) $R^3$ is hydrogen;
(b) $R^3$ is $C_{1-6}$alkyl;
(c) $R^3$ is $C_{1-6}$alkoxy$C_{1-6}$alkyl or $C_{3-7}$cycloalkyl.

Preferred embodiments of the invention are compounds of formula (I) or any of the subgroups of compounds of formula (I) wherein $R^3$ is hydrogen, or $C_{1-6}$alkyl, more preferably hydrogen or methyl.

Embodiments of the invention are compounds of formula (I) or any of the subgroups of compounds of formula (I) wherein $R^4$ is aryl or Het, each independently, optionally substituted with any of the substituents of Het or aryl mentioned in the definitions of the compounds of formula (I) or of any of the subgroups of compounds of formula (I); or specifically said aryl or Het being each, independently, optionally substituted with $C_{1-6}$alkyl, halo, amino, mono- or di$C_{1-6}$alkylamino, pyrrolidinyl, piperidinyl, morpholinyl, piperazinyl, 4-$C_{1-6}$alkylpiperazinyl; and wherein the morpholinyl and piperidinyl groups may optionally substituted with one or two $C_{1-6}$alkyl radicals;

Embodiments of the invention are compounds of formula (I) or any of the subgroups of compounds of formula (I) wherein $R^4$ is a radical

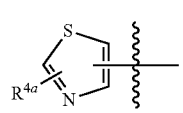

(q)

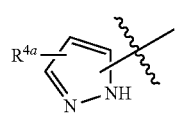

(q')

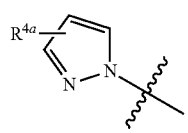

(q'-1)

or, in particular, wherein $R^4$ is selected from the group consisting of:

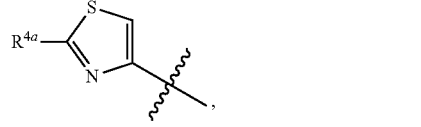

(q-1)

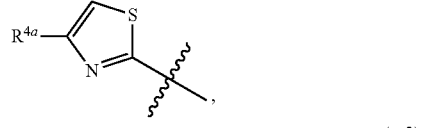

(q-2)

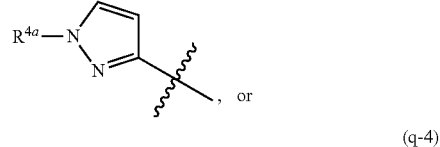

, or (q-3)

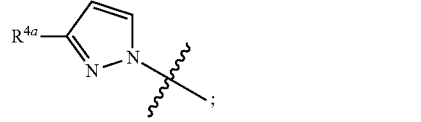

(q-4)

wherein, where possible a nitrogen may bear an $R^{4a}$ substituent or a link to the remainder of the molecule; each $R^{4a}$ in any of the $R^4$ substituents may be selected from those mentioned as possible substituents on Het, as specified in the definitions of the compounds of formula (I) or of any of the subgroups of compounds of formula (I);

more specifically each $R^{4a}$ may be hydrogen, halo, $C_{1-6}$alkyl, amino, or mono- or di-$C_{1-6}$alkylamino, pyrrolidinyl, piperidinyl, morpholinyl, piperazinyl, 4-$C_{1-6}$alkyl-piperazinyl; and wherein the morpholinyl and piperidinyl groups may optionally substituted with one or two $C_{1-6}$alkyl radicals;

more specifically each $R^{4a}$ is, each independently, hydrogen, halo, $C_{1-6}$alkyl, amino, or mono- or di-$C_{1-6}$alkylamino;

and where $R^{4a}$ is substituted on a nitrogen atom, it preferably is a carbon containing substituent that is connected to the nitrogen via a carbon atom or one of its carbon atoms; and wherein in that instance $R^{4a}$ preferably is $C_{1-6}$alkyl.

Embodiments of the invention are compounds of formula (I) or any of the subgroups of compounds of formula (I) wherein $R^4$ is phenyl or pyridiyl (in particular 4-pyridyl) which each may be substituted with 1, 2 or 3 substituents selected from those mentioned for aryl in the definitions of the compounds of formula (I) or of any of the subgroups thereof. In particular said phenyl or pyridyl is substituted with 1-3 (or with 1-2, or with one) substituent or substituents selected from halo, $C_{1-6}$alkyl or $C_{1-6}$alkoxy.

Embodiments of the invention are compounds of formula (I) or any of the subgroups of compounds of formula (I) wherein $R^5$ is halo, or $C_{1-6}$alkyl, preferably methyl, ethyl, isopropyl, tert-butyl, fluoro, chloro, or bromo. include poluhalo$C_{1-6}$alkyl Embodiments of the invention are compounds of formula (I) or any of the subgroups of compounds of formula (I) wherein $R^6$ is $C_{1-6}$alkoxy or di$C_{1-6}$alkylamino; preferably $R^6$ is methoxy or dimethylamino; more preferably $R^6$ is methoxy.

The compounds of formula (I) consist of three building blocks P1, P2, P3. Building block P1 further contains a P1' tail. The carbonyl group marked with an asterisk in compound (I-c) below may be part of either building block P2 or of building block P3. For reasons of chemistry, building block P2 of the compounds of formula (I) wherein X is C incorporates the carbonyl group attached to the position 1'.

The linking of building blocks P1 with P2, P2 with P3, and P1 with P1' (when R¹ is —NH—SO₂R⁸ or —OR) involves forming an amide bond. The linking of blocks P1 and P3 involves double bond formation. The linking of building blocks P1, P2 and P3 to prepare compounds (I-i) or (I-j) can be done in any given sequence. One of the steps involves a cyclization whereby the macrocycle is formed.

Represented herebelow are compounds (I-i) which are compounds of formula (I) wherein carbon atoms C7 and C8 are linked by a double bond, and compounds (I-j) which are compounds of formula (I) wherein carbon atoms C7 and C8 are linked by a single bond. The compounds of formula (I-j) can be prepared from the corresponding compounds of formula (I-I) by reducing the double bond in the macrocycle.

It should be noted that in compounds of formula (I-c), the amide bond formation between blocks P2 and P3 may be accomplished at two different positions of the urea fragment. A first amide bond encompasses the nitrogen of the pyrrolidine ring and the adjacent carbonyl (marked with an asterisk). An alternative second amide bond formation involves the reaction of the asterisked carbonyl with a —NHR³ group. Both amide bond formations between building blocks P2 and P3 are feasible.

The synthesis procedures described hereinafter are meant to be applicable for as well the racemates, stereochemically pure intermediates or end products, or any stereoisomeric mixtures. The racemates or stereochemical mixtures may be separated into stereoisomeric forms at any stage of the synthesis procedures. In one embodiment, the intermediates and end products have the stereochemistry specified above in the compounds of formula (I-a) and (I-b).

In order to simplify the structural representation of the compounds of formula (I) or the intermediates the group

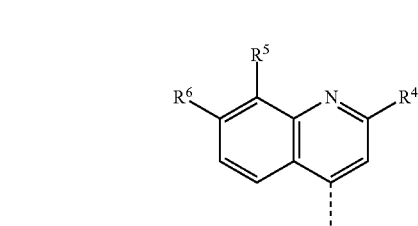

is represented by R⁹ and the dotted line represents the bond linking said group represented by R⁹ to the remainder of the molecule.

In one embodiment, compounds (I-i) are prepared by first forming the amide bonds and subsequent forming the double bond linkage between P3 and P1 with concomitant cyclization to the macrocycle.

In a preferred embodiment, compounds (I) wherein the bond between C₇ and C₈ is a double bond, which are compounds of formula (I-i), as defined above, may be prepared as outlined in the following reaction scheme:

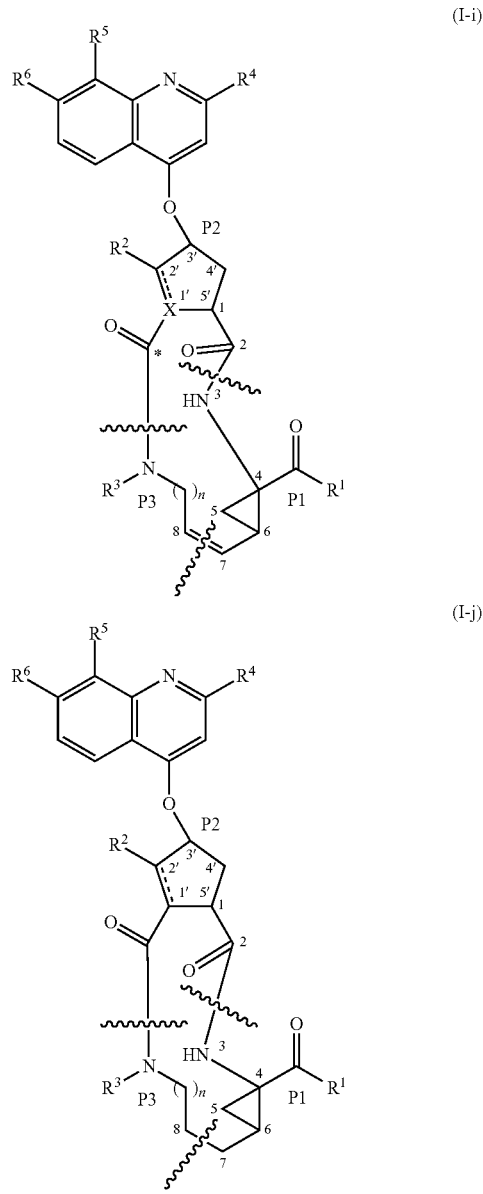

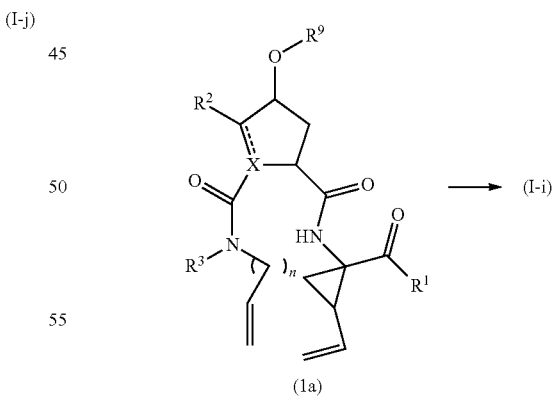

Formation of the macrocycle can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Air-stable ruthenium catalysts such as bis(tricyclohexylphosphine)-3-phenyl-1H-inden-1-ylidene ruthenium chloride (Neolyst M1®) or bis(tricyclohexylphosphine)-[(phenylthio)methylene]ruthenium (IV) dichloride can be used. Other catalysts that can be used are Grubbs first and second generation catalysts, i.e. Benzylidene-bis(tricycle-hexylphosphine)dichlororuthenium and (1,3-bis-(2,4,6-trimethylphenyl)-2-imidazolidinylidene)dichloro(phenylmethylene)-(tricyclohexylphosphine)ruthenium, respectively. Of particular interest are the Hoveyda-Grubbs first and second generation catalysts, which are dichloro(o-isopropoxyphenylmethylene)(tricyclohexylphosphine)-ruthenium(II) and 1,3-bis-(2,4,6-trimethylphenyl)-2-imidazolidinylidene) dichloro-(o-isopropoxyphenylmethylene)ruthenium respectively. Also other catalysts containing other transition metals such as Mo can be used for this reaction.

The metathesis reactions may be conducted in a suitable solvent such as for example ethers, e.g. THF, dioxane; halogenated hydrocarbons, e.g. dichoromethane, CHCl$_3$, 1,2-dichloroethane and the like, hydrocarbons, e.g. toluene. In a preferred embodiment, the metathesis reaction is conducted in toluene. These reactions are conducted at increased temperatures under nitrogen atmosphere.

Compounds of formula (I) wherein the link between C7 and C8 in the macrocycle is a single bond, i.e. compounds of formula (I-j), can be prepared from the compounds of formula (I-i) by a reduction of the C7-C8 double bond in the compounds of formula (I-i). This reduction may be conducted by catalytic hydrogenation with hydrogen in the presence of a noble metal catalyst such as, for example, Pt, Pd, Rh, Ru or Raney nickel. Of interest is Rh on alumina. The hydrogenation reaction preferably is conducted in a solvent such as, e.g. an alcohol such as methanol, ethanol, or an ether such as THF, or mixtures thereof. Water can also be added to these solvents or solvent mixtures.

The R$^1$ group can be connected to the P1 building block at any stage of the synthesis, i.e. before or after the cyclization, or before or after the cyclization and reduction as described herein above. The compounds of formula (I) wherein R$^1$ represents —NHSO$_2$R$^8$, said compounds being represented by formula (I-k-1), can be prepared by linking the R$^1$ group to P1 by forming an amide bond between both moieties. Similarly, the compounds of formula (I) wherein R$^1$ represents —OR$^7$, i.e. compounds (I-k-2), can be prepared by linking the R$^1$ group to P1 by forming an ester bond. In one embodiment, the —OR$^5$ groups are introduced in the last step of the synthesis of the compounds (I) as outlined in the following reaction schemes wherein G represents a group:

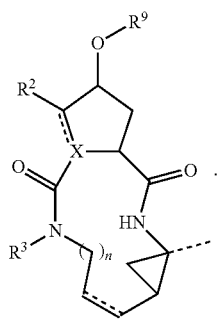

(a)

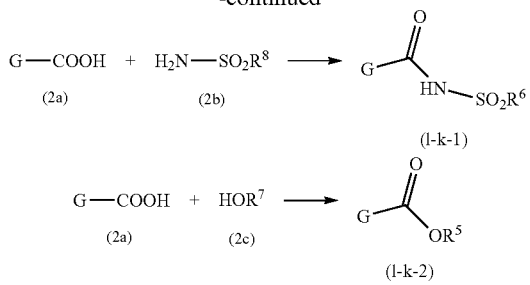

Intermediate (2a) can be coupled with the amine (2b) by an amide forming reaction such as any of the procedures for the formation of an amide bond described hereinafter. In particular, (2a) may be treated with a coupling agent, for example N,N'-carbonyl-diimidazole (CDI), EEDQ, IIDQ, EDCI or benzotriazol-1-yl-oxy-tris-pyrrolidino-phosphonium hexafluorophosphate (commercially available as PyBOP®), in a solvent such as an ether, e.g. THF, or a halogenated hydrocarbon, e.g. dichloromethane, chlorophorm, dichloroethane, and reacted with the desired sulfonamide (2b), preferably after reacting (2a) with the coupling agent. The reactions of (2a) with (2b) preferably are conducted in the presence of a base, for example a trialkylamine such as triethylamine or diisopropylethylamine, or 1,8-diazabicycle [5.4.0]undec-7-ene (DBU). Intermediate (2a) can also be converted into an activated form, e.g. an activated form of general formula G-CO—Z, wherein Z represents halo, or the rest of an active ester, e.g. Z is an aryloxy group such as phenoxy, p.nitrophenoxy, pentafluorophenoxy, trichlorophenoxy, pentachlorophenoxy and the like; or Z can be the rest of a mixed anhydride. In one embodiment, G-CO—Z is an acid chloride (G-CO—Cl) or a mixed acid anhydride (G-CO—O—CO—R or G-CO—O—CO—OR, R in the latter being e.g. C$_{1-4}$alkyl, such as methyl, ethyl, propyl, i.propyl, butyl, t.butyl, i.butyl, or benzyl). The activated form G-CO—Z is reacted with the sulfonamide (2b).

The activation of the carboxylic acid in (2a) as described in the above reactions may lead to an internal cyclization reaction to an azalactone intermediate of formula

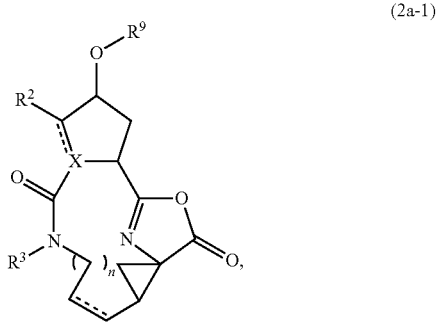

(2a-1)

wherein X, R$^2$, R$^3$, R$^9$, n are as specified above and wherein the stereogenic centers may have the stereochemical configuration as specified above, for example as in (I-a) or (I-b). The intermediates (2a-1) can be isolated from the reaction mixture, using conventional methodology, and the isolated intermediate (2a-1) is then reacted with (2b), or the reaction mixture containing (2a-1) can be reacted further with (2b) without isolation of (2a-1). In one embodiment, where the reaction with the coupling agent is conducted in a waterimmiscible solvent, the reaction mixture containing (2a-1) may be washed with water or with slightly basic water in order to remove all water-soluble side products. The thus obtained washed solution may then be reacted with (2b) without additional purification steps. The isolation of intermediates (2a-1) on the other hand may provide certain advantages in that the isolated product, after optional further purification, may be reacted with (2b), giving rise to less side products and an easier work-up of the reaction.

Intermediate (2a) can be coupled with the alcohol (2c) by an ester forming reaction. For example, (2a) and (2c) are reacted together with removal of water either physically, e.g. by azeotropical water removal, or chemically by using a dehydrating agent. Intermediate (2a) can also be converted into an activated form G-CO—Z, such as the activated forms mentioned above, and subsequently reacted with the alcohol (2c). The ester forming reactions preferably are conducted in the presence of a base such as an alkali metal carbonate or hydrogen carbonate, e.g. sodium or potassium hydrogen carbonate, or a tertiary amine such as the amines mentioned herein in relation to the amide forming reactions, in particular a trialkylamine, e.g. triethylamine Solvents that can be used in the ester forming reactions comprise ethers such as THF; halogenated hydrocarbons such as dichoromethane, $CH_2Cl_2$; hydrocarbons such as toluene; polar aprotic solvents such as DMF, DMSO, DMA; and the like solvents.

The compounds of formula (I) wherein $R^3$ is hydrogen, said compounds being represented by (I-1), can also be prepared by removal of a protecting group PG, from a corresponding nitrogen-protected intermediate (3a), as in the following reaction scheme. The protecting group PG in particular is any of the nitrogen protecting groups mentioned hereinafter and can be removed using procedures also mentioned hereinafter:

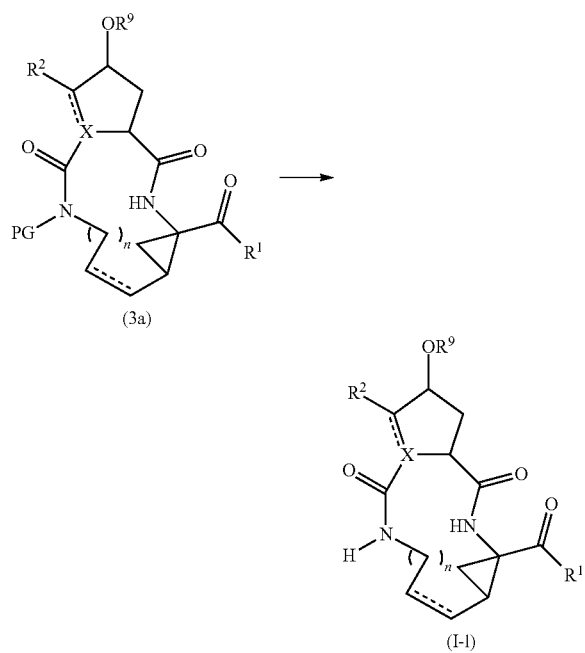

The starting materials (3a) in the above reaction can be prepared following the procedures for the preparation of compounds of formula (I), but using intermediates wherein the group $R^3$ is PG.

The compounds of formula (I) can also be prepared by reacting an intermediate (4a) with intermediate (4b) as outlined in the following reaction scheme wherein the various radicals have the meanings specified above:

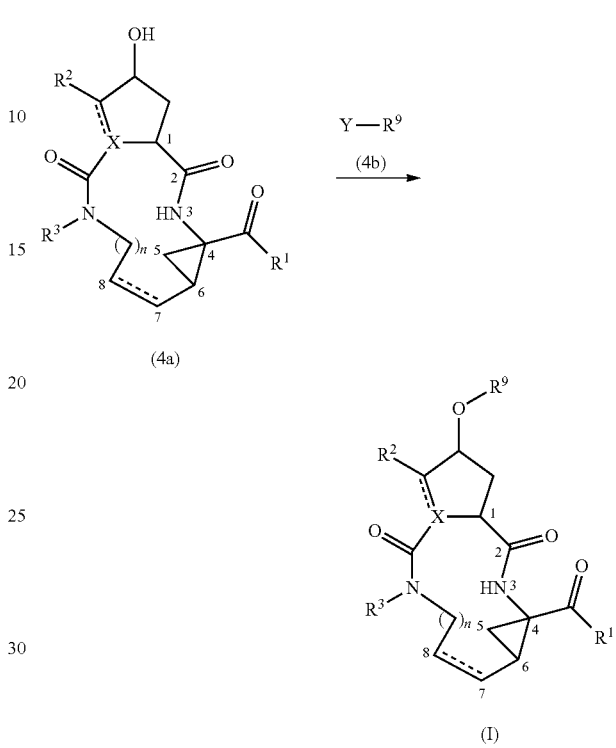

Y in (4b) represents hydroxy or a leaving group LG such as a halide, e.g. bromide or chloride, or an arylsulfonyl group, e.g. mesylate, triflate or tosylate and the like.

In one embodiment, the reaction of (4a) with (4b) is an O-arylation reaction and Y represents a leaving group. This reaction can be conducted following the procedures described by E. M. Smith et al. (J. Med. Chem. (1988), 31, 875-885). In particular, this reaction is conducted in the presence of a base, preferably a strong base, in a reaction-inert solvent, e.g. one of the solvents mentioned for the formation of an amide bond.

In a particular embodiment, starting material (4a) is reacted with (4b) in the presence of a base which is strong enough to detract a hydrogen from the hydroxy group, for example an alkali of alkaline metal hydride such as LiH or sodium hydride, or alkali metal alkoxide such as sodium or potassium methoxide or ethoxide, potassium tert-butoxide, in a reaction inert solvent like a dipolar aprotic solvent, e.g. DMA, DMF and the like. The resulting alcoholate is reacted with the arylating agent (4b), wherein Y is a suitable leaving group as mentioned above. The conversion of (4a) to (I) using this type of O-arylation reaction does not change the stereochemical configuration at the carbon bearing the hydroxy group.

Alternatively, the reaction of (4a) with (4b) can also be conducted via a Mitsunobu reaction (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706). This reaction comprises treatment of intermediate (4a) with (4b) wherein Y is hydroxyl, in the presence of triphenylphosphine and an activating agent such as a dialkyl azocarboxylate, e.g. diethyl azodicarboxylate (DEAD), diisopropyl azodicarboxylate (DIAD) or the like. The Mitsunobu reaction changes the stereochemical configuration at the carbon bearing the hydroxy group.

Alternatively, in order to prepare the compounds of formula (I), first an amide bond between building blocks P2 and P1 is formed, followed by coupling of the P3 building block to the P1 moiety in P1-P2, and a subsequent carbamate or ester bond formation between P3 and the P2 moiety in P2-P1-P3 with concomitant ring closure.

Yet another alternative synthetic methodology is the formation of an amide bond between building blocks P2 and P3, followed by the coupling of building block P1 to the P3 moiety in P3-P2, and a last amide bond formation between P1 and P2 in P1-P3-P2 with concomitant ring closure.

Building blocks P1 and P3 can be linked to a P1-P3 sequence. If desired, the double bond linking P1 and P3 may be reduced. The thus formed P1-P3 sequence, either reduced or not, can be coupled to building block P2 and the thus forming sequence P1-P3-P2 subsequently cyclized, by forming an amide bond.

Building blocks P1 and P3 in any of the previous approaches can be linked via double bond formation, e.g. by the olefin metathesis reaction described hereinafter, or a Wittig type reaction. If desired, the thus formed double bond can be reduced, similarly as described above for the conversion of (I-i) to (I-j). The double bond can also be reduced at a later stage, i.e. after addition of a third building block, or after formation of the macrocycle. Building blocks P2 and P1 are linked by amide bond formation and P3 and P2 are linked by carbamate or ester formation.

The tail P1' can be bonded to the P1 building block at any stage of the synthesis of the compounds of formula (I), for example before or after coupling the building blocks P2 and P1; before or after coupling the P3 building block to P1; or before or after ring closure.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

The formation of amide bonds can be carried out using standard procedures such as those used for coupling amino acids in peptide synthesis. The latter involves the dehydrative coupling of a carboxyl group of one reactant with an amino group of the other reactant to form a linking amide bond. The amide bond formation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions with amide bond formation include the azide method, mixed carbonic-carboxylic acid anhydride (isobutyl chloroformate) method, the carbodiimide (dicyclohexylcarbodiimide, diisopropylcarbodiimide, or water-soluble carbodiimide such as N-ethyl-N'-[(3-dimethylamino)propyl]carbodiimide) method, the active ester method (e.g. p-nitrophenyl, p-chlorophenyl, trichlorophenyl, pentachloro-phenyl, pentafluorophenyl, N-hydroxysuccinic imido and the like esters), the Woodward reagent K-method, the 1,1-carbonyldiimidazole (CDI or N,N'-carbonyl-diimidazole) method, the phosphorus reagents or oxidation-reduction methods. Some of these methods can be enhanced by adding suitable catalysts, e.g. in the carbodiimide method by adding 1-hydroxybenzotriazole, DBU (1,8-diazabicyclo[5.4.0]undec-7-ene), or 4-DMAP. Further coupling agents are (benzotriazol-1-yloxy)tris-(dimethylamino) phosphonium hexafluorophosphate, either by itself or in the presence of 1-hydroxy-benzotriazole or 4-DMAP; or 2-(1H-benzotriazol-1-yl)-N,N,N',N'-tetra-methyluronium tetrafluoroborate, or O-(7-azabenzotriazol-1-yl)-N,N,N',N'-tetramethyluronium hexafluorophosphate. These coupling reactions can be performed in either solution (liquid phase) or solid phase.

A preferred amide bond formation is performed employing N-ethyloxycarbonyl-2-ethyloxy-1,2-dihydroquinoline (EEDQ) or N-isobutyloxy-carbonyl-2-isobutyloxy-1,2-dihydroquinoline (IIDQ). Unlike the classical anhydride procedure, EEDQ and IIDQ do not require base nor low reaction temperatures. Typically, the procedure involves reacting equimolar amounts of the carboxyl and amine components in an organic solvent (a wide variety of solvents can be used). Then EEDQ or IIDQ is added in excess and the mixture is allowed to stir at room temperature.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicyclo[5.4.0]undec-7-ene (DBU). The reaction temperature may range between 0° C. and 50° C. and the reaction time may range between 15 min and 24 h.

The functional groups in the building blocks that are linked together may be protected to avoid formation of undesired bonds. Appropriate protecting groups that can be used are listed for example in Greene, "Protective Groups in Organic Chemistry", John Wiley & Sons, New York (1999) and "The Peptides: Analysis, Synthesis, Biology", Vol. 3, Academic Press, New York (1987).

Carboxyl groups can be protected as an ester that can be cleaved off to give the carboxylic acid. Protecting groups that can be used include 1) alkyl esters such as methyl, trimethylsilyl and tert-butyl; 2) arylalkyl esters such as benzyl and substituted benzyl; or 3) esters that can be cleaved by a mild base or mild reductive means such as trichloroethyl and phenacyl esters.

Amino groups can be protected by a variety of N-protecting groups, such as:
1) acyl groups such as formyl, trifluoroacetyl, phthalyl, and p-toluenesulfonyl;
2) aromatic carbamate groups such as benzyloxycarbonyl (Cbz or Z) and substituted benzyloxycarbonyls, and 9-fluorenylmethyloxycarbonyl (Fmoc);
3) aliphatic carbamate groups such as tert-butyloxycarbonyl (Boc), ethoxycarbonyl, diisopropylmethoxy-carbonyl, and allyloxycarbonyl;
4) cyclic alkyl carbamate groups such as cyclopentyloxycarbonyl and adamantyloxycarbonyl;
5) alkyl groups such as triphenylmethyl, benzyl or substituted benzyl such as 4-methoxybenzyl;
6) trialkylsilyl such as trimethylsilyl or t.Bu dimethylsilyl; and
7) thiol containing groups such as phenylthiocarbonyl and dithiasuccinoyl. Interesting amino protecting groups are Boc and Fmoc.

Preferably the amino protecting group is cleaved off prior to the next coupling step. Removal of N-protecting groups can be done following art-known procedures. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethyl-formamide. When the Fmoc group is used, the reagents of choice are piperidine or substituted piperidine in dimethylformamide, but any secondary amine can be used. The deprotection is carried out at a temperature between 0° C. and room temperature, usually around 15-25° C., or 20-22° C.

Other functional groups that can interfere in the coupling reactions of the building blocks may also be protected. For example hydroxyl groups may be protected as benzyl or substituted benzyl ethers, e.g. 4-methoxybenzyl ether, benzoyl or substituted benzoyl esters, e.g. 4-nitrobenzoyl ester, or with trialkylsilyl groups (e.g. trimethylsilyl or tert-butyldimethylsilyl).

Further amino groups may be protected by protecting groups that can be cleaved off selectively. For example, when Boc is used as the α-amino protecting group, the following side chain protecting groups are suitable: p-toluenesulfonyl (tosyl) moieties can be used to protect further amino groups; benzyl (Bn) ethers can be used to protect hydroxy groups; and benzyl esters can be used to protect further carboxyl groups. Or when Fmoc is chosen for the α-amino protection, usually tert-butyl based protecting groups are acceptable. For instance, Boc can be used for further amino groups; tert-butyl ethers for hydroxyl groups; and tert-butyl esters for further carboxyl groups.

Any of the protecting groups may be removed at any stage of the synthesis procedure but preferably, the protecting groups of any of the functionalities not involved in the reaction steps are removed after completion of the build-up of the macrocycle. Removal of the protecting groups can be done in whatever manner is dictated by the choice of protecting groups, which manners are well known to those skilled in the art.

The intermediates of formula (1a) wherein X is N, said intermediates being represented by formula (1a-1), may be prepared starting from intermediates (5a) which are reacted with an alkenamine (5b) in the presence of a carbonyl introducing agent as outlined in the following reaction scheme.

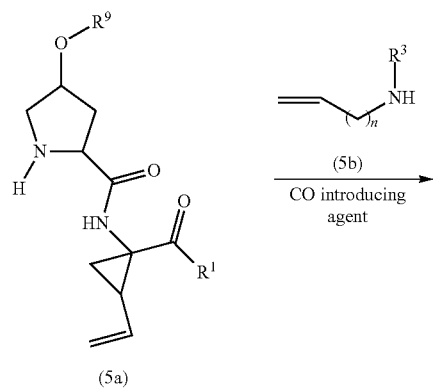

(5a)

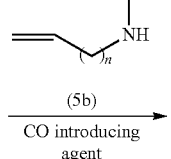

(5b)

CO introducing agent

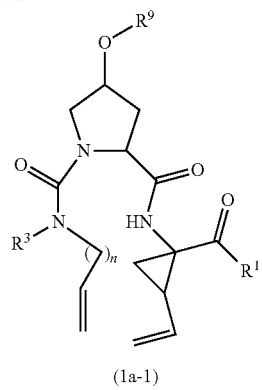

(1a-1)

Carbonyl (CO) introducing agents include phosgene, or phosgene derivatives such as carbonyl diimidazole (CDI), and the like. In one embodiment (5a) is reacted with the CO introducing agent in the presence of a suitable base and a solvent, which can be the bases and solvents used in the amide forming reactions as described above. In a particular embodiment, the base is a hydrogencarbonate, e.g. NaHCO$_3$, or a tertiary amine such as triethylamine and the like, and the solvent is an ether or halogenated hydrocarbon, e.g. THF, CH$_2$Cl$_2$, CHCl$_3$, and the like. Thereafter, the amine (5b) is added thereby obtaining intermediates (1a-1) as in the above scheme. An alternative route using similar reaction conditions involves first reacting the CO introducing agent with the alkenamine (5b) and then reacting the thus formed intermediate with (5a).

The intermediates (1a-1) can alternatively be prepared as follows:

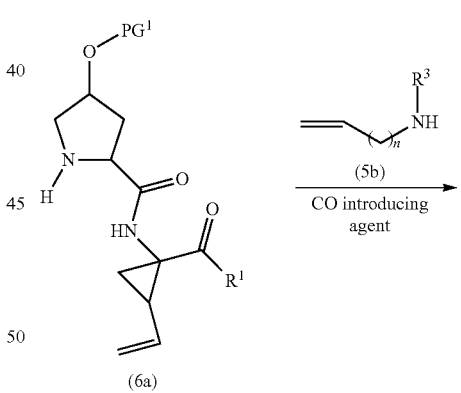

(6a)

CO introducing agent

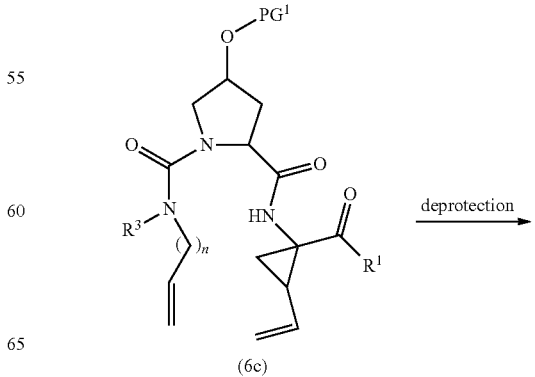

(6c)

deprotection

-continued

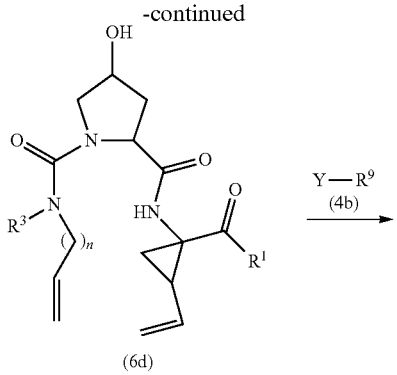

(6d)

PG[1] is an O-protecting group, which can be any of the groups mentioned herein and in particular is a benzoyl or substituted benzoyl group such as 4-nitrobenzoyl. In the latter instance this group can be removed by reaction with a an alkali metal hydroxide (LiOH, NaOH, KOH), in particular where PG[1] is 4-nitrobenzoyl, with LiOH, in an aqueous medium comprising water and a water-soluble organic solvent such as an alkanol (methanol, ethanol) and THF.

Intermediates (6a) are reacted with (5b) in the presence of a carbonyl introducing agent, similar as described above, and this reaction yields intermediates (6c). These are deprotected, in particular using the reaction conditions mentioned above. The resulting alcohol (6d) is reacted with intermediates (4b) as described above for the reaction of (4a) with (4b) and this reaction results in intermediates (1a-1).

The intermediates of formula (1a) wherein X is C, said intermediates being represented by formula (1a-2), may be prepared by an amide forming reaction starting from intermediates (7a) which are reacted with an amine (5b) as shown in the following reaction scheme, using reaction conditions for preparing amides such as those described above.

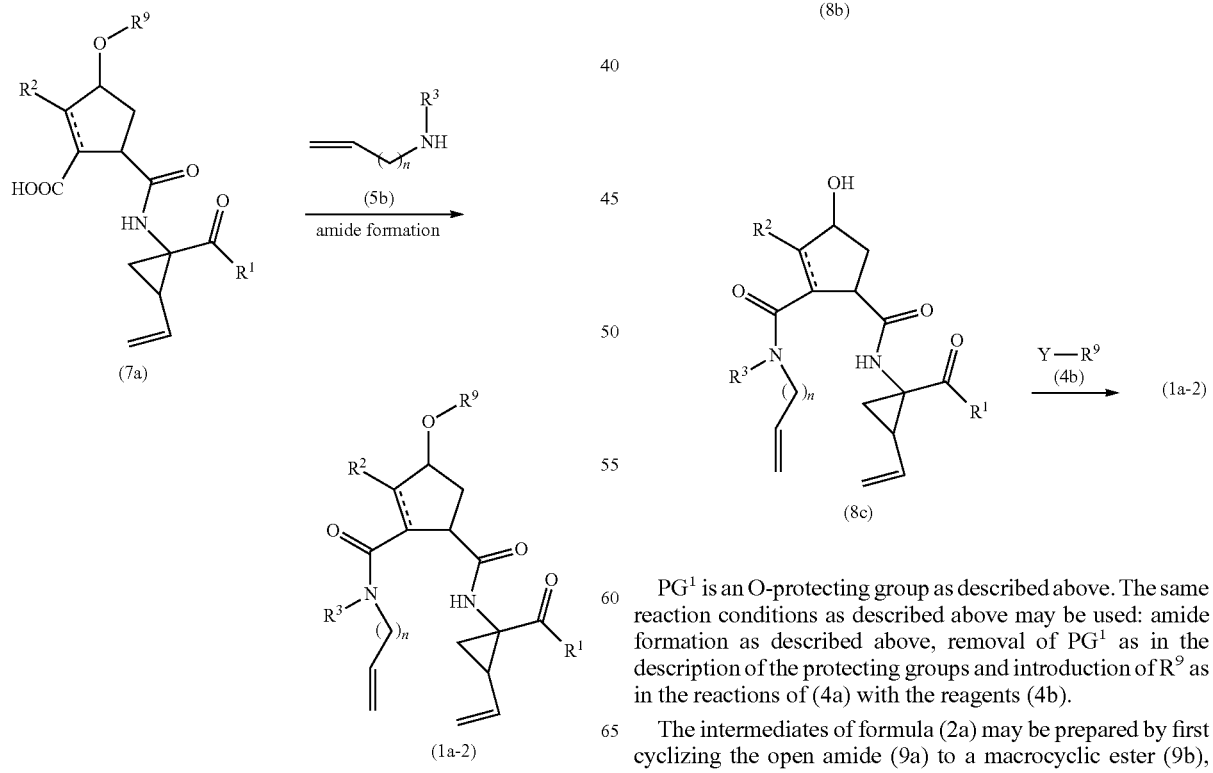

The intermediates (1a-1) can alternatively be prepared as follows:

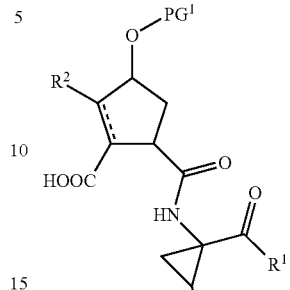

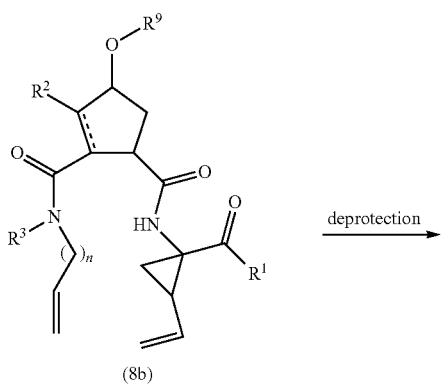

PG[1] is an O-protecting group as described above. The same reaction conditions as described above may be used: amide formation as described above, removal of PG[1] as in the description of the protecting groups and introduction of R[9] as in the reactions of (4a) with the reagents (4b).

The intermediates of formula (2a) may be prepared by first cyclizing the open amide (9a) to a macrocyclic ester (9b), which in turn is converted to (2a) as follows:

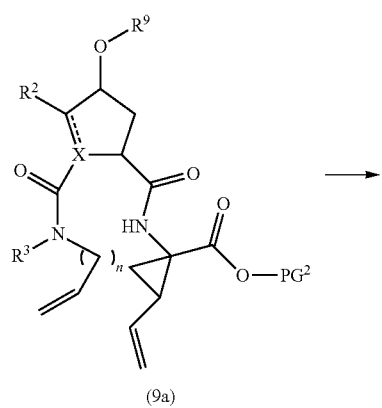

(9a)

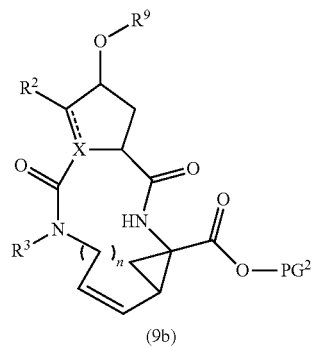

(9b)

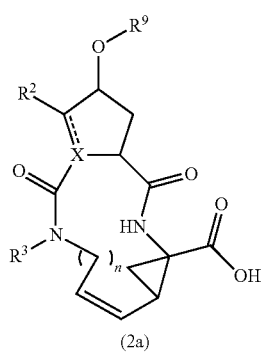

(2a)

PG² is a carboxyl protecting group, e.g. one of the carboxyl protecting groups mentioned above, in particular a $C_{1-4}$alkyl or benzyl ester, e.g. a methyl, ethyl or t.butyl ester. The reaction of (9a) to (9b) is a metathesis reaction and is conducted as described above. The group PG² is removed following procedures also described above. Where PG¹ is a $C_{1-4}$alkyl ester, it is removed by alkaline hydrolysis, e.g. with NaOH or preferably LiOH, in an aqueous solvent, e.g. a $C_{1-4}$alkanol/water mixture. A benzyl group can be removed by catalytic hydrogenation.

In an alternative synthesis, intermediates (2a) can be prepared as follows:

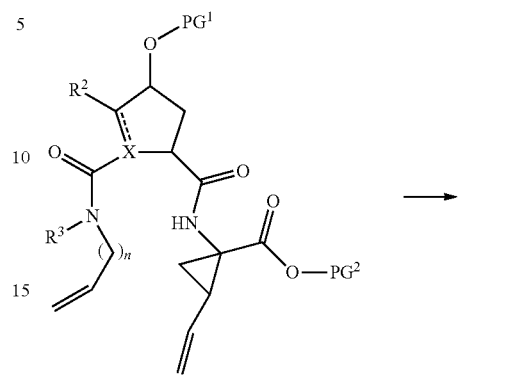

(10a)

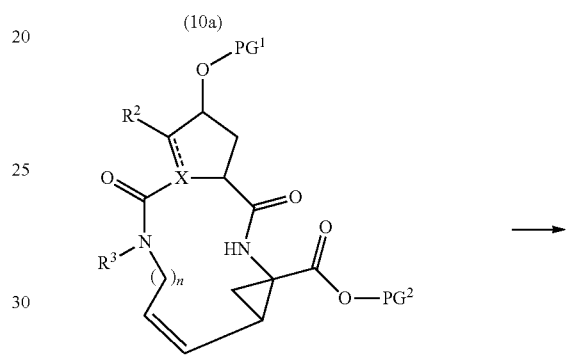

(10b)

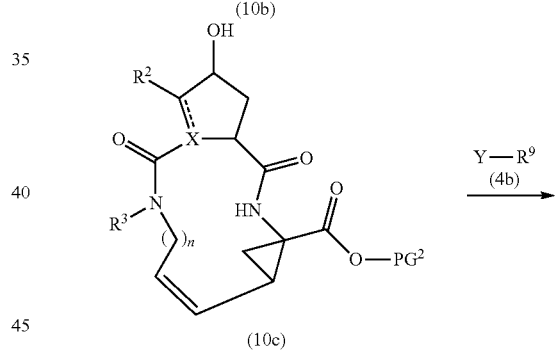

(10c)

(9b) ⟶ (2a)

The PG¹ group is selected such that it is selectively cleavable towards PG². PG² may be e.g. methyl or ethyl esters, which can be removed by treatment with an alkali metal hydroxide in an aqueous medium, in which case PG¹ e.g. is t.butyl or benzyl. PG² may be t.butyl esters removable under weakly acidic conditions or PG¹ may be benzyl esters removable with strong acid or by catalytic hydrogenation, in the latter two cases PG¹ e.g. is a benzoic ester such as a 4-nitrobenzoic ester.

First, intermediates (10a) are cyclized to the macrocyclic esters (10b), the latter are deprotected by removal of the PG¹ group to (10c), which are reacted with intermediates (4b), followed by removal of carboxyl protecting group PG². The cyclization, deprotection of PG¹ and PG² and the coupling with (4b) are as described above.

The R¹ groups can be introduced at any stage of the synthesis, either as the last step as described above, or earlier, before the macrocycle formation. In the following scheme, the groups R¹ being —NH—SO₂R⁸ or —OR⁷ (which are as specified above) are introduced:

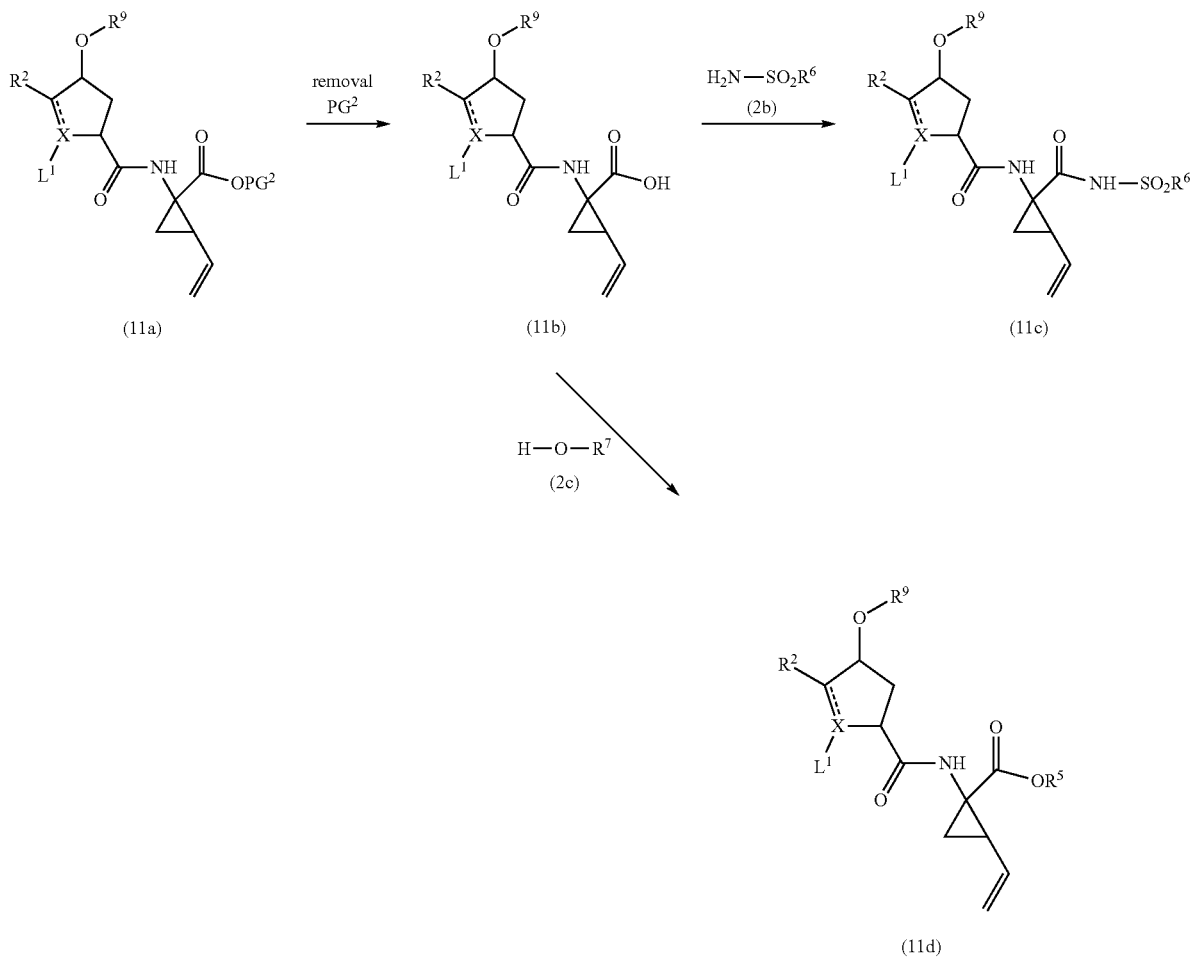

In the above scheme, PG² is as defined above and L¹ is a P3 group

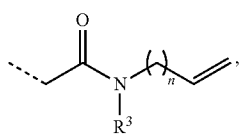

wherein n and R³ are as defined above and where X is N, L¹ may also be a nitrogen-protecting group (PG, as defined above) and where X is C, L¹ may also be a group —COOPG²ᵃ, wherein the group PG²ᵃ is a carboxyl protecting group similar as PG², but wherein PG²ᵃ is selectively cleavable towards PG². In one embodiment PG²ᵃ is t.butyl and PG² is methyl or ethyl.

The intermediates (11c) and (11d) wherein L¹ represents a group (b) correspond to the intermediates (1a) and may be processed further as specified above.

Coupling of P1 and P2 Building Blocks

The P1 and P2 building blocks are linked using an amide forming reaction following the procedures described above. The P1 building block may have a carboxyl protecting group PG² (as in (12b)) or may already be linked to P1' group (as in (12c)). L² is a N-protecting group (PG), or a group (b), as specified above. L³ is hydroxy, —OPG¹ or a group —O—R⁹ as specified above. Where in any of the following reaction schemes L³ is hydroxy, prior to each reaction step, it may be protected as a group —OPG¹ and, if desired, subsequently deprotected back to a free hydroxy function. Similarly as described above, the hydroxy function may be converted to a group —O—R⁹.

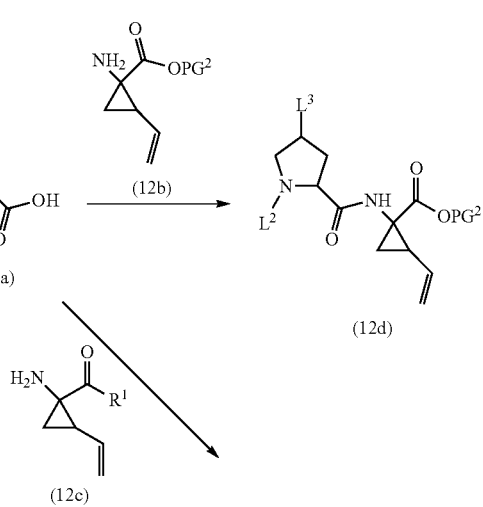

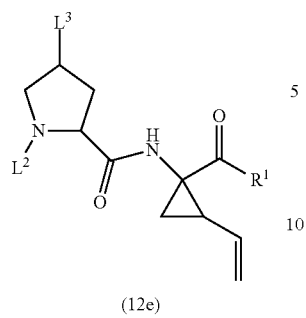

(12e)

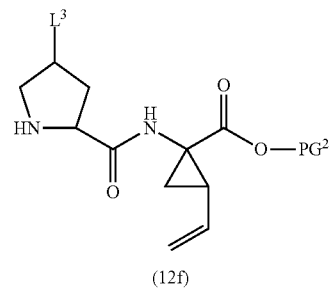

(12f)

In the procedure of the above scheme, a cyclopropyl amino acid (12b) or (12c) is coupled to the acid function of the P2 building block (12a) with the formation of an amide linkage, following the procedures described above. Intermediates (12d) or (12e) are obtained. Where in the latter $L^2$ is a group (b), the resulting products are P3-P2-P1 sequences encompassing some of the intermediates (11c) or (11d) in the previous reaction scheme. Removal of the acid protecting group in (12d), using the appropriate conditions for the protecting group used, followed by coupling with an amine $H_2N$—$SO_2R^8$ (2b) or with $HOR^7$ (2c) as described above, again yields the intermediates (12e), wherein —$COR^1$ are amide or ester groups. Where $L^2$ is a N-protecting group, it can be removed yielding intermediates (5a) or (6a). In one embodiment, PG in this reaction is a BOC group and $PG^2$ is methyl or ethyl. Where additionally $L^3$ is hydroxy, the starting material (12a) is Boc-L-hydroxyproline. In a particular embodiment, PG is BOC, $PG^2$ is methyl or ethyl and $L^3$ is —O—$R^9$.

In one embodiment, $L^2$ is a group (b) and these reactions involve coupling P1 to P2-P3, which results in the intermediates (1a-1) or (1a) mentioned above. In another embodiment, $L^2$ is a N-protecting group PG, which is as specified above, and the coupling reaction results in intermediates (12d-1) or (12e-1), from which the group PG can be removed, using reaction conditions mentioned above, obtaining intermediates (12-f) or respectively (12 g), which encompass intermediates (5a) and (6a) as specified above:

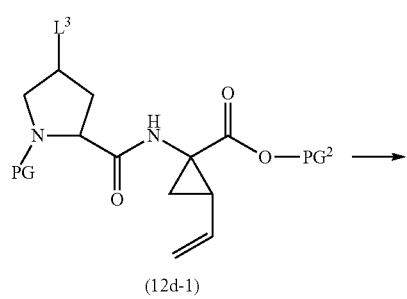

(12d-1)

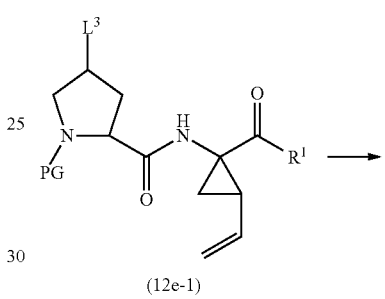

(12e-1)

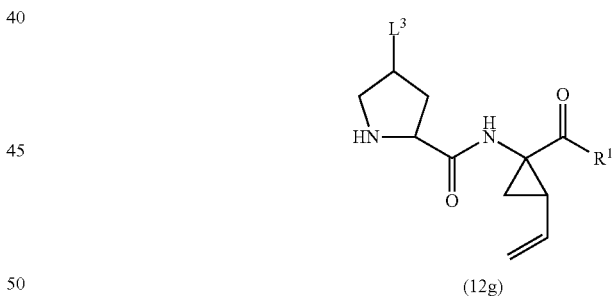

(12g)

In one embodiment, the group $L^3$ in the above schemes represents a group —O-$PG^1$ which can be introduced on a starting material (12a) wherein $L^3$ is hydroxy. In this instance $PG^1$ is chosen such that it is selectively cleavable towards group $L^2$ being PG.

In a similar way, P2 building blocks wherein X is C, which are cyclopentane or cyclopentene derivatives, can be linked to P1 building blocks as outlined in the following scheme wherein $R^1$, $R^2$, $L^3$ are as specified above and $PG^2$ and $PG^{2a}$ are carboxyl protecting groups. $PG^{2a}$ typically is chosen such that it is selectively cleavable towards group $PG^2$. Removal of the $PG^{2a}$ group in (13c) yields intermediates (7a) or (8a), which can be reacted with (5b) as described above.

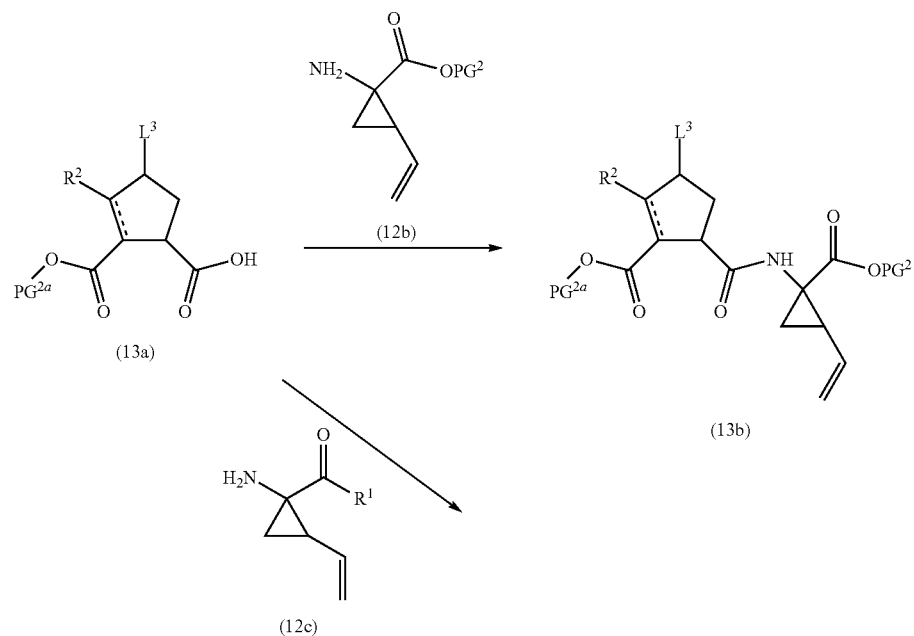
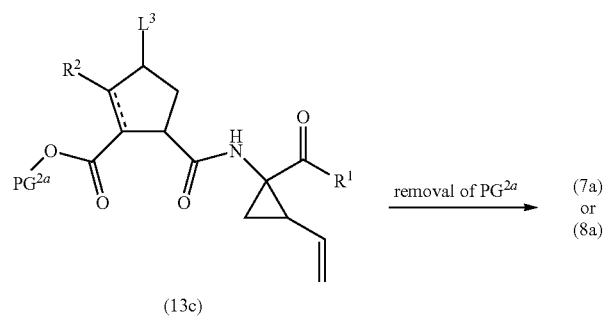

In a particular embodiment, where X is C, $R^2$ is H, and where X and the carbon bearing $R^2$ are linked by a single bond (P2 being a cyclopentane moiety), $PG^{2a}$ and $L^3$ taken together form a bond and the P2 building block is represented by formula:

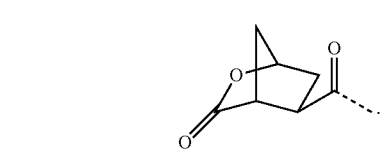

(c)

Bicyclic acid (14a) is reacted with (12b) or (12c) similar as described above to (14b) and (14c) respectively, wherein the lactone is opened giving intermediates (14c) and (14e). The lactones can be opened using ester hydrolysis procedures, for example using the reaction conditions described above for the alkaline removal of a $PG^1$ group in (9b), in particular using basic conditions such as an alkali metal hydroxide, e.g. NaOH, KOH, in particular LiOH.

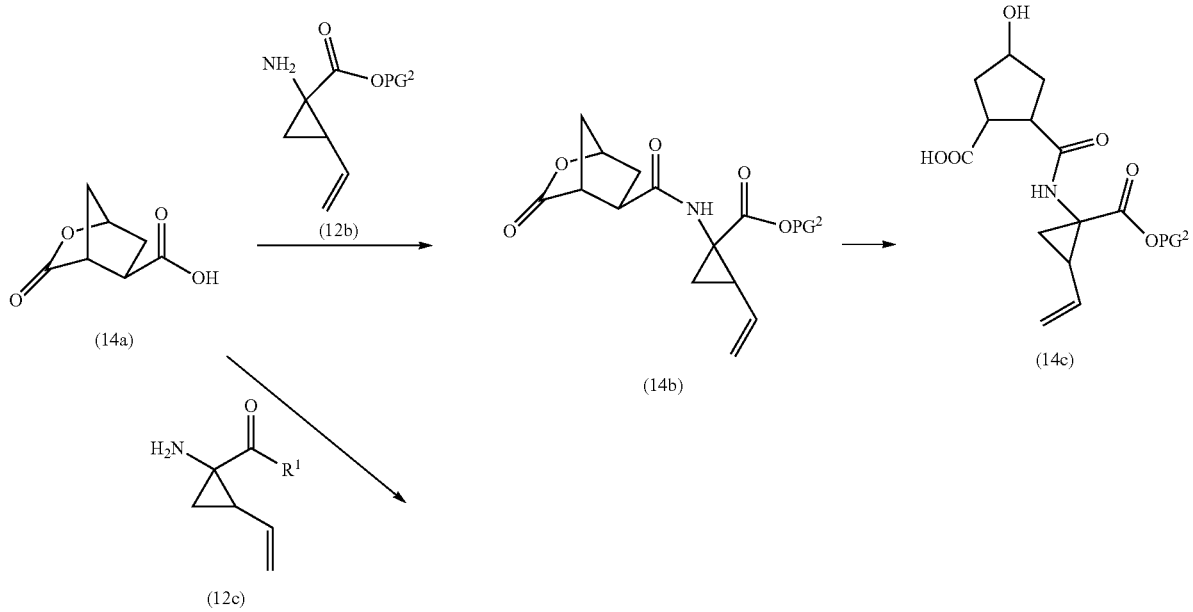

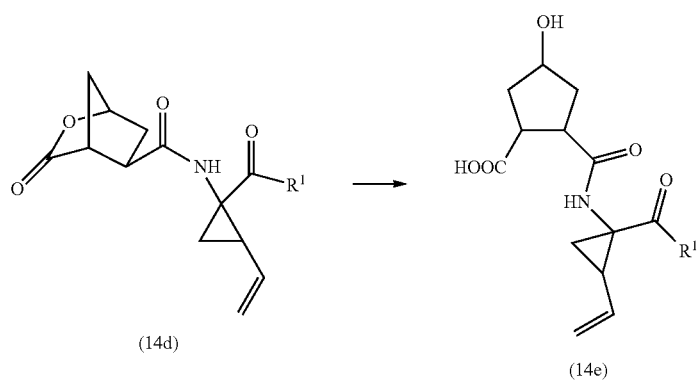

Intermediates (14c) and (14e) can be processed further as described hereinafter.

Coupling of P3 and P2 Building Blocks

For P2 building blocks that have a pyrrolidine moiety, the P3 and P2 or P3 and P2-P1 building blocks are linked using a carbamate forming reaction following the procedures described above for the coupling of (5a) with (5b). A general procedure for coupling P2 blocks having a pyrrolidine moiety is represented in the following reaction scheme wherein $L^3$ is as specified above and $L^4$ is a group —O-$PG^2$, a group (d)

or a group (e)

In one embodiment $L^4$ in (15a) is a group —$OPG^2$, the $PG^2$ group may be removed and the resulting acid coupled with cyclopropyl amino acids (12a) or (12b), yielding intermediates (12d) or (12e) wherein $L^2$ is a radical (d) or (e).

A general procedure for coupling P3 blocks with a P2 block or a with a P2-P1 block wherein the P2 is a cyclopentane or cyclopentene is shown in the following scheme. $L^3$ and $L^4$ are as specified above.

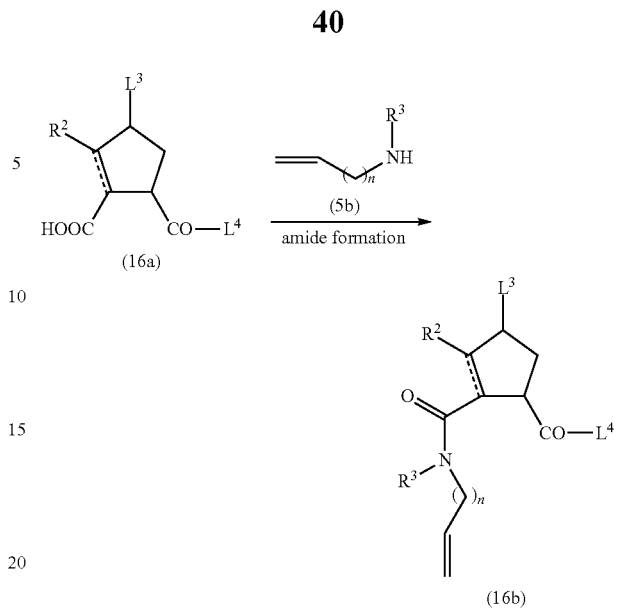

In a particular embodiment $L^3$ and $L^4$ taken together may form a lactone bridge as in (14a), and the coupling of a P3 block with a P2 block is as follows:

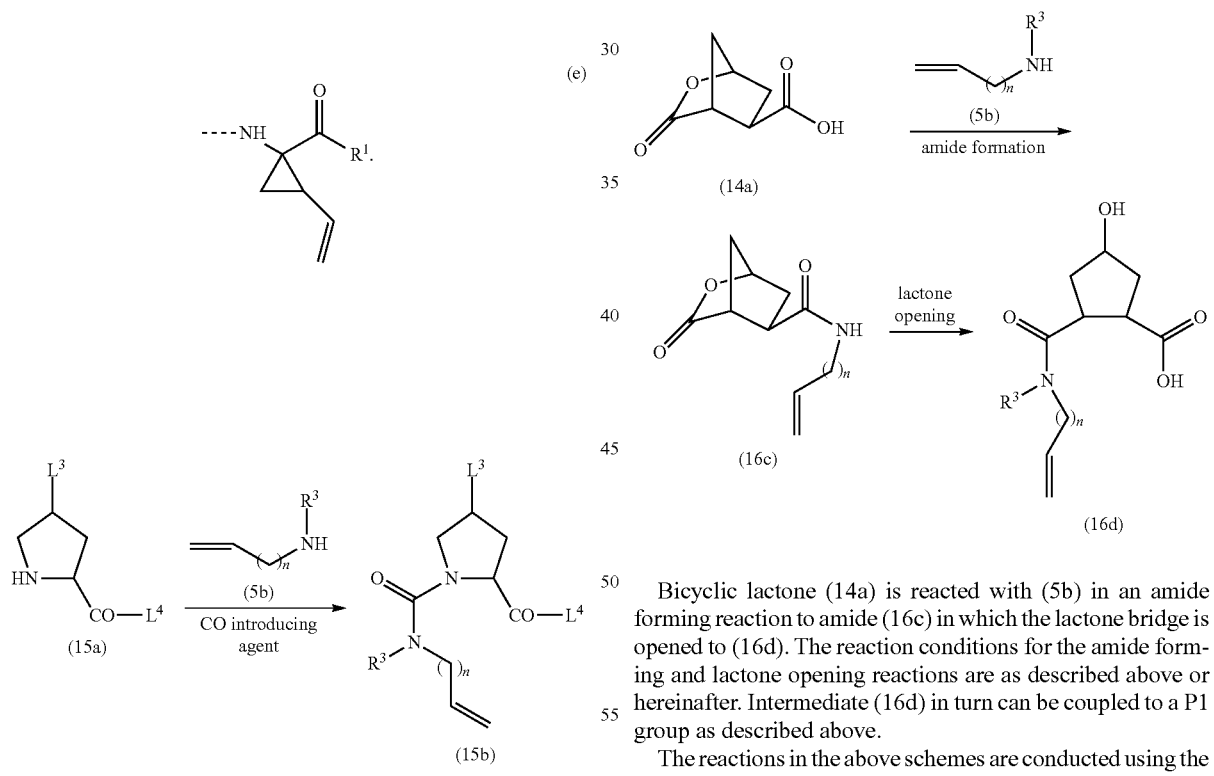

Bicyclic lactone (14a) is reacted with (5b) in an amide forming reaction to amide (16c) in which the lactone bridge is opened to (16d). The reaction conditions for the amide forming and lactone opening reactions are as described above or hereinafter. Intermediate (16d) in turn can be coupled to a P1 group as described above.

The reactions in the above schemes are conducted using the same procedures as described above for the reactions of (5a), (7a) or (8a) with (5b) and in particular the above reactions wherein $L^4$ is a group (d) or (e) correspond to the reactions of (5a), (7a) or (8a) with (5b), as described above.

The building blocks P1, P1', P2 and P3 used in the preparation of the compounds of formula (I) can be prepared starting from art-known intermediates. A number of such syntheses are described hereafter in more detail.

The individual building blocks can first be prepared and subsequently coupled together or alternatively, precursors of the building blocks can be coupled together and modified at a later stage to the desired molecular composition.

The functionalities in each of the building blocks may be protected to avoid side reactions.

Synthesis of P2 Building Blocks

The P2 building blocks contain either a pyrrolidine, a cyclopentane, or a cyclopentene moiety substituted with a group —O—$R^4$.

P2 building blocks containing a pyrrolidine moiety can be derived from commercially available hydroxy proline.

The preparation of P2 building blocks that contain a cylopentane ring may be performed as shown in the scheme below.

a base such as a tertiary amine like dimethylamino-pyridine or triethylamine in a solvent like dichloromethane. Lactone opening of (17c) using reaction conditions described above, in particular with lithium hydroxide, yields the acid (17d), which can be used further in coupling reactions with P1 building blocks. The free acid in (17d) may also be protected, preferably with an acid protecting group $PG^{2a}$ that is selectively cleavable towards $PG^2$, and the hydroxy function may be converted to a group —$OPG^1$ or to a group —O—$R^9$. The products obtained upon removal of the group $PG^2$ are intermediates (17 g) and (17i) which correspond to intermediates (13a) or (16a) specified above.

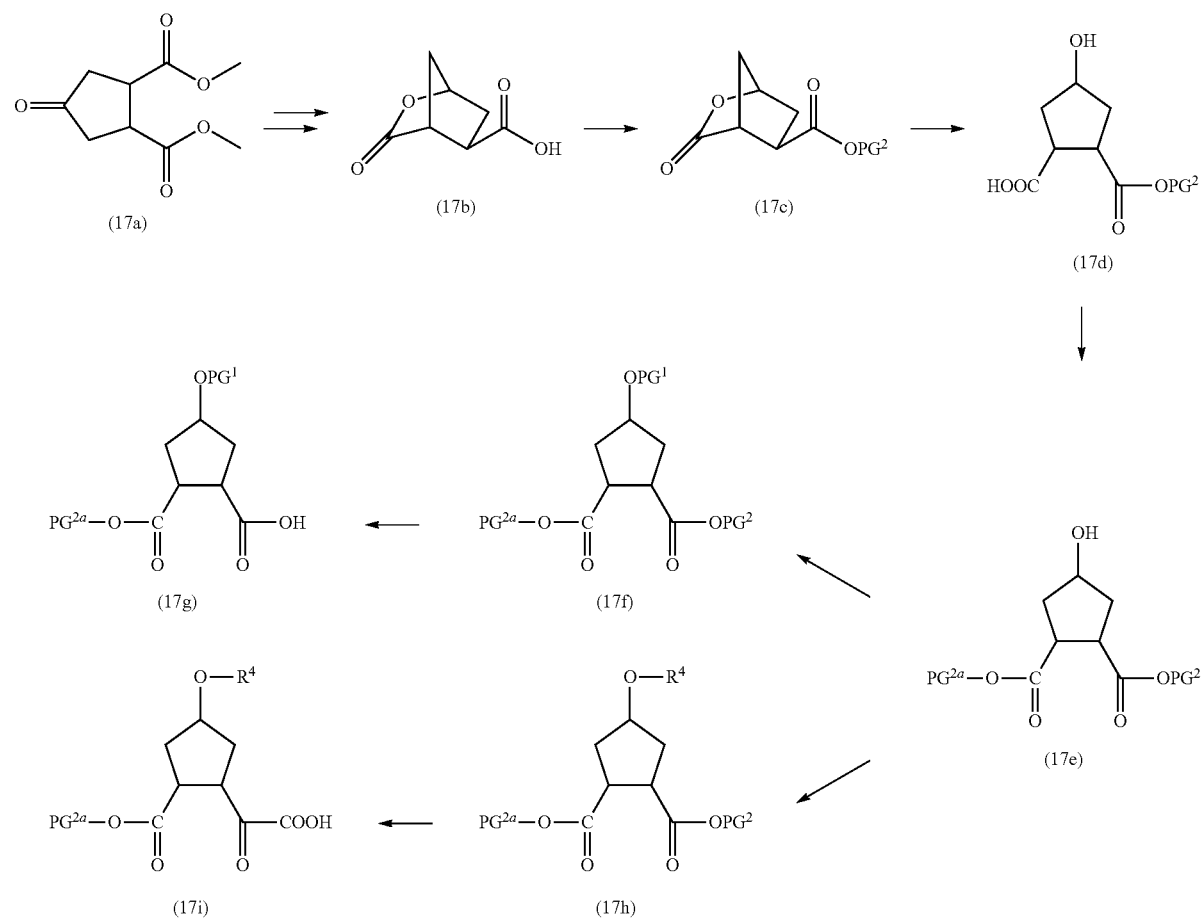

The bicyclic acid (17b) can be prepared, for example, from 3,4-bis(methoxycarbonyl)-cyclopentanone (17a), as described by Rosenquist et al. in Acta Chem. Scand. 46 (1992) 1127-1129. A first step in this procedure involves the reduction of the keto group with a reducing agent like sodium borohydride in a solvent such as methanol, followed by hydrolysis of the esters and finally ring closure to the bicyclic lactone (17b) using lactone forming procedures, in particular by using acetic anhydride in the presence of a weak base such as pyridine. The carboxylic acid functionality in (17b) can then be protected by introducing an appropriate carboxyl protecting group, such as a group $PG^2$, which is as specified above, thus providing bicyclic ester (17c). The group $PG^2$ in particular is acid-labile such as a t.butyl group and is introduced e.g. by treatment with isobutene in the presence of a Lewis acid or with di-tert-butyl dicarbonate in the presence of Intermediates with specific stereochemistry may be prepared by resolving the intermediates in the above reaction sequence. For example, (17b) may be resolved following art-known procedures, e.g. by salt form action with an optically active base or by chiral chromatography, and the resulting stereoisomers may be processed further as described above. The OH and COOH groups in (17d) are in cis position. Trans analogs can be prepared by inverting the stereochemistry at the carbon bearing the OH function by using specific reagents in the reactions introducing $OPG^1$ or O—$R^9$ that invert the stereochemistry, such as, e.g. by applying a Mitsunobu reaction.

In one embodiment, the intermediates (17d) are coupled to P1 blocks (12b) or (12c), which coupling reactions correspond to the coupling of (13a) or (16a) with the same P1 blocks, using the same conditions. Subsequent introduction of a —O—R⁹ substituent as described above followed by removal of the acid protection group PG² yields intermediates (8a-1), which are a subclass of the intermediates (7a), or part of the intermediates (16a). The reaction products of the PG² removal can be further coupled to a P3 building block. In one embodiment PG² in (17d) is t.butyl which can be removed under acidic conditions, e.g. with trifluoroacetic acid.

An unsaturated P2 building block, i.e. a cyclopentene ring, may be prepared as illustrated in the scheme below.

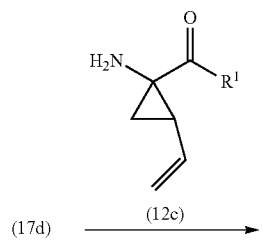

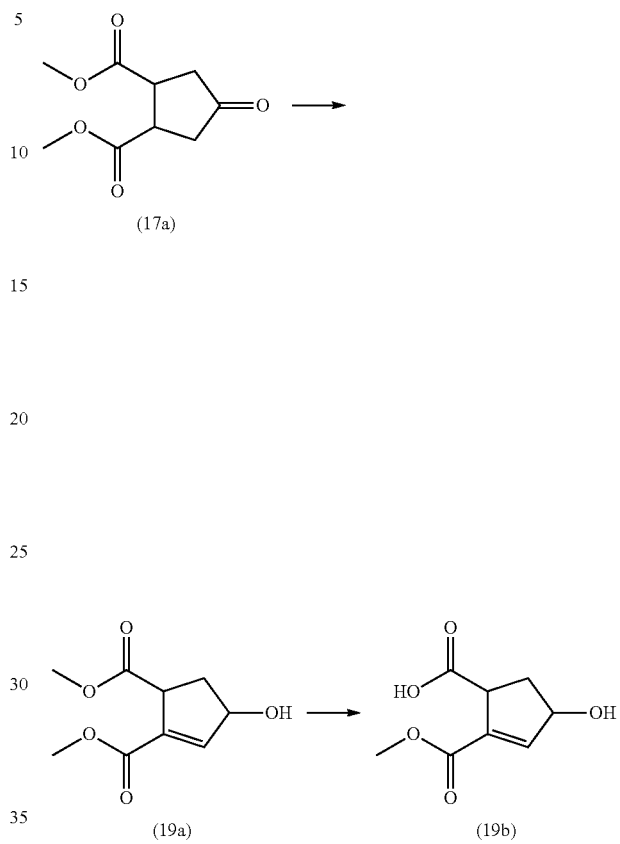

A bromination-elimination reaction of 3,4-bis(methoxycarbonyl)cyclopentanone (17a) as described by Dolby et al. in J. Org. Chem. 36 (1971) 1277-1285 followed by reduction of the keto functionality with a reducting agent like sodium borohydride provides the cyclopentenol (19a). Selective ester hydrolysis using for example lithium hydroxide in a solvent like a mixture of dioxane and water, provides the hydroxy substituted monoester cyclopentenol (19b).

An unsaturated P2 building block wherein R² can also be other than hydrogen, may be prepared as shown in the scheme below.

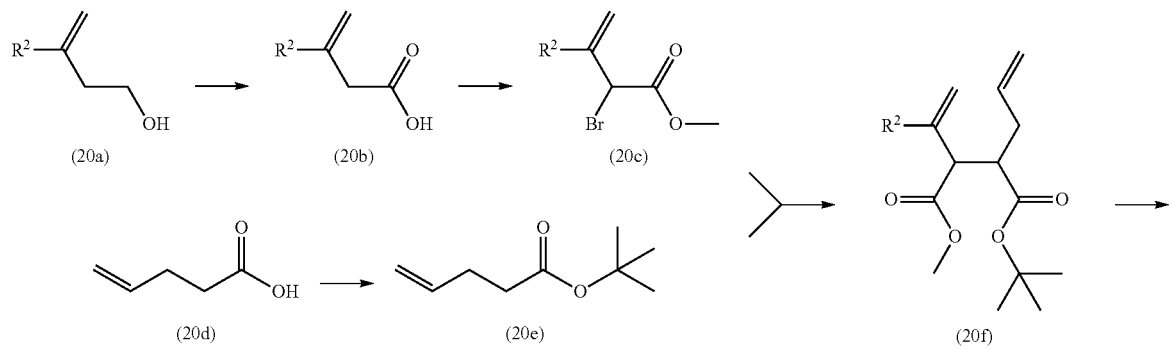

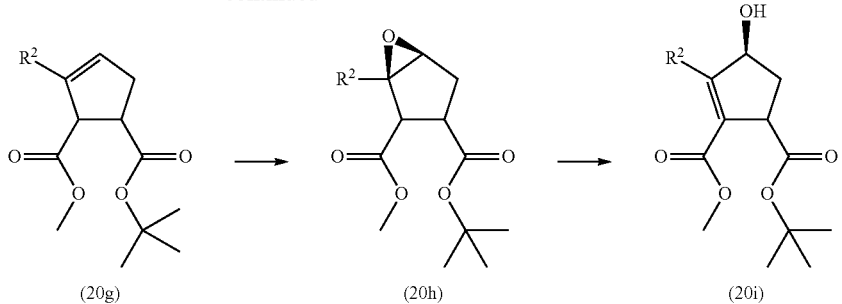

Oxidation of commercially available 3-methyl-3-buten-1-ol (20a), in particular by an oxidizing agent like pyridinium chlorochromate, yields (20b), which is converted to the corresponding methyl ester, e.g. by treatment with acetyl chloride in methanol, followed by a bromination reaction with bromine yielding the α-bromo ester (20c). The latter can then be condensed with the alkenyl ester (20e), obtained from (20d) by an ester forming reaction. The ester in (20e) preferably is a t.butyl ester which can be prepared from the corresponding commercially available acid (20d), e.g. by treatment with di-tert-butyl dicarbonate in the presence of a base like dimethylaminopyridine.

Intermediate (20e) is treated with a base such as lithium diisopropyl amide in a solvent like tetrahydrofuran, and reacted with (20c) to give the alkenyl diester (20f). Cyclisation of (20f) by an olefin metathesis reaction, performed as described above, provides cyclopentene derivative (20 g). Stereoselective epoxidation of (20 g) can be carried out using the Jacobsen asymmetric epoxidation method to obtain epoxide (20 h). Finally, an epoxide opening reaction under basic conditions, e.g. by addition of a base, in particular DBN (1,5-diazabicyclo-[4.3.0]non-5-ene), yields the alcohol (20i). Optionally, the double bond in intermediate (20i) can be reduced, for example by catalytic hydrogenation using a catalyst like palladium on carbon, yielding the corresponding cyclopentane compound. The t.butyl ester may be removed to the corresponding acid, which subsequently is coupled to a P1 building block.

The —$R^9$ group can be introduced on the pyrrolidine, cyclopentane or cyclopentene rings at any convenient stage of the synthesis of the compounds according to the present invention. One approach is to first introduce the —$R^9$ group to the said rings and subsequently add the other desired building blocks, i.e. P1 (optionally with the P1' tail) and P3, followed by the macrocycle formation. Another approach is to couple the building blocks P2, bearing no —O—$R^9$ substituent, with each P1 and P3, and to add the —$R^9$ group either before or after the macrocycle formation. In the latter procedure, the P2 moieties have a hydroxy group, which may be protected by a hydroxy protecting group $PG^1$.

$R^9$ groups can be introduced on building blocks P2 by reacting hydroxy substituted intermediates (21a) or (21b) with intermediates (4b) similar as described above for the synthesis of (I) starting from (4a). These reactions are represented in the schemes below, wherein $L^2$ is as specified above and $L^5$ and $L^{5a}$ independently from one another, represent hydroxy, a carboxyl protecting group —$OPG^2$ or —$OPG^{2a}$, or $L^5$ may also represent a P1 group such as a group (d) or (e) as specified above, or $L^{5a}$ may also represent a P3 group such as a group (b) as specified above The groups $PG^2$ and $PG^{2a}$ are as specified above. Where the groups $L^5$ and $L^{5a}$ are $PG^2$ or $PG^{2a}$, they are chosen such that each group is selectively cleavable towards the other. For example, one of $L^5$ and $L^{5a}$ may be a methyl or ethyl group and the other a benzyl or t.butyl group.

In one embodiment in (21a), $L^2$ is PG and $L^5$ is —$OPG^2$, or in (21d), $L^{5a}$ is —$OPG^2$ and $L^5$ is —$OPG^2$ and the $PG^2$ groups are removed as described above.

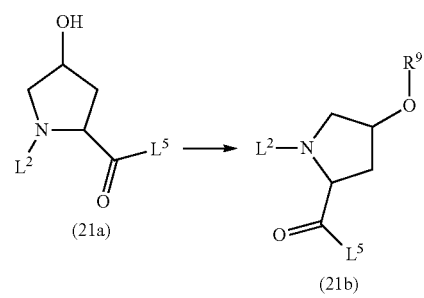

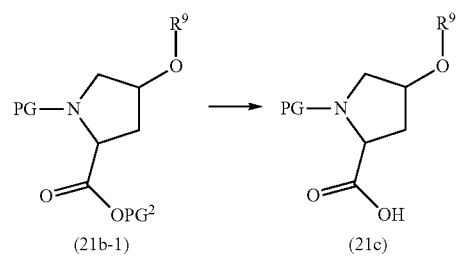

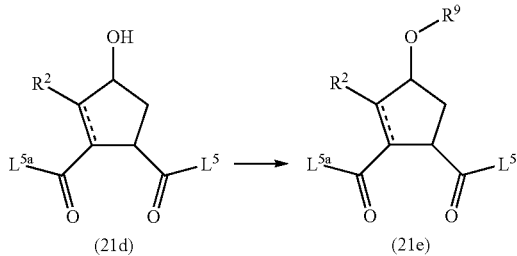

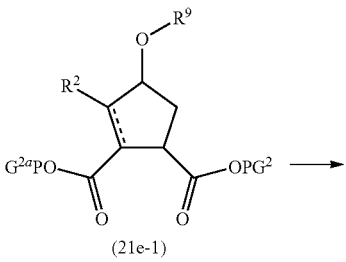

-continued

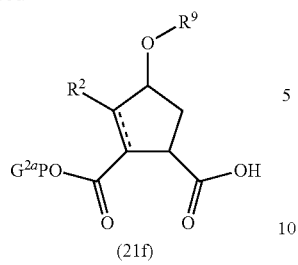

(21f)

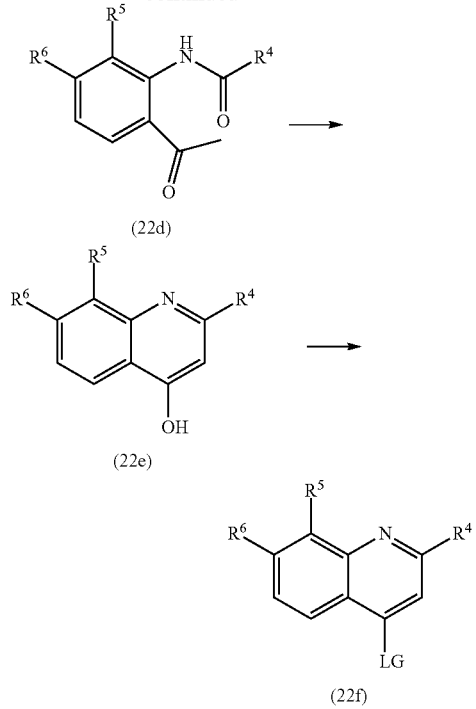

Alternatively, when handling hydroxy substituted cyclopentane analogues, the quinoline substituent can be introduced via a similar Mitsunobu reaction by reacting the hydroxy group of compound (2a') with the desired alcohol (3b) in the presence of triphenylphosphine and an activating agent like diethyl azodicarboxylate (DEAD), diisopropyl azodicarboxylate (DIAD) or the like.

In another embodiment the group $L^2$ is BOC, $L^5$ is hydroxy and the starting material (21a) is commercially available BOC-hydroxyproline, or any other stereoisomeric form thereof, e.g. BOC-L-hydroxyproline, in particular the trans isomer of the latter. Where $L^5$ in (21b) is a carboxyl-protecting group, it may be removed following procedures described above to (21c). In still another embodiment PG in (21b-1) is Boc and $PG^2$ is a lower alkyl ester, in particular a methyl or ethyl ester. Hydrolysis of the latter ester to the acid can be done by standard procedures, e.g. acid hydrolysis with hydrochloric acid in methanol or with an alkali metal hydroxide such as NaOH, in particular with LiOH. In another embodiment, hydroxy substituted cyclopentane or cyclopentene analogs (21d) are converted to (21e), which, where $L^5$ and $L^{5a}$ are —$OPG^2$ or —$OPG^{2a}$, may be converted to the corresponding acids (21f) by removal of the group $PG^2$. Removal of $PG^{2a}$ in (21e-1) leads to similar intermediates.

The intermediates Y—$R^9$ (4b) can be prepared following art-known methods using known starting materials. A number of synthesis pathways for such intermediates will be described hereafter in somewhat more detail. For example the preparation of the above mentioned intermediate quinolines is shown below in the following scheme.

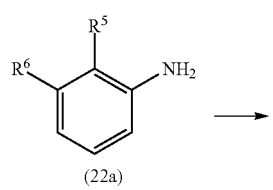

(22a)

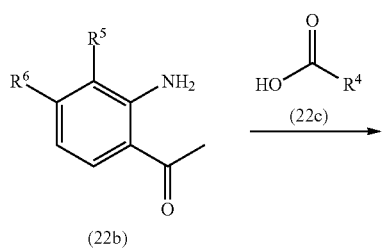

(22b)

Friedel-Craft acylation of a suitable substituted aniline (22a), available either commercially or via art-known procedures, using an acylating agent such as acetyl chloride or the like in the presence of one or more Lewis acid such as boron trichloride and aluminum trichloride in a solvent like dichloromethane provides (22b). Coupling of (22b) with a carboxylic acid (22c), preferably under basic conditions, such as in pyridine, in the presence of an activating agent for the carboxylate group, for instance POCl₃, followed by ring closure and dehydration under basic conditions like potassium tert-butoxide in tert-butanol yields quinoline derivative (22e). The latter can be converted to (22f) wherein LG is a leaving group, e.g. by reaction of (22e) with a halogenating agent, for example phosphoryl chloride or the like, or with an arylsulfonyl chloride, e.g. with tosyl chloride. Quinoline derivative (22e) can be coupled in a Mitsunobu reaction to an alcohol as described above, or quinoline (22f) can be reacted with (1a) in an O-arylation reaction as described above.

A variety of carboxylic acids with the general structure (22c) can be used in the above synthesis. These acids are available either commercially or can be prepared via art-known procedures. An example of the preparation of 2-(substituted)aminocarboxy-aminothiazole derivatives (23a-1), following the procedure described by Berdikhina et al. in Chem. Heterocycl. Compd. (Engl. Transl.) (1991), 427-433, is shown in the following reaction scheme which illustrates the preparation of 2-carboxy-4-isopropyl-thiazole (22c-1):

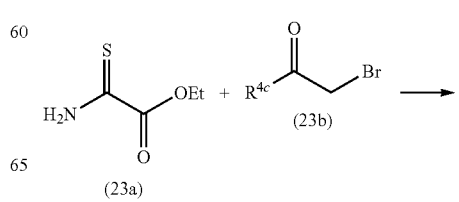

(23a) (23b)

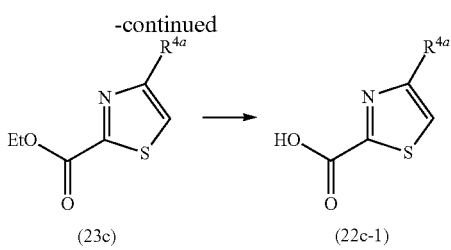

Synthesis of P1 Building Blocks

The cyclopropane amino acid used in the preparation of the P1 fragment is commercially available or can be prepared using art-known procedures.

In particular the amino-vinyl-cyclopropyl ethyl ester (12b) may be obtained according to the procedure described in WO 00/09543 or as illustrated in the following scheme, wherein $PG^2$ is a carboxyl protecting group as specified above:

Ethyl thiooxamate (23a) is reacted with the β-bromoketone (23b) to form the thiazolyl carboxylic acid ester (23c), which is hydrolyzed to the corresponding acid (25c-1). The ethyl ester in these intermediates may be replaced by other carboxyl protecting groups $PG^2$, as defined above. In the above scheme $R^{4a}$ is as defined above and in particular is $C_{1-4}$alkyl, more in particular i.propyl.

The bromoketone (23b) may be prepared from 3-methylbutan-2-one (MIK) with a sililating agent (such as TMSCl) in the presence of a suitable base (in particular LiHMDS) and bromine The synthesis of further carboxylic acids (22c), in particular of substituted amino thiazole carboxylic acids (25a-2) is illustrated herebelow:

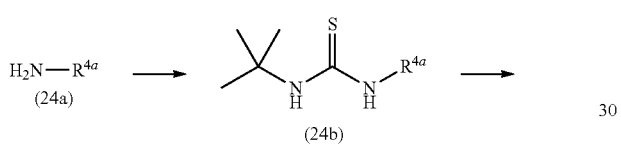

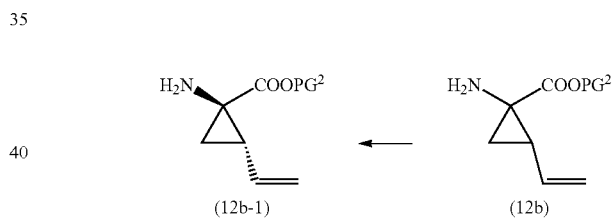

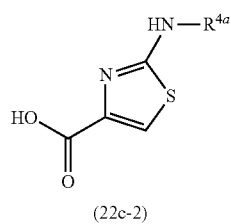

Thiourea (24c) with various substituents $R^{4a}$, which in particular are $C_{1-6}$alkyl, can be formed by reaction of the appropriate amine (24a) with tert-butylisothiocyanate in the presence of a base like diisopropylethylamine in a solvent like dichloromethane followed by removal of the tert-butyl group under acidic conditions. Subsequent condensation of thiourea derivative (24c) with 3-bromopyruvic acid provides the thiazole carboxylic acid (22c-2).

Treatment of commercially available or easily obtainable imine (25a) with 1,4-dihalo-butene in presence of a base produces (25b), which after hydrolysis yields cyclopropyl amino acid (12b), having the allyl substituent syn to the carboxyl group. Resolution of the enantiomeric mixture (12b) results in (12b-1). The resolution is performed using art-known procedures such as enzymatic separation; crystallization with a chiral acid; or chemical derivatization; or by chiral column chromatography. Intermediates (12b) or (12b-1) may be coupled to the appropriate P2 derivatives as described above.

P1 building blocks for the preparation of compounds according to general formula (I) wherein $R^1$ is —$OR^7$ or —NH—$SO_2R^8$ can be prepared by reacting amino acids (23a) with the appropriate alcohol or amine respectively under standard conditions for ester or amide formation. Cyclopropyl amino acids (23a) are prepared by introducing a N-protecting group PG, and removal of $PG^2$ and the amino acids (a) are converted to the amides (12c-1) or esters (12c-2), which are subgroups of the intermediates (12c), as outlined in the following reaction scheme, wherein PG is as specified above.

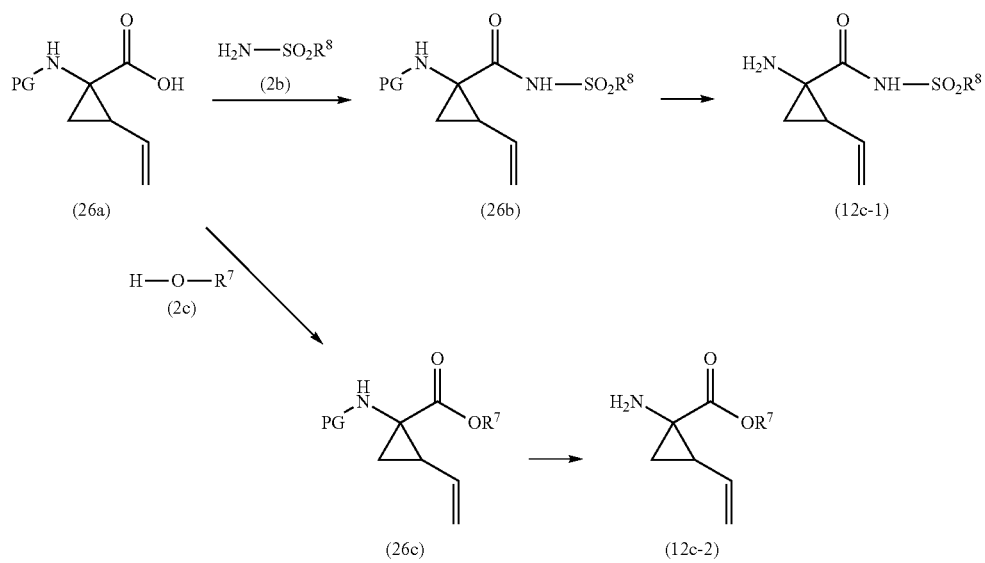

The reaction of (26a) with amine (2b) is an amide forming procedure. The similar reaction with (2c) is an ester forming reaction. Both can be performed following the procedures described above. This reaction yields intermediates (26b) or (26c) from which the amino protecting group is removed by standard methods such as those described above. This in turn results in the desired intermediate (12c-1). Starting materials (26a) may be prepared from the above-mentioned intermediates (12b) by first introducing a N-protecting group PG and subsequent removal of the group $PG^2$.

In one embodiment the reaction of (26a) with (2b) is done by treatment of the amino acid with a coupling agent, for example N,N'-carbonyl-diimidazole (CDI) or the like, in a solvent like THF followed by reaction with (2b) in the presence of a base such as 1,8-diazabicyclo[5.4.0]undec-7-ene (DBU). Alternatively the amino acid can be treated with (2b) in the presence of a base like diisopropylethylamine followed by treatment with a coupling agent such as benzotriazole-1-yl-oxy-tris-pyrrolidino-phosphonium hexafluorophosphate (commercially available as PyBOP®) to effect the introduction of the sulfonamide group.

Intermediates (12c-1) or (12c-2) in turn may be coupled to the appropriate proline, cyclopentane or cyclopentene derivatives as described above.

Synthesis of the P3 Building Blocks

The P3 building blocks are available commercially or can be prepared according to methodologies known to the skilled in the art. One of these methodologies is shown in the scheme below and uses monoacylated amines, such as trifluoroacetamide or a Boc-protected amine

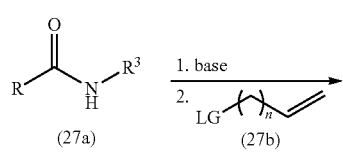

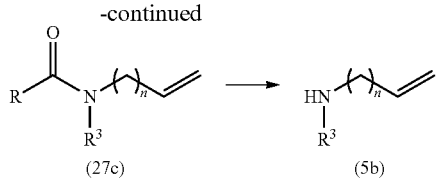

In the above scheme, R together with the CO group forms a N-protecting group, in particular R is t-butoxy, trifluoromethyl; $R^3$ and n are as defined above and LG is a leaving group, in particular halogen, e.g. chloro or bromo.

The monoacylated amines (27a) are treated with a strong base such as sodium hydride and are subsequently reacted with a reagent LG-$C_{5-8}$alkenyl (27b), in particular halo$C_{5-8}$alkenyl, to form the corresponding protected amines (27c). Deprotection of (27c) affords (5b), which are building blocks P3. Deprotection will depend on the functional group R, thus if R is t-butoxy, deprotection of the corresponding Boc-protected amine can be accomplished with an acidic treatment, e.g. trifluoroacetic acid. Alternatively, when R is for instance trifluoromethyl, removal of the R group is accomplished with a base, e.g. sodium hydroxide.

The following scheme illustrates yet another method for preparing a P3 building block, namely a Gabriel synthesis of primary $C_{5-8}$alkenylamines, which can be carried out by the treatment of a phthalimide (28a) with a base, such as NaOH or KOH, and with (27b), which is as specified above, followed by hydrolysis of the intermediate N-alkenyl imide to generate a primary $C_{5-8}$alkenylamine (5b-1).

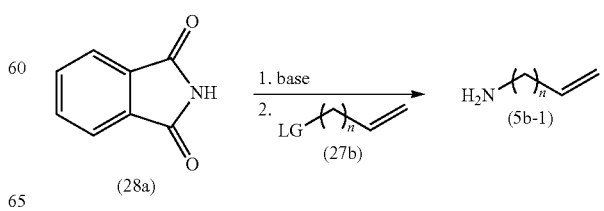

In the above scheme, n is as defined above.

Compounds of formula (I) may be converted into each other following art-known functional group transformation reactions. For example, amino groups may be N-alkylated, nitro groups reduced to amino groups, a halo atom may be exchanged for another halo.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis. A number of the compounds of this invention moreover are active against mutated strains of HCV. Additionally, many of the compounds of this invention show a favorable pharmacokinetic profile and have attractive properties in terms of bioavailabilty, including an acceptable half-life, AUC (area under the curve) and peak values and lacking unfavorable phenomena such as insufficient quick onset and tissue retention.

The in vitro antiviral activity against HCV of the compounds of formula (I) was tested in a cellular HCV replicon system based on Lohmann et al. (1999) Science 285:110-113, with the further modifications described by Krieger et al. (2001) Journal of Virology 75: 4614-4624, which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

Also, the combination of previously known anti-HCV compound, such as, for instance, interferon-α (IFN-α), pegylated interferon-α and/or ribavirin, and a compound of formula (I) can be used as a medicine in a combination therapy. The term "combination therapy" relates to a product containing mandatory (a) a compound of formula (I), and (b) optionally another anti-HCV compound, as a combined preparation for simultaneous, separate or sequential use in treatment of HCV infections, in particular, in the treatment of infections with HCV.

Anti-HCV compounds encompass agents selected from an HCV polymerase inhibitor, an HCV protease inhibitor, an inhibitor of another target in the HCV life cycle, and immunomodulatory agent, an antiviral agent, and combinations thereof.

HCV polymerase inhibitors include, but are not limited to, NM283 (valopicitabine), R803, JTK-109, JTK-003, HCV-371, HCV-086, HCV-796 and R-1479.

Inhibitors of HCV proteases (NS2-NS3 inhibitors and NS3-NS4A inhibitors) include, but are not limited to, the compounds of WO02/18369 (see, e.g., page 273, lines 9-22 and page 274, line 4 to page 276, line 11); BILN-2061, VX-950, GS-9132 (ACH-806), SCH-503034, and SCH-6. Further agents that can be used are those disclosed in WO-98/17679, WO-00/056331 (Vertex); WO 98/22496 (Roche); WO 99/07734, (Boehringer Ingelheim), WO 2005/073216, WO2005073195 (Medivir) and structurally similar agents.

Inhibitors of other targets in the HCV life cycle, including NS3 helicase; metallo-protease inhibitors; antisense oligonucleotide inhibitors, such as ISIS-14803, AVI-4065 and the like; siRNA's such as SIRPLEX-140-N and the like; vector-encoded short hairpin RNA (shRNA); DNAzymes; HCV specific ribozymes such as heptazyme, RPI.13919 and the like; entry inhibitors such as HepeX-C, HuMax-HepC and the like; alpha glucosidase inhibitors such as celgosivir, UT-231B and the like; KPE-02003002; and BIVN 401.

Immunomodulatory agents include, but are not limited to; natural and recombinant interferon isoform compounds, including α-interferon, β-interferon, γ-interferon, ω-interferon and the like, such as Intron A®, Roferon-A®, Canferon-A300®, Advaferon®, Infergen®, Humoferon®, Sumiferon MP®, Alfaferone®, IFN-beta®, Feron® and the like; polyethylene glycol derivatized (pegylated) interferon compounds, such as PEG interferon-α-2a (Pegasys®), PEG interferon-α-2b (PEG-Intron®), pegylated IFN-α-con1 and the like; long acting formulations and derivatizations of interferon compounds such as the albumin-fused interferon albuferon α and the like; compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isatoribine and the like; thymosin α-1; ANA-245; ANA-246; histamine dihydrochloride; propagermanium; tetrachlorodecaoxide; ampligen; IMP-321; KRN-7000; antibodies, such as civacir, XTL-6865 and the like; and prophylactic and therapeutic vaccines such as InnoVac C, HCV E1E2/MF59 and the like.

Other antiviral agents include, but are not limited to, ribavirin, amantadine, viramidine, nitazoxanide; telbivudine;

NOV-205; taribavirin; inhibitors of internal ribosome entry; broad-spectrum viral inhibitors, such as IMPDH inhibitors (e.g., compounds of U.S. Pat. No. 5,807,876, U.S. Pat. No. 6,498,178, U.S. Pat. No. 6,344,465, U.S. Pat. No. 6,054,472, WO97/40028, WO98/40381, WO00/56331, and mycophenolic acid and derivatives thereof, and including, but not limited to VX-950, merimepodib (VX-497), VX-148, and/or VX-944); or combinations of any of the above.

Thus, to combat or treat HCV infections, the compounds of formula (I) may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and another HCV inhibitory compound, e.g. (pegylated) IFN-α and/or ribavirin.

In still another aspect there are provided combinations of a compound of formula (I) as specified herein and an anti-HIV compound. The latter preferably are those HIV inhibitors that have a positive effect on drug metabolism and/or pharmacokinetics that improve bioavailabilty. An example of such an HIV inhibitor is ritonavir.

As such, the present invention further provides a combination comprising (a) an HCV NS3/4a protease inhibitor of formula (I) or a pharmaceutically acceptable salt thereof; and (b) ritonavir or a pharmaceutically acceptable salt thereof.

The compound ritonavir, and pharmaceutically acceptable salts thereof, and methods for its preparation are described in WO94/14436. For preferred dosage forms of ritonavir, see U.S. Pat. No. 6,037,157, and the documents cited therein: U.S. Pat. No. 5,484,801, U.S. Ser. No. 08/402,690, and WO95/07696 and WO95/09614. Ritonavir has the following formula:

invention provides a process wherein the combination comprises one or more additional agent as described herein.

The combinations of the present invention may be used as medicaments. Said use as a medicine or method of treatment comprises the systemic administration to HCV-infected subjects of an amount effective to combat the conditions associated with HCV and other pathogenic flavi- and pestiviruses. Consequently, the combinations of the present invention can be used in the manufacture of a medicament useful for treating, preventing or combating infection or disease associated with HCV infection in a mammal, in particular for treating conditions associated with HCV and other pathogenic flavi- and pestiviruses.

In one embodiment of the present invention there is provided a pharmaceutical composition comprising a combination according to any one of the embodiments described herein and a pharmaceutically acceptable excipient. In particular, the present invention provides a pharmaceutical composition comprising (a) a therapeutically effective amount of an HCV NS3/4a protease inhibitor of the formula (I) or a pharmaceutically acceptable salt thereof, (b) a therapeutically effective amount of ritonavir or a pharmaceutically acceptable salt thereof, and (c) a pharmaceutically acceptable excipient. Optionally, the pharmaceutical composition further comprises an additional agent selected from an HCV polymerase inhibitor, an HCV protease inhibitor, an inhibitor of another target in the HCV life cycle, and immunomodulatory agent, an antiviral agent, and combinations thereof.

The compositions may be formulated into suitable pharmaceutical dosage forms such as the dosage forms described above. Each of the active ingredients may be formulated separately and the formulations may be co-administered or one formulation containing both and if desired further active ingredients may be provided.

As used herein, the term "composition" is intended to encompass a product comprising the specified ingredients, as well as any product which results, directly or indirectly, from the combination of the specified ingredients.

In one embodiment the combinations provided herein may also be formulated as a combined preparation for simultaneous, separate or sequential use in HIV therapy. In such a

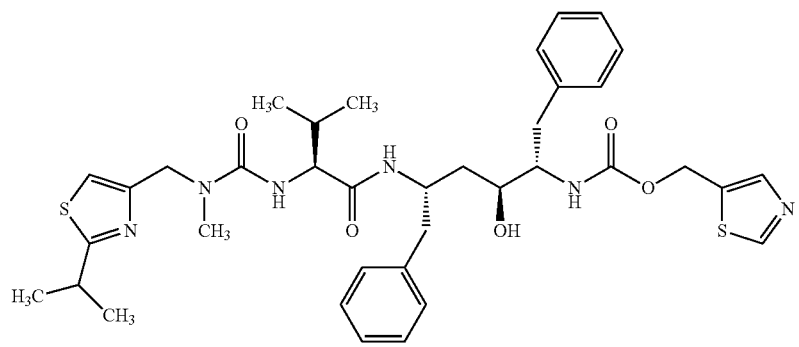 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1]

In a further embodiment, the combination comprising (a) an HCV NS3/4a protease inhibitor of formula (I) or a pharmaceutically acceptable salt thereof; and (b) ritonavir or a pharmaceutically acceptable salt thereof; further comprises an additional anti-HCV compound selected from the compounds as described herein.

In one embodiment of the present invention there is provided a process for preparing a combination as described herein, comprising the step of combining an HCV NS3/4a protease inhibitor of formula (I) or a pharmaceutically acceptable salt thereof, and ritonavir or a pharmaceutically acceptable salt thereof. An alternative embodiment of this case, the compound of general formula (I) or any subgroup thereof, is formulated in a pharmaceutical composition containing other pharmaceutically acceptable excipients, and ritonavir is formulated separately in a pharmaceutical composition containing other pharmaceutically acceptable excipients. Conveniently, these two separate pharmaceutical compositions can be part of a kit for simultaneous, separate or sequential use.

Thus, the individual components of the combination of the present invention can be administered separately at different times during the course of therapy or concurrently in divided or single combination forms. The present invention is therefore to be understood as embracing all such regimes of simultaneous or alternating treatment and the term "administering" is to be interpreted accordingly. In a preferred embodiment, the separate dosage forms are administered about simultaneously.

In one embodiment, the combination of the present invention contains an amount of ritonavir, or a pharmaceutically acceptable salt thereof, which is sufficient to clinically improve the bioavailability of the HCV NS3/4a protease inhibitor of formula (I) relative to the bioavailability when said HCV NS3/4a protease inhibitor of formula (I) is administered alone.

In another embodiment, the combination of the present invention contains an amount of ritonavir, or a pharmaceutically acceptable salt thereof, which is sufficient to increase at least one of the pharmacokinetic variables of the HCV NS3/4a protease inhibitor of formula (I) selected from $t_{1/2}$, $C_{min}$, $C_{max}$, $C_{ss}$, AUC at 12 hours, or AUC at 24 hours, relative to said at least one pharmacokinetic variable when the HCV NS3/4a protease inhibitor of formula (I) is administered alone.

A further embodiment relates to a method for improving the bioavailability of a HCV NS3/4a protease inhibitor comprising administering to an individual in need of such improvement a combination as defined herein, comprising a therapeutically effective amount of each component of said combination.

In a further embodiment, the invention relates to the use of ritonavir or a pharmaceutically acceptable salt thereof, as an improver of at least one of the pharmacokinetic variables of a HCV NS3/4a protease inhibitor of formula (I) selected from $t_{1/2}$, $C_{min}$, $C_{max}$, $C_{ss}$, AUC at 12 hours, or AUC at 24 hours; with the proviso that said use is not practised in the human or animal body.

The term "individual" as used herein refers to an animal, preferably a mammal, most preferably a human, who has been the object of treatment, observation or experiment.

Bioavailability is defined as the fraction of administered dose reaching systemic circulation. $t_{1/2}$ represents the half life or time taken for the plasma concentration to fall to half its original value. $C_{ss}$ is the steady state concentration, i.e. the concentration at which the rate of input of drug equals the rate of elimination. $C_{min}$ is defined as the lowest (minimum) concentration measured during the dosing interval. $C_{max}$ represents the highest (maximum) concentration measured during the dosing interval. AUC is defined as the area under the plasma concentration-time curve for a defined period of time.

The combinations of this invention can be administered to humans in dosage ranges specific for each component comprised in said combinations. The components comprised in said combinations can be administered together or separately. The NS3/4a protease inhibitors of formula (I) or any subgroup thereof, and ritonavir or a pharmaceutically acceptable salt or ester thereof, may have dosage levels of the order of 0.02 to 5.0 grams-per-day.

When the HCV NS3/4a protease inhibitor of formula (I) and ritonavir are administered in combination, the weight ratio of the HCV NS3/4a protease inhibitor of formula (I) to ritonavir is suitably in the range of from about 40:1 to about 1:15, or from about 30:1 to about 1:15, or from about 15:1 to about 1:15, typically from about 10:1 to about 1:10, and more typically from about 8:1 to about 1:8. Also useful are weight ratios of the HCV NS3/4a protease inhibitors of formula (I) to ritonavir ranging from about 6:1 to about 1:6, or from about 4:1 to about 1:4, or from about 3:1 to about 1:3, or from about 2:1 to about 1:2, or from about 1.5:1 to about 1:1.5. In one aspect, the amount by weight of the HCV NS3/4a protease inhibitors of formula (I) is equal to or greater than that of ritonavir, wherein the weight ratio of the HCV NS3/4a protease inhibitor of formula (I) to ritonavir is suitably in the range of from about 1:1 to about 15:1, typically from about 1:1 to about 10:1, and more typically from about 1:1 to about 8:1. Also useful are weight ratios of the HCV NS3/4a protease inhibitor of formula (I) to ritonavir ranging from about 1:1 to about 6:1, or from about 1:1 to about 5:1, or from about 1:1 to about 4:1, or from about 3:2 to about 3:1, or from about 1:1 to about 2:1 or from about 1:1 to about 1.5:1.

The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms of the disease being treated. Since the instant invention refers to combinations comprising two or more agents, the "therapeutically effective amount" is that amount of the agents taken together so that the combined effect elicits the desired biological or medicinal response. For example, the therapeutically effective amount of a composition comprising (a) the compound of formula (I) and (b) ritonavir, would be the amount of the compound of formula (I) and the amount of ritonavir that when taken together have a combined effect that is therapeutically effective.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

According to one embodiment, the HCV NS3/4a protease inhibitor of formula (I) and ritonavir may be co-administered once or twice a day, preferably orally, wherein the amount of the compounds of formula (I) per dose is from about 1 to about 2500 mg, and the amount of ritonavir per dose is from Ito about 2500 mg. In another embodiment, the amounts per dose for once or twice daily co-administration are from about 50 to about 1500 mg of the compound of formula (I) and from about 50 to about 1500 mg of ritonavir. In still another embodiment, the amounts per dose for once or twice daily co-administration are from about 100 to about 1000 mg of the compound of formula (I) and from about 100 to about 800 mg of ritonavir. In yet another embodiment, the amounts per dose for once or twice daily co-administration are from about 150 to about 800 mg of the compound of formula (I) and from about 100 to about 600 mg of ritonavir. In yet another embodiment, the amounts per dose for once or twice daily co-administration are from about 200 to about 600 mg of the compound of formula (I) and from about 100 to about 400 mg of ritonavir. In yet another embodiment, the amounts per dose for once or twice daily co-administration are from about 200 to about 600 mg of the compound of formula (I) and from about 20 to about 300 mg of ritonavir. In yet another embodiment, the amounts per dose for once or twice daily co-administration are from about 100 to about 400 mg of the compound of formula (I) and from about 40 to about 100 mg of ritonavir.

Exemplary combinations of the compound of formula (I) (mg)/ritonavir (mg) for once or twice daily dosage include 50/100, 100/100, 150/100, 200/100, 250/100, 300/100, 350/100, 400/100, 450/100, 50/133, 100/133, 150/133, 200/133, 250/133, 300/133, 50/150, 100/150, 150/150, 200/150, 250/150, 50/200, 100/200, 150/200, 200/200, 250/200, 300/200, 50/300, 80/300, 150/300, 200/300, 250/300, 300/300, 200/600, 400/600, 600/600, 800/600, 1000/600, 200/666, 400/666, 600/666, 800/666, 1000/666, 1200/666, 200/800, 400/800, 600/800, 800/800, 1000/800, 1200/800, 200/1200, 400/1200, 600/1200, 800/1200, 1000/1200, and 1200/1200. Other exemplary combinations of the compound of formula (I) (mg)/ritonavir (mg) for once or twice daily dosage include 1200/400, 800/400, 600/400, 400/200, 600/200, 600/100, 500/100, 400/50, 300/50, and 200/50.

In one embodiment of the present invention there is provided an article of manufacture comprising a composition effective to treat an HCV infection or to inhibit the NS3 protease of HCV; and packaging material comprising a label which indicates that the composition can be used to treat infection by the hepatitis C virus; wherein the composition comprises a compound of the formula (I) or any subgroup thereof, or the combination as described herein.

Another embodiment of the present invention concerns a kit or container comprising a compound of the formula (I) or any subgroup thereof, or a combination according to the invention combining an HCV NS3/4a protease inhibitor of formula (I) or a pharmaceutically acceptable salt thereof, and ritonavir or a pharmaceutically acceptable salt thereof, in an amount effective for use as a standard or reagent in a test or assay for determining the ability of potential pharmaceuticals to inhibit HCV NS3/4a protease, HCV growth, or both. This aspect of the invention may find its use in pharmaceutical research programs.

The compounds and combinations of the present invention can be used in high-throughput target-analyte assays such as those for measuring the efficacy of said combination in HCV treatment.

EXAMPLES

The following examples are intended to illustrate the present invention and not to limit it thereto.

Example 1

Preparation of Representative Intermediates

Synthesis of 4-hydroxy-7-methoxy-8-methyl-2-(thiazol-2-yl)quinoline (4)

Step A

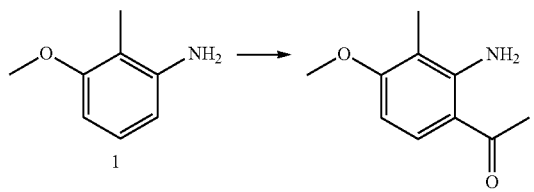

A solution of BCl$_3$ (1.0 M in CH$_2$Cl$_2$, 194 mL) was added dropwise by canula over 20 min, under argon pressure, at 0° C. to a solution of 3-methoxy-2-methylaniline (25.4 g, 185 mmol) in xylene (300 mL). The temperature was maintained between 0° C. and 10° C. until the addition was completed. After an additional 30 min at 0° C., acetonitrile (12.6 mL, 241 mmol) was added dropwise under argon at 0° C. After 30 min at 0° C., the resulting suspension was transferred into a dropping funnel, and diluted with CH$_2$Cl$_2$ (40 mL). This mixture was added at 0° C. under argon over 20 min to a suspension of AlCl$_3$ (25.9 g, 194 mmol) in CH$_2$Cl$_2$ (40 mL). The resulting orange solution was heated in an oil bath at 70° C. under a nitrogen stream for 12 h. Then, the reaction mixture was cooled down to room temperature, and ice-cold water and CH$_2$Cl$_2$ were added. This mixture was heated at reflux for 6 h, and then cooled to room temperature. After 12 h, the pH was adjusted at 0° C. to 3 with 6N NaOH. The solution was extracted with CH$_2$Cl$_2$, successively washed with water, 1N NaOH, and brine. The organic layer was dried (Na$_2$SO$_4$), filtered and concentrated in vacuo. The residue was triturated at room temperature in diisopropyl ether (50 mL) for 0.5 h. Then, the suspension was cooled at 0° C., filtered, and washed with small portion of diisopropyl ether and dried under high vacuum to give 15.4 g (46%) of the desired product 2: m/z=180 (M+H)$^+$.

Step B

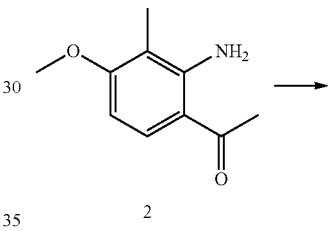

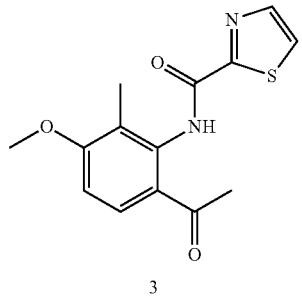

EDCI (257 mg, 1.34 mmol) and HOAt (152 mg, 1.12 mmol) were added to a stirred solution of 2 (200 mg, 1.12 mmol) in CH$_2$Cl$_2$ (10 mL) and dry DMF (1 mL). The resulting solution was stirred at room temperature for 3 days. Then, the reaction mixture was partitioned between CH$_2$Cl$_2$ and 1N NaHCO$_3$. The organic layer was successively washed with 1N NH$_4$Cl, and water, dried (Na$_2$SO$_4$), and evaporated. Purification by flash chromatography (gradient AcOEt/heptane, 10:90 to 50:50) afforded 62 mg (19%) of the target product: m/z=291 (M+H)+.

Step C

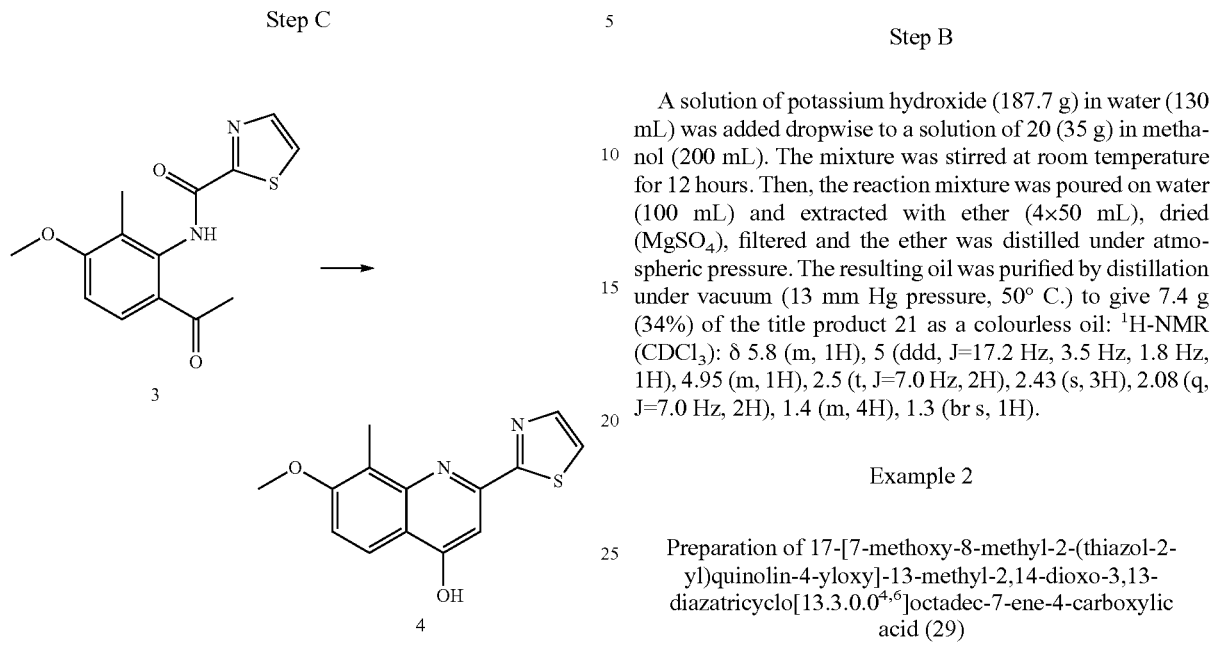

tBuOK (50 mg, 0.448 mmol) was added to a suspension of acetophenone 3 (62 mg, 0.213 mmol) in tBuOH (5 mL). The resulting mixture was stirred at 80° C. overnight, then cooled at room temperature. The reaction mixture was diluted with AcOEt, acidified with KHSO$_4$, and successively washed with water and brine. Organic layer was dried (Na$_2$SO$_4$) and evaporated to give 43 mg (74%) of the target product as a white powder: m/z=273 (M+H)+.

Synthesis of (hex-5-enyl)(methyl)amine (21)

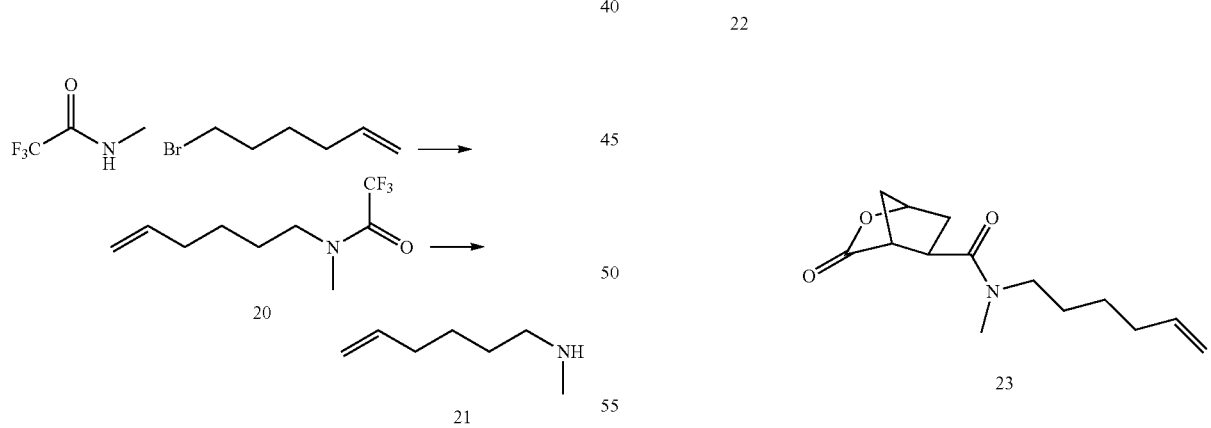

Step A

Sodium hydride (1.05 eq) was slowly added at 0° C. to a solution of N-methyltrifluoro-acetamide (25 g) in DMF (140 mL). The mixture was stirred for 1 h at room temperature under nitrogen. Then, a solution of bromohexene (32.1 g) in DMF (25 mL) was added dropwise and the mixture was heated to 70° C. for 12 hours. The reaction mixture was poured on water (200 mL) and extracted with ether (4×50 mL), dried (MgSO$_4$), filtered and evaporated to give 35 g of the target product 20 as a yellowish oil which was used without further purification in the next step.

Step B

A solution of potassium hydroxide (187.7 g) in water (130 mL) was added dropwise to a solution of 20 (35 g) in methanol (200 mL). The mixture was stirred at room temperature for 12 hours. Then, the reaction mixture was poured on water (100 mL) and extracted with ether (4×50 mL), dried (MgSO$_4$), filtered and the ether was distilled under atmospheric pressure. The resulting oil was purified by distillation under vacuum (13 mm Hg pressure, 50° C.) to give 7.4 g (34%) of the title product 21 as a colourless oil: $^1$H-NMR (CDCl$_3$): δ 5.8 (m, 1H), 5 (ddd, J=17.2 Hz, 3.5 Hz, 1.8 Hz, 1H), 4.95 (m, 1H), 2.5 (t, J=7.0 Hz, 2H), 2.43 (s, 3H), 2.08 (q, J=7.0 Hz, 2H), 1.4 (m, 4H), 1.3 (br s, 1H).

Example 2

Preparation of 17-[7-methoxy-8-methyl-2-(thiazol-2-yl)quinolin-4-yloxy]-13-methyl-2,14-dioxo-3,13-diazatricyclo[13.3.0.0$^{4,6}$]octadec-7-ene-4-carboxylic acid (29)

Step A

3-Oxo-2-oxa-bicyclo[2.2.1]heptane-5-carboxylic acid 22 (500 mg, 3.2 mmol) in 4 ml DMF was added at 0° C. to HATU (1.34 g, 3.52 mmol) and N-methylhex-5-enylamine (435 mg, 3.84 mmol) in DMF (3 mL), followed by DIPEA. After stirring for 40 min at 0° C., the mixture was stirred at room temperature for 5 h. Then, the solvent was evaporated, the residue dissolved in EtOAc (70 mL) and washed with saturated NaHCO$_3$ (10 mL). The aqueous layer was extracted with EtOAc (2×25 mL). The organic layers were combined, washed with saturated NaCl (20 mL), dried (Na$_2$SO$_4$), and evaporated. Purification by flash chromatography (EtOAc/ petroleum ether, 2:1) afforded 550 mg (68%) of the target product 23 as a colorless oil: m/z=252 (M+H)+.

Step B

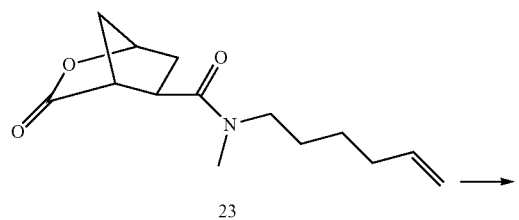

23

A solution of LiOH (105 mg in 4 ml of water) was added at 0° C. to the lactone amide 23. After 1 h, the conversion was completed (HPLC). The mixture was acidified to pH 2-3 with 1N HCl, extracted with AcOEt, dried (MgSO$_4$), evaporated, co-evaporated with toluene several times, and dried under high vacuum overnight to give 520 mg (88%) of the target product 24: m/z=270 (M+H)+.

Step C

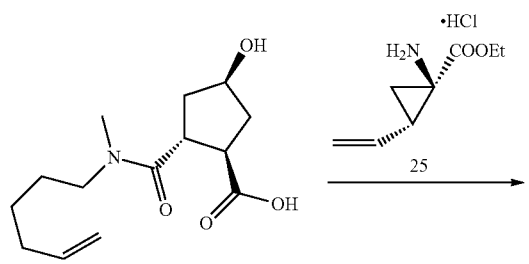

The 1-(amino)-2-(vinyl)cyclopropanecarboxylic acid ethyl ester hydrochloride 25 (4.92 g, 31.7 mmol) and HATU (12.6 g, 33.2 mmol) were added to 24 (8.14 g, 30.2 mmol). The mixture was cooled in an ice bath under argon, and then DMF (100 mL) and DIPEA (12.5 mL, 11.5 mmol) were successively added. After 30 min at 0° C., the solution was stirred at room temperature for an additional 3 h. Then, the reaction mixture was partitioned between EtOAc and water, washed successively with 0.5 N HCl (20 mL) and saturated NaCl (2×20 mL), and dried (Na$_2$SO$_4$). Purification by flash chromatography (AcOEt/CH$_2$Cl$_2$/Petroleum ether, 1:1:1) afforded 7.41 g (60%) of the target product 26 as a colorless oil: m/z=407 (M+H)+.

Step D

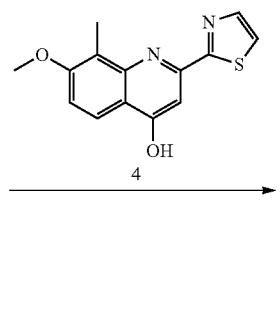

26

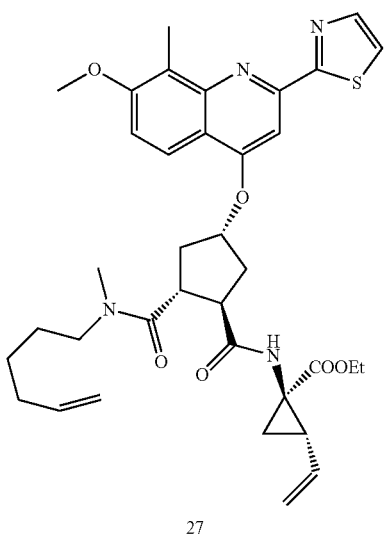

27

DIAD (218 µL, 1.11 mmol) is added at −20° C. under nitrogen atmosphere to a solution of 26 (300 mg, 0.738 mmol), quinoline 4 (420 mg, 1.03 mmol) and triphenylphosphine (271 mg, 1.03 mmol) in dry THF (15 mL). Then, the reaction is warmed up to room temperature. After 1.5 h, the solvent is evaporated and the crude product is purified by flash column chromatography (gradient of petroleum ether/CH$_2$Cl$_2$/ether, 3:1.5:0.5 to 1:1:1) to give the target product 27: m/z=661 (M+H)$^+$.

the residue purified by silica gel chromatography (Petroleum ether/CH$_2$Cl$_2$/Et$_2$O; 3:1:1) to give the target product 28: m/z=633 (M+H)$^+$.

Step E

Step F

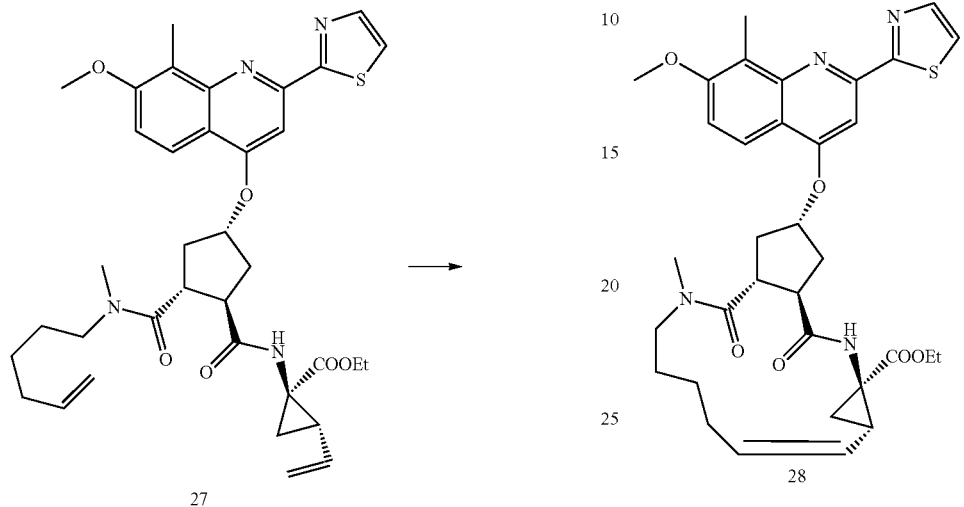

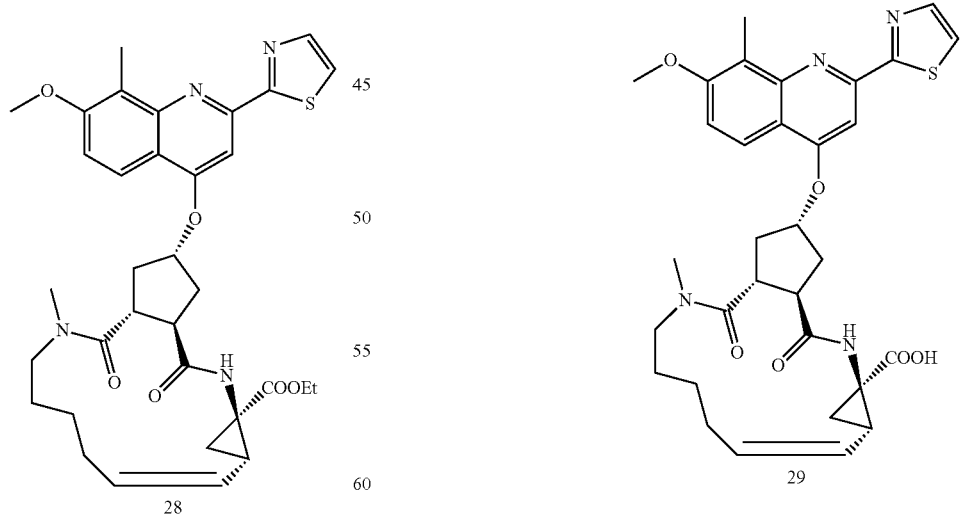

A solution of 27 (200 mg, 0.30 mmol) and Hoveyda-Grubbs 1$^{st}$ generation catalyst (18 mg, 0.030 mmol) in dried and degassed 1,2-dichloroethane (300 mL) is heated at 70° C. under nitrogen for 12 h. Then, the solvent is evaporated and A solution of LiOH (327 mg) in water (3 mL) is added to a stirred solution of 28 (150 mg, 0.237 mmol) in THF (15 mL) and MeOH (10 mL). After 48 h, solvent is evaporated and the residue partitioned between water and ether. Aqueous layer is acidified (pH=3) and extracted with AcOEt, dried (MgSO$_4$)

and evaporated. The residue is crystallized from ether to give the target compound 29: m/z=605 (M+H)+.

Example 3

Preparation of N-[17-[7-methoxy-8-methyl-2-(thiazol-2-yl)quinolin-4-yloxy]-13-methyl-2,14-dioxo-3,13-diazatricyclo[13.3.0.0$^{4,6}$]octadec-7-ene-4-carbonyl](cyclopropyl)sulfonamide (30)

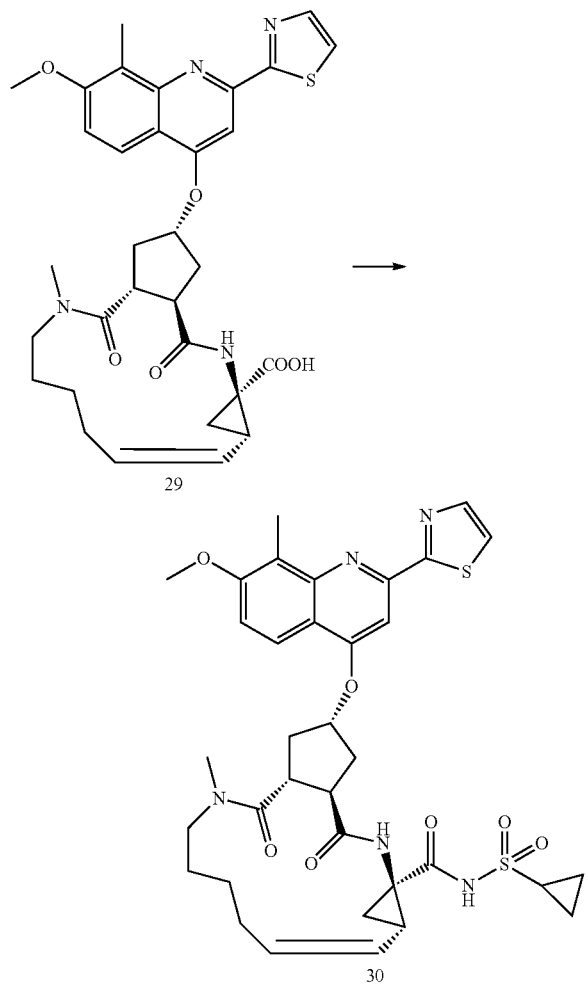

A mixture of 29 (85 mg, 0.14 mmol) and CDI (47 mg, 0.29 mmol) in dry THF (7 mL) is heated at reflux for 2 h under nitrogen. LCMS analysis shows one peak of the intermediate (RT=5.37). The reaction mixture is cooled to room temperature and cyclopropylsulfonamide (52 mg, 0.43 mmol) is added. Then, DBU (50 µL, 0.33 mmol) is added and the reaction mixture is stirred at room temperature for 1 h, and then heated at 55° C. for 24 h. Solvent is evaporated, and the residue partitioned between AcOEt and acidic water (pH=3). The crude material is purified by column chromatography (AcOEt/CH$_2$Cl$_2$/Petroleum ether, 1:1:1). The residue is crystallized in Et$_2$O, filtered to give the target compound contaminated with the cyclopropyl-sulfonamide. This material is triturated in 3 ml of water, filtered, washed with water and dried overnight in the high vacuum pump to give the target compound 30 as a white powder: m/z=708 (M+H)+.

Example 4

Preparation of 17-[2-(4-isopropylthiazole-2-yl)-7-methoxy-8-methyl-quinolin-4-yloxy]-13-methyl-2,14-dioxo-3,13-diazatricyclo[13.3.0.0$^{4,6}$]octadec-7-ene-4-carboxylic acid (46)

Synthesis of 4-hydroxy-2-(4-isopropylthiazole-2-yl)-7-methoxy-8-methylquinoline (36)

Step 1: synthesis of N-(tert-butyloxycarbonyl)-3-methoxy-2-methylaniline (32)

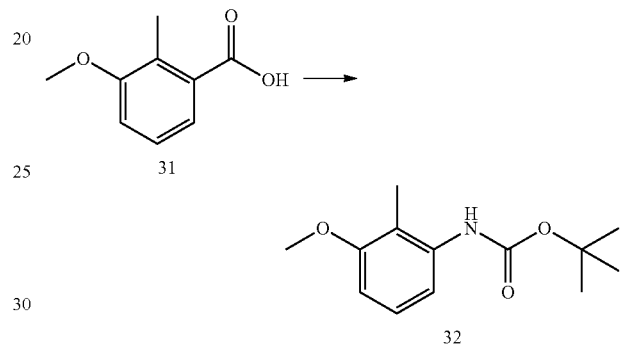

Triethylamine (42.4 mL, 302 mmol) was added to a suspension of 3-methoxy-2-methylbenzoic acid (45.6 g, 274 mmol) in dry toluene (800 mL). A clear solution was obtained. Then, dppa (65.4 mL, 302 mmol) in toluene (100 mL) was slowly added. After 1 h at room temperature, the reaction mixture was successively heated at 50° C. for 0.5 h, at 70° C. for 0.5 h then at 100° C. for 1 h. To this solution, t-BuOH (30.5 g, 411 mmol) in toluene (40 mL) was added at 100° C. and the resulting mixture was refluxed for 7 h. The solution was cooled to room temperature then successively washed with water, 0.5 N HCl, 0.5 N NaOH and brine, dried (Na$_2$SO$_4$), and evaporated to give 67 g of the target product: m/z=237 (M)+.

Step 2: synthesis of 3-methoxy-2-methylaniline (33)

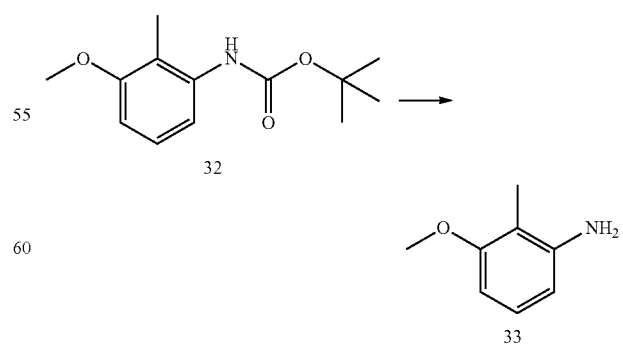

TFA (40.7 mL, 548 mmol) was added to a solution of N-(tert-butyloxycarbonyl)-3-methoxy-2-methylaniline, in dichloromethane (500 mL). After 2 h at room temperature, TFA (40.7 mL, 548 mmol) was added and the resulting mixture was stirred at room temperature overnight. Then, volatiles were evaporated. The residue was triturated with toluene (100 mL) and diisopropylether (250 mL), filtered off and washed with diisopropyl ether (100 mL) to give 56.3 g of the title product as a TFA salt: m/z=138 (M+H)⁺. The TFA salt was transformed to the free aniline by treatment with NaHCO₃.

Step 3: synthesis of (2-amino-4-methoxy-3-methylphenyl)(methyl)ketone (34)

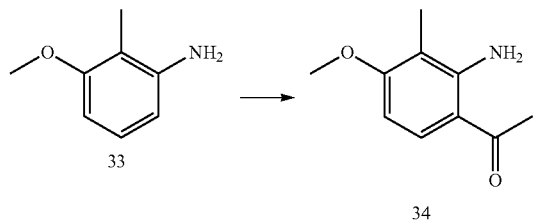

A solution of BCl₃ (1.0 M, 200 mL, 200 mmol) in CH₂Cl₂ was slowly added under nitrogen to a solution of 3-methoxy-2-methylaniline (26.0 g, 190 mmol) in xylene (400 mL). The temperature was monitored during the addition and was kept below 10° C. The reaction mixture was stirred at 5° C. for 0.5 h. Then, dry acetonitrile (13 mL, 246 mmol) was added at 5° C. After 0.5 h at 5° C., the solution was transferred into a dropping funnel and slowly added at 5° C. to a suspension of AlCl₃ (26.7 g, 200 mmol) in CH₂Cl₂ (150 mL). After 45 min at 5° C., the reaction mixture was heated at 70° C. under a nitrogen stream. After evaporation of CH₂Cl₂, the temperature of the reaction mixture reached 65° C. After 12 h at 65° C., the reaction mixture was cooled at 0° C., poured onto ice (300 g), and slowly heated to reflux for 7 h. After 2 days at room temperature, 6 N NaOH (50 mL) was added. The pH of the resulting solution was 2-3. The xylene layer was decanted. The organic layer was extracted with CH₂Cl₂. The xylene and CH₂Cl₂ layers were combined, successively washed with water, 1N NaOH, and brine, dried (Na₂SO₄) and evaporated. The residue was triturated in diisopropyl ether at 0° C., filtered off and washed with diisopropylether to give 13.6 g (40%) of the title product as a yellowish solid: m/z=180 (M+H)⁺.

Step 4: synthesis of 2'-[[(4-isopropylthiazole-2-yl)(oxo)methyl]amino]-4'-methoxy-3'-methylacetophenone (35)

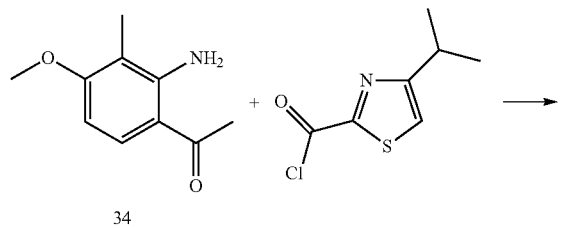

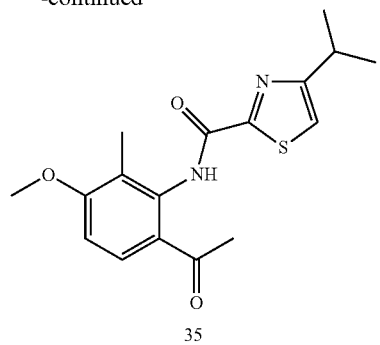

A solution of (2-amino-4-methoxy-3-methylphenyl)(methyl)ketone (18.6 g, 104 mmol) in dioxane (50 mL) was added under nitrogen to a suspension of 4-isopropylthiazole-2-carbonyl chloride in dioxane (250 mL). After 2 h at room temperature, the reaction mixture was concentrated to dryness. Then, the residue was partitioned between an aqueous solution of NaHCO₃ and AcOEt, organic layer was washed with brine, dried (Na₂SO₄), and evaporated. The residue was triturated in diisopropyl ether, filtered off and washed with diisopropyl ether to give 30.8 g (90%) of the title product 35.

Step 5: synthesis of 4-hydroxy-2-(4-isopropylthiazole-2-yl)-7-methoxy-8-methylquinoline (36)

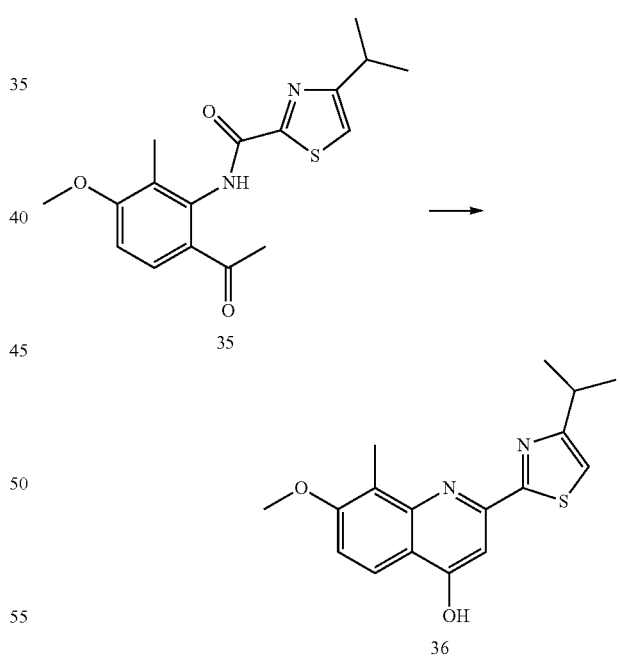

Potassium tert-butoxide (21.8 g, 195 mmol) was added to a suspension of 2'-[[(4-iso-propylthiazole-2-yl)(oxo)methyl]amino]-4'-methoxy-3'-methylacetophenone (35, 30.8 g, 92.7 mmol) in tert-butanol. The resulting reaction mixtures was heated at 100° C. overnight. Then, the reaction mixture was cooled at room temperature and diluted with ether (100 mL). The precipitate was filtered off and washed with Et₂O to give a powder (fraction A). The mother liquor was concentrated in vacuo, triturated in ether, filtered off, and washed with ether to give a powder (fraction 2). Fractions 1 and 2 were mixed and poured into water (250 mL). The pH of the resulting solution was adjusted to 6-7 (control with pH paper) with HCl 1N. The precipitate was filtered off, washed with water and dried. Then, the solid was triturated in diisopropyl ether, filtered off and dried to give 26 g (88%) of the title product 36 as a brownish solid: m/z=315 (M+H)+.

Synthesis of (hex-5-enyl)(methyl)amine (38)

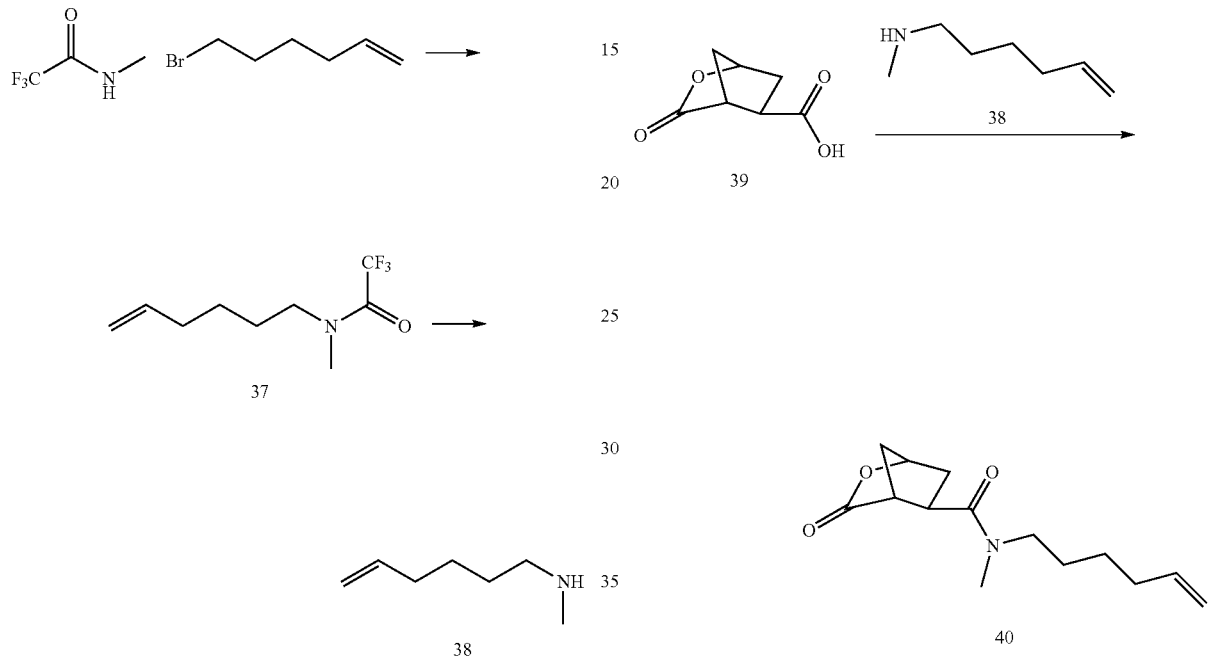

Step A

Sodium hydride (1.05 eq) was slowly added at 0° C. to a solution of N-methyltrifluoro-acetamide (25 g) in DMF (140 mL). The mixture was stirred for 1 h at room temperature under nitrogen. Then, a solution of bromohexene (32.1 g) in DMF (25 mL) was added dropwise and the mixture was heated to 70° C. for 12 hours. The reaction mixture was poured on water (200 mL) and extracted with ether (4×50 mL), dried (MgSO₄), filtered and evaporated to give 35 g of the target product 37 as a yellowish oil which was used without further purification in the next step.

Step B

A solution of potassium hydroxide (187.7 g) in water (130 mL) was added dropwise to a solution of 37 (35 g) in methanol (200 mL). The mixture was stirred at room temperature for 12 hours. Then, the reaction mixture was poured on water (100 mL) and extracted with ether (4×50 mL), dried (MgSO₄), filtered and the ether was distilled under atmospheric pressure. The resulting oil was purified by distillation under vacuum (13 mm Hg pressure, 50° C.) to give 7.4 g (34%) of the title product 38 as a colourless oil: ¹H-NMR (CDCl₃): δ 5.8 (m, 1H), 5 (ddd, J=17.2 Hz, 3.5 Hz, 1.8 Hz, 1H), 4.95 (m, 1H), 2.5 (t, J=7.0 Hz, 2H), 2.43 (s, 3H), 2.08 (q, J=7.0 Hz, 2H), 1.4 (m, 4H), 1.3 (br s, 1H).

Preparation of 17-[2-(4-isopropylthiazole-2-yl)-7-methoxy-8-methylquinolin-4-yloxy]-3-methyl-2,14-dioxo-3,13-diazatricyclo[13.3.0.0⁴,⁶]octadec-7-ene-4-carboxylic acid (46)

Step A

3-Oxo-2-oxa-bicyclo[2.2.1]heptane-5-carboxylic acid 39 (500 mg, 3.2 mmol) in 4 ml DMF was added at 0° C. to HATU (1.34 g, 3.52 mmol) and N-methylhex-5-enylamine (435 mg, 3.84 mmol) in DMF (3 mL), followed by DIPEA. After stirring for 40 min at 0° C., the mixture was stirred at room temperature for 5 h. Then, the solvent was evaporated, the residue dissolved in EtOAc (70 mL) and washed with saturated NaHCO₃ (10 mL). The aqueous layer was extracted with EtOAc (2×25 mL). The organic phases were combined, washed with saturated NaCl (20 mL), dried (Na₂SO₄), and evaporated. Purification by flash chromatography (EtOAc/petroleum ether, 2:1) afforded 550 mg (68%) of the target product 40 as a colorless oil: m/z=252 (M+H)+.

Step B

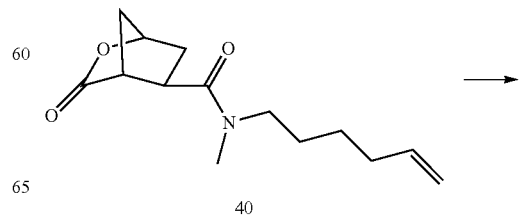

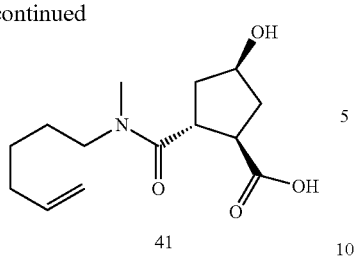

A solution of LiOH (105 mg in 4 ml of water) was added at 0° C. to the lactone amide 40. After 1 h, the conversion was completed (HPLC). The mixture was acidified to pH 2-3 with 1N HCl, extracted with AcOEt, dried (MgSO₄), evaporated, co-evaporated with toluene several times, and dried under high vacuum overnight to give 520 mg (88%) of the target product 41: m/z=270 (M+H)⁺.

Step C

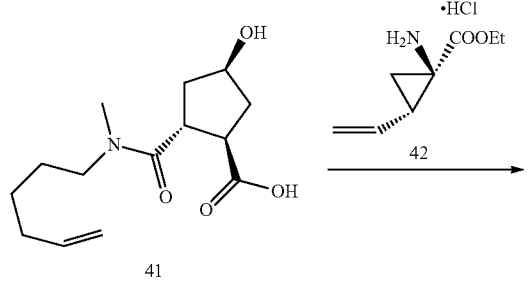

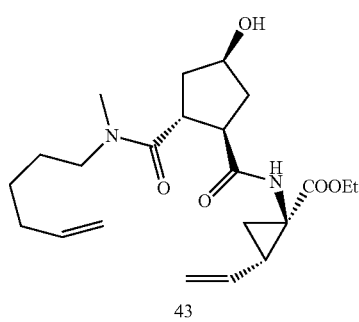

The 1-(amino)-2-(vinyl)cyclopropanecarboxylic acid ethyl ester hydrochloride 42 (4.92 g, 31.7 mmol) and HATU (12.6 g, 33.2 mmol) were added to 41 (8.14 g, 30.2 mmol). The mixture was cooled in an ice bath under argon, and then DMF (100 mL) and DIPEA (12.5 mL, 11.5 mmol) were successively added. After 30 min at 0° C., the solution was stirred at room temperature for an additional 3 h. Then, the reaction mixture was partitioned between EtOAc and water, washed successively with 0.5 N HCl (20 mL) and saturated NaCl (2×20 mL), and dried (Na₂SO₄). Purification by flash chromatography (AcOEt/CH₂Cl₂/Petroleum ether, 1:1:1) afforded 7.41 g (60%) of the target product 43 as a colorless oil: m/z=407 (M+H)⁺.

Step D

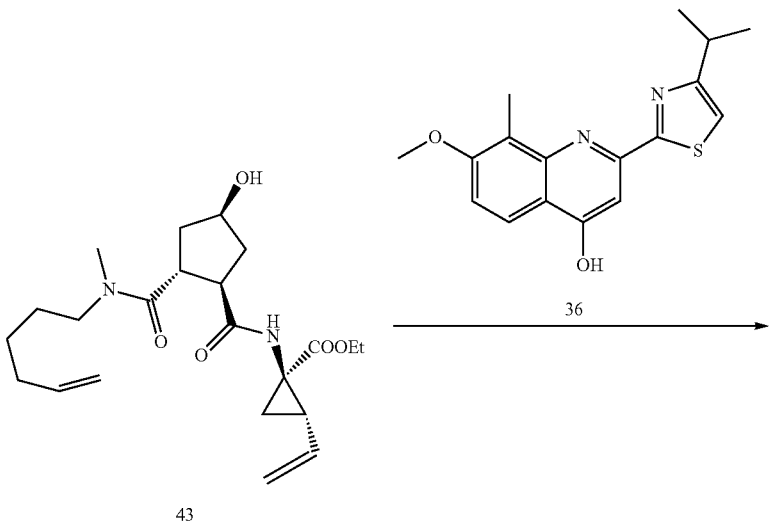

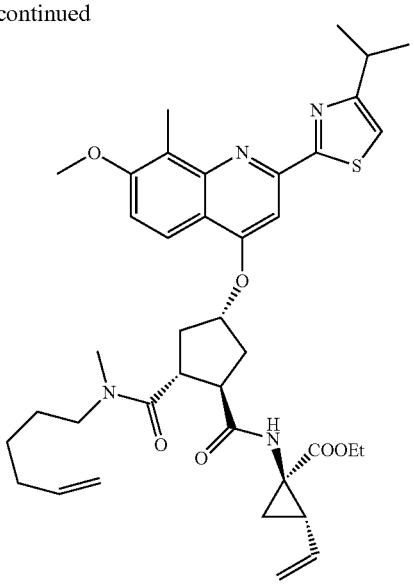

44

DIAD (1.02 mL, 5.17 mmol) was added at −15° C. under nitrogen atmosphere to a solution of 43 (1.5 g, 3.69 mmol), quinoline 36 (1.39 g, 4.43 mmol) and triphenyl-phosphine (1.26 g, 4.80 mmol) in dry THF (40 mL). After 4.5 h, at −15° C., the reaction mixture was partitioned between ice-cold water and AcOEt, dried (Na$_2$SO$_4$) and evaporated. The crude material was purified by flash column chromatography (gradient of petroleum AcOEt/CH$_2$Cl$_2$, 1:9 to 2:8) to give 1.45 g (56%) of the target product 44: m/z=703 (M+H)$^+$.

Step E

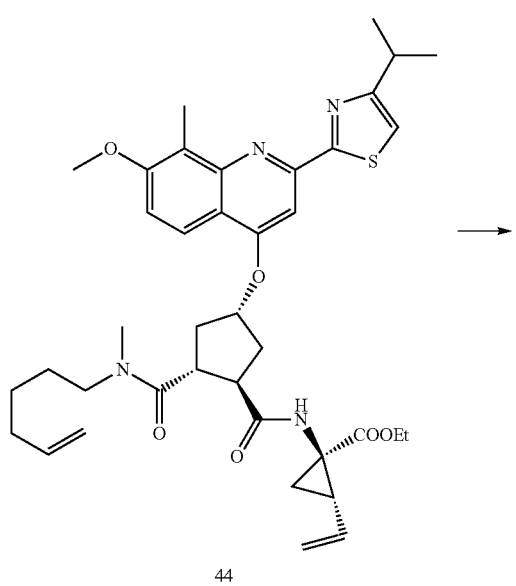

44

-continued

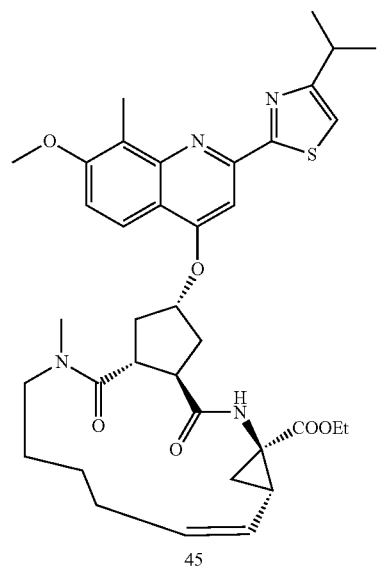

45

A solution of 44 (1.07 g, 1.524 mmol) and Hoveyda-Grubbs 1$^{st}$ generation catalyst (33 mg, 0.03 eq) in dried and degassed 1,2-dichloroethane (900 mL) was heated at 75° C. under nitrogen for 12 h. Then, the solvent was evaporated and the residue purified by silica gel chromatography (25% EtOAc in CH$_2$Cl$_2$). 620 mg (60%) of pure macrocycle 45 were obtained. m/z=674 (M+H)$^+$. $^1$H NMR (CDCl$_3$): 1.18-1.39 (m, 12H), 1.59 (m, 1H), 1.70-2.08 (m, 5H), 2.28 (m, 1H), 2.38 (m, 1H), 2.62 (m, 2H), 2.68 (s, 3H), 2.83 (m, 1H), 3.06 (s, 3H), 3.19 (sept, J=6.7 Hz, 1H), 3.36 (m, 1H), 3.83 (m, 1H), 3.97 (s, 3H), 4.09 (m, 2H), 4.65 (td, J=4 Hz, 14 Hz, 1H), 5.19

(dd, J=4 Hz, 10 Hz, 1H), 5.31 (m, 1H), 5.65 (td, J=4 Hz, 8 Hz, 1H), 7.00 (s, 1H), 7.18 (s, 1H), 7.46 (d, J=9 Hz, 1H), 7.48 (s, 1H), 8.03 (d, J=9 Hz, 1H).

(m, 2H), 5.66 (m, 1H), 7.01 (s, 1H), 7.10 (s, 1H), 7.22 (d, J=10 Hz, 1H), 7.45 (s, 1H), 8.00 (d, J=10 Hz, 1H).

Step F

Step G

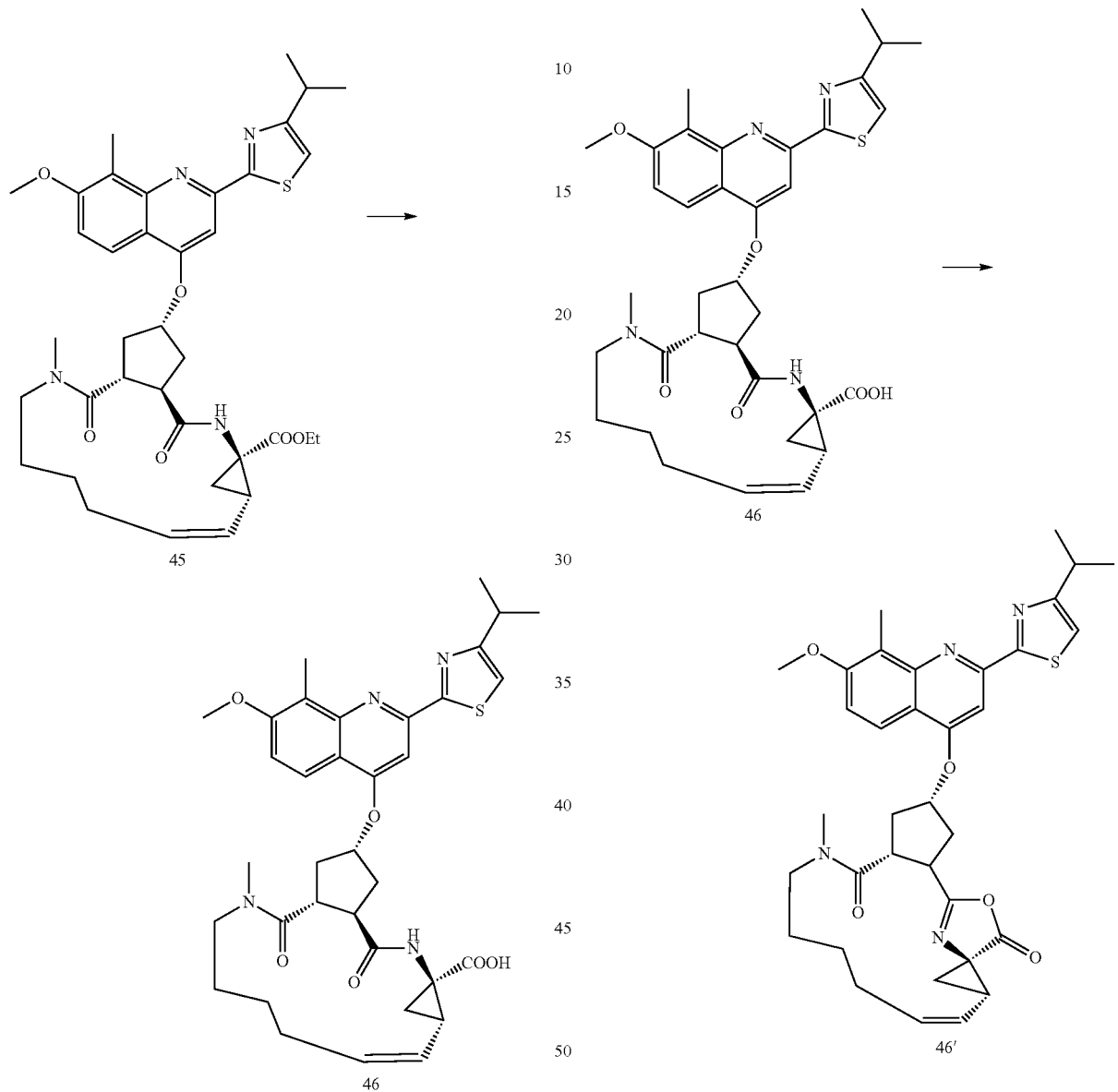

A solution of lithium hydroxide (1.65 g, 38.53 mmol) in water (15 mL) was added to a stirred solution of ester 45 (620 mg, 0.920 mmol) in THF (30 mL) and MeOH (20 mL). After 16 h at room temperature, the reaction mixture was quenched with NH$_4$Cl sat., concentrated under reduced pressure, acidified to pH 3 with HCl 1N and extracted with CH$_2$Cl$_2$, dried (MgSO$_4$) and evaporated to give 560 mg (88%) of carboxylic acid 46. m/z=647 (M+H)$^+$. $^1$H NMR (CDCl$_3$): 1.11-1.40 (m, 8H), 1.42-1.57 (m, 2H), 1.74 (m, 2H), 1.88-2.00 (m, 2H), 2.13 (m, 1H), 2.28 (m, 1H), 2.40 (m, 1H), 2.59 (m, 2H), 2.67 (s, 3H), 2.81 (m, 1H), 2.97 (s, 3H), 3.19 (m, 1H), 3.31 (m, 1H), 3.71 (m, 1H), 3.96 (s, 3H), 4.56 (dt, J=4 Hz, 12 Hz, 1H), 5.23

A solution of 17-[2-(4-isopropylthiazole-2-yl)-7-methoxy-8-methylquinolin-4-yloxy]-13-methyl-2,14-dioxo-3,13-diazatricyclo[13.3.0.04,6]octadec-7-ene-4-carboxylic acid 46 (138.3 mg, 0.214 mmol) prepared according to the procedure described above, and carbonyldiimidazole (96.9 mg, 0.598 mmol) in dry THF (5 mL) was stirred at reflux under nitrogen for 2 h. The reaction mixture was cooled down at room temperature and concentrated under reduced pressure. The residue was partitioned between EtOAc and HCl 1 N, the organic layer was washed with brine, dried (Na2SO$_4$) and evaporated. Then the solid was triturated in i-Pr ether to get 46' as a white powder: m/z=629 (M+H)$^+$. $^1$H NMR (CDCl$_3$): 0.99-1.00 (m, 1H), 1.20-1.35 (m, 2H), 1.39 (d, J=6.9 Hz, 6H), 1.55-1.7 (m, 1H), 1.9-2 (m, 2H), 2.15-2.25 (m, 2H), 2.3-2.60 (m, 4H), 2.68 (s, 3H), 2.71-2.82 (m, 1H), 2.82-

2.9 (m, 1H), 3.08 (s, 3H), 3.1-3.2 (m, 1H), 3.4-3.5 (m, 1H), 3.65-3.71 (m, 1H), 3.91 (s, 3H), 4.28-4.4 (m, 1H), 5.32-5.46 (m, 2H), 5.85-5.95 (m, 1H), 7.00 (s, 1H), 7.22 (d, J=9.2 Hz, 1H), 7.45 (s, 1H), 8.09 (d, J=9.2 Hz, 1H).

Example 5

Preparation of N-[17-[2-(4-isopropylthiazole-2-yl)-7-methoxy-8-methylquinolin-4-yloxy]-13-methyl-2,14-dioxo-3,13-diazatricyclo[13.3.0.0$^{4,6}$]octadec-7-ene-4-carbonyl](cyclopropyl)sulfonamide (47)

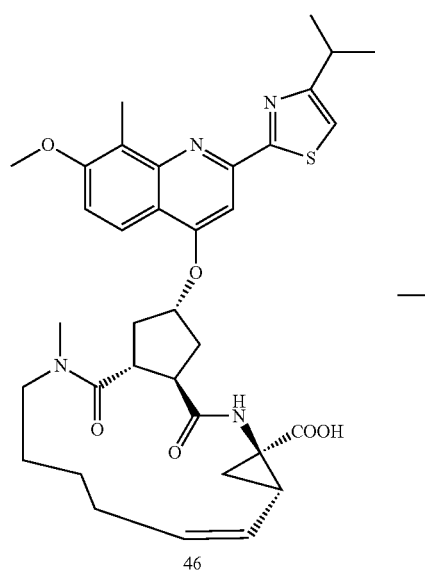

46

A solution of 17-[2-(4-isopropylthiazole-2-yl)-7-methoxy-8-methylquinolin-4-yloxy]-13-methyl-2,14-dioxo-3,13-diazatricyclo[13.3.0.04,6]octadec-7-ene-4-carboxylic acid 46 (560 mg, 0.867 mmol) prepared according to Example 4, and carbonyldiimidazole (308 mg, 1.90 mmol) in dry THF (10 mL) was stirred at reflux under nitrogen for 2 h. The reaction mixture was cooled to room temperature and cyclopropylsulfonamide (400 mg, 3.301 mmol) and DBU (286 mg, 1.881 mmol) were added. This solution was heated at 50° C. for 15 h. Then, the reaction mixture was cooled down at room temperature and concentrated under reduced pressure. The residue was partitioned between $CH_2Cl_2$ and HCl 1 N, the organic layer was washed with brine, dried ($MgSO_4$) and evaporated. Purification by flash chromatography (gradient of EtOAc (0 to 25%) in $CH_2Cl_2$) afforded 314 mg of an off-white solid which was further washed with water, then isopropylether, and dried in the vacuum oven to deliver 282 mg (40%) of the pure title product 47 as a white powder: m/z=750 (M+H)$^+$. $^1$H NMR (CDCl$_3$): 0.99-1.52 (m, 14H), 1.64-2.05 (m, 4H), 2.77 (m, 1H), 2.41 (m, 2H), 2.59 (m, 2H), 2.69 (s, 3H), 2.92 (m, 2H), 3.04 (s, 3H), 3.19 (m, 1H), 3.40 (m, 2H), 3.98 (s, 3H), 4.60 (t, J=13 Hz, 1H), 5.04 (t, J=11 Hz, 1H), 5.37 (m, 1H), 5.66 (m, 1H), 6.21 (s, 1H), 7.02 (s, 1H), 7.22 (d, J=10 Hz, 1H), 7.45 (s, 1H), 7.99 (d, J=10 Hz, 1H), 10.82 (broad s, 1H).

Example 6

Preparation of N-[17-[2-(4-isopropylthiazole-2-yl)-7-methoxy-8-methylquinolin-4-yloxy]-13-methyl-2,14-dioxo-3,13-diazatricyclo[13.3.0.0$^{4,6}$]octadec-7-ene-4-carbonyl](1-methylcyclopropyl)sulfonamide (48)

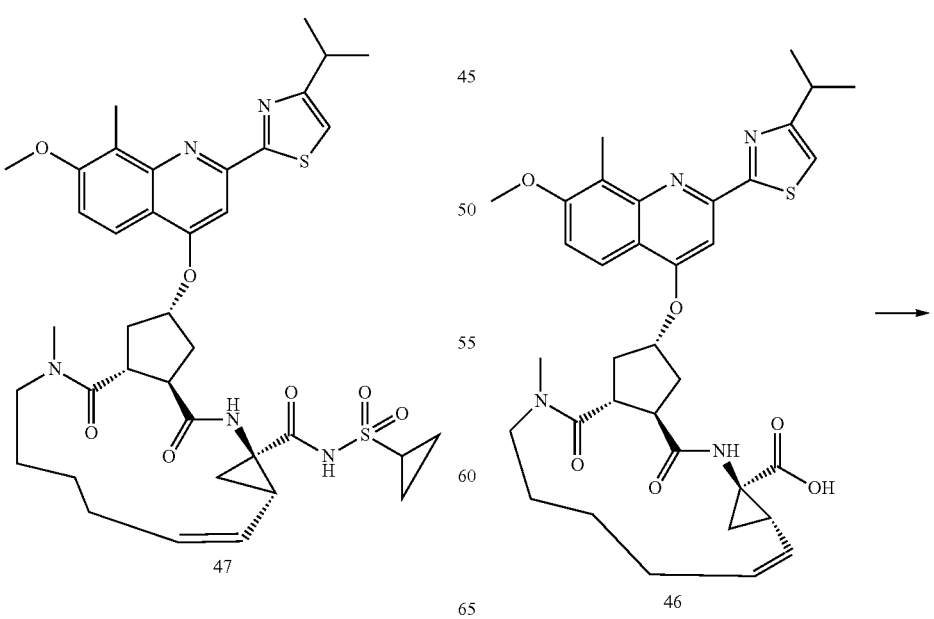

47

46

Example 7

Preparation of 17-[8-chloro-2-(4-isopropylthiazole-2-yl)-7-methoxyquinolin-4-yloxy]-13-methyl-2,14-dioxo-3,13-diazatricyclo[13.3.0.0$^{4,6}$]octadec-7-ene-4-carboxylic acid (25)

Step A: Synthesis of (2-amino-3-chloro-4-methoxyphenyl)(methyl)ketone (50)

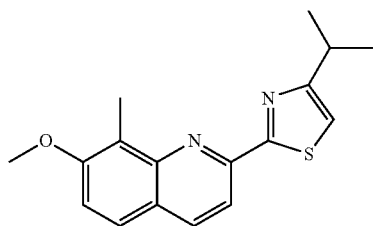

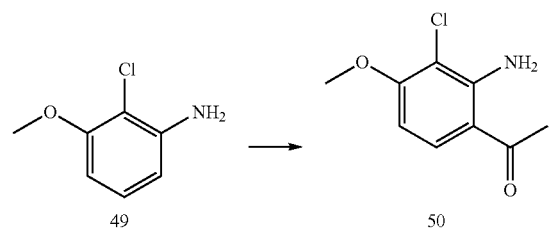

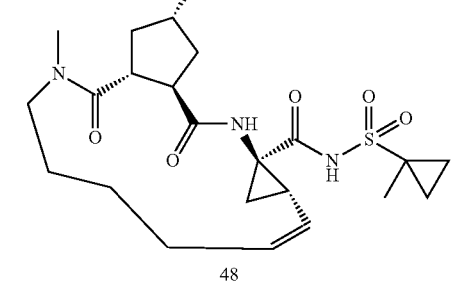

48

A solution of carboxylic acid 46 (240 mg, 0.38 mmol) and carbonyldiimidazole (2 eq) in dry THF (5 mL) was stirred at reflux under nitrogen for 2 h. The reaction mixture was cooled to room temperature and 1-methylcyclopropylsulfonamide (2 eq) and DBU (2 eq) were added. This solution was heated at 50° C. for 15 h. Then, the reaction mixture was cooled down to room temperature and concentrated under reduced pressure. The residue was partitioned between CH$_2$Cl$_2$ and HCl 1N, the organic layer was washed with brine, dried (MgSO$_4$) and evaporated. Purification by flash chromatography (gradient of EtOAc (0 to 25%) in CH$_2$Cl$_2$) afforded 170 mg (58%) of the title compound 48 as an off-white solid which was further washed with water, then isopropylether, and dried in the vacuum oven: m/z=764 (M+H)$^+$. $^1$H NMR (acetone-d6): 0.86 (m, 2H), 1.15-1.78 (m, 19H), 1.87 (m, 2H), 2.13-2.54 (m, 3H), 2.57-2.71 (m, 4H), 2.96-3.25 (m, 4H), 3.54 (m, 2H), 4.02 (s, 3H), 4.58 (t, J=13 Hz, 1H), 5.04 (m, 1H), 5.46 (m, 1H), 5.62 (m, 1H), 7.31 (s, 1H), 7.43 (d, J=9 Hz, 1H), 7.58 (s, 1H), 8.07 (d, J=13 Hz, 1H), 8.19 (broad s, 1H), 11.44 (broad s, 1H).

A solution of BCl$_3$ (1.0 M, 138 mL, 138 mmol) in CH$_2$Cl$_2$ was slowly added under nitrogen to a solution of 2-chloro-3-methoxyaniline 49 (20.6 g, 131 mmol) in xylene (225 mL). The temperature was monitored during the addition and was kept below 10° C. The reaction mixture was stirred at 5° C. for 0.5 h. Then, dry acetonitrile (9.0 mL, 170 mmol) was added at 5° C. After 0.5 h at 5° C., the solution was transferred into a dropping funnel and slowly added at 5° C. to a suspension of AlCl$_3$ (18.4 g, 138 mmol) in CH$_2$Cl$_2$ (80 mL). After 45 min at 5° C., the reaction mixture was heated at 70° C. under a nitrogen stream. After evaporation of CH$_2$Cl$_2$, the temperature of the reaction mixture reached 65° C. After 12 h at 65° C., the reaction mixture was cooled to 0° C., poured onto ice (200 g), and slowly heated to reflux for 7 h. After 2 days at room temperature, 6 N NaOH (25 mL) and CH$_2$Cl$_2$ (100 mL) were added. The mixture was filtered, the filtered washed with CH$_2$Cl$_2$. The organic layer was decanted, and successively washed with water, 1N NaOH, and brine, dried (Na$_2$SO$_4$) and evaporated. The residue was triturated in diisopropyl ether at 0° C., filtered off and washed with diisopropylether to give 19.0 g (73%) of the title product 50 as a white solid: m/z=200 (M+H)$^+$.

Step B: Synthesis of 2'-[[(4-isopropylthiazole-2-yl)(oxo)methyl]amino]-3'-chloro-4'-methoxyacetophenone (51)

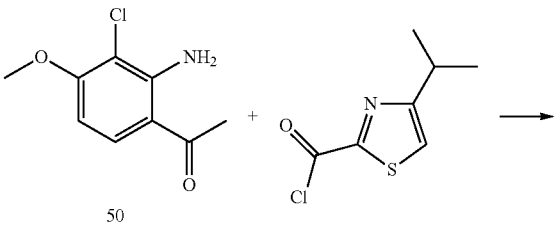

-continued

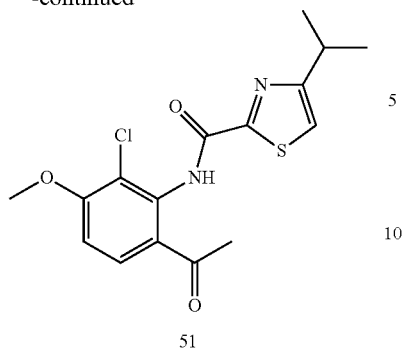

The title product 51 was prepared (79%) from (2-amino-3-chloro-4-methoxyphenyl)-(methyl)ketone (50) following the procedure reported for 2'-[[(4-isopropylthiazole-2-yl)(oxo)methyl]amino]-4'-methoxy-3'-methylacetophenone (35): m/z=353 (M+H)⁺.

Step C: synthesis of 8-chloro-4-hydroxy-2-(4-isopropylthiazole-2-yl)-7-methoxy-quinoline (52)

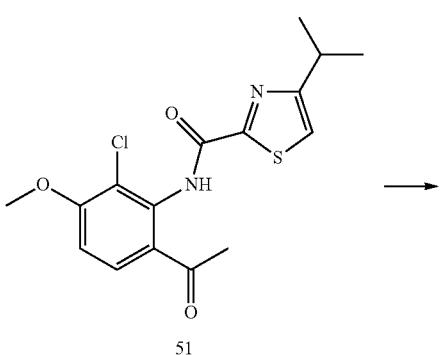

The title product 52 was prepared (58%) from 2'-[[(4-isopropylthiazole-2-yl)(oxo)-methyl]amino]-3'-chloro-4'-methoxyacetophenone (51) following the procedure reported for 4-hydroxy-2-(4-isopropylthiazole-2-yl)-7-methoxy-8-methylquinoline (36): m/z=335 (M+H)⁺.

Step D: Preparation of compound 53

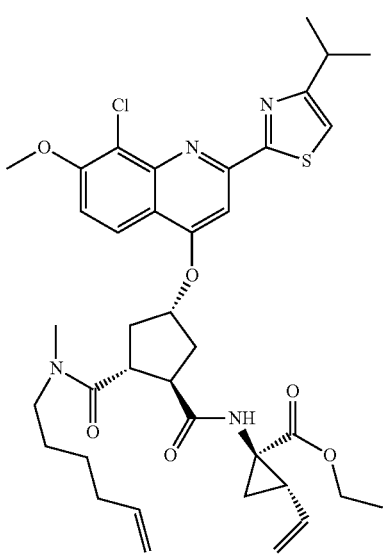

Compound 53 was prepared from alcohol 43 and 8-chloro-4-hydroxy-2-(4-isopropyl-thiazole-2-yl)-7-methoxy-quinoline (52) following the procedure described for 44: m/z=723 (M+H)⁺.

Step E: Preparation of Compound 54

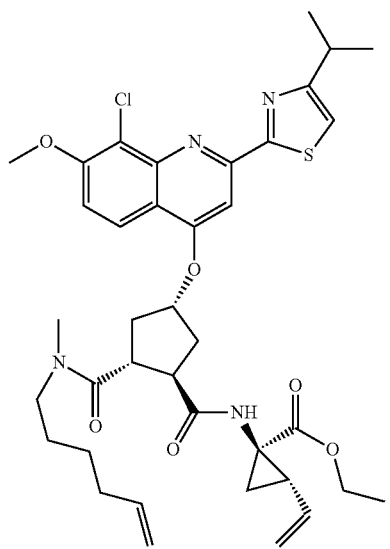

-continued

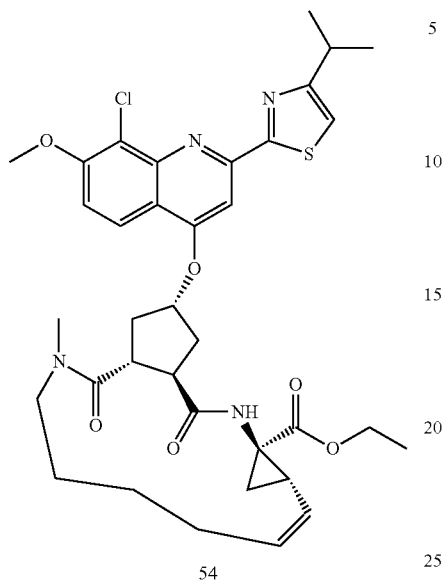

54

Compound 54 was prepared from 53 following the procedure described for 45: m/z=695 (M+H)+.

Step F: Preparation of Compound 55

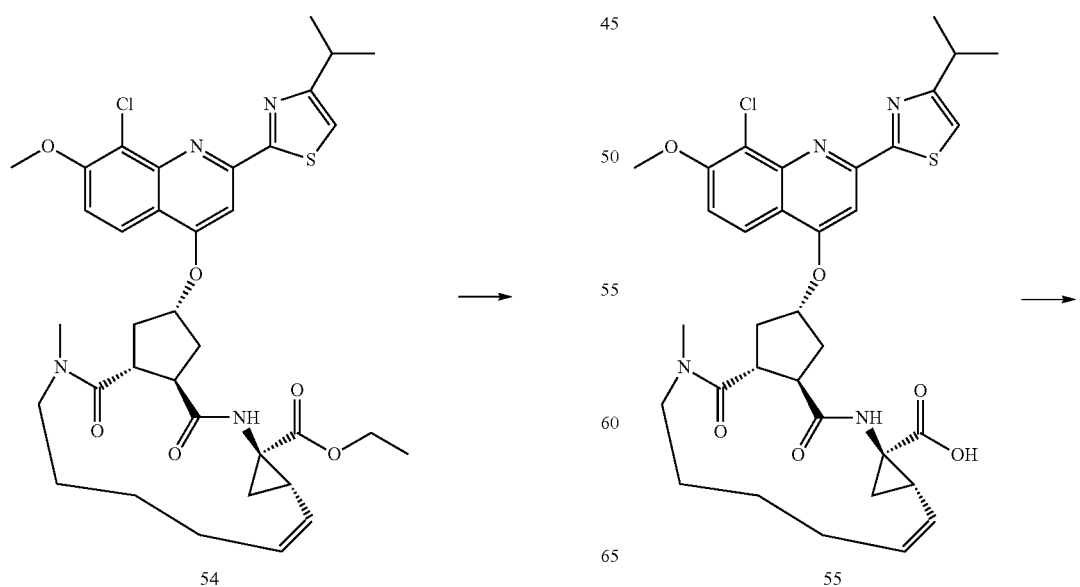

-continued

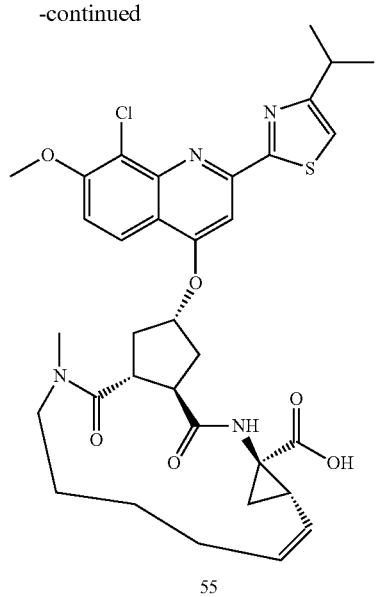

55

A solution of lithium hydroxide (3.85 g, 90.1 mmol) in water (30 mL) was added to a stirred solution of ester 54 (1.64 g, 2.36 mmol) in THF (55 mL) and MeOH (40 mL). After 16 h at room temperature, more LiOH (1.0 g) was added. After 20 h at room temperature, the reaction mixture was quenched with a saturated solution of NH$_4$Cl, concentrated under reduced pressure, acidified to pH 5 with HCl 1N, extracted with EtOAc, dried (MgSO$_4$) and evaporated to give 1.37 g (87%) of the carboxylic acid 55. m/z=667 (M+H)+.

Example 8

Preparation of N-[17-[8-chloro-2-(4-isopropylthiazole-2-yl)-7-methoxyquinolin-4-yloxy]-13-methyl-2,14-dioxo-3,13-diazatricyclo[13.3.0.0$^{4,6}$]-octadec-7-ene-4-carbonyl](cyclopropyl)sulfonamide (56)

89
-continued

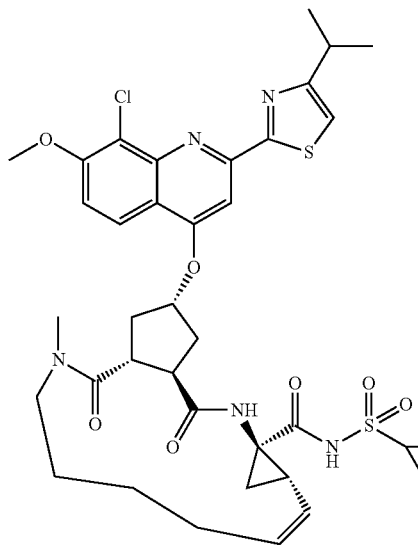

56

A solution of carboxylic acid 55 (1.37 g, 2.52 mmol) and carbonyldiimidazole (2 eq) in dry THF (75 mL) was stirred at reflux under nitrogen for 2 h. The reaction mixture was cooled to room temperature and cyclopropylsulfonamide (2 eq) and DBU (2 eq) were added. This solution was heated at 50° C. for 36 h. Then, the reaction mixture was cooled down to room temperature and concentrated under reduced pressure. The residue was partitioned between EtOAc and HCl 1N, the organic layer was washed with brine, dried (MgSO$_4$) and evaporated. Purification by flash chromatography (gradient of EtOAc (0 to 25%) in CH$_2$Cl$_2$) afforded 880 mg (55%) of the title compound 56 as an off-white solid: m/z=770 (M+H)$^+$. $^1$H NMR (CDCl$_3$, major rotamer): 0.93-1.52 (m, 13H), 1.60-2.07 (m, 5H), 2.21-2.64 (m, 5H), 2.92 (m, 2H), 3.04 (s, 3H), 3.19 (m, 1H), 3.41 (m, 2H), 4.07 (s, 3H), 4.60 (t, J=13 Hz, 1H), 5.04 (t, J=11 Hz, 1H), 5.37 (m, 1H), 5.66 (m, 1H), 6.33 (s, 1H), 7.07 (s, 1H), 7.24 (d, J=9 Hz, 1H), 7.52 (s, 1H), 8.05 (d, J=9 Hz, 1H), 10.81 (broad s, 1H).

90

Example 9

Preparation of N-[17-[8-chloro-2-(4-isopropylthiazole-2-yl)-7-methoxy-quinolin-4-yloxy]-13-methyl-2,14-dioxo-3,13-diazatricyclo[13.3.0.0$^{4,6}$]octadec-7-ene-4-carbonyl] (1-methylcyclopropyl)sulfonamide (57)

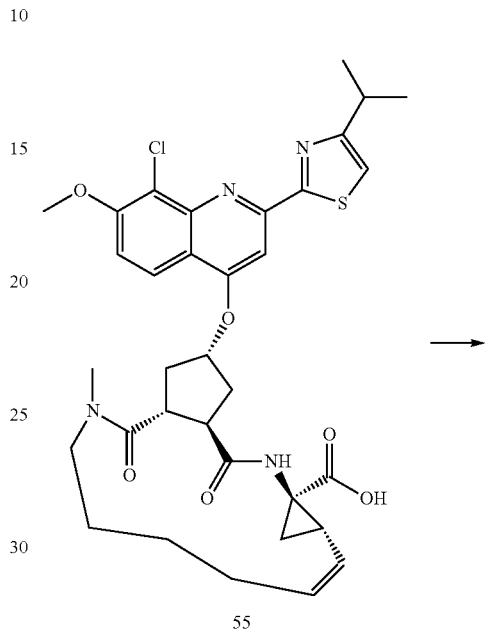

55

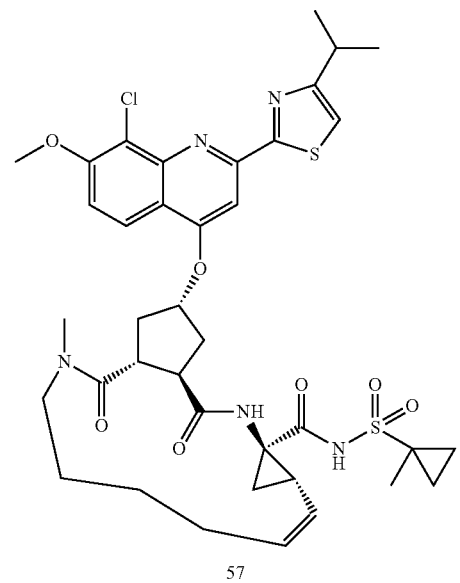

57

A solution of carboxylic acid 55 (49 mg, 0.073 mmol) and carbonyldiimidazole (2 eq) in dry THF (5 mL) was stirred at reflux under nitrogen for 2 h. The reaction mixture was cooled to room temperature and 1-methylcyclopropylsulfonamide (2 eq) and DBU (2 eq) were added. This solution was heated at 50° C. for 15 h. Then, the reaction mixture was cooled down to room temperature and concentrated under reduced pressure. The residue was partitioned between EtOAc and HCl 1N, the organic layer was washed with brine, dried (MgSO$_4$)

and evaporated. Purification by flash chromatography (gradient of EtOAc (0 to 25%) in DCM) afforded 10 mg (20%) of the title compound 57: m/z=784 (M+H)⁺.

Example 10

Preparation of 17-[2-(3-isopropylpyrazol-1-yl)-7-methoxy-8-methylquinolin-4-yloxy]-13-methyl-2,14-dioxo-3,13-diazatricyclo[13.3.0.0$^{4,6}$]octadec-7-ene-4-carboxylic acid (65)

Step 1: Synthesis of ethyl 4-hydroxy-7-methoxy-8-methylquinoline-3-carboxylate (58)

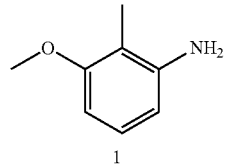

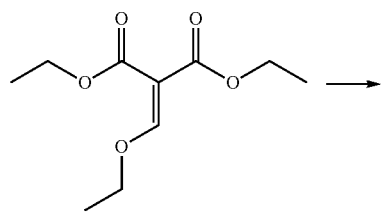

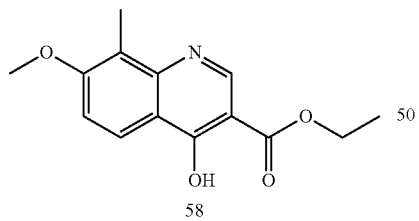

Diethyl ethoxymethylenemalonate (17.2 g, 79.6 mmol) was added to 2-methyl-m-anisidine (8.4 g, 61.2 mmol) (exothermic reaction). Then, diethylether (100 mL) was added and the mixture was stirred overnight at room temperature. The solvent was evaporated and the residue re-dissolved in ether (50 mL), filtered, washed with heptane and dried to give 12 g of an intermediate. This intermediate was added portion wise to diphenyl ether (50 mL) pre-heated at 230° C. The reaction mixture was successively heated to 250° C. for 1.5 h, cooled at room temperature, and diluted with heptane (200 mL). The precipitate was filtered off, and successively washed with heptane and ether to give 9.2 g (57.5%) of the target product 58 as a yellow powder: m/z=262 (M+H)⁺.

Step 2: Synthesis of 4-Hydroxy-7-methoxy-8-methylquinoline (59)

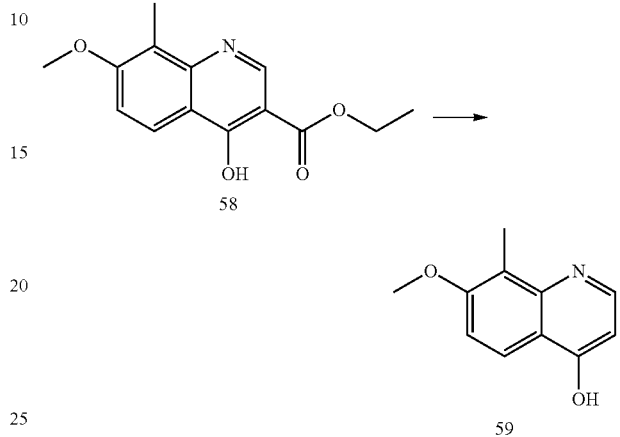

A suspension of ethyl 4-hydroxy-7-methoxy-8-methylquinoline-3-carboxylate (58, 9.2 g, 35.2 mmol) in 5N NaOH (150 mL) was refluxed for 1.5 h (until a clear solution was obtained). Then, the solution was cooled to 0° C. and the pH adjusted to 2-3 with concentrated HCl. The solid was filtered off and successively washed with water, acetone and ether. This powder was added in small portions to diphenylether (40 mL), pre-heated at 250° C. The resulting suspension became a solution after 20 min ($CO_2$ formation was observed). After 1 h at 250° C., the brown solution was cooled to room temperature and diluted with heptanes (200 mL). The precipitate was filtered off and washed with heptanes and ether to give 6.4 g (96%) of the target product 59 as a yellow powder: m/z=190 (M+H)⁺.

Step 3: Synthesis of 4-Chloro-7-methoxy-8-methylquinoline (60)

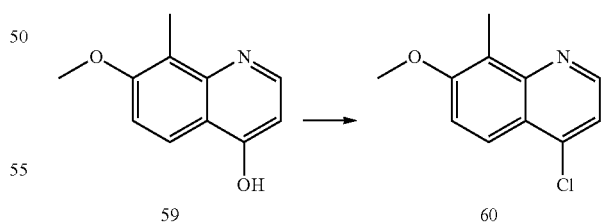

A solution of 4-hydroxy-7-methoxy-8-methylquinoline (59, 6.4 g, 33.8 mmol) in $POCl_3$ (17.2 g, 111.6 mmol) was heated at reflux for 1 h under nitrogen. Then, the resulting solution was cooled down to room temperature and the excess of $POCl_3$ was evaporated under reduced pressure. The residue was partitioned between ice-cold 1N NaOH and AcOEt. The organic layer was dried ($Na_2SO_4$), and evaporated. The residue was purified by silica-gel filtration (AcOEt/$CH_2Cl_2$/Hep-

Step 4: Synthesis of 4-Chloro-7-methoxy-8-methylquinoline N-oxide (61)

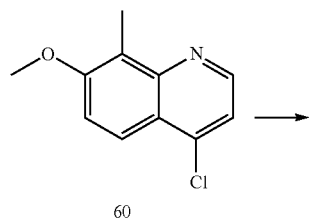

60

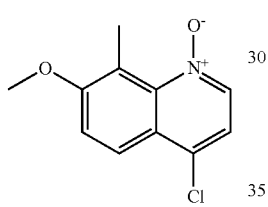

61

Metachloroperbenzoic acid (90.2 g, 366.0 mmol) was added portion wise over 3 h to a solution of 4-chloro-7-methoxy-8-methylquinoline (60, 15.2 g, 73.2 mmol) in CHCl$_3$ (1 L). Then, the solution was partitioned between ice-cooled NaOH 1N and CH$_2$Cl$_2$ (8 successive extractions). The organic layers were combined, dried (Na$_2$SO$_4$) and evaporated. The residue was purified by column chromatography (gradient of AcOEt/CH$_2$Cl$_2$, 1:2 to 1:0) to give 3.0 g (18.3%) of the title product 61 as a pale yellow powder: m/z=224 (M+H)$^+$.

Step 5: Synthesis of 4-Benzyloxy-7-methoxy-8-methylquinoline N-oxide (62)

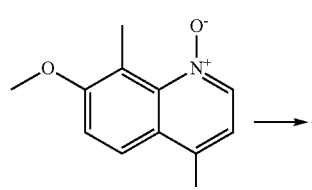

61

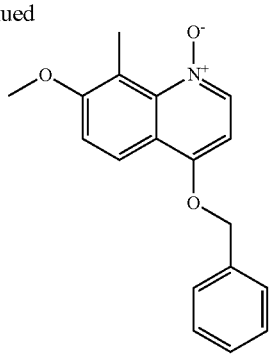

62

NaH (973 mg, 60% in mineral oil, 24.3 mmol) was added at 0° C., under inert atmosphere, to benzylalcohol (2.96 mL, 28.6 mmol) in DMF (10 mL). After 5 min at 0° C., the solution was warmed up to room temperature. After 10 min at room temperature, 4-chloro-7-methoxy-8-methylquinoline N-oxide (61, 3.2 g, 14.3 mmol) was added in one potion. The resulting black solution was stirred at room temperature under inert atmosphere for another 30 min, then poured into ice-cooled water, and extracted 4 times with AcOEt. Combined organic layers were dried (Na$_2$SO$_4$) and evaporated. The residue was purified by column chromatography (gradient AcOEt/CH$_2$Cl$_2$, 1:1 to 1:0, then AcOEt/MeOH 9:1) to give 2.5 g (59%) of the target product 62 as a yellow powder: m/z=296 (M+H)$^+$.

Step 6: Synthesis of 4-benzyloxy-2-chloro-7-methoxy-8-methylquinoline (63)

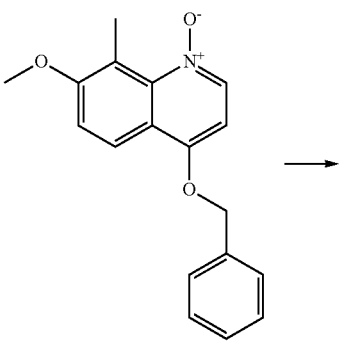

62

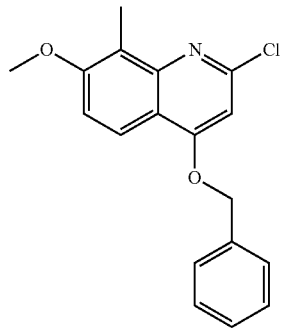

63 tane, 4:4:2) to give 6.5 g (92.5%) of the target product 60 as yellow needles: m/z=208 (M+H)$^+$.

POCl₃ was added under inert atmosphere at −78° C. to 4-benzyloxy-7-methoxy-8-methylquinoline N-oxide (62, 2.5 g, 8.47 mmol). Then the reaction mixture was allowed to warm up to room temperature, then heated to reflux. After 35 min, the solution was cooled to room temperature and the excess of POCl₃ was evaporated under reduced pressure. The residue was partitioned between ice-cooled water and AcOEt, dried (Na₂SO₄) and evaporated. The residue was triturated in ether, then filtered and successively washed with small portions of methanol and ether to give 2.4 g (90.4%) of the target product 63 as a white powder: m/z=314 (M+H)⁺.

Step 7: Synthesis of 4-hydroxy-2-(3-isopropylpyrazol-1-yl)-7-methoxy-8-methyl-quinoline (64)

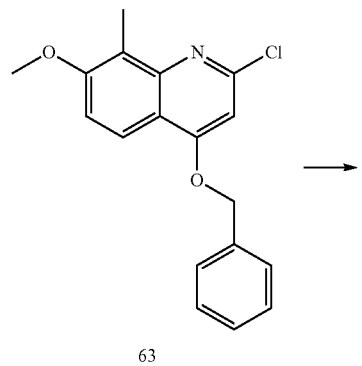

63

A mixture of 4-benzyloxy-2-chloro-7-methoxy-8-methylquinoline (63, 1.00 g, 3.19 mmol) and 3-isopropylpyrazole was heated at 155° C. for 12 h. Then, the reaction mixture was partitioned between AcOEt and water, dried (Na₂SO₄) and evaporated. The residue was purified by column chromatography (AcOEt/CH₂Cl₂, 1:1) to give 900 mg (95%) of the target product 64 as a yellowish powder: m/z=298 (M+H)⁺.

Step 8: Synthesis of 17-[2-(3-isopropylpyrazol-1-yl)-7-methoxy-8-methylquinolin-4-yl-oxy]-13-methyl-2,14-dioxo-3,13-diazatricyclo[13.3.0.0⁴,⁶]octadec-7-ene-4-carboxylic acid (65)

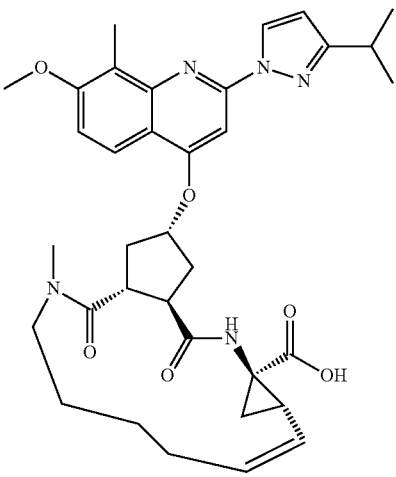

65

The title compound was prepared from 4-hydroxy-2-(3-isopropylpyrazol-1-yl)-7-methoxy-8-methylquinoline (64) and intermediate 26 following the procedure (Step D-F) reported for the preparation of 17-[7-methoxy-8-methyl-2-(thiazol-2-yl)quinolin-4-yloxy]-13-methyl-2,14-dioxo-3,13-diazatricyclo[13.3.0.0⁴,⁶]octadec-7-ene-4-carboxylic acid (29): m/z=630 (M+H)⁺.

Example 11

Preparation of N-[17-[2-(3-isopropylpyrazol-1-yl)-7-methoxy-8-methyl-quinolin-4-yloxy]-13-methyl-2,14-dioxo-3,13-diazatricyclo[13.3.0.0⁴,⁶]octadec-7-ene-4-carbonyl](cyclopropyl)sulfonamide (66)

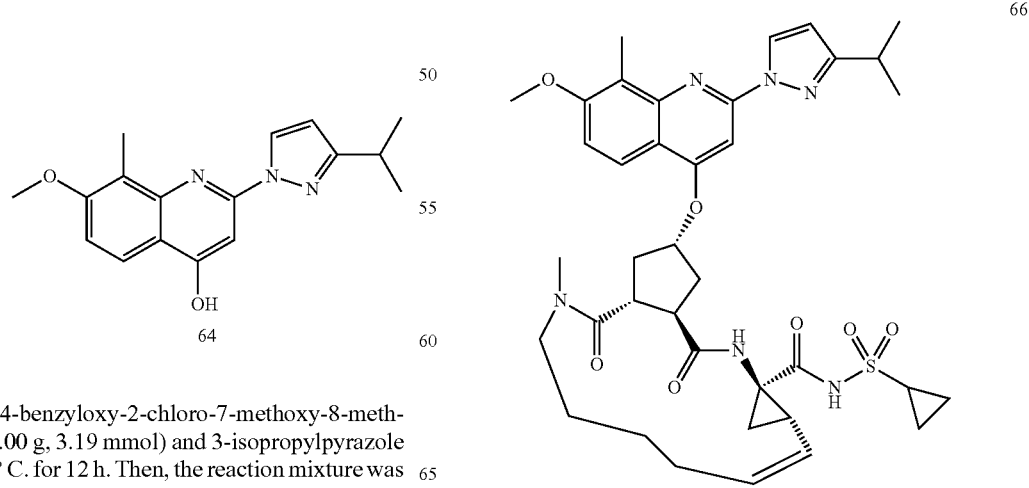

66

The title compound was prepared from 17-[2-(3-isopropylpyrazol-1-yl)-7-methoxy-8-methylquinolin-4-yloxy]-13-methyl-2,14-dioxo-3,13-diazatricyclo[13.3.0.0$^{4,6}$]octadec-7-ene-4-carboxylic acid (65) and cyclopropylsulfonamide following the procedure reported for the preparation of N-[17-[8-chloro-2-(4-isopropylthiazole-2-yl)-7-methoxyquinolin-4-yloxy]-13-methyl-2,14-dioxo-3,13-diazatricyclo[13.3.0.0$^{4,6}$]-octadec-7-ene-4-carbonyl](cyclopropyl)sulfonamide (56): m/z=733 (M+H)$^+$. $^1$H NMR (CDCl$_3$): 0.80-1.50 (m, 12H), 1.65-1.78 (m, 1H), 1.79-2.05 (m, 4H), 2.15-2.31 (m, 1H), 2.32-2.48 (m, 2H), 2.49-2.63 (m, 5H), 2.84-2.96 (m, 2H), 3.03 (s, 3H), 3.05-3.14 (m, 1H), 3.33-3.42 (m, 2H), 3.61-3.70 (m, 1H), 3.96 (s, 3H), 4.60 (t, J=12.3 Hz, 1H), 5.04 (t, J=10.6 Hz, 1H), 5.26-5.46 (m, 1H), 5.61-5.69 (m, 1H), 6.32 (d, J=2.5 Hz, 1H), 6.37 (br s, 1H), 7.13 (d, J=9.0 Hz, 1H), 7.30 (s, 1H), 7.95 (d, J=9.0 Hz, 1H), 8.68 (d, J=2.5 Hz, 1H), 10.88 (br s, 1H).

Example 12

Preparation of 17-[8-ethyl-2-(4-isopropylthiazole-2-yl)-7-methoxy-quinolin-4-yloxy]-13-methyl-2,14-dioxo-3,13-diazatricyclo[13.3.0.0$^{4,6}$]octadec-7-ene-4-carboxylic acid (70)

Step 1: Synthesis of N-[2-(1-hydroxyethyl)-3-methoxyphenyl]pivaloylamide (66)

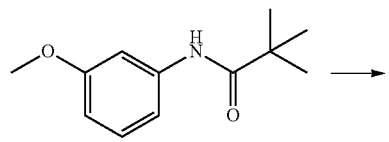

A solution of N-butyllithium (2.5 M in hexanes, 4.4 mL, 11.1 mmol) was added dropwise at 0° C. under nitrogen to a stirred solution of N-(3-methoxyphenyl)-pivaloylamide. After 1 h at room temperature, the reaction mixture was cooled down to −78° C. Then, a solution of acetaldehyde (544 μL, 9.64 mmol) in THF (1 mL) was added. After 10 min, the reaction mixture was allowed to warm up to room temperature for 30 min. Then, the reaction mixture was partitioned between AcOEt and water, dried (Na$_2$SO$_4$) and evaporated to afford 500 mg (45%) of the target product 66 as a yellow solid: m/z=252 (M+H)$^+$.

Step 2: Synthesis of N-[2-ethyl-3-methoxyphenyl]pivaloylamide (67)

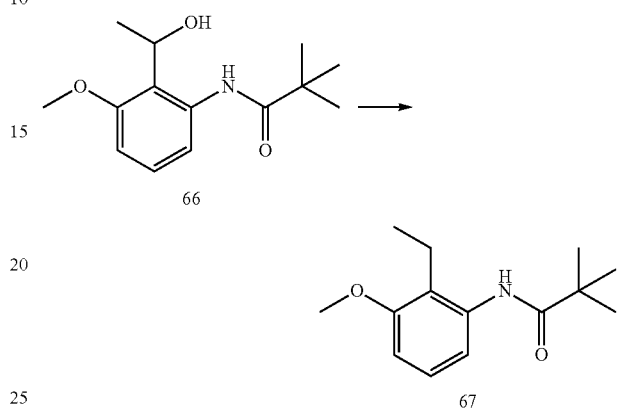

A mixture of N-[2-(1-hydroxyethyl)-3-methoxyphenyl]pivaloylamide (66, 42 g, 167 mmol), Pd/C (10%, 2.00 g) and H$_2$SO$_4$ (10 mL) in acetic acid (400 mL) was stirred at room temperature for 30 minutes. Then, the resulting reaction mixture was hydrogenated for 4 days, after which the catalyst was eliminated by filtration on kieselghur. The filtrate was concentrated to 300 mL, then poured into 1.0 L of water. The solid formed was filtered off, washed with water to give the target product 67 as a yellow solid: m/z=236 (M+H)$^+$.

Step 3: Synthesis of 2-ethyl-m-anisidine (68)

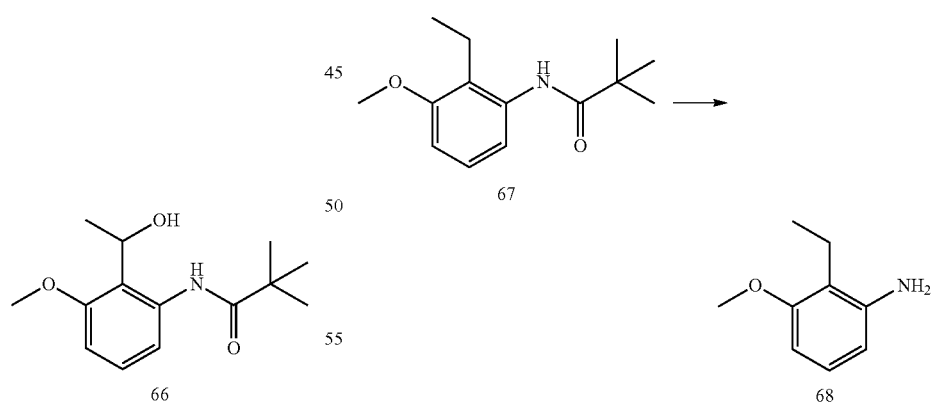

A solution of N-[2-ethyl-3-methoxyphenyl]pivaloylamide (67, 167 mmol) and 37% HCl (700 mL) in EtOH (700 mL) was refluxed for 48 h. Then, the reaction mixture was cooled to room temperature and concentrated under reduced pressure (⅓ of volume). This solution was maintained at 5° C. for 6 h. The solid that appeared was filtered off, and washed with diisopropylether to give 22.35 g of the target product as its HCl salt. The free based was generated by treatment with K₂CO₃ to give 20.85 g (83%) of the target product 68: m/z=152 (M+H)⁺.

Step 4: Synthesis of 8-ethyl-4-hydroxy-2-(4-isopropylthiazole-2-yl)-7-methoxyquinoline (69)

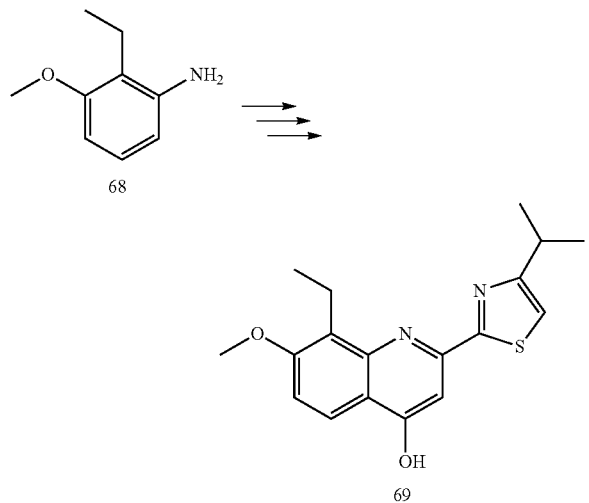

The title compound was prepared from 2-ethyl-m-anisidine (68) following the procedure (Steps 3-5) reported for the preparation of 4-hydroxy-2-(4-isopropylthiazole-2-yl)-7-methoxy-8-methylquinoline (36): m/z=329 (M+H)⁺.

Step 5: Synthesis of 17-[8-ethyl-2-(4-isopropylthiazole-2-yl)-7-methoxyquinolin-4-yl-oxy]-13-methyl-2,14-dioxo-3,13-diazatricyclo[13.3.0.0⁴,⁶]octadec-7-ene-4-carboxylic acid (70)

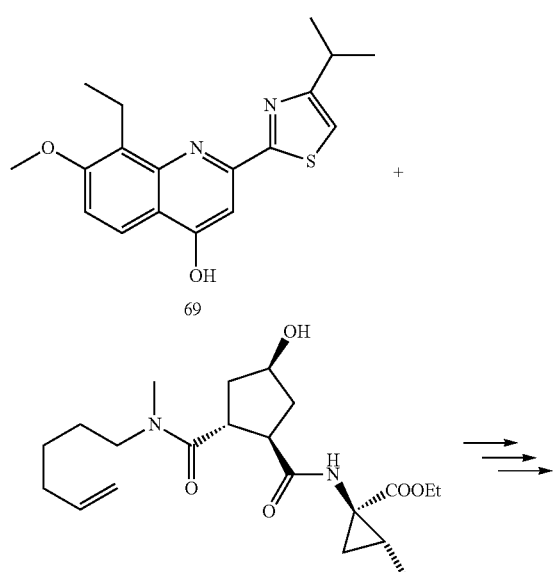

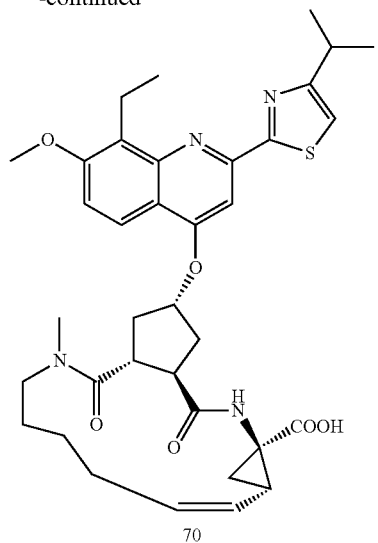

The title compound was prepared from 8-ethyl-4-hydroxy-2-(4-isopropylthiazole-2-yl)-7-methoxyquinoline (69) and intermediate 43 following the procedure (Steps D-F) reported for the preparation of 17-[2-(4-isopropylthiazole-2-yl)-7-methoxy-8-methyl-quinolin-4-yloxy]-13-methyl-2,14-dioxo-3,13-diazatricyclo[13.3.0.0⁴,⁶]octadec-7-ene-4-carboxylic acid (46): m/z=661 (M+H)⁺.

Example 13

N-[17-[8-ethyl-2-(4-isopropylthiazole-2-yl)-7-methoxyquinolin-4-yloxy]-13-methyl-2,14-dioxo-3,13-diazatricyclo[13.3.0.0⁴,⁶]octadec-7-ene-4-carbonyl](cyclo-propyl)sulfonamide (71)

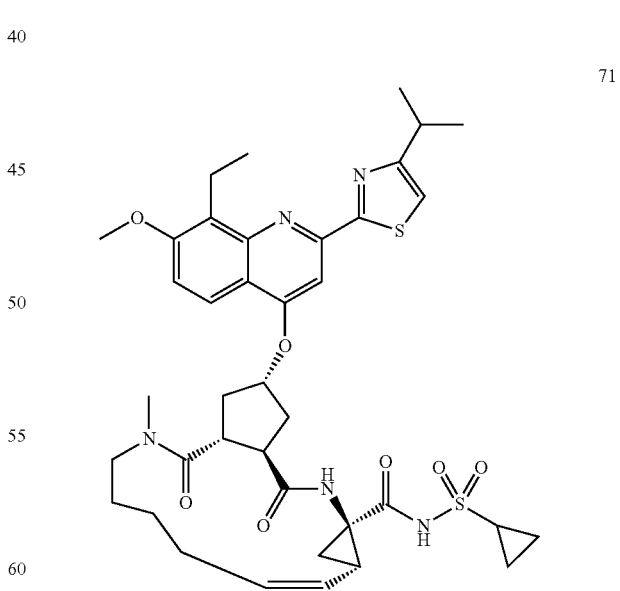

The title compound was prepared from 17-[8-ethyl-2-(4-isopropylthiazole-2-yl)-7-methoxyquinolin-4-yloxy]-13-methyl-2,14-dioxo-3,13-diazatricyclo[13.3.0.0⁴,⁶]-octadec-7-ene-4-carboxylic acid (70) and cyclopropylsulfonamide following the procedure reported for the preparation of N-[17-[8-chloro-2-(4-isopropylthiazole-2-yl)-7-methoxyquinolin-4-yloxy]-13-methyl-2,14-dioxo-3,13-diazatricyclo[13.3.0.0$^{4,6}$]-octadec-7-ene-4-carbonyl](cyclopropyl)sulfonamide (56): m/z=764 (M+H)$^+$.

Example 14

Preparation of 17-[8-fluoro-2-(4-isopropylthiazole-2-yl)-7-methoxy-quinolin-4-yloxy]-13-methyl-2,14-dioxo-3,13-diazatricyclo[13.3.0.0$^{4,6}$]-octadec-7-ene-4-carboxylic acid (73)

Step 1: 8-fluoro-4-hydroxy-2-(4-isopropylthiazole-2-yl)-7-methoxyquinoline (72)

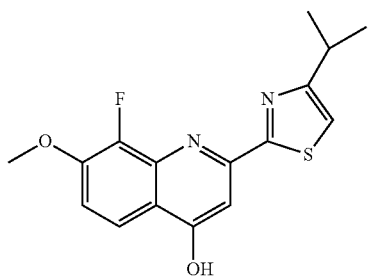

72

The title compound was prepared from 2-fluoro-3-methoxybenzoic acid following the procedure (steps 1-5) reported for the preparation of 4-hydroxy-2-(4-isopropylthiazole-2-yl)-7-methoxy-8-methylquinoline (36): m/z=319 (M+H)$^+$.

Step 2: Synthesis of 17-[8-fluoro-2-(4-isopropylthiazole-2-yl)-7-methoxyquinolin-4-yloxy]-13-methyl-2,14-dioxo-3,13-diazatricyclo[13.3.0.0$^{4,6}$]octadec-7-ene-4-carboxylic acid (73)

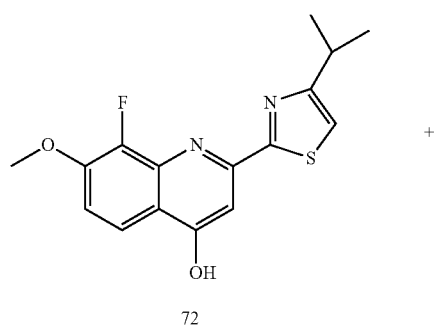

72

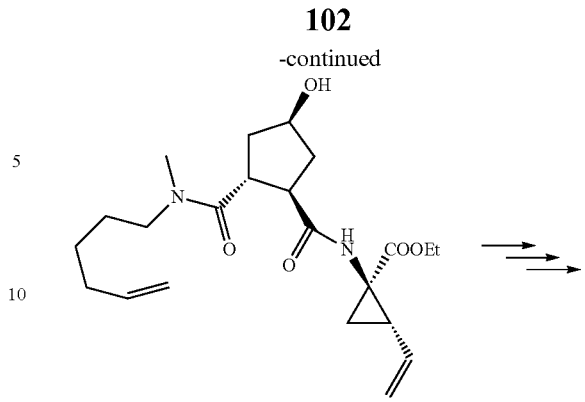

43

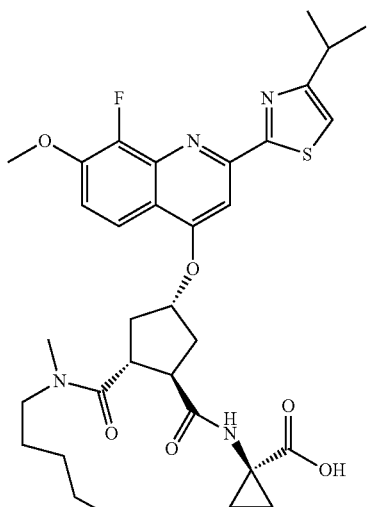

73

The title compound was prepared from 8-fluoro-4-hydroxy-2-(4-isopropylthiazole-2-yl)-7-methoxyquinoline (72) and alcohol 43 following the procedure (steps D-F) reported for the preparation of 17-[2-(4-isopropylthiazole-2-yl)-7-methoxy-8-methyl-quinolin-4-yloxy]-13-methyl-2, 14-dioxo-3,13-diazatricyclo[13.3.0.0$^{4,6}$]octadec-7-ene-4-carboxylic acid (46): m/z=651 (M+H)$^+$.

Example 15

N-[17-[8-fluoro-2-(4-isopropylthiazole-2-yl)-7-methoxyquinolin-4-yl-oxy]-13-methyl-2,14-dioxo-3,13-diazatricyclo[13.3.0.0$^{4,6}$]octadec-7-ene-4-carbonyl]-(cyclopropyl)sulfonamide (74)

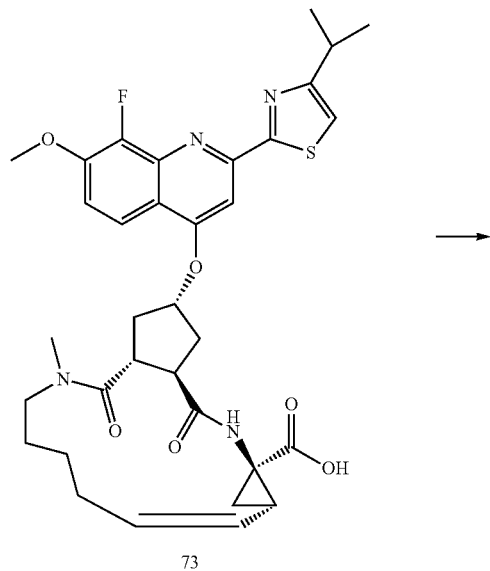

The title compound was prepared from 17-[8-fluoro-2-(4-isopropylthiazole-2-yl)-7-methoxyquinolin-4-yloxy]-13-methyl-2,14-dioxo-3,13-diazatricyclo[13.3.0.0$^{4,6}$]-octadec-7-ene-4-carboxylic acid (73) and cyclopropylsulfonamide following the procedure reported for the preparation of N-[17-[8-chloro-2-(4-isopropylthiazole-2-yl)-7-methoxyquinolin-4-yloxy]-13-methyl-2,14-dioxo-3,13-diazatricyclo[13.3.0.0$^{4,6}$]-octadec-7-ene-4-carbonyl](cyclopropyl)sulfonamide (56): m/z=754 (M+H)$^+$. $^1$H NMR (CDCl$_3$): $^1$H NMR (CDCl$_3$): 0.75-1.52 (m, 15H), 1.64-2.05 (m, 4H), 2.77 (m, 1H), 2.41 (m, 2H), 2.59 (m, 2H), 2.92 (m, 2H), 3.04 (s, 3H), 3.19 (m, 1H), 3.40 (m, 2H), 4.07 (s, 3H), 4.60 (m, 1H), 5.05 (t, J=10.5 Hz, 1H), 5.37 (m, 1H), 5.66 (m, 1H), 6.17 (s, 1H), 7.07 (s, 1H), 7.54 (s, 1H), 7.86 (m, 1H), 10.77 (broad s, 1H).

Example 16

18-[2-(4-isopropylthiazole-2-yl)-7-methoxy-8-methylquinolin-4-yloxy]-2,15-dioxo-3,14-diazatricyclo[14.3.0.0$^{4,6}$]nonadec-7-ene-4-carboxylic acid (80)

Step 1. Synthesis of N-(hept-6-enyl)phthalimide (75)

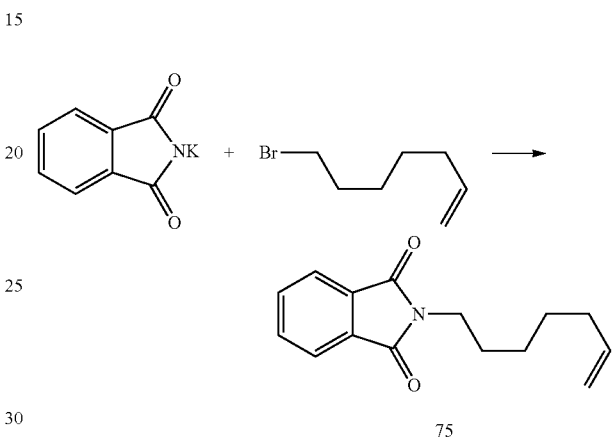

A solution of potassium phthalimide (627 mg, 3.38 mmol) and 7-bromohept-1-ene in dry DMF (10 mL) was stirred at 100° C. under nitrogen for 1 h. Then, the reaction mixture was successively cooled to room temperature, filtered, diluted with ether, and filtered again. The filtrate was concentrated under reduced pressure to give the target product 75 as an oil, which was used without further purifications in the next step: m/z=244 (M+H)$^+$.

Step 2. Synthesis of 6-heptenylamine (76)

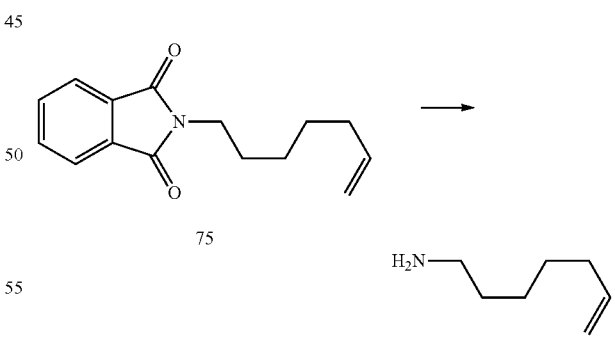

A solution of N-(hept-6-enyl)phthalimide (75, 66.2 g, 272 mmol) and hydrazine hydrate (19.8 mL, 408 mmol) in MeOH (1.0 L) was stirred at room temperature overnight. Then, the reaction mixture was cooled to room temperature and the solid discarded by filtration. The filtrate was diluted with ether and the solid formed discarded by filtration. The ether was evaporated under reduced pressure. Then, 5N HCl (50 mL) was added and the resulting mixture was stirred at reflux. After 45 min., the reaction mixture was cooled down to room temperature and the solid formed filtered. The pH of the filtrate was adjusted to 3 at 0° C. with NaOH. Then, the reaction mixture was extracted with ether and dried (Na$_2$SO$_4$) and evaporated. The crude was purified by distillation to give 34.57 g of the target product 76 as an oil: m/z=114 (M+H)$^+$.

Step 3. Synthesis of intermediate 77

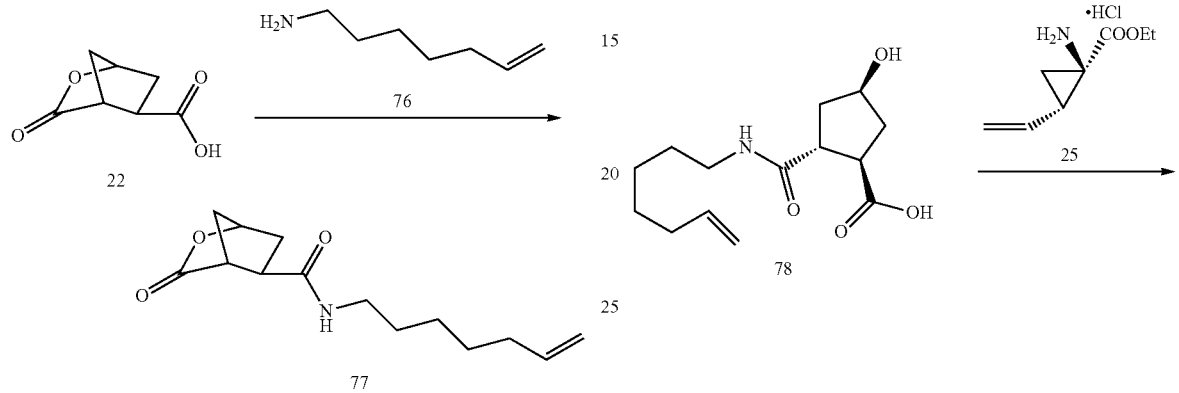

The title compound was prepared from 6-heptenylamine (76) and 3-Oxo-2-oxa-bicyclo[2.2.1]heptane-5-carboxylic acid (22) following the procedure reported for the preparation of intermediate 23: m/z=252 (M+H)$^+$. The title compound was also prepared (82% isolated yield) using other coupling conditions (EDCI.HCl (1.1 eq.), HOAT (1.1 eq.) and diisopropylethylamine in dry DMF).

Step 4. Synthesis of intermediate 78

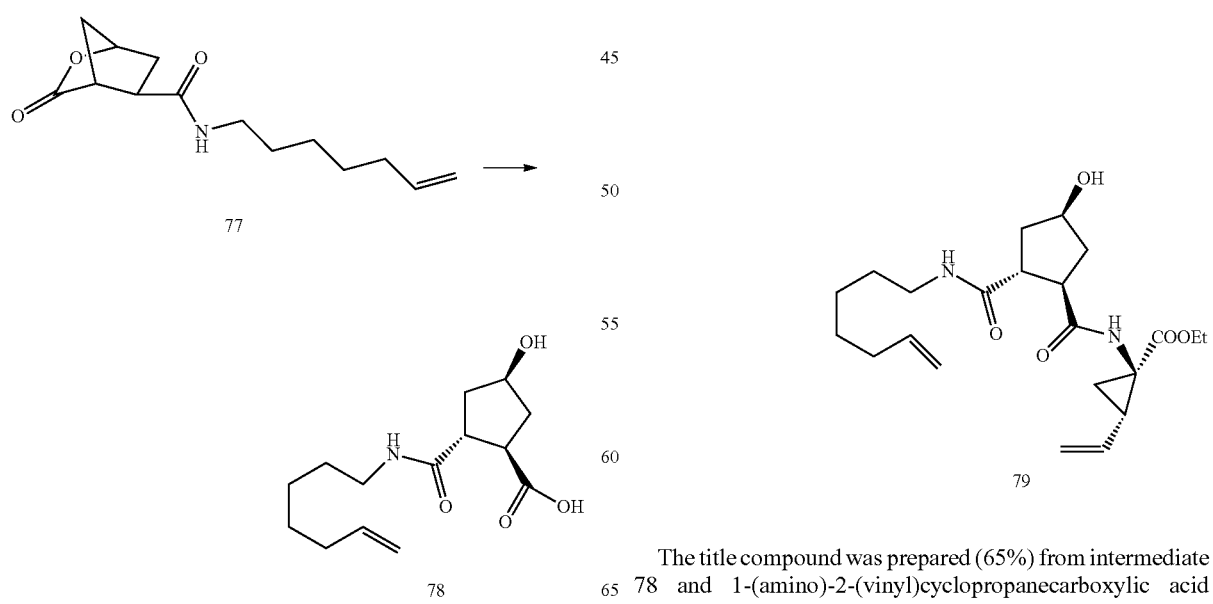

The title compound was prepared (65%) from intermediate 77 and LiOH following the procedure reported for the preparation of intermediate 24: m/z=270 (M+H)$^+$.

Step 5. Synthesis of intermediate 79

The title compound was prepared (65%) from intermediate 78 and 1-(amino)-2-(vinyl)cyclopropanecarboxylic acid ethyl ester hydrochloride 25 following the procedure reported for the preparation of intermediate 26: m/z=407 (M+H)$^+$.

Step 6. Synthesis of 18-[2-(4-isopropylthiazole-2-yl)-7-methoxy-8-methylquinolin-4-yloxy]-2,15-dioxo-3,14-diazatricyclo[14.3.0.0^{4,6}]nonadec-7-ene-4-carboxylic acid (80)

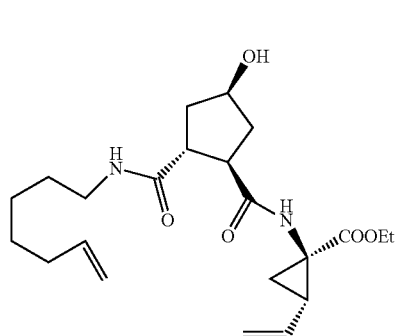
79

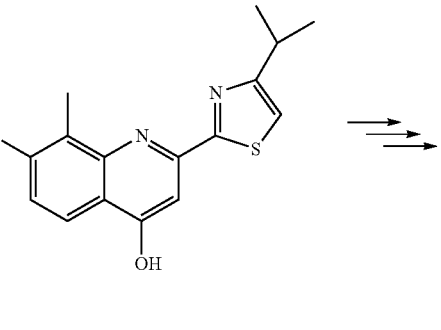
36

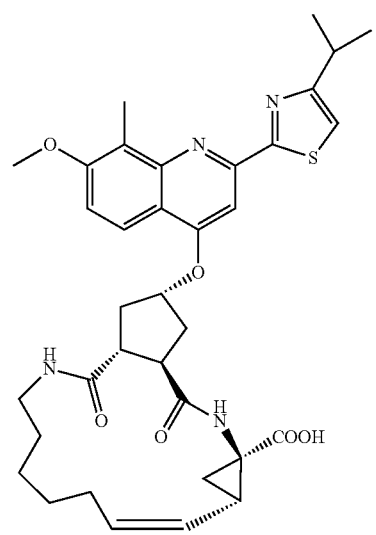
80

The title compound was prepared from intermediate 79 and quinoline 36 following the procedure (Steps D-F) reported for the preparation of 17-[2-(4-isopropylthiazole-2-yl)-7-methoxy-8-methylquinolin-4-yloxy]-13-methyl-2,14-dioxo-3,13-diazatricyclo-[13.3.0.0^{4,6}]octadec-7-ene-4-carboxylic acid (46): m/z=647 (M+H)$^+$.

Example 17

N-[18-[2-(4-isopropylthiazole-2-yl)-7-methoxy-8-methylquinolin-4-yl-oxy]-2,15-dioxo-3,14-diazatricyclo[14.3.0.0^{4,6}]nonadec-7-ene-4-carbonyl](cyclopropyl)sulfonamide (81)

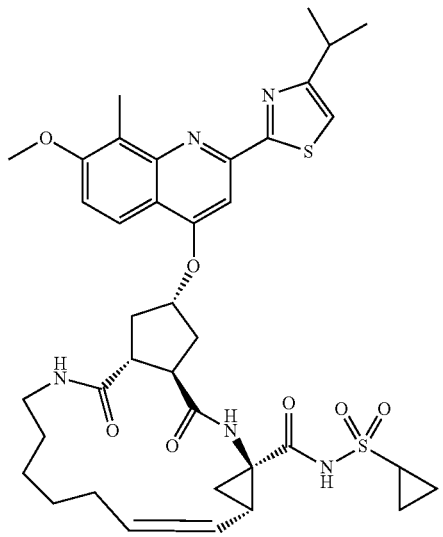

81

The title compound was prepared from 18-[2-(4-isopropylthiazole-2-yl)-7-methoxy-8-methylquinolin-4-yloxy]-2,15-dioxo-3,14-diazatricyclo[14.3.0.0^{4,6}]nonadec-7-ene-4-carboxylic acid (80) and cyclopropylsulfonamide following the procedure reported for the preparation of N-[17-[2-(4-isopropylthiazole-2-yl)-7-methoxy-8-methylquinolin-4-yloxy]-13-methyl-2,14-dioxo-3,13-diazatricyclo[13.3.0.0^{4,6}]octadec-7-ene-4-carbonyl](cyclopropyl)sulfonamide (47): m/z=750 (M+H)+. $^1$H NMR (CDCl$_3$): 0.90-0.96 (m, 1H), 1.1-1.2 (m, 4H), 1.39 (d, J=6.9 Hz, 6H), 1.4-1.55 (m, 5H), 1.80-1.92 (m, 5H), 2.15-2.25 (m, 1H), 2.30-2.40 (m, 1H), 2.45-2.55 (m, 2H), 2.68 (s, 3H), 2.85-2.92 (m, 1H), 3.15-3.30 (m, 2H), 3.45-3.55 (m, 2H), 3.96 (s, 3H), 4.09 (dd, J=11.5 Hz, J=3.8 Hz, 1H), 4.61 (t, J=7.9 Hz, 1H), 4.99 (t, J=9.0 Hz, 1H), 5.51-5.53 (m, 1H), 5.71 (dd, J=18.6 Hz, J=8.2 Hz, 1H), 6.86 (s, 1H), 7.03 (s, 1H), 7.20 (d, J=9.2 Hz, 1H), 7.50 (s, 1H), 7.88 (d, J=9.2 Hz, 1H), 9.40 (br s, 1H).

Example 18

N-[[18-[2-[4-(isopropyl)thiazol-2-yl]-7-methoxy-8-methylquinolin-4-yloxy]-2,15-dioxo-14-(4-methoxybenzyl)-3,14,16-triazatricyclo[14.3.0.0^{4,6}]nonadec-7-en-4-yl]carbonyl](cyclopropyl)sulfonamide (90)

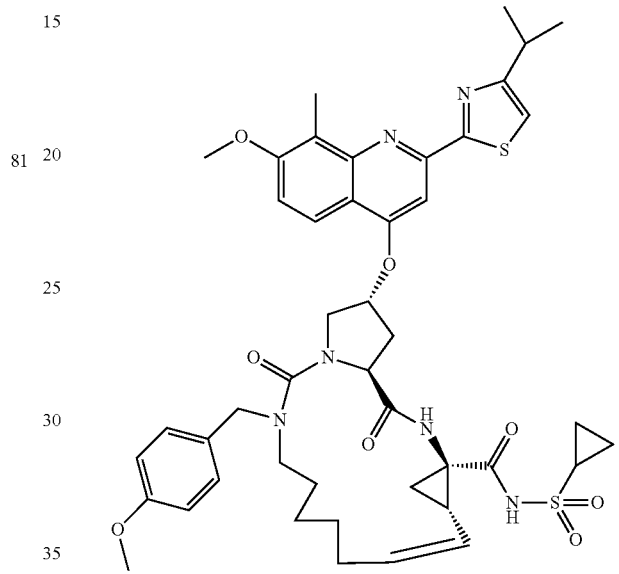

Step A: Synthesis of intermediate 82

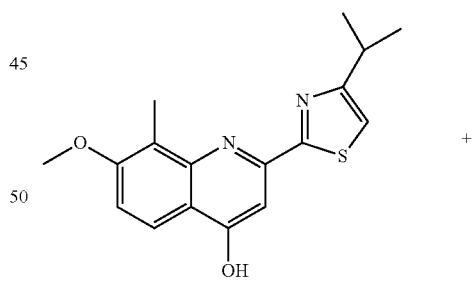

36

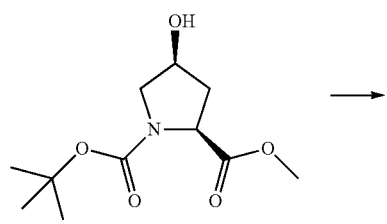

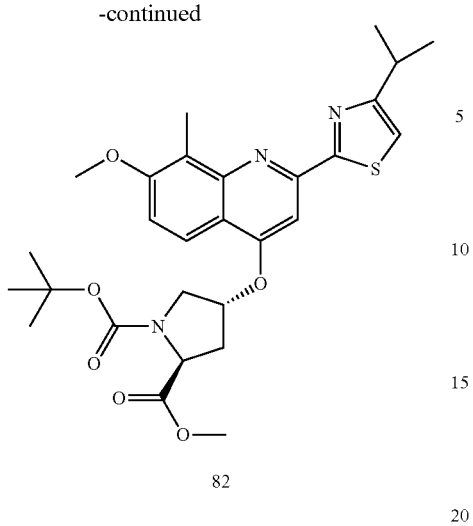

82

Boc-cis-hydroxy-L-Proline methyl ester (500 mg, 2.04 mmol), 4-hydroxy-2-[4-(iso-propyl)thiazol-2-yl]-7-methoxy-8-methylquinoline (36, 769 mg, 2.04 mmol) and 2-diphenylphosphanylpyridine (751 mg, 2.86 mmol) were dried under high vacuum for 1 h. Dry THF was then added under nitrogen and the resulting reaction mixture was cooled to −15° C. Then, DIAD was added drop wise. After 1 h at −5° C. the solution was allowed to warm up to room temperature. After 16 h, the reaction mixture was partitioned between ice-cold water and AcOEt. The organic layer was successively washed vigorously with HCl 1M and brine, dried (MgSO$_4$), filtered and evaporated. Purification by column chromatography on silica gel (gradient AcOEt/CH$_2$Cl$_2$, 0:10 to 5:95) afforded 940 mg (85%) of the desired product 82 as a colorless oil: m/z=542 (M+H)$^+$.

Step B: Synthesis of intermediate 83

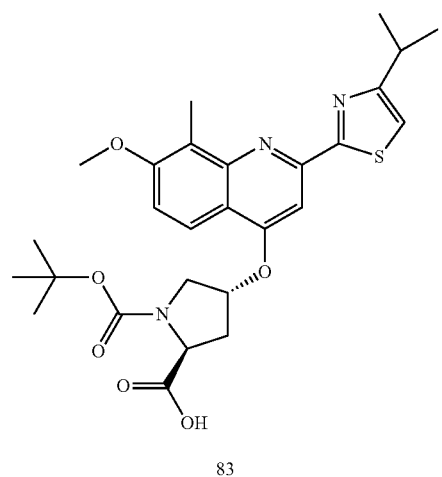

83

A solution of LiOH (592 mg, 13.8 mmol) in water was added to a solution of intermediate 82 (1.5 g, 2.77 mmol) in MeOH/THF 1:1. After 16 h at room temperature, the reaction mixture was acidified to pH 3-4 with diluted HCl, extracted with AcOEt, washed with brine, dried (MgSO$_4$) and evaporated. The residue was purified by flash chromatography (Gradient AcOEt/CH$_2$Cl$_2$, 1:9 to 4:6) to give 1.26 g (86%) of the title product 83 as an orange oil: m/z=528 (M+H)$^+$.

Step C: Synthesis of intermediate 84

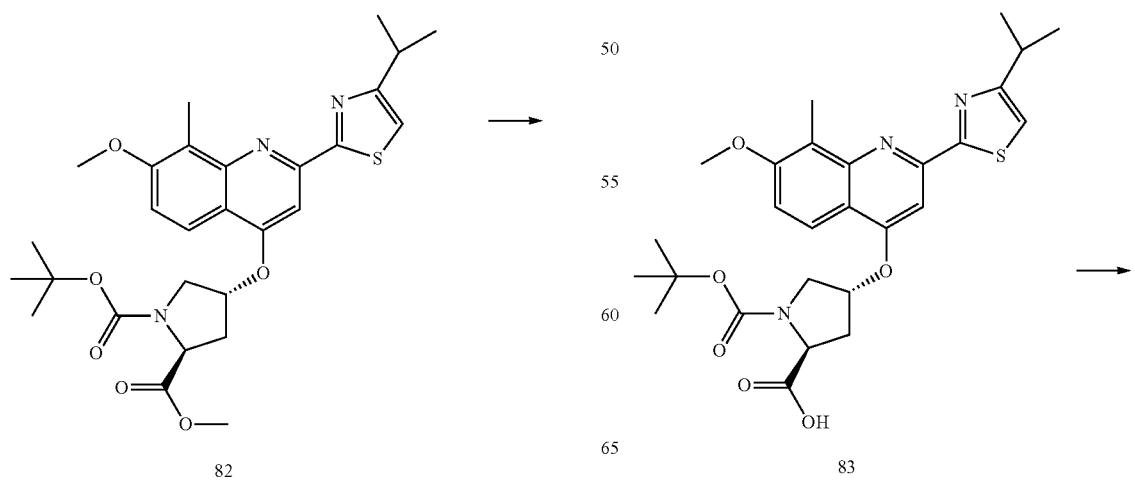

82    83

-continued

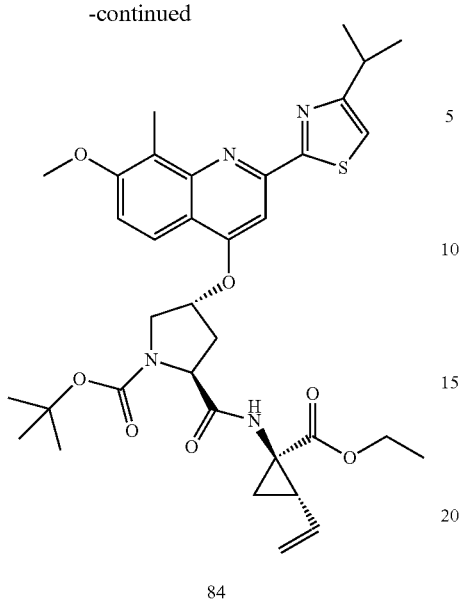

84

To a stirred solution of carboxylic acid 83 (1.26 g, 2.39 mmol) in dry DMF (20 mL) was added (1R,2S)-1-amino-2-vinylcyclopropanecarboxylic acid ethyl ester tosylate (860 mg, 2.63 mmol) and diisopropylethylamine (1.04 mL, 5.98 mmol). Then, HATU (999 mg, 2.63 mmol) was added at 0° C. under nitrogen. The resulting solution was stirred at 0° C. for 30 minutes, then at room temperature. After 4 h, the reaction mixture was diluted with water and extracted with AcOEt. The organic layers were combined and successively washed with a saturated solution of NaHCO$_3$, water and brine, dried (MgSO$_4$), and evaporated. Purification by column chromatography (gradient AcOEt/CH$_2$Cl$_2$, 0:1 to 2:8) afforded 1.44 g (90%) of the title product 84 as a white solid: m/z=665 (M+H)$^+$.

Step D: Synthesis of intermediate 85

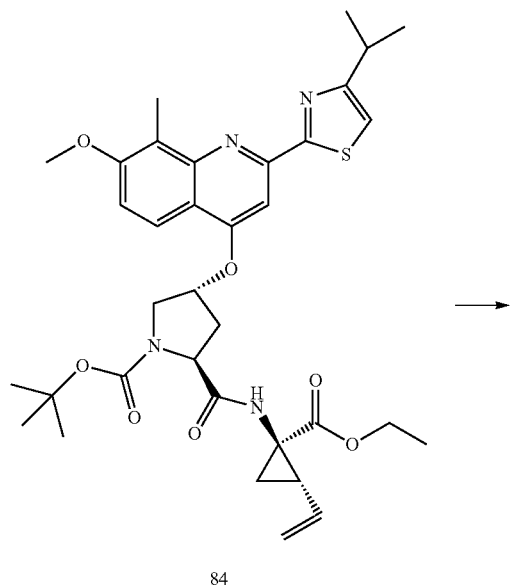

84

-continued

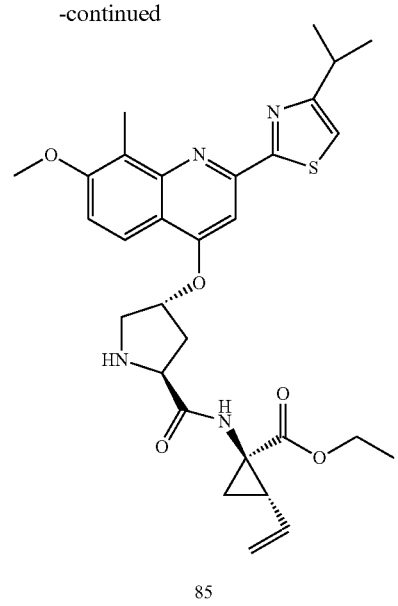

85

To a stirred solution of Boc-protected proline derivative 84 (1.44 g, 2.16 mmol) in CH$_2$Cl$_2$ (20 mL) was added trifluoroacetic acid (5 mL). After 2 h at room temperature, the reaction mixture was concentrated and the residue was partitioned between a saturated solution of NaHCO$_3$ and CH$_2$Cl$_2$. The organic layer was dried (MgSO$_4$) filtered and concentrated to give 1.0 g (81%) of the title product 85 as a colorless oil: m/z=565 (M+H)$^+$.

Step E: Synthesis of
N-(hept-6-enyl)-N-(4-methoxybenzyl)amine 86

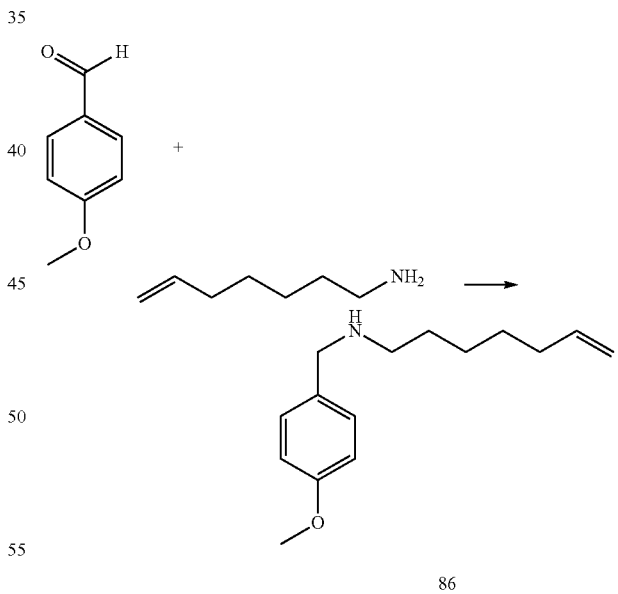

86

A solution of hept-6-enylamine (2.0 g, 13.4 mmol) and anisaldehyde (1.79 mL, 14.7 mmol) in EtOH (50 mL) was stirred at room temperature for 1 h. Then, NaBH$_4$ (556 mg, 14.7 mmol) was added at 0° C. under nitrogen. The resulting solution was allowed to warm up to room temperature for 4 h. Then, the reaction mixture was partitioned between ice-cold water and CH$_2$Cl$_2$, washed with brine, dried (Na$_2$SO$_4$) and evaporated. The residue was purified by chromatography (gradient AcOEt/CH$_2$Cl$_2$ 0:1 to 2:8, then CH$_2$Cl$_2$/MeOH 9:1) to give 1.8 g (34%) of the title product 86 as a colorless oil: m/z=234 (M+H)$^+$.

Step F: Synthesis of intermediate 87
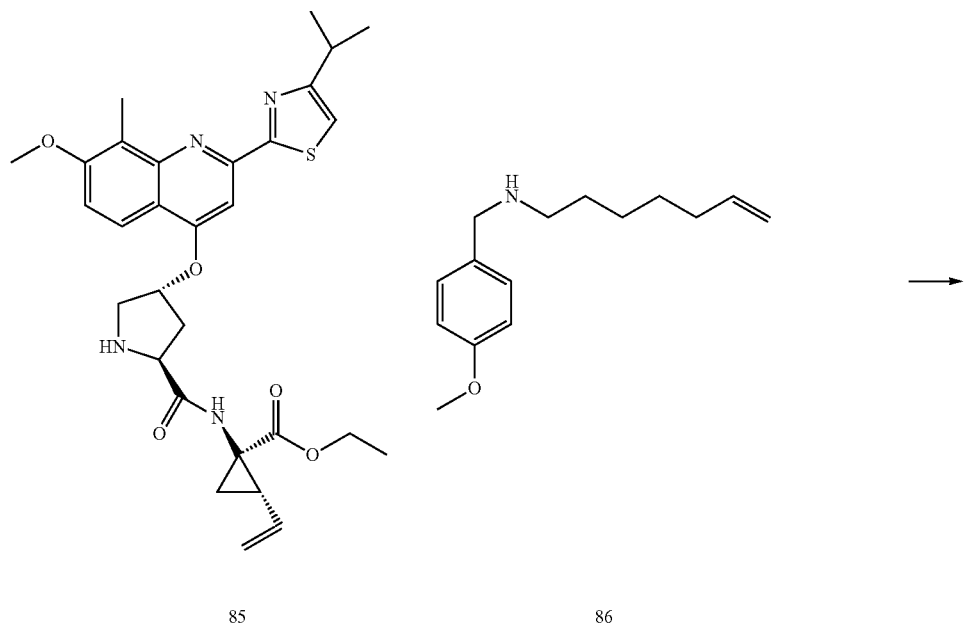
85 86
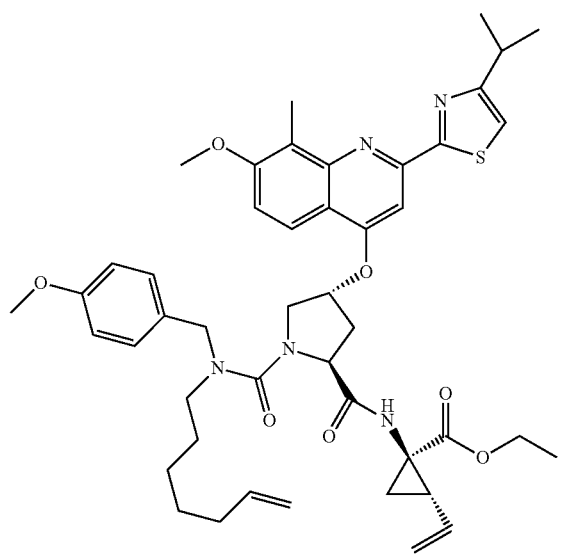
87

To a solution of proline derivative 85 in THF (50 mL) was added NaHCO$_3$ (1.0 g). Then, phosgene (4.7 mL, 20% solution in toluene) was added at 0° C. under nitrogen. After 1.5 h, the white solid was filtered off and washed with THF and CH$_2$Cl$_2$. Then, the filtrate was concentrated under reduced pressure and the residue was re-dissolved in dry dichloromethane (50 mL). To this solution, NaHCO$_3$ (1.0 g) and protected amine 86 were successively added. After 16 h at room temperature, the reaction mixture was filtered off. The filtrate was concentrated under reduced pressure and the resulting residue was purified by silica chromatography (gradient AcOEt/CH$_2$Cl$_2$, 0:1 to 2:8) to give 1.36 g (90%) of the title product 87: m/z=824 (M+H)$^+$.

Step G: Synthesis of intermediate 88 mixture was concentrated and purified by flash chromatography (gradient AcOEt/CH$_2$Cl$_2$, 0:1 to 2:8) to give 900 mg (65%) of the title product 88 as a brownish foam: m/z=796 (M+H)$^+$.

Step H: Synthesis of intermediate 89

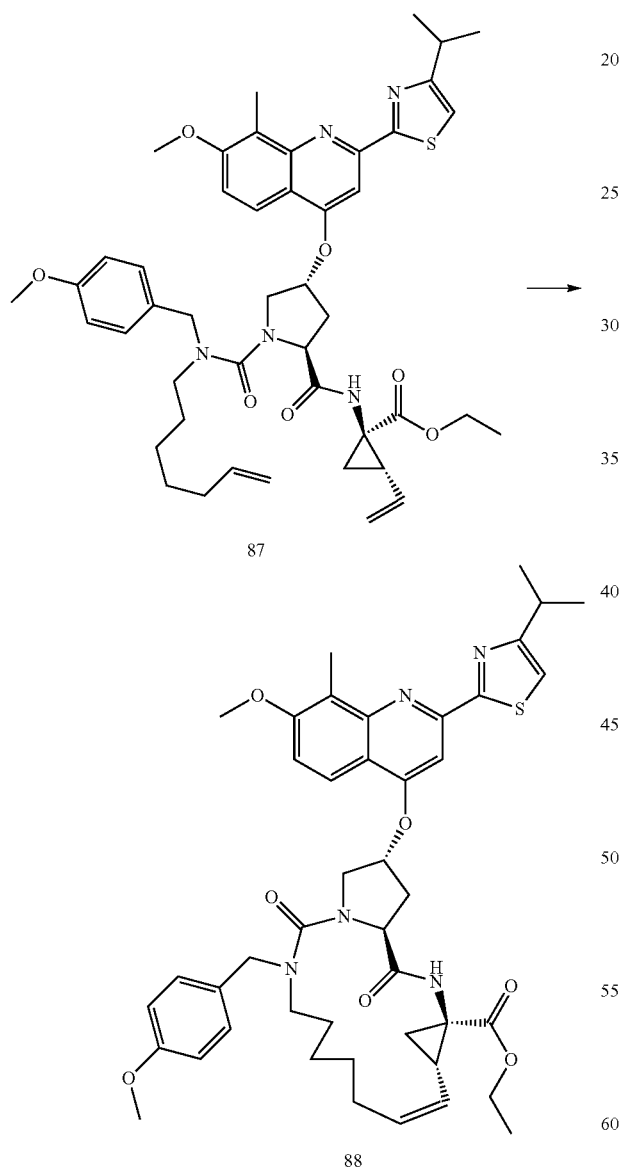

Hoveyda-Grubbs 1$^{st}$ generation catalyst (50 mg, 0.082 mmol) was added to a degassed solution of diene 87 (1.36 g, 1.65 mmol) in toluene (170 mL). The resulting solution was heated at 80° C. under nitrogen for 4 h. Then, the reaction A solution of LiOH (242 mg, 5.65 mmol) in water (20 mL) was added to a solution of ester 88 (900 mg, 1.13 mmol) in MeOH/THF 1:1. The reaction mixture was stirred at 50° C. for 2 h, then cooled down to room temperature, acidified to pH 3-4 with diluted HCl, and extracted with AcOEt. The organic layers were successively combined, washed with brine, dried (MgSO$_4$), filtered and evaporated to give 840 mg (97%) of the title product 89 as a slightly yellow solid: m/z=768 (M+H)$^+$.

Step I: Synthesis of N-[[18-[2-[4-(isopropyl)thiazol-2-yl]-7-methoxy-8-methylquinolin-4-yloxy]-2,15-dioxo-14-(4-methoxybenzyl)-3,14,16-triazatricyclo[14.3.0.0$^{4,6}$]nonadec-7-en-4-yl]carbonyl](cyclopropyl)sulfonamide (90)

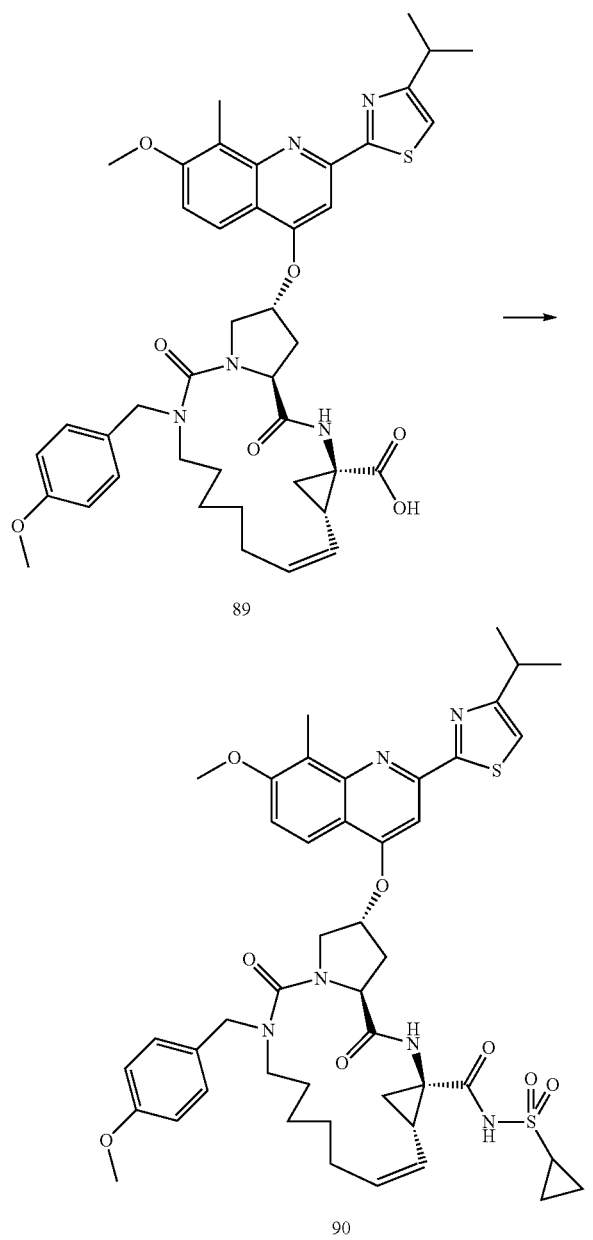

A solution of carboxylic acid 65 (830 mg, 1.03 mmol) and carbonyldiimidazole (333 mg, 2.06 mmol) in dry THF (20 mL) was stirred at reflux under nitrogen for 2 h. Then, the reaction mixture was cooled to room temperature and cyclopropyl-sulfonamide (249 mg, 2.06 mmol) and DBU (313 mg, 2.06 mmol) were added. The resulting solution was stirred at 50° C. for 12 h, then cooled to room temperature. The reaction mixture was quenched with water and extracted with CH$_2$Cl$_2$, washed with diluted HCl, dried (MgSO$_4$), filtered and evaporated. The crude material was purified by column chromatography (CH$_2$Cl$_2$/EtOAc, 80:20) and recrystallized from CH$_2$Cl$_2$/ether to give 450 mg (50%) of the title product 90 as a white powder: m/z=871 (M+H)$^+$; $^1$H-NMR (CDCl$_3$): 1.05-1.61 (m, 18H), 2.00 (m, 1H), 2.12-2.22 (m, 2H), 2.59-2.70 (m, 5H), 2.96 (m, 1H), 3.15-3.20 (m, 3H), 3.63 (s, 3H), 3.71-3.78 (m, 2H), 3.88-3.94 (m, 4H), 4.54 (d, J=15 Hz, 1H), 5.08 (t, J=8.5 Hz, 1H), 5.16 (t, J=9.4 Hz, 1H), 5.38 (m, 1H), 5.75 (m, 1H), 6.45 (d, J=8.4 Hz, 2H), 6.65 (d, J=8.4 Hz, 2H), 7.03 (s, 1H), 7.10 (d, J=9.1 Hz, 1H), 7.41 (s, 1H), 7.73 (d, J=9.1 Hz, 1H), 7.76 (br s, 1H), 10.15 (br s, 1H).

Example 19

N-[[18-[2-[4-(isopropyl)thiazol-2-yl]-7-methoxy-8-methylquinolin-4-yloxy]-2,15-dioxo-3,14,16-triazatricyclo[14.3.0.0$^{4,6}$]nonadec-7-en-4-yl]carbonyl]-(cyclopropyl)sulfonamide (91)

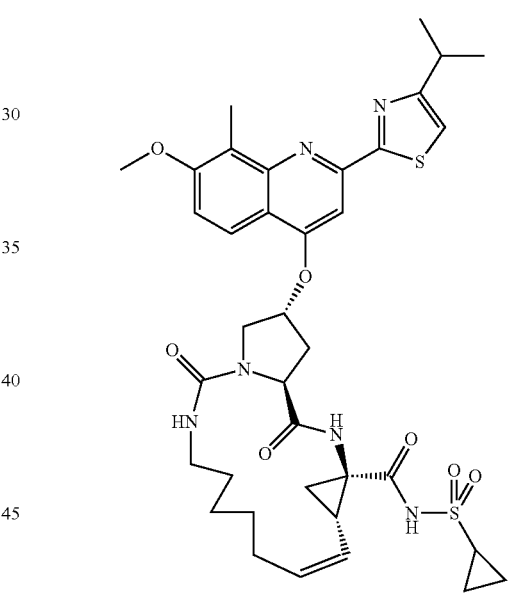

TFA (10 mL) was added to a solution of N-[[18-[2-[4-(isopropyl)thiazol-2-yl]-7-methoxy-8-methylquinolin-4-yloxy]-2,15-dioxo-14-(4-methoxybenzyl)-3,14,16-triazatricyclo[14.3.0.0$^{4,6}$]nonadec-7-en-4-yl]carbonyl](cyclopropyl)sulfonamide (90) in DCM (20 mL). After 30 min at room temperature, water (20 mL) was added to the reaction mixture and the pH was adjusted to 3-4 with NaHCO$_3$. The organic layer was washed with brine, dried (Na$_2$SO$_4$), filtered and evaporated. The residue was purified by column chromatography (gradient MeOH/CH$_2$Cl$_2$, 0:1 to 1:99, then AcOEt/CH$_2$Cl$_2$ 1:1) to afford 313 mg (73%) of the desired title product 91 as a yellowish solid: m/z=751 (M+H)$^+$. $^1$H-NMR (CDCl$_3$): 0.88-1.64 (m, 16H), 1.96 (m, 2H), 2.52 (m, 1H), 2.68 (m s, 5H), 2.79-2.92 (m, 3H), 3.18 (m, 1H), 3.63-3.69 (m, 2H), 3.86 (m, 1H), 3.97 (s, 3H), 4.34 (m, 1H), 4.59 (m, 1H), 5.08 (m, 1H), 5.40 (m, 1H), 5.80 (m, 1H), 6.73 (s, 1H), 7.03 (s, 1H), 7.21 (d, J=8.9 Hz, 1H), 7.26 (br s, 1H), 7.47 (s, 1H), 7.92 (d, J=8.9 Hz, 1H), 10.20 (br s, 1H).

Example 20

N-[[18-[8-chloro-2-[4-(isopropyl)thiazol-2-yl]-7-methoxyquinolin-4-yloxy]-2,15-dioxo-3,14,16-triazatricyclo[14.3.0.0$^{4,6}$]nonadec-7-en-4-yl]carbonyl]-(cyclopropyl)sulfonamide (94)

Step A: Synthesis of 4,8-dichloro-2-(4-isopropylthiazole-2-yl)-7-methoxyquinoline (92)

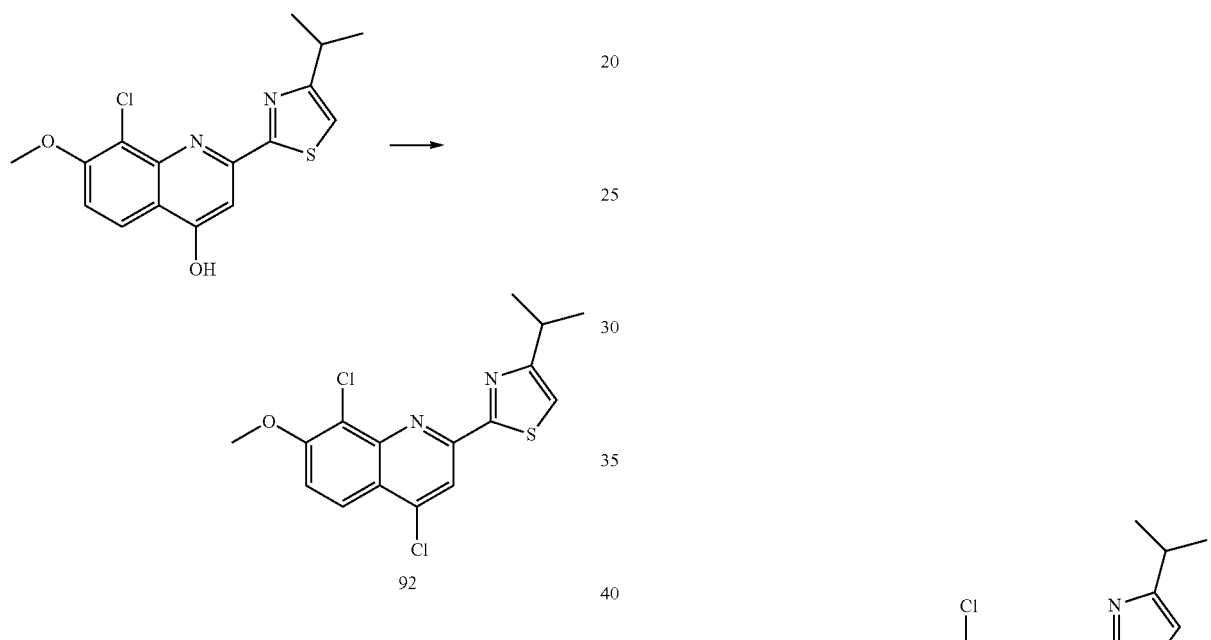

A solution of 8-chloro-4-hydroxy-2-(4-isopropylthiazole-2-yl)-7-methoxy-quinoline (2.0 g, 5.97 mmol) in POCl$_3$ (10 mL) was heated at 85° C. during 30 min. Then, the reaction mixture was concentrated under reduced pressure. The residue was poured into ice-cooled water (20 mL), the pH was adjusted to 10 with 50% NaOH, and extracted with CH$_2$Cl$_2$. The organic layer was washed with brine, dried (MgSO$_4$), filtered, and evaporated to give 2.05 g (97%) of the title compound 92 as a yellow solid: m/z=353 (M+H)$^+$.

Step B: Synthesis of intermediate 93

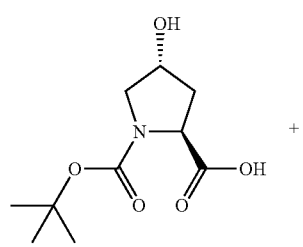 +

NaH (60% in mineral oil, 679 mg, 17.0 mmol) was added under nitrogen to a solution of Boc-trans-hydroxy-L-Proline-OH (2.0 g, 5.661 mmoles) in dry DMF (50 mL). After 30 min at room temperature, a solution of 4,8-dichloro-2-(4-isopropylthiazole-2-yl)-7-methoxyquinoline (92, 1.38 g, 5.94 mmol) in dry DMF was added and the resulting solution was stirred overnight at room temperature. Then, the reaction mixture was quenched with diluted HCl until pH 2, extracted twice with AcOEt, and the combined organic layers were washed with brine, dried (MgSO$_4$) and evaporated. The residue was purified by column chromatography (gradient AcOEt/CH$_2$Cl$_2$, 0:1 to 1:1) to give 2.35 g (75%) of the title 93: m/z=548 (M+H)$^+$.

Step C: Synthesis of N-[[18-[8-chloro-2-[4-(isopropyl)thiazol-2-yl]-7-methoxy-quinolin-4-yloxy]-2,15-dioxo-3,14,16-triazatricyclo[14.3.0.0$^{4,6}$]nonadec-7-en-4-yl]carbonyl](cyclopropyl)sulfonamide (94)

9.9 Hz, 1H), 5.51 (m, 1H), 5.79 (m, 1H), 7.03 (m, 1H), 7.08 (s, 1H), 7.22 (d, J=9.3 Hz, 1H), 7.54 (s, 1H), 7.95 (d, J=9.3 Hz, 1H).

Example 21

N-[[18-[8-chloro-2-[4-(isopropyl)thiazol-2-yl]-7-methoxyquinolin-4-yloxy]-2,15-dioxo-3,14,16-triazatricyclo[14.3.0.0$^{4,6}$]nonadec-7-en-4-yl]carbonyl](1-methylcyclopropyl)sulfonamide (95)

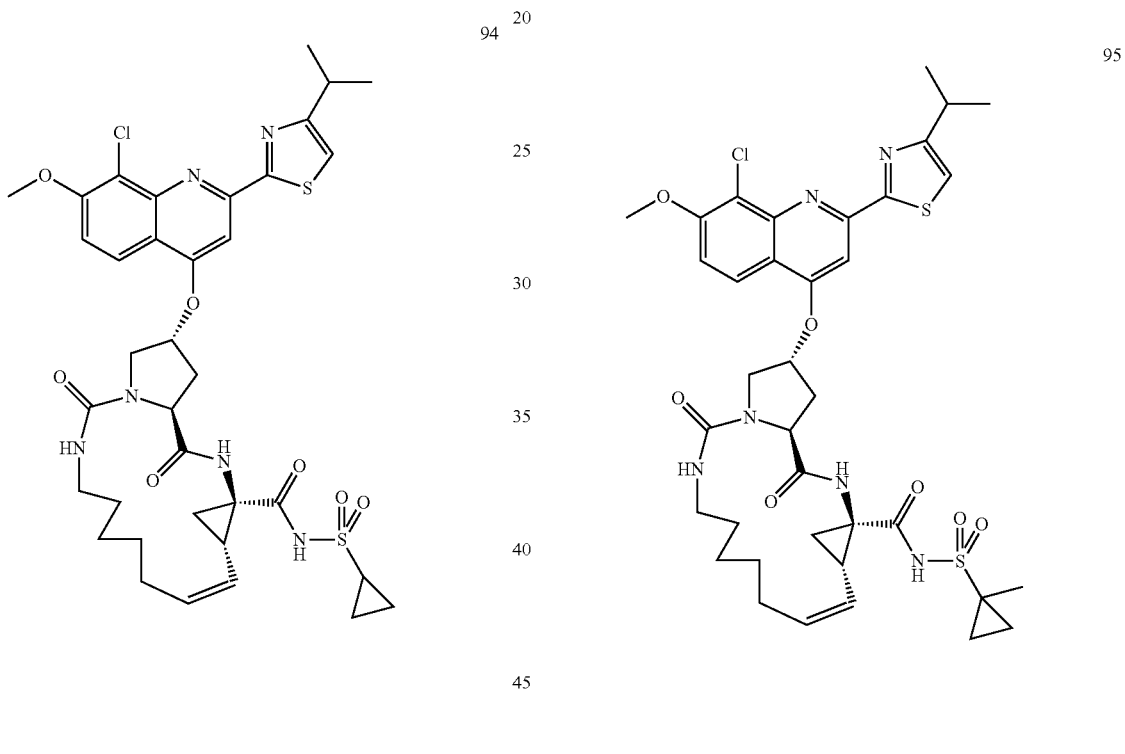

The title compound was synthesized from intermediate 93 following the procedure (Steps C-I) reported for N-[[18-[2-[4-(isopropyl)thiazol-2-yl]-7-methoxy-8-methyl-quinolin-4-yloxy]-2,15-dioxo-14-(4-methoxybenzyl)-3,14,16-triazatricyclo-[14.3.0.0$^{4,6}$]nonadec-7-en-4-yl]carbonyl](cyclopropyl)sulfonamide (90) and for N-[[18-[2-[4-(isopropyl)thiazol-2-yl]-7-methoxy-8-methylquinolin-4-yloxy]-2,15-dioxo-3,14,16-triazatricyclo[14.3.0.0$^{4,6}$]nonadec-7-en-4-yl]carbonyl](cyclopropyl)-sulfonamide (91): m/z=771 (M)$^+$; $^1$H-NMR (CDCl$_3$): 0.93 (m, 1H), 1.06-1.63 (m, 15H), 1.92 (m, 3H), 2.50 (m, 1H), 2.64 (m, 2H), 2.76 (m, 1H), 2.87 (m, 2H), 3.20 (m, J=6.9 Hz, 1H), 3.70 (m, 1H), 3.77-3.87 (m, 1H), 4.00 (dd, J=4.0 Hz, 10.1 Hz, 1H), 4.04 (s, 3H), 4.42 (m, 1H), 4.59 (t, J=7.3 Hz, 1H), 5.05 (dd, J=8.3 Hz, The title compound was synthesized from intermediate 93 and 1-Methyl-cyclopropyl-sulfonamide following the procedure (Steps C-I) reported for N-[[18-[2-[4-(isopropyl)-thiazol-2-yl]-7-methoxy-8-methylquinolin-4-yloxy]-2,15-dioxo-14-(4-methoxybenzyl)-3,14,16-triazatricyclo[14.3.0.0$^{4,6}$]nonadec-7-en-4-yl]carbonyl](cyclopropyl)-sulfonamide (90) and for N-[[18-[2-[4-(isopropyl)thiazol-2-yl]-7-methoxy-8-methyl-quinolin-4-yloxy]-2,15-dioxo-3,14,16-triazatricyclo[14.3.0.0$^{4,6}$]-nonadec-7-en-4-yl]carbonyl](cyclopropyl)sulfonamide (91): m/z=785 (M)$^+$. $^1$H-NMR (CDCl$_3$): 0.90 (m, 1H), 1.12-1.60 (m, 16H), 1.74 (m, 1H), 1.90-1.99 (m, 4H), 2.51 (m, 1H), 2.65-2.78 (m, 3H), 2.88 (m, 1H), 3.20 (m, J=6.7 Hz, 1H), 3.69 (m, 1H), 3.84 (m, 1H), 3.96-4.00 (m, 1H), 4.01 (s, 3H), 4.46 (m, 1H), 4.63 (t, J=7.4 Hz, 1H), 5.09

(t, J=9.1 Hz, 1H), 5.50 (m, 1H), 5.79 (m, 1H), 7.08 (m, 2H), 7.22 (d, J=9.2 Hz, 1H), 7.52 (s, 1H), 7.95 (d, J=9.2 Hz, 1H), 10.08 (br s, 1H).

Example 22

Cyclopropanesulfonic acid {17-[2-(6-methyl-2-pyridyl)-7-methoxy-8-methyl-quinolin-4-yloxy]-13-methyl-2,14-dioxo-3,13-diaza-tricyclo[13.3.0.0$^{4,6}$] octadec-7-ene-4-carbonyl}-amide (103)

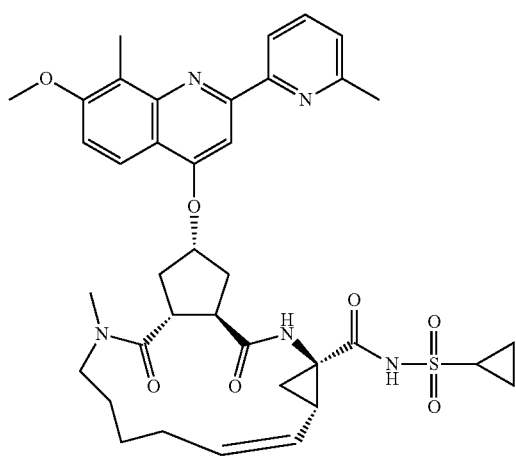

103

Step A: Synthesis of 6-methylpyridine-2-carboxylic acid (6-acetyl-3-methoxy-2-methylphenyl)-amide (96)

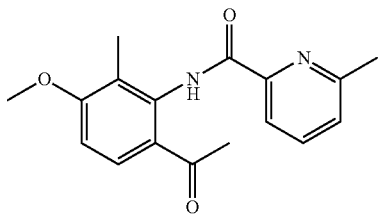

96

6-Methylpicolinic acid (1.12 g, 8.167 mmol) was dissolved in dry DCM (100 ml) and kept on an ice-bath. Then, 6-acetyl-3-methoxy-2-methylaniline (1.48 g, 8.17 mmol) and pyridine (6.6 mL, 0.082 mol) were added followed by drop wise addition of POCl$_3$ (1.53 mL, 0.016 mol) over 15 minutes. The resulting solution was stirred at −5° C. for 1 h. Then, water (100 mL) was added carefully and after 5 min of stirring, NaOH (40%, 20 mL) was subsequently added drop wise followed by the separation of the organic layer. The water layer was extracted three times with CH$_2$Cl$_2$, and the combined organic layers were washed with brine, dried (MgSO$_4$), filtered and evaporated. The residue was purified by column chromatography (Heptane/AcOEt, 3:1) to give the title compound (2.1 g, 86%): m/z=299 (M+H)$^+$.

Step B: Synthesis of 4-hydroxy-2-(6-methyl-2-pyridyl)-7-methoxy-8-methylquinoline (97)

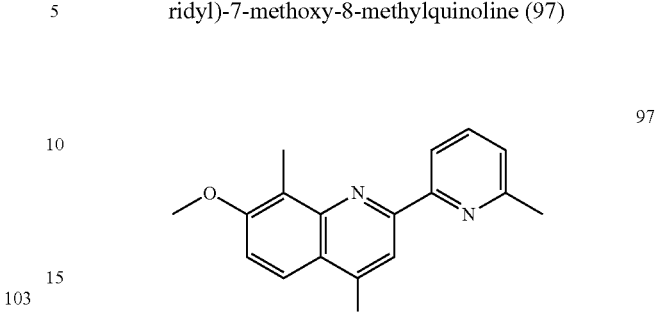

97

To a solution of 6-methylpyridine-2-carboxylic acid (6-acetyl-3-methoxy-2-methyl-phenyl)-amide (96) in pyridine (15 mL) was added 2.5 equivalent of freshly grounded KOH along with water (200 μL). The mixture was heated by microwave irradiation at 150° C. for 30 min, then 80-85% of the pyridine was evaporated under reduced pressure. The residue was poured on ice and neutralized with acetic acid. The precipitate was filtered off, then dried to give the title compound (1.8 g, 95%): m/z=299 (M+H)$^+$.

Step C: Synthesis of 2-(1-ethoxycarbonyl-2-vinylcyclopropylcarbamoyl)-4-[2-(6-methyl-2-pyridyl)-7-methoxy-8-methylquinolin-4-yloxy]cyclopentanecarboxylic acid tert-butyl ester (98)

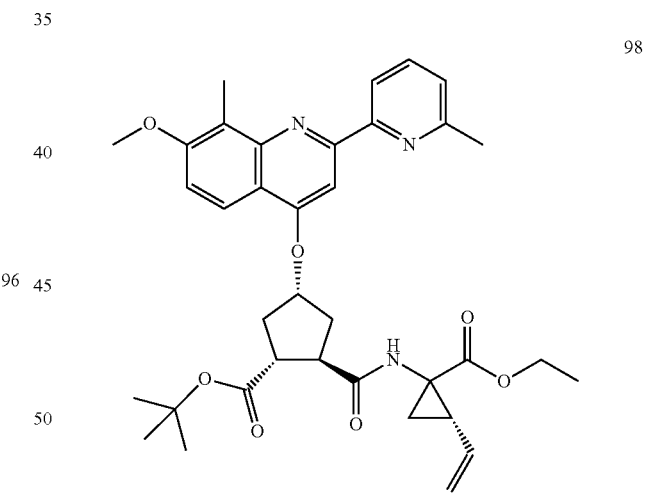

98

A solution of 2-(1-ethoxycarbonyl-2-vinylcyclopropylcarbamoyl)-4-hydroxycyclo-pentanecarboxylic acid tert-butyl ester (500 mg, 1.5 mmol), prepared as described in WO2005/073195, 4-hydroxy-2-(6-methyl-2-pyridyl)-7-methoxy-8-methylquinoline (97, 504 mg, 1.8 mmol) and triphenylphosphine (990 mg, 3.75 mmol) were stirred in dry THF (40 mL) at 0° C. for 10 min. Then, DIAD (0.74 mL, 3.75 mmol) was added drop wise. The resulting reaction mixture was stirred at a temperature from 0° C. to 22° C. overnight. Then, volatiles were evaporated and the residue was purified by column chromatography on silica gel (gradient CH$_2$Cl$_2$/AcOEt, 1:0 to 95:5) to give 1.1 g (88%) of the title compound 98: m/z=630 (M+H)$^+$.

Step D: Synthesis of 2-(1-ethoxycarbonyl-2-vinylcyclopropylcarbamoyl)-4-[2-(6-methyl-2-pyridyl)-7-methoxy-8-methylquinolin-4-yloxy]cyclopentanecarboxylic acid (99)

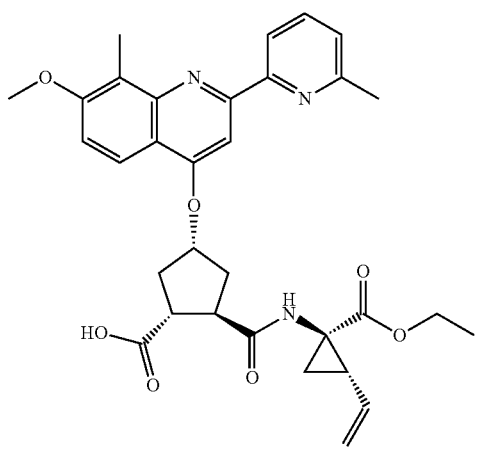

99

TFA (24 mL) was added at room temperature to a solution of 2-(1-ethoxycarbonyl-2-vinylcyclopropylcarbamoyl)-4-[2-(6-methyl-2-pyridyl)-7-methoxy-8-methylquinolin-4-yloxy]cyclopentanecarboxylic acid tert-butyl ester (98, 1.1 g, 1.75 mmol) and triethylsilane (510 mg, 2.5 eq) in $CH_2Cl_2$ (24 mL). After 2 h, the reaction mixture was concentrated under reduced pressure, and then co-evaporated with toluene. The residue was re-dissolved in AcOEt and successively washed with a solution of $NaHCO_3$ and brine. The organic layer was dried ($MgSO_4$), filtered and evaporated, to give 800 mg (80%) of the title compound 99 (800 mg, 80%): m/z=574 (M+H)$^+$.

Step E: Synthesis of 1-{2-(hex-5-enylmethylcarbamoyl)-4-[2-(6-methyl-2-pyridyl)-7-methoxy-8-methylquinolin-4-yloxy]cyclopentanecarbonyl}amino-2-vinylcyclopropanecarboxylic acid ethyl ester (100)

100

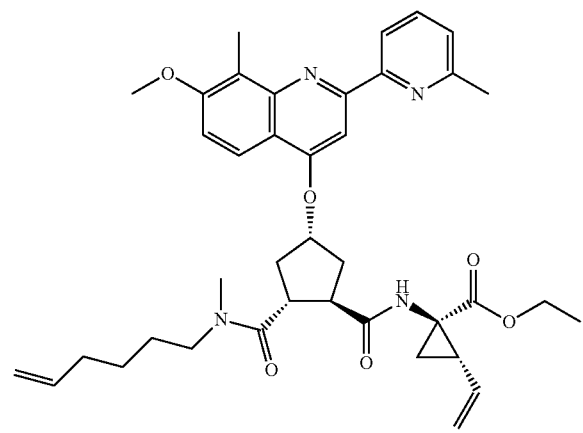

A solution of 2-(1-ethoxycarbonyl-2-vinylcyclopropylcarbamoyl)-4-[2-(6-methyl-2-pyridyl)-7-methoxy-8-methylquinolin-4-yloxy]cyclopentanecarboxylic acid (99, 0.77 g, 1.344 mmol), N-methylhex-5-enylamine hydrochloride (221 mg, 1.95 mmol) and diisopropylethylamine (1.17 mL, 6.72 mmol) in DMF (25 mL) was stirred at 0° C. under inert atmosphere. After 30 min HATU (741 mg, 1.95 mmol) was added and the reaction mixture was allowed to warm up to room temperature overnight. Then, DMF was evaporated and the residue was partitioned between AcOEt and a solution of $NaHCO_3$. Organic layer was successively washed with water and brine, dried ($MgSO_4$), filtered and evaporated. The crude product was purified by silica gel chromatography (gradient Heptane/AcOEt 80:20 to 50:50) to give 735 mg (82%) of the title compound: m/z=669 (M+H)$^+$.

Step F: Synthesis of 17-[2-(6-methylpyridin-2-yl)-7-methoxy-8-methyl-quinolin-4-yloxy]-13-methyl-2,14-dioxo-3,13-diaza-tricyclo[13.3.0.0$^{4,6}$]octadec-7-ene-4-carboxylic acid ethyl ester (101)

101

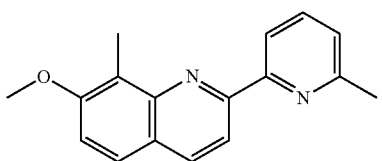

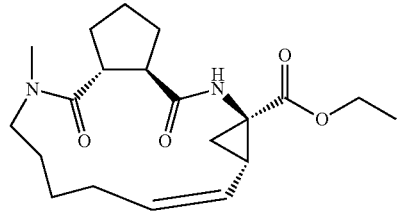

1-{2-(Hex-5-enylmethylcarbamoyl)-4-[2-(6-methyl-2-pyridyl)-7-methoxy-8-methyl-quinolin-4-yloxy]cyclopentanecarbonyl}amino-2-vinylcyclopropanecarboxylic acid ethyl ester (100, 250 mg, 0.37 mmol) was dissolved in dry 1,2-dichloroethane (250 mL). Then, nitrogen gas was bubbled through the solution for 30 min before Hoveyda-Grubbs 2$^{nd}$ generation (25 mg) was added. The resulting solution was refluxed overnight, then cooled down to room temperature and evaporated. The residue was purified by column chromatography on silica gel (gradient AcOEt/Heptane, 3:7 to 5:5) to give 139 mg (58%) of the title compound 101.

Step G: Synthesis of 17-[2-(6-methyl-2-pyridyl)-7-methoxy-8-methylquinolin-4-yl-oxy]-13-methyl-2,14-dioxo-3,13-diazatricyclo[13.3.0.0⁴,⁶]octadec-7-ene-4-carboxylic acid (102)

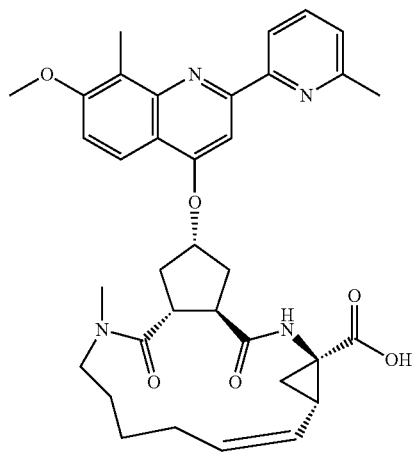

102

LiOH (0.42 mL, 1M) was added to a solution of 17-[2-(6-methylpyridin-2-yl)-7-methoxy-8-methyl-quinolin-4-yloxy]-13-methyl-2,14-dioxo-3,13-diaza-tricyclo-[13.3.0.0⁴,⁶]octadec-7-ene-4-carboxylic acid ethyl ester (101, 27 mg, 0.042 mmol) in a mixture of THF:MeOH:H₂O, 2:1:1 (6 mL). The resulting solution was stirred at room temperature overnight, then the pH was adjusted to 6 with acetic acid. The reaction mixture was successively diluted with water, extracted with CH₂Cl₂, dried (MgSO₄), filtered and evaporated to give 17 mg (65%) of the title compound: m/z=613 (M+H)⁺.

Step H: Synthesis of cyclopropanesulfonic acid {17-[2-(6-methyl-2-pyridyl)-7-methoxy-8-methyl-quinolin-4-yloxy]-13-methyl-2,14-dioxo-3,13-diaza-tricyclo-[13.3.0.0⁴,⁶]octadec-7-ene-4-carbonyl}-amide (103)

103

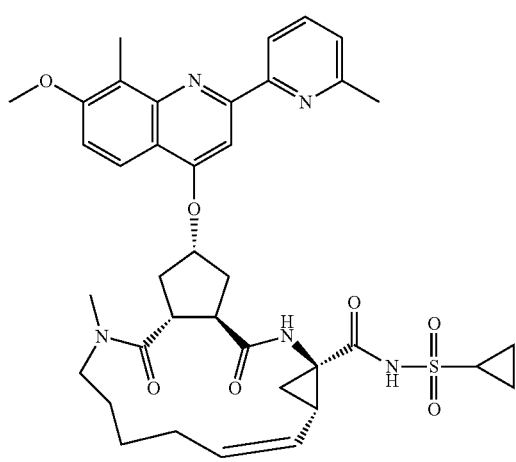

A mixture of the acid 17-[2-(6-methyl-2-pyridyl)-7-methoxy-8-methylquinolin-4-yl-oxy]-13-methyl-2,14-dioxo-3,13-diazatricyclo[13.3.0.0⁴,⁶]octadec-7-ene-4-carboxylic acid (102, 28 mg, 0.046 mmol) and CDI (15 mg, 0.092 mmol) in dry THF (3 mL) was heated at reflux for 2 h under nitrogen. The activation was monitored by LC-MS. The reaction mixture was cooled at room temperature and cyclopropylsulfonamide (17 mg, 0.137 mmol) was added. Then, DBU (16 µL, 0.105 mmol) was added and the reaction was heated at 55° C. After 24 h, the pH of the reaction mixture was adjusted to 3 with citric acid (5%). Then, the solvent was evaporated, and the residue partitioned between AcOEt and water. The crude material was purified by preparative HPLC to give 17 mg (52%) of the target compound 103: m/z=716 (M+H)⁺.

Example 23

Cyclopropanesulfonic acid {17-[2-(6-isopropyl-2-pyridyl)-7-methoxy-8-methyl-quinolin-4-yloxy]-13-methyl-2,14-dioxo-3,13-diaza-tricyclo[13.3.0.0⁴,⁶]-octadec-7-ene-4-carbonyl}-amide (114)

114

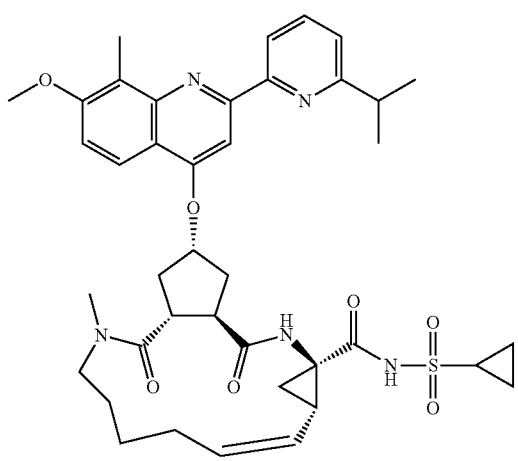

Step A: Synthesis of 2-isopropylpyridine-N-oxide (104)

104

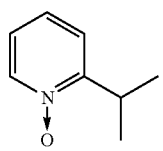

A mixture of isopropylpyridine (2.1 g, 17.75 mmol) and m-CPBA (5.0 g, 1.3 eq.) in CH₂Cl₂ was stirred overnight at room temperature. Then, the reaction mixture was diluted with CH₂Cl₂ (twice the volume) and successively washed with aqueous sodium bicarbonate (twice) and brine, dried (Na$_2$SO$_4$) and evaporated to give 2.0 g (85%) of the title compound 104.

Step B: Synthesis of 2-cyano-6-isopropylpyridine (105)

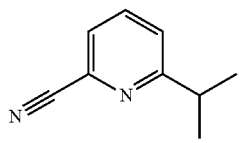

A mixture of 2-isopropylpyridine-N-oxide (104, 1.33 g, 9.7 mmol), cyanotrimethyl-silane (TMS-CN) (1.42 mL, 1.06 g, 11.0 mmol) in 1,2-dichloroethane (40 mL) was stirred at room temperature for 5 min. Then, diethylcarbamoylchloride (Et$_2$NCOCl, 1.23 mL, 9.7 mmol) was added and the mixture was stirred at room temperature under inert atmosphere. After 2 days, a aqueous solution of potassium carbonate (10%) was added and the stirring was continued for 10 min. The organic layer was separated, and the water layer was extracted twice with 1,2-dichloroethane. The combined organic layers were washed with brine, dried (Na$_2$SO$_4$) and evaporated. The residue was purified by column chromatography on silica gel (Hexanes/AcOEt, 3:1) to give 1.06 g (74%) of the title compound: m/z=147 (M+H)$^+$.

Step C: Synthesis of 6-isopropylpyridine-2-carboxylic acid (106)

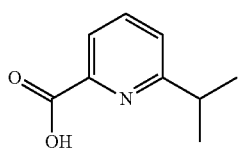

A solution of 2-cyano-6-isopropylpyridine (105, 1.06 g, 7.3 mmol) in 37% aqueous HCl-MeOH (1:2) was heated to reflux overnight. Then, the solvent was evaporated, and the residue was poured into a saturated solution of KOH. The resulting solution was refluxed overnight. Then, the solution was successively cooled down to room temperature and the pH of was adjusted to 5 by addition of aqueous HCl. The resulting reaction mixture was successively extracted with chloroform, washed with brine, dried (Na$_2$SO$_4$) and evaporated to give 0.97 g (81%) of the title compound 106: m/z=166 (M+H)$^+$.

Step D: Synthesis of 6-isopropylpyridine-2-carboxylic acid (6-acetyl-3-methoxy-2-methylphenyl)amide (107)

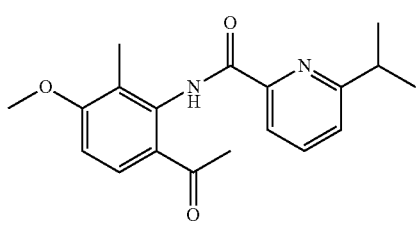

POCl$_3$ (0.88 mL, 9.53 mmol) was added at −25° C. drop wise over 5 min under nitrogen, to a stirred solution of 6-isopropylpyridine-2-carboxylic acid (106, 1.43 g, 8.66 mmol) and 6-acetyl-3-metoxy-2-methylaniline (1.55 g, 8.66 mmol) in dry pyridine (70 mL). The resulting solution was stirred at −10° C. for 2.5 h. Then, the reaction mixture was poured on ice, neutralized with aqueous sodium bicarbonate and extracted 3 times with AcOEt. The organic layers were combined, washed with brine, dried (Na$_2$SO$_4$) and evaporated. The residue was purified by column chromatography (hexanes/AcOEt, 3:1) to give 3.54 g (72%) of the title compound 107: m/z=327 (M+H)$^+$.

Step E: Synthesis of 4-hydroxy-2-(6-isopropyl-2-pyridyl)-7-methoxy-8-methyl-quinoline (108)

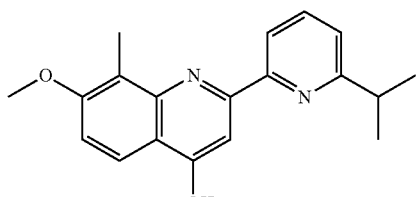

To a solution of 6-isopropylpyridine-2-carboxylic acid (6-acetyl-3-methoxy-2-methyl-phenyl)amide (107, 0.70 g, 2.14 mmol) in pyridine (5 mL) were added 2.5 equivalents of freshly grounded KOH along with water (50 µL). The mixture was heated by microwave irradiation at 133° C. for 55 min, then 80-85% of the pyridine was evaporated under reduced pressure. The residue was poured on ice and neutralized with acetic acid. The precipitate was filtered off, then dried to give 0.62 g (95%) of the title compound 108 (1.8 g, 95%): m/z=309 (M+H)⁺.

Step F: Synthesis of 2-(1-ethoxycarbonyl-2-vinyl-cyclopropylcarbamoyl)-4-[2-(6-iso-propyl-pyridin-2-yl)-7-methoxy-8-methyl-quinolin-4-yloxy]-cyclopentanecarboxylic acid tert-butyl ester (109)

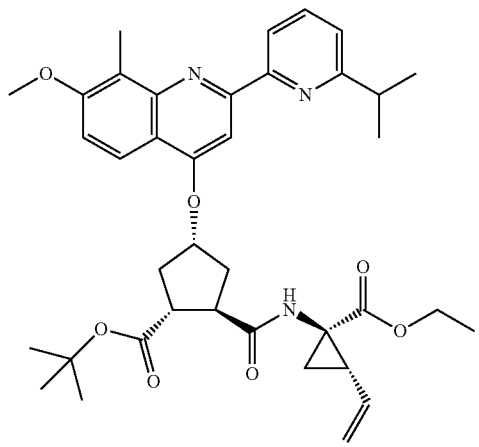

109

The title compound was prepared in 62% isolated yield from 2-(1-ethoxycarbonyl-2-vinylcyclopropylcarbamoyl)-4-hydroxycyclopentanecarboxylic acid tert-butyl ester and 4-hydroxy-2-(6-isopropyl-2-pyridyl)-7-methoxy-8-methylquinoline (108) following the procedure reported for the preparation 2-(1-ethoxycarbonyl-2-vinylcyclopropyl-carbamoyl)-4-[2-(6-methyl-2-pyridyl)-7-methoxy-8-methylquinolin-4-yloxy]cyclo-pentanecarboxylic acid tert-butyl ester (98): m/z=658 (M+H)⁺.

Step G: Synthesis of 2-(1-ethoxycarbonyl-2-vinylcyclopropylcarbamoyl)-4-[2-(6-iso-propyl-2-pyridyl)-7-methoxy-8-methylquinolin-4-yloxy]cyclopentanecarboxylic acid (110)

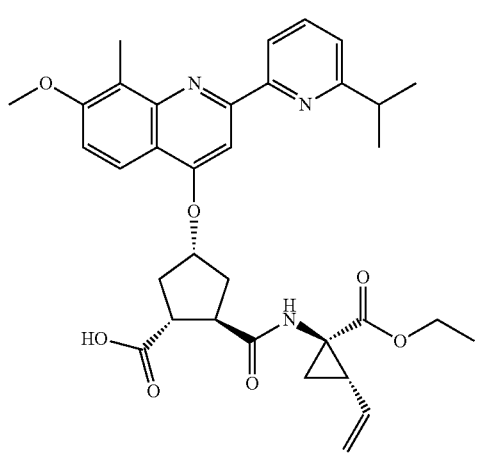

110

TFA (5 mL) was added at room temperature to a solution of 2-(1-ethoxycarbonyl-2-vinyl-cyclopropylcarbamoyl)-4-[2-(6-isopropyl-pyridin-2-yl)-7-methoxy-8-methyl-quinolin-4-yloxy]-cyclopentanecarboxylic acid tert-butyl ester (109, 590 mg, 0.90 mmol) and triethylsilane (280 mg, 2.5 eq) in CH₂Cl₂ (5 mL). After 2 h, the reaction mixture was concentrated under reduced pressure to afford the desired product 110, which was used in the next step without further purifications.

Step H: Synthesis of 1-{2-(hex-5-enylmethylcarbamoyl)-4-[2-(6-isopropyl-2-pyridyl)-7-methoxy-8-methylquinolin-4-yloxy]cyclopentanecarbonyl}amino-2-vinyl-cyclopropanecarboxylic acid ethyl ester (111)

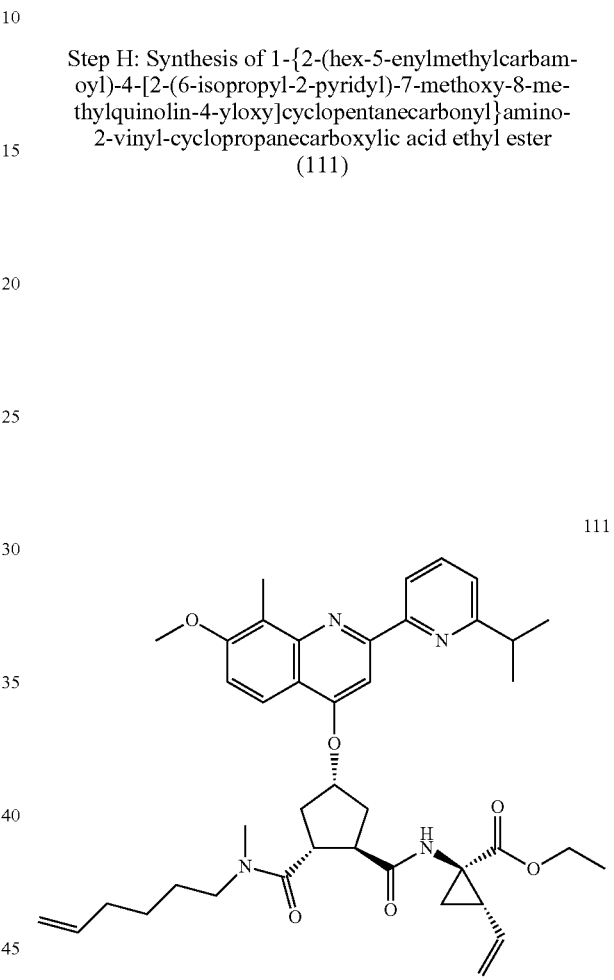

111

The title compound 111 was prepared in 70% isolated yield from 2-(1-ethoxycarbonyl-2-vinylcyclopropylcarbamoyl)-4-[2-(6-isopropyl-2-pyridyl)-7-methoxy-8-methyl-quinolin-4-yloxy]cyclopentanecarboxylic acid (110) following the procedure reported for the preparation of 1-{2-(hex-5-enylmethylcarbamoyl)-4-[2-(6-methyl-2-pyridyl)-7-methoxy-8-methylquinolin-4-yloxy] cyclopentanecarbonyl}amino-2-vinylcyclopropanecarboxylic acid ethyl ester (100): m/z=697 (M+H)⁺.

Step I: Synthesis of 17-[2-(6-isopropyl-2-pyridyl)-7-methoxy-8-methylquinolin-4-yl-oxy]-13-methyl-2,14-dioxo-3,13-diazatricyclo[13.3.0.0⁴,⁶]octadec-7-ene-4-carboxylic acid ethyl ester (112)

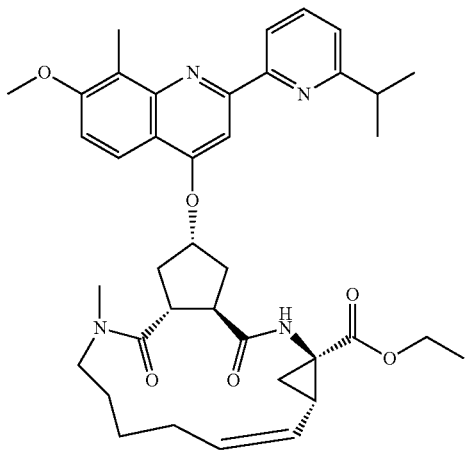

112

1-{2-(hex-5-enylmethylcarbamoyl)-4-[2-(6-isopropyl-2-pyridyl)-7-methoxy-8-methyl-quinolin-4-yloxy]cyclopentanecarbonyl}amino-2-vinyl-cyclopropanecarboxylic acid ethyl ester (111, 438 mg, 0.50 mmol) was dissolved in dry 1,2-dichloroethane. Then, nitrogen gas was bubbled through the solution for 30 min before Hoveyda-Grubbs 1$^{st}$ generation (15 mg) was added. The resulting solution was refluxed for 3 h, then more catalyst (20 mg) was added. After 2 h at reflux, another 10 mg of the catalyst was added. After 12 h at reflux, the reaction mixture was cooled down to room temperature. Then, scavenger MP-TMT (Agronaut Technologies Inc.) was added (~300 mg) and the mixture was stirred at room temperature for 45 min. The catalyst was discarded by filtration on silica gel (gradient of CHCl₃/MeOH, 1:0 to 98:2) to give 220 mg (66%) of the title compound 112: m/z=669 (M+H)⁺.

Step J: Synthesis of 17-[2-(6-isopropyl-2-pyridyl)-7-methoxy-8-methylquinolin-4-yloxy]-13-methyl-2,14-dioxo-3,13-diazatricyclo[13.3.0.0⁴,⁶]octadec-7-ene-4-carboxylic acid (113)

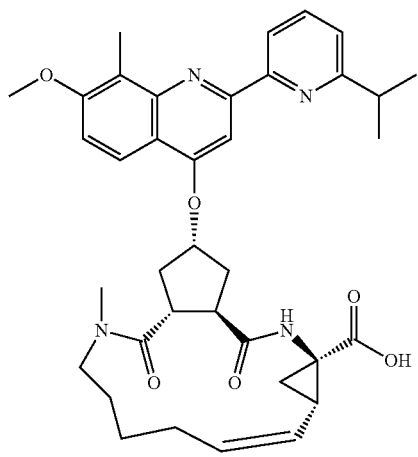

113

A solution LiOH (40 mg) in water (1.5 mL) was added to a solution of 17-[2-(6-iso-propyl-2-pyridyl)-7-methoxy-8-methylquinolin-4-yloxy]-13-methyl-2,14-dioxo-3,13-diazatricyclo[13.3.0.0⁴,⁶]octadec-7-ene-4-carboxylic acid ethyl ester (112, 220 mg, 0.33 mmol) in a mixture of MeOH (3 mL) and THF (1 mL). The resulting solution was successively heated to 55° C. for 3 h, then stirred at room temperature for 5 h. Then, the pH of the reaction mixture was adjusted to pH 6 with acetic acid and water (3 mL) was added. The resulting solution was extracted with CHCl₃. Then, the organic layer was dried (Na₂SO₄), filtered and evaporated to give 200 mg (95%) of the title compound 113 as a white powder: m/z=641 (M+H)⁺.

Step K: Synthesis of cyclopropanesulfonic acid {17-[2-(6-isopropyl-2-pyridyl)-7-methoxy-8-methyl-quinolin-4-yloxy]-13-methyl-2,14-dioxo-3,13-diazatricyclo-[13.3.0.0⁴,⁶]octadec-7-ene-4-carbonyl}amide (114)

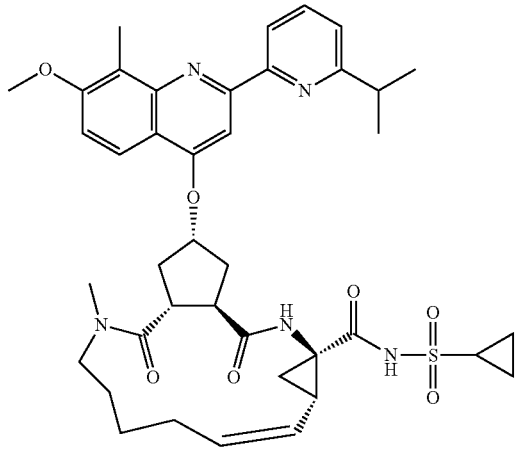

114

A solution of 17-[2-(6-isopropyl-2-pyridyl)-7-methoxy-8-methylquinolin-4-yloxy]-13-methyl-2,14-dioxo-3,13-diazatricyclo[13.3.0.0⁴,⁶]octadec-7-ene-4-carboxylic acid (113, 200 mg, 0.31 mmol), DMAP (76.5 mg, 0.62 mmol), and EDC (151 mg, 0.78 mmol) in DMF (5 mL) was stirred at room temperature overnight (the activation of the acid was monitored by LC-MS). Then, cyclopropylsulfonamide (191 mg, 1.56 mmol) was added, followed by DBU (228 µL, 1.56 mmol). The resulting solution was stirred overnight at room temperature, then neutralized with acetic acid and evaporated. The residue was re-dissolved in MeOH and purified by preparative HPLC to give 90 mg (39%) of the title compound 114: m/z=744 (M+H)⁺.

Example 24

(6S)-Cyclopropanesulfonic acid {17-[2-(2-cyclohexylthiazol-4-yl)-7-methoxy-8-methylquinolin-4-yloxy]-13-methyl-2,14-dioxo-3,13-diaza-tricyclo-[13.3.0.0$^{4,6}$]octadec-7-ene-4-carbonyl}amide (123) and (6R)-Cyclopropanesulfonic acid {17-[2-(2-cyclohexylthiazol-4-yl)-7-methoxy-8-methylquinolin-4-yloxy]-13-methyl-2,14-dioxo-3,13-diaza-tricyclo [13.3.0.0$^{4,6}$]octadec-7-ene-4-carbonyl}amide (124)

Step A: Synthesis of cyclohexanecarbothioic acid amide (115)

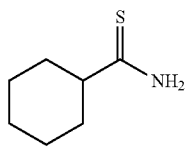

115

To a suspension of cyclohexanecarboxamide (10 g, 78.6 mmol) in diethyl ether (300 mL) was added phosphorous pentasulfide (9.0 g, 200 mmol) in three portions over 5 h. After stirring overnight the reaction mixture was filtered. The mother-liquor was evaporated to give 5.5 g (49%) of the title compound 115.

Step B: Synthesis of 2-cyclohexylthiazole-4-carboxylic acid ethyl ester (116)

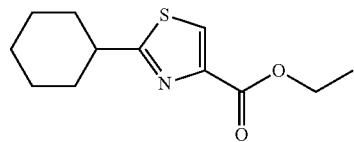

116

A solution of cyclohexanecarbothioic acid amide (115, 5.5 g, 38.3 mmol) and ethyl 3-bromopyruvate (90%, 8.3 g, 38.3 mmol) in THF (200 mL) was heated to reflux. After 2 h, the reaction mixture was cooled to room temperature for 12 h. Then, the solvent was evaporated and the residue was purified by column chromatography (gradient of heptane/AcOEt, 90:10 to 75:25) to afford 6.8 g (74%) of the title compound 116 as a clear liquid.

Step C: Synthesis of 2-cyclohexylthiazole-4-carboxylic acid (117)

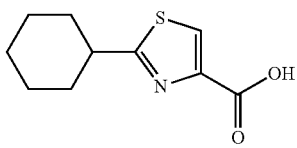

117

To a solution of 2-cyclohexylthiazole-4-carboxylic acid ethyl ester (116, 6.8 g, 28.5 mmol) in water was added 1M LiOH (50 mL). The solution was kept at room temperature and monitored by LC-MS. When the hydrolysis was completed the reaction mixture was neutralized with myriatic acid and extracted with ethyl acetate and diethyl ether. The organic phase was dried (Na$_2$SO$_4$), filtered and concentrated under reduced pressure to give 5.0 g (83%) of the title compound 117: m/z=212 (M+H)$^+$.

Step D: Synthesis of 2-cyclohexylthiazole-4-carboxylic acid (6-acetyl-3-methoxy-2-methylphenyl) amide (118)

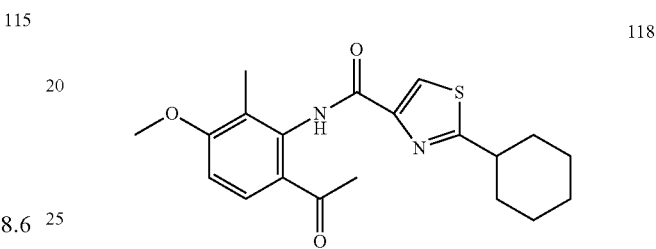

118

POCl$_3$ (1.4 mL, 14.9 mmol) was added drop wise at −35° C. over 5 min, to a stirred solution of 2-cyclohexylthiazole-4-carboxylic acid (117, 1.5 g, 7.1 mmol) and 2-acetyl-5-methoxy-6-methylaniline (1.27 g, 7.1 mmol) in dry pyridine (40 mL). After 1 h, the reaction mixture was successively warmed up to room temperature for 2.5 h, evaporated and neutralized with an aqueous solution of sodium bicarbonate. The precipitate was filtered, washed with water and dried to give 2.6 g (95%) of the title compound 118: m/z=373 (M+H)$^+$.

Step E: Synthesis of 2-(2-cyclohexylthiazol-4-yl)-4-hydroxy-7-methoxy-8-methylquinoline (119)

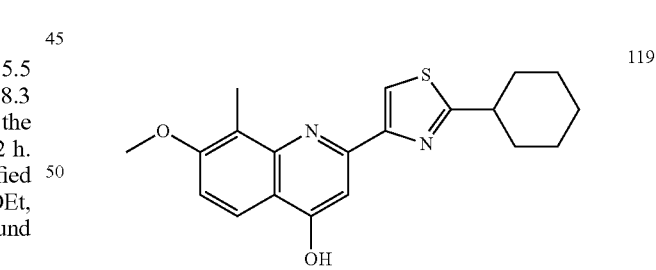

119

Freshly grounded KOH (2 mmol, 112 mg) was added to a solution of 2-cyclohexyl-thiazole-4-carboxylic acid (6-acetyl-3-methoxy-2-methylphenyl)amide (118, 373 mg, 2 mmol) in pyridine (20 mL). The mixture was divided into several batches and each batch was individually heated by microwave irradiation at 150° C. for 30 min. Then, the different batches were combined and pyridine was evaporated. The residue was treated with aqueous citric acid to give a suspension, which was subsequently diluted with a small volume of EtOH, then partitioned between water and CH$_2$Cl$_2$. Organic layer was dried (Na$_2$SO$_4$), and evaporated. The residue was purified by column chromatography (gradient of CH$_2$Cl$_2$:MeOH, 1:0 to 93:7) to give 1.8 g (72.5%) of the title compound 119 as a white powder: m/z=355 (M+H)$^+$.

Step F: Synthesis of 1-{[4-[2-(2-cyclohexylthiazol-4-yl)-7-methoxy-8-methyl-quinolin-4-yloxy]-2-(hex-5-enylmethylcarbamoyl)cyclopentanecarbonyl]amino}-2-vinylcyclo-propanecarboxylic acid ethyl ester (120)

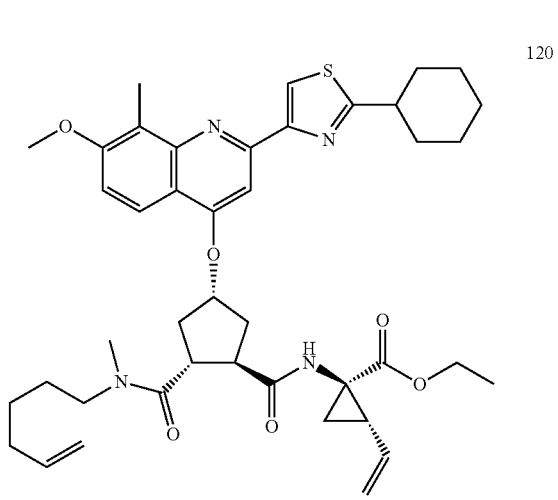 [SMILES: C=CCCCCN(C)C(=O)[C@@H]1C[C@H](Oc2cc(-c3csc(C4CCCCC4)n3)nc3c(C)c(OC)ccc23)C[C@H]1C(=O)N[C@]1(C(=O)OCC)C[C@H]1C=C]

120

The title compound 120 was prepared in 42% yield from 1-{[4-[2-(2-cyclohexylthiazol-4-yl)-7-methoxy-8-methyl-quinolin-4-yloxy]-2-(hex-5-enylmethylcarbamoyl)-cyclo-pentanecarbonyl]amino}-2-vinylcyclopropanecarboxylic acid ethyl ester (120) following the procedure reported for the preparation of 1-{2-(hex-5-enylmethyl-carbamoyl)-4-[2-(6-isopropyl-2-pyridyl)-7-methoxy-8-methylquinolin-4-yloxy]cyclo-pentanecarbonyl}amino-2-vinyl-cyclopropanecarboxylic acid ethyl ester (111): m/z=743 (M+H)$^+$.

Step G: Synthesis of 17-[2-(2-cyclohexylthiazol-4-yl)-7-methoxy-8-methyl-quinolin-4-yloxy]-13-methyl-2,14-dioxo-3,13-diazatricyclo[13.3.0.0$^{4,6}$]octadec-7-ene-4-carboxylic acid ethyl ester (121)

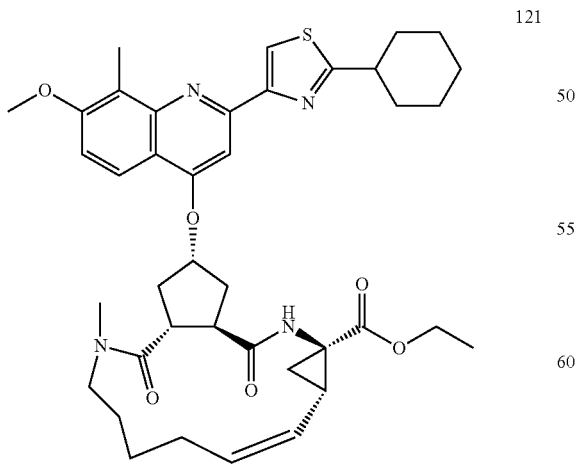

121

The title compound 121 was prepared in 50% yield from 2-(2-cyclohexylthiazol-4-yl)-4-hydroxy-7-methoxy-8-methylquinoline (119) and 2-(1-ethoxycarbonyl-2-vinylcyclopropylcarbamoyl)-4-hydroxycyclopentanecarboxylic acid tert-butyl ester following the procedure reported for the preparation of 17-[2-(6-methylpyridin-2-yl)-7-methoxy-8-methyl-quinolin-4-yloxy]-13-methyl-2,14-dioxo-3,13-diaza-tricyclo[13.3.0.0$^{4,6}$]-octadec-7-ene-4-carboxylic acid ethyl ester (101): m/z=715 (M+H)$^+$.

Step H: Synthesis of 17-[2-(2-cyclohexylthiazol-4-yl)-7-methoxy-8-methylquinolin-4-yloxy]-13-methyl-2,14-dioxo-3,13-diazatricyclo[13.3.0.0$^{4,6}$]octadec-7-ene-4-carboxylic acid (122)

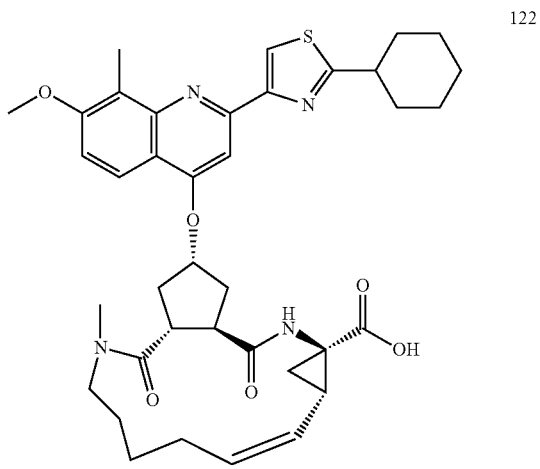 [SMILES: COc1ccc2c(O[C@@H]3C[C@H]4C(=O)N[C@]5(C(=O)O)C[C@H]5/C=C\CCCCN(C)C(=O)[C@@H]4C3)cc(-c3csc(C4CCCCC4)n3)nc2c1C]

122

An aqueous solution of LiOH (1M, 5 mL) was added to a solution of 17-[2-(2-cyclo-hexylthiazol-4-yl)-7-methoxy-8-methyl-quinolin-4-yloxy]-13-methyl-2,14-dioxo-3,13-diazatricyclo[13.3.0.0$^{4,6}$]octadec-7-ene-4-carboxylic acid ethyl ester (121) in MeOH (10 mL), THF (20 mL) and water (5 mL). The resulting solution was stirred at 50° C. for 19 h. Then, the pH of the reaction mixture was adjusted to 6 with myriatic acid (3M, 1.7 mL). The resulting solution was evaporated on silica and purified by column chromatography (AcOEt/MeOH/AcOH, 74:25:1) to give 273 mg (95%) of the title compound 122 as a white powder: m/z=687 (M+H)⁺.

Step I: Synthesis of (6S)-cyclopropanesulfonic acid {17-[2-(2-cyclohexylthiazol-4-yl)-7-methoxy-8-methylquinolin-4-yloxy]-13-methyl-2,14-dioxo-3,13-diaza-tricyclo-[13.3.0.0⁴,⁶]octadec-7-ene-4-carbonyl}amide (123) and (6R)-cyclopropanesulfonic acid {17-[2-(2-cyclohexylthiazol-4-yl)-7-methoxy-8-methylquinolin-4-yloxy]-13-methyl-2,14-dioxo-3,13-diaza-tricyclo[13.3.0.0⁴,⁶]octadec-7-ene-4-carbonyl}amide (124)

mixture was neutralized with acetic acid, evaporated. The residue was re-dissolved in water and acetonitrile, then purified by preparative HPLC to give 21 mg (11%) of the title compound (123, first isomer): m/z=790 (M+H)⁺ and 35 mg (18%) of the second isomer 124: m/z=790 (M+H)⁺.

Example 25

Preparation of N-[17-[2-(3-isopropylpyrazol-1-yl)-7-methoxy-8-methyl-quinolin-4-yloxy]-13-methyl-2,14-dioxo-3,13-diazatricyclo[13.3.0.0⁴,⁶]octadec-7-ene-4-carbonyl][1-(methyl)cyclopropyl]sulfonamide (125)

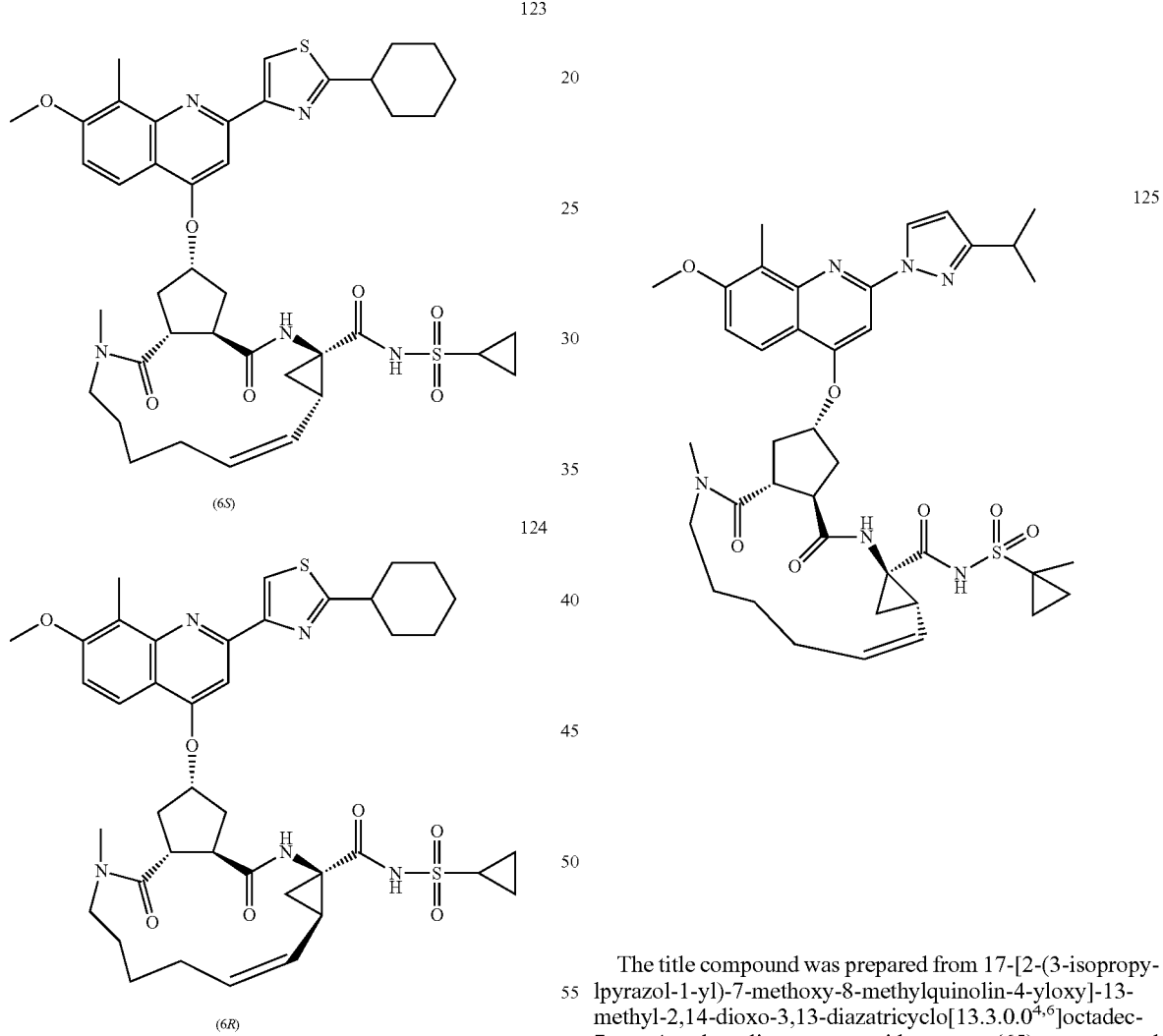

A solution of 17-[2-(2-cyclohexylthiazol-4-yl)-7-methoxy-8-methylquinolin-4-yloxy]-13-methyl-2,14-dioxo-3,13-diazatricyclo[13.3.0.0⁴,⁶]octadec-7-ene-4-carboxylic acid (122, 173 mg, 0.25 mmol) and CDI (81 mg, 0.5 mmol) in THF (7.5 mL) was heated to reflux for 2 h (the activation of the acid was monitored by LC-MS). Then, the reaction mixture was cooled down to room temperature, and cyclopropylsulfonamide (91 mg, 0.75 mmol) and DBU (8 mL, 0.575 mmol) were successively added. After 12 h, the reaction The title compound was prepared from 17-[2-(3-isopropylpyrazol-1-yl)-7-methoxy-8-methylquinolin-4-yloxy]-13-methyl-2,14-dioxo-3,13-diazatricyclo[13.3.0.0⁴,⁶]octadec-7-ene-4-carboxylic acid (65) and 1-methylcyclopropylsulfonamide following the procedure reported for the preparation of N-[17-[8-chloro-2-(4-isopropylthiazole-2-yl)-7-methoxyquinolin-4-yloxy]-13-methyl-2,14-dioxo-3,13-diazatricyclo[13.3.0.0⁴,⁶]-octadec-7-ene-4-carbonyl](cyclopropyl)sulfonamide (56): m/z=747 (M+H)⁺.
¹H NMR (CDCl₃): 0.79-0.92 (m, 2H), 1.20-2.03 (m, 19H), 2.20-2.32 (m, 1H), 2.35-2.48 (m, 2H), 2.52-2.64 (m, 5H), 2.85-2.93 (m, 1H), 3.04 (s, 3H), 3.05-3.14 (m, 1H), 3.35-3.46 (m, 2H), 3.97 (s, 3H), 4.60 (td, J=13.2 Hz, J=2.2 Hz, 1H), 5.04 (t, J=10.5 Hz, 1H), 5.30-5.47 (m, 1H), 5.61-5.69 (m, 1H), 6.30 (s, 1H), 6.32 (d, J=2.4 Hz, 1H), 7.12 (d, J=9.2 Hz, 1H), 7.30 (s, 1H), 7.95 (d, J=9.0 Hz, 1H), 8.61 (d, J=2.5 Hz, 1H), 10.9 (br s, 1H).

Example 26

Preparation of 17-[2-(3-tert-butylpyrazol-1-yl)-7-methoxy-8-methyl-quinolin-4-yloxy]-13-methyl-2,14-dioxo-3,13-diazatricyclo[13.3.0.0$^{4,6}$]octadec-7-ene-4-carboxylic acid (127)

Step 1: Synthesis of 4-hydroxy-2-(3-tert-butylpyrazol-1-yl)-7-methoxy-8-methylquinoline (126)

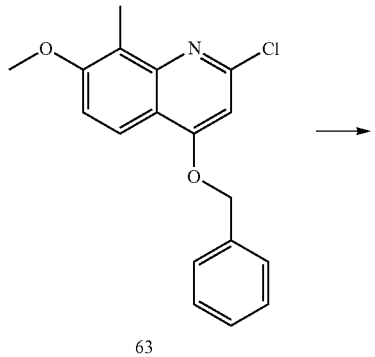

63

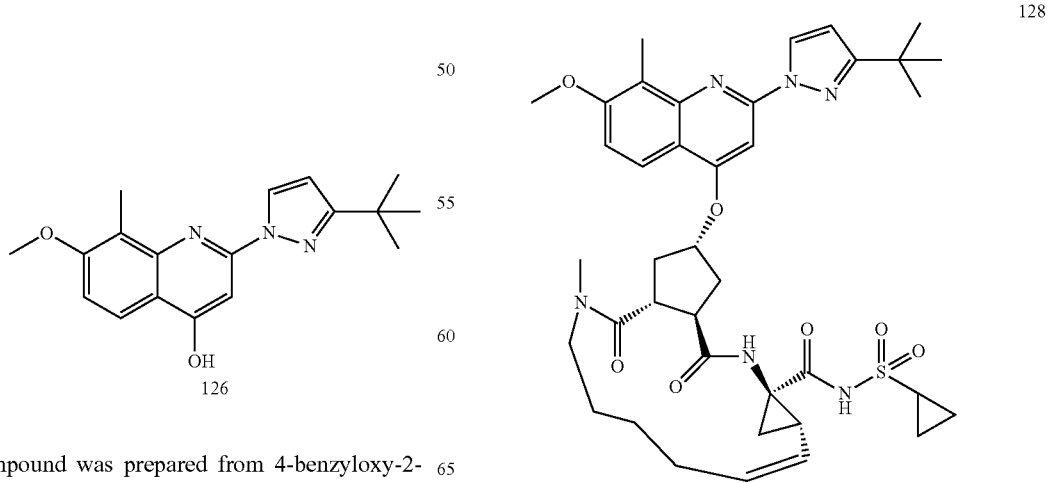

126

The title compound was prepared from 4-benzyloxy-2-chloro-7-methoxy-8-methyl-quinoline (63) and 3-tert-butylpyrazole following the procedure reported for the preparation of 4-hydroxy-2-(3-isopropylpyrazol-1-yl)-7-methoxy-8-methylquinoline (64): m/z=312 (M+H)$^+$.

Step 2: Synthesis of 17-[2-(3-tert-butylpyrazol-1-yl)-7-methoxy-8-methylquinolin-4-yl-oxy]-13-methyl-2,14-dioxo-3,13-diazatricyclo[13.3.0.0$^{4,6}$]octadec-7-ene-4-carboxylic acid (127)

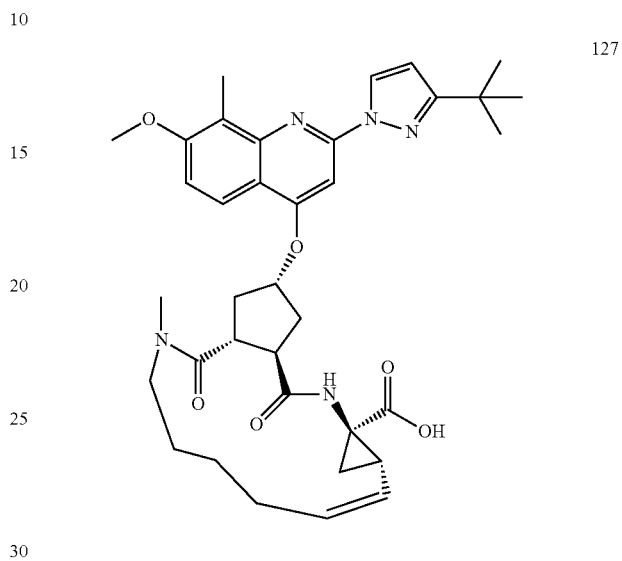

127

The title compound was prepared from 4-hydroxy-2-(3-tert-butylpyrazol-1-yl)-7-methoxy-8-methylquinoline (126) and intermediate 26 following the procedure (Step D-F) reported for the preparation of 17-[7-methoxy-8-methyl-2-(thiazol-2-yl)quinolin-4-yloxy]-13-methyl-2,14-dioxo-3,13-diazatricyclo[13.3.0.0$^{4,6}$]octadec-7-ene-4-carboxylic acid (29): m/z=644 (M+H)$^+$.

Example 27

Preparation of N-[17-[2-(3-tert-butylpyrazol-1-yl)-7-methoxy-8-methyl-quinolin-4-yloxy]-13-methyl-2,14-dioxo-3,13-diazatricyclo[13.3.0.0$^{4,6}$]octadec-7-ene-4-carbonyl](cyclopropyl)sulfonamide (128)

128

The title compound was prepared from 17-[2-(3-tert-butylpyrazol-1-yl)-7-methoxy-8-methylquinolin-4-yloxy]-13-methyl-2,14-dioxo-3,13-diazatricyclo[13.3.0.0$^{4,6}$]octadec-7-ene-4-carboxylic acid (127) and cyclopropylsulfonamide following the procedure reported for the preparation of N-[17-[8-chloro-2-(4-isopropylthiazole-2-yl)-7-methoxyquinolin-4-yloxy]-13-methyl-2,14-dioxo-3,13-diazatricyclo[13.3.0.0$^{4,6}$]-octadec-7-ene-4-carbonyl](cyclopropyl)sulfonamide (56): m/z=747 (M+H)$^+$. $^1$H NMR (CDCl$_3$): 0.95-1.12 (m, 2H), 1.13-1.30 (m, 2H), 1.31-1.55 (m, 11H), 1.63-2.05 (m, 4H), 2.20-2.55 (m, 9H), 2.80-2.98 (m, 1H), 3.03 (s, 3H), 3.36-3.47 (m, 2H), 3.61-3.70 (m, 1H), 3.97 (s, 3H), 4.60 (t, J=12.2 Hz, 1H), 5.04 (t, J=10.3 Hz, 1H), 5.26-5.46 (m, 1H), 5.61-5.69 (m, 1H), 6.35 (d, J=2.5 Hz, 1H), 6.42 (br s, 1H), 7.13 (d, J=9.1 Hz, 1H), 7.32 (s, 1H), 7.95 (d, J=9.1 Hz, 1H), 8.67 (d, J=2.5 Hz, 1H), 10.9 (br s, 1H).

Example 28

Preparation of 17-[2-(3,5-dimethylpyrazol-1-yl)-7-methoxy-8-methyl-quinolin-4-yloxy]-13-methyl-2,14-dioxo-3,13-diazatricyclo[13.3.0.0$^{4,6}$]octadec-7-ene-4-carboxylic acid (130)

Step 1: Synthesis of 4-hydroxy-2-(3,5-dimethylpyrazol-1-yl)-7-methoxy-8-methylquinoline (129)

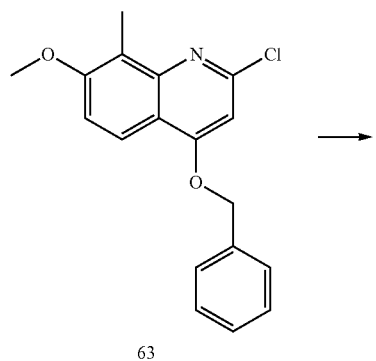

63

The title compound was prepared from 4-benzyloxy-2-chloro-7-methoxy-8-methyl-quinoline (63) and 3,5-dimethylpyrazole following the procedure reported for the preparation of 4-hydroxy-2-(3-isopropylpyrazol-1-yl)-7-methoxy-8-methylquinoline (64): m/z=284 (M+H)$^+$.

Step 2: Synthesis of 17-[2-(3,5-dimethylpyrazol-1-yl)-7-methoxy-8-methylquinolin-4-yloxy]-13-methyl-2,14-dioxo-3,13-diazatricyclo[13.3.0.0$^{4,6}$]octadec-7-ene-4-carboxylic acid (130)

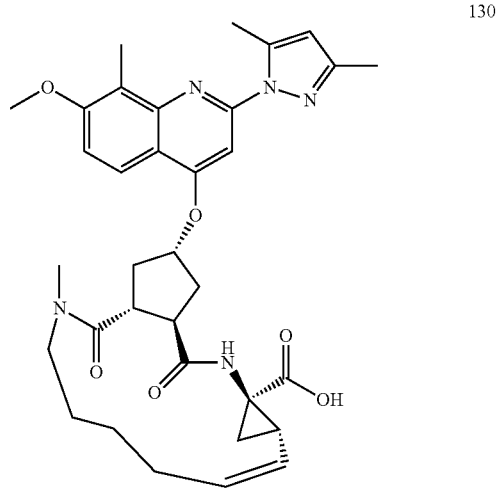

130

The title compound was prepared from 4-hydroxy-2-(3,5-dimethylpyrazol-1-yl)-7-methoxy-8-methylquinoline (129) and intermediate 26 following the procedure (Step D-F) reported for the preparation of 17-[7-methoxy-8-methyl-2-(thiazol-2-yl)quinolin-4-yloxy]-13-methyl-2,14-dioxo-3,13-diazatricyclo[13.3.0.0$^{4,6}$]octadec-7-ene-4-carboxylic acid (29): m/z=616 (M+H)$^+$.

Example 29

Preparation of N-[17-[2-(3,5-dimethylpyrazol-1-yl)-7-methoxy-8-methyl-quinolin-4-yloxy]-13-methyl-2,14-dioxo-3,13-diazatricyclo[13.3.0.0$^{4,6}$]octadec-7-ene-4-carbonyl](cyclopropyl)sulfonamide (131)

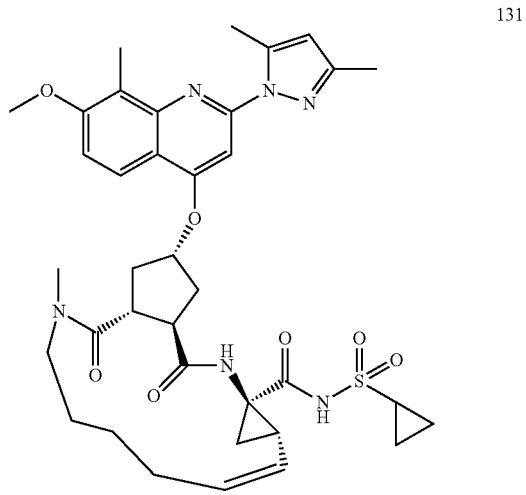 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-n3nc(C)cc3C)nc2c1C]

131

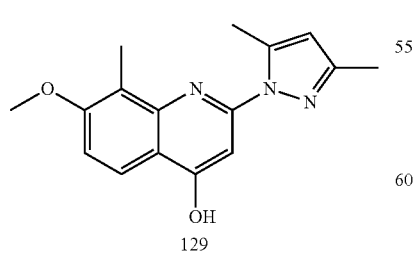

129

The title compound was prepared from 17-[2-(3,5-dimethylpyrazol-1-yl)-7-methoxy-8-methylquinolin-4-yloxy]-13-methyl-2,14-dioxo-3,13-diazatricyclo[13.3.0.0$^{4,6}$]octadec-7-ene-4-carboxylic acid (130) and cyclopropylsulfonamide following the procedure reported for the preparation of N-[17-[8-chloro-2-(4-isopropylthiazole-2-yl)-7-methoxyquinolin-4-yloxy]-13-methyl-2,14-dioxo-3,13-diazatricyclo[13.3.0.0$^{4,6}$]-octadec-7-ene-4-carbonyl](cyclopropyl)sulfonamide (56): m/z=719 (M+H)$^+$. $^1$H NMR (CDCl$_3$): 0.70-0.96 (m, 1H), 1.1-1.2 (m, 5H), 1.4-1.55 (m, 2H), 1.80-1.93 (m, 4H), 2.15-2.25 (m, 1H), 2.30-2.40 (m, 2H), 3.30 (s, 3H), 2.45-2.55 (m, 2H), 2.52 (s, 3H), 2.80 (s, 3H), 2.82-2.91 (m, 2H), 3.00 (s, 3H), 3.45-3.55 (m, 2H), 3.95 (s, 3H), 4.51-4.60 (m, 1H), 4.99-5.1 (m, 1H), 5.21-5.33 (m, 1H), 5.51 (m, 1H), 6.00 (s, 1H), 7.03 (s, 1H), 7.10 (d, J=9.1 Hz, 1H), 7.20 (s, 1H), 7.98 (d, J=9.1 Hz, 1H), 10.80 (br s, 1H).

Example 30

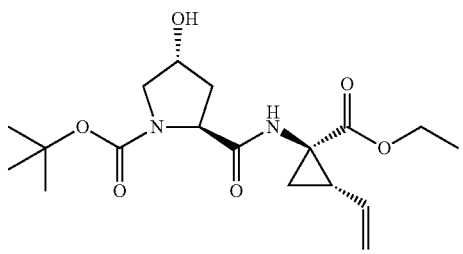 [SMILES: C=C[C@@H]1C[C@]1(NC(=O)[C@@H]1C[C@@H](O)CN1C(=O)OC(C)(C)C)C(=O)OCC]

2-(1-Ethoxycarbonyl-2-vinyl-cyclopropylcarbamoyl)-4-hydroxy-pyrrolidine-1-carboxylic acid tert-butyl ester (132)

Boc-protected proline (4 g, 17.3 mmol), HATU (6.9 g, 18.2 mmol) and 1-amino-2-vinyl-cyclopropanecarboxylic acid ethyl ester prepared as described in WO03/099274, (3.5 g, 18.3 mmol) were dissolved in DMF (60 ml) and cooled to 0° on an ice-bath. Diisopropylethyl amine (DIPEA) (6 ml) was added. The ice-bath was removed and the mixture was left at ambient temperature over-night. Dichloromethane (~80 ml) was then added and the organic phase was washed with aqueous sodium hydrogen carbonate, citric acid, water, brine and dried over sodium sulfate. Purification by flash chromatography (ether→7% methanol in ether) gave pure title compound (6.13 g, 96%)

Example 31

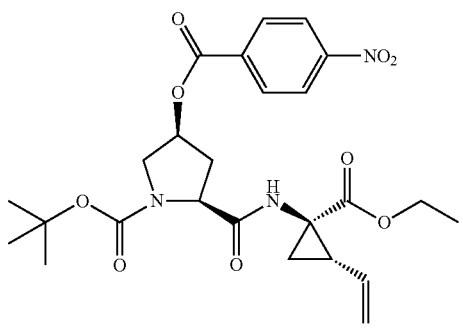 [SMILES: C=C[C@@H]1C[C@]1(NC(=O)[C@@H]1C[C@H](OC(=O)c2ccc([N+](=O)[O-])cc2)CN1C(=O)OC(C)(C)C)C(=O)OCC]

2-(1-Ethoxycarbonyl-2-vinyl-cyclopropylcarbamoyl)-4-(4-nitro-benzoyloxy)-pyrrolidine-1-carboxylic acid tert-butyl ester (133)

Compound 132 (6.13 g, 16.6 mmol), 4-nitrobenzoic acid (4.17 g, 25 mmol) and PPh$_3$ (6.55 g, 25 mmol) was dissolved in THF (130 ml). The solution was cooled to ~0° and diisopropyl azidocarboxylate (5.1 g, 25 mmol) was added slowly. The cooling was then removed and the mixture was left overnight at ambient condition. Aqueous sodium hydrogen carbonate (60 ml) was added and the mixture was extracted with dichloromethane. Purification by flash chromatography (pentane-ether, 2:1→pentane-ether, 1:2→2% methanol in ether) gave pure title compound (6.2 g, 72%).

Example 32

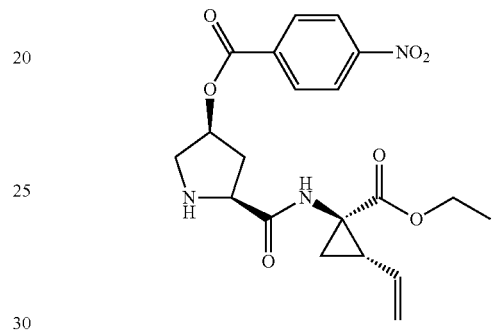

4-Nitro-benzoic acid 5-(1-ethoxycarbonyl-2-vinyl-cyclopropylcarbamoyl)-pyrrolidin-3-yl ester (134)

Compound 133 (6.2 g, 12 mmol) was dissolved in an ice-cold mixture of trifluoro-methanesulfonic acid 33% in dichloromethane. The ice-bath was then removed and the mixture was left at room temperature for ~1.5 h. The solvent was evaporated and 0.25 M sodium carbonate added and the mixture was extracted with dichloromethane. Evaporation gave the title compound (4.8 g, 95%) as a yellowish powder.

Example 33

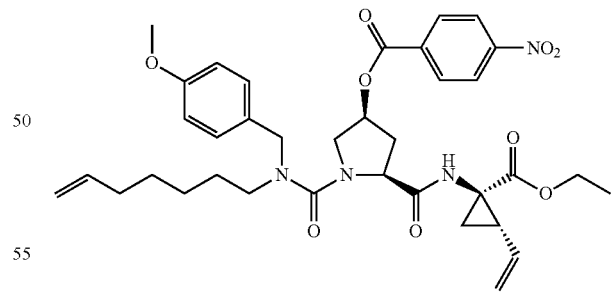

4-Nitro-benzoic acid 5-(1-ethoxycarbonyl-2-vinyl-cyclopropylcarbamoyl)-1-[hept-6-enyl-(4-methoxy-benzyl)-carbamoyl]-pyrrolidin-3-yl ester (135)

To a solution of compound 134 (4.5 g, 10.8 mmol) in THF (160 mL) were added NaHCO$_3$ (1 tablespoon) and phosgene in toluene (1.93 M, 11.5 mL, 22 mmol). The mixture was vigorously stirred for 1 h at room temperature, and then filtered and evaporated. The residue was dissolved in CH$_2$Cl$_2$ (160 mL), and NaHCO$_3$ (1 tablespoon) and hept-5-enyl-(p-methoxybenzyl)-amine (4.3 g, 18.5 mmol) were added. After stirring overnight at room temperature the reaction mixture was filtered and evaporated to dryness. Flash column chromatography on silica gel (EtOAc:toluene 25:75→40:60) gave the title compound (6.59 g, 90%) as a light brown syrup.

Example 34

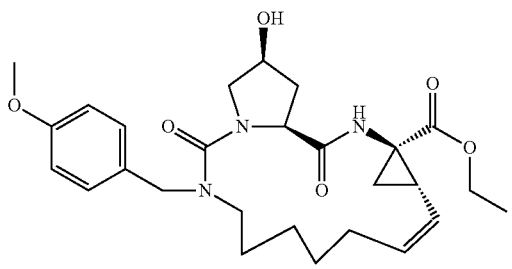 [SMILES: CCOC(=O)[C@@]12C[C@H]1/C=C\CCCCCN(Cc1ccc(OC)cc1)C(=O)N1C[C@@H](O)C[C@H]1C(=O)N2]

18-Hydroxy-14-(4-methoxy-benzyl)-2,15-dioxo-3,14,16-triaza-tricyclo[14.3.0.0*4,6]nonadec-7-ene-4-caroxylic acid ethyl ester (136)

Compound 135 (1 g, 1.48 mmol) was dissolved in 1,2-dichloroethane (2 l). The mixture was degassed for 15 min using a stream of argon. Hoveyda-Grubbs catalyst (II) (50 mg, 5 mol %) was added and the mixture was refluxed for 4 h. The solvent was evaporated and the crude ester was dissolved in tetrahydrofuran (100 ml), methanol (50 ml) and water (50 ml). The mixture was cooled 0° C. on ice-bath. Aqueous lithium hydroxide (20 ml, 1M) was added and the mixture was stirred at 0° C. for 4 h. The volume was then doubled with water and the mixture acidified with acetic acid. Extraction (dichloromethane) followed by flash chromatography (methanol 1→5% in ether) gave pure title compound (450 mg, 61%).

MS (M+H)$^+$ 500

Example 35

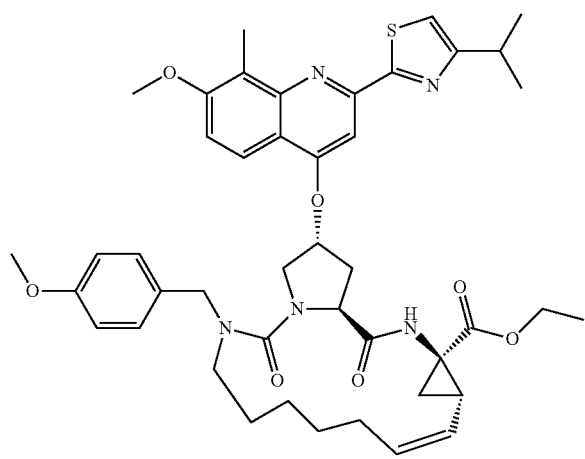 [SMILES: CCOC(=O)[C@@]12C[C@H]1/C=C\CCCCCN(Cc1ccc(OC)cc1)C(=O)N1C[C@H](Oc3cc(-c4nc(C(C)C)cs4)nc4c(C)c(OC)ccc34)C[C@H]1C(=O)N2]

18-[2-(4-Isopropyl-thiazol-2-yl)-7-methoxy-8-methyl-quinolin-4-yloxy]-14-(4-methoxy-benzyl)-2,15-dioxo-3,14,16-triaza-tricyclo[14.3.0.0*4,6*]nonadec-7-ene-4-carboxylic acid ethyl ester (137)

Alcohol 136 (230 mg, 0.460 mmol), quinolinol 36 (218 mg, 0.690 mmol), and triphenylphosphine (182 mg, 0.690 mmol) were dissolved in dry THF and the mixture was cooled to 0° C. DIAD (130 μL, 0.690 mmol) was added dropwise to the stirred solution at 0° C. during 30 minutes after which the solution was allowed to attain room temperature and was subsequently stirred overnight. The solvent was evaporated and the crude material was purified by flash column chromatography (toluene/ethyl acetate 1:1) to give the title compound (366 mg) (M+H)$^+$ calcd: 796.4. found: 796.7.

Example 36

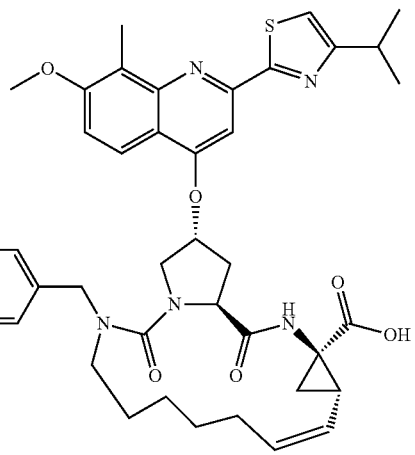

18-[2-(4-Isopropyl-thiazol-2-yl)-7-methoxy-8-methyl-quinolin-4-yloxy]-14-(4-methoxybenzyl)-2,15-dioxo-3,14,16-triaza-tricyclo[14.3.0.0*4,6*]nonadec-7-ene-4-carboxylic acid (138)

Ethyl ester 137 (366 mg, 0.460 mmol) was dissolved in THF/MeOH/H$_2$O 2:1:1 (30 mL) and 1M LiOH (4.6 mL, 4.40 mmol) was added dropwise at room temperature during 5 minutes after which the solution was stirred overnight. The mixture was acidified to pH 3-4 by addition of solid citric acid and the organic solvents were evaporated. The water phase was diluted with brine (50 mL) and was then extracted trice with DCM. The combined organic phase was washed twice with brine and was thereafter dried, filtered and concentrated. The crude was then purified by flash column chromatography (ethyl actetate/methanol 7:1) to give the title compound (212 mg, 60%). (M+H)+ calcd: 768.3. found: 768.7.

Example 37

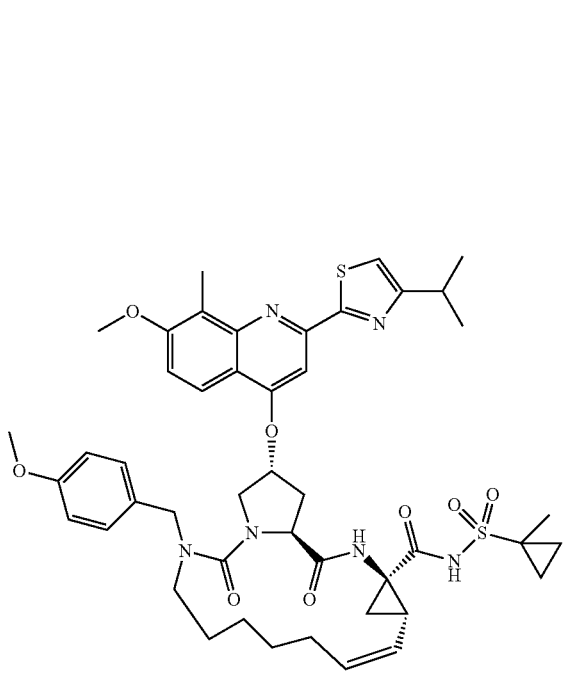 [SMILES: COc1ccc(CN2CCCCC/C=C\[C@@H]3C[C@@]3(C(=O)NS(=O)(=O)C3(C)CC3)NC(=O)[C@@H]3C[C@@H](Oc4cc(-c5nc(C(C)C)cs5)nc5c(C)c(OC)ccc45)CN3C2=O)cc1]

1-Methyl-cyclopropanesulfonic acid [18-[2-(4-iso-propyl-thiazol-2-yl)-7-methoxy-8-methyl-quinolin-4-yloxy]-14-(4-methoxy-benzyl)-2,15-dioxo-3,14,16-triaza-tricyclo-[14.3.0.0*4,6*]nonadec-7-ene-4-carbonyl]-amide (139)

To acid 138 (212 mg, 0.276 mmol) dissolved in dichloromethane (7 mL) was added EDC (69 mg, 0.359 mmol) and the reaction mixture was stirred at room temperature. After 7 hours TLC and LC-MS indicated complete conversion of the starting material into the corresponding oxazolidinone. The reaction mixture was diluted with dichloro-methane (20 mL) and the organic phase was washed twice with water after which the organic phase was dried, filtered, and concentrated. The residue was dissolved in dichloromethane (5 mL) and cyclopropylmethyl sulfonamide (53 mg, 0.394 mmol) and DBU (78 μL, 0.525 mmol) were added and the reaction mixture was stirred at room temperature for 20 hours. The mixture was diluted with dichloromethane (30 mL) and the organic phase was washed twice with 10% citric acid and once with brine. The organic phase was dried, filtered and concentrated and the crude product was purified by flash column chromatography (toluene/ethyl acetate 1:1, 1:2, ethyl acetate, ethyl acetate/methanol 9:1) to give the title compound (108 mg, 44%) as a colorless solid. LC-MS purity: >95%. (M+H)+ calcd: 885.4. found: 885.7.

Example 38

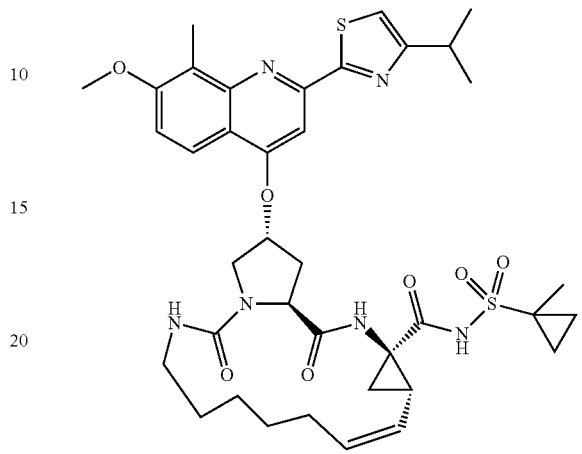

1-Methyl-cyclopropanesulfonic acid {18-[2-(4-iso-propyl-thiazol-2-yl)-7-methoxy-8-methyl-quinolin-4-yloxy]-2,15-dioxo-3,14,16-triaza-tricyclo [14.3.0.0*4,6*]nonadec-7-ene-4-carbonyl}-amide (140)

To compound 139 (106 mg, 0.120 mmol) dissolved in dichloromethane (18 mL) were added triethylsilane (38 μL, 0.240 mmol) and TFA (9 mL) and the reaction mixture was stirred at room temperature for 1 hour. The solvents were evaporated and co-evaporated trice with toluene. The residue was dissolved in dichloromethane and the organic phase was washed twice with saturated NaHCO3 solution. The organic phase was dried, filtered, and concentrated and the crude product was purified by flash column chromatography (toluene/ethyl acetate 1:1) to yield the title compound (73 mg, 80%) as a slightly yellow solid. LC-MS purity: >95%. (M+H)+ cald: 765.3. found: 765.7.

Example 39

Alternative Route for the Preparation of Compound 34

Step A: Synthesis of 4-Amino-5-cyano-2-hydroxy-3-methylbenzoic acid ethyl ester (141)

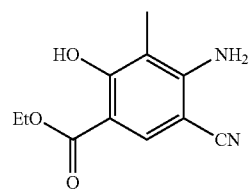 [SMILES: CCOC(=O)c1cc(C#N)c(N)c(C)c1O]

To a solution of sodium ethoxide (1.3 L) (freshly prepared by addition of sodium metal (7.9 g, 0.35 mol) to ethanol (1.3

L)) at 0° C. was added ethylpropionyl acetate (25 g, 0.17 mol) and the solution was stirred at RT for 1 h. To the above solution was added ethoxymethylene malononnitrile (21 g, 0.17 mol) at RT and the reaction mixture was refluxed at 80° C. for 2 h. The reaction mixture was cooled, neutralized to pH=7 by addition of 1.5 N HCl and concentrated under vacuum. The obtained residue was diluted with water (100 mL) and filtered. The solid was washed with water and dried under vacuum at 50° C. to give the crude product (27 g). The crude solid was washed with 5% ethyl acetate in pet. ether which gave pure title compound (22.5 g, 59%). TLC: EtOAc/Pet. ether, 3:7, $R_f$=0.4

Step B: Synthesis of
4-Amino-5-cyano-2-hydroxy-3-methylbenzoic acid
(142)

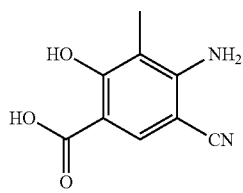

To a solution of LiOH×H$_2$O (8.4 g, 0.2 mol) in ethanol/water (1:1, 300 mL) was added compound 74 (22 g, 0.1 mol) at RT and the reaction mixture was refluxed at 80° C. for 4 h. The reaction mixture was concentrated under vacuum, the obtained residue was diluted with water (100 mL), washed with pet. ether/ethyl acetate (1:1, 2×200 mL). The aqueous layer was separated, acidified to pH=5 using 1.5N HCl and the obtained solid product was filtered off. The aqueous layer was further extracted with ethyl acetate (2×300 mL), dried and concentrated to give more product. The combined products was washed with 5% ethyl acetate in pet. ether to give the pure title compound (19 g, >95%).

TLC: MeOH/Chloroform, 1:4, $R_f$=0.2

Step C: Synthesis of
2-Amino-4-hydroxy-3-methylbenzonitrile (143)

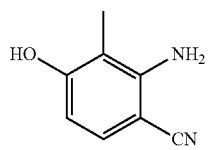

A mixture of compound 75 (19 g, 0.1 mol) in quinoline (50 mL) was heated to 170° C. for 2 h (until effervescence ceased). The reaction mixture was cooled to RT and aqueous NaOH solution was added (1M, 500 mL) followed by pet. ether (500 mL). The reaction mixture was stirred for 15 min and the aqueous layer was separated. The aqueous layer was further washed with pet. ether (2×300 mL) to remove quinoline completely. The aqueous layer was acidified with 1.5N HCl to pH=5, the solid was filtered off and dried under vacuum. The obtained solid was further washed with 5% ethyl acetate in pet. ether to give pure title compound (12 g, 82%).

TLC: EtOAc/Pet ether, 3:7, $R_f$=0.35

Step D: Synthesis of
2-Amino-4-methoxy-3-methylbenzonitrile (144)

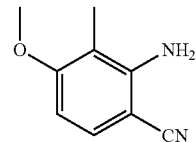

A mixture of compound 76 (12 g, 0.08 mol), K$_2$CO$_3$ (11 g, 0.08 mol) in dry DMF (200 mL) was stirred for 15 min at RT. To this was added MeI (13.6 g, 0.096 mol) and the mixture was stirred for 4 h at RT. The reaction mixture was diluted with water (800 mL), extracted with 30% ethyl acetate in pet. ether (3×300 mL). The combined organic layers were washed with water and brine, dried and concentrated to give a crude product. The crude product was washed with pet. ether to give pure title compound (12 g, 93%).

TLC: Pet. ether/EtOAc, 7:3, $R_f$=0.4

Step E: Synthesis of 1-(2-Amino-4-methoxy-3-methyl-phenyl)-ethanone (34)

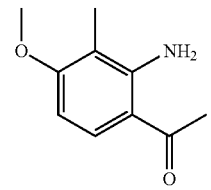

To a solution of compound 77 (12 g, 0.074 mol) in THF (150 mL) was added MeMgBr in diethyl ether (3M, 100 mL, 0.296 mol) at 0° C. drop-wise. The reaction mixture was stirred at RT for 1 h and then at 55° C. for 3 h. The reaction mixture was cooled to 0° C., quenched with ice-cold 1.5N HCl till the effervescence ceases (pH=6). The reaction mixture was diluted with water (100 mL), extracted with ethyl acetate (2×300 mL). The combined organic layers were washed with brine, dried and concentrated to give brown solid. The crude solid was dissolved in ethyl acetate (150 mL), added pet. ether (150 mL) and passed through a bed of silica gel to remove color impurities and concentrated. The solid obtained was washed with 5% ethyl acetate in pet. ether which gave pure title compound (9 g, 68%) as a yellow solid.

TLC: Pet. ether/EtOAc, 7:3, $R_f$=0.4.

Example 40

Synthesis of 3-Oxo-2-oxa-bicyclo[2.2.1]heptane-5-carboxylic acid tert-butyl ester (146)

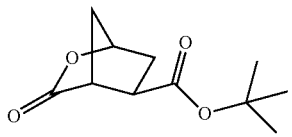

DMAP (14 mg, 0.115 mmol) and Boc$_2$O (252 mg, 1.44 mmol) was added to a stirred solution of 145 (180 mg, 1.15 mmol) in 2 mL CH$_2$Cl$_2$ under inert argon atmosphere at 0° C. The reaction was allowed to warm to room temperature and was stirred overnight. The reaction mixture was concentrated and the crude product was purified by flash column chromatography (toluene/ethyl acetate gradient 15:1, 9:1, 6:1, 4:1, 2:1) which gave the title compound (124 mg, 51%) as white crystals.

$^1$H-NMR (300 MHz, CD$_3$OD) δ 1.45 (s, 9H), 1.90 (d, J=11.0 Hz, 1H), 2.10-2.19 (m, 3H), 2.76-2.83 (m, 1H), 3.10 (s, 1H), 4.99 (s, 1H); $^{13}$C-NMR (75.5 MHz, CD$_3$OD) δ 27.1, 33.0, 37.7, 40.8, 46.1, 81.1, 81.6, 172.0, 177.7.

Alternative Method for the Preparation of Compound 146

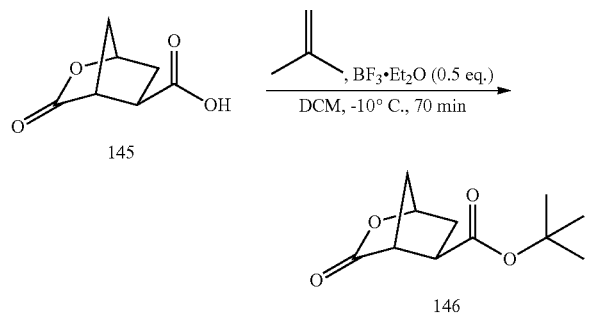

Compound 145 (13.9 g, 89 mmol) was dissolved in dichloromethane (200 ml) and then cooled to approximately −10° C. under nitrogen. Isobutylene was then bubbled into the solution until the total volume had increased to approximately 250 ml which gave a turbid solution. BF$_3$.Et$_2$O (5.6 ml, 44.5 mmol, 0.5 eq.) was added and the reaction mixture was kept at approximately −10° C. under nitrogen. After 10 min, a clear solution was obtained. The reaction was monitored by TLC (EtOAc-Toluene 3:2 acidified with a few drops of acetic acid and hexane-EtOAc 4:1, staining with basic permanganate solution). At 70 min only traces of compound 145 remained and aq. saturated NaHCO$_3$ (200 ml) was added to the reaction mixture, which was then stirred vigorously for 10 min. The organic layer was washed with saturated NaHCO$_3$ (3×200 ml) and brine (1×150 ml), then dried with sodium sulfite, filtered and the residue was evaporated to an oily residue. Upon addition of hexane to the residue, the product precipitated. Addition of more hexane and heating to reflux gave a clear solution from which the product crystallized. The crystals were collected by filtration and was washed with hexane (rt), then air-dried for 72 h giving colourless needles (12.45 g, 58.7 mmol, 66%).

Synthesis of (1R,2R,4S)-2-((1R,2S)-1-Ethoxycarbonyl-2-vinyl-cyclopropylcarbamoyl)-4-hydroxy-cyclopentanecarboxylic acid tert-butyl ester (147)

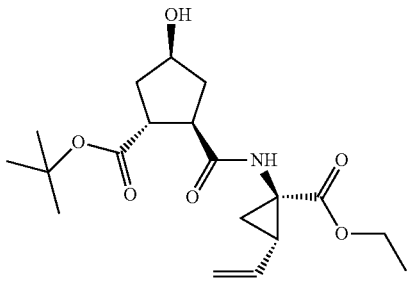 [SMILES: C=C[C@@H]1C[C@]1(NC(=O)[C@@H]1C[C@H](O)C[C@H]1C(=O)OC(C)(C)C)C(=O)OCC]

Compound 146 (56 mg, 0.264 mmol) was dissolved in dioxane/water 1:1 (5 mL) and the mixture was cooled to 0° C. 1 M lithium hydroxide (0.52 mL, 0.520 mmol) was added and the mixture was stirred at 0° C. for 45 minutes, after which the mixture was neutralized with 1M hydrochloric acid and evaporated and coevaporated with toluene. The crystalline residue was dissolved in DMF (5 mL) and (1R,2S)-1-amino-2-vinyl-cyclopropane carboxylic acid ethyl ester hydrochloride (60 mg, 0.313 mmol) and diisopropylethylamine (DIEA) (138 µL, 0.792 mmol) were added and the solution was cooled to 0° C. HATU (120 mg, 0.316 mmol) was added and the mixture was stirred for 0.5 h at 0° C. and for an additional 2 h at room temperature. The mixture was then evaporated and extracted with EtOAc, washed with brine, dried, filtered and concentrated. Purification by flash column chromatography (toluene/EtOAc 1:1) provided the title compound (86 mg, 89%) as a colourless oil. The afforded oil was crystallised from ethyl acetate-hexane.

Example 41

Activity of Compounds of Formula (I)

Replicon Assay

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV type 1b. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease by 50% the level of detected luciferase activity, or more specifically, the ability of the genetically linked HCV replicon RNA to replicate.

Inhibition Assay

The aim of this in vitro assay was to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-NH$_2$ (AnaSpec, San José, USA), was measured spectrofluorometrically in the presence of a peptide cofactor, KKGSVVIVGRIVLSGK (Åke Engström, Department of Medical Biochemistry and Microbiology, Uppsala University, Sweden). [Landro, 1997 #Biochem 36 9340-9348]. The enzyme (1 nM) was incubated in 50 mM HEPES, pH 7.5, 10 mM DTT, 40% glycerol, 0.1% n-octyl-D-glucoside, with 25 µM NS4A cofactor and inhibitor at 30° C. for 10 min, whereupon the reaction was initiated by addition of 0.5 µM substrate. Inhibitors were dissolved in DMSO, sonicated for 30 sec. and vortexed. The solutions were stored at −20° C. between measurements.

The final concentration of DMSO in the assay sample was adjusted to 3.3%. The rate of hydrolysis was corrected for inner filter effects according to published procedures. [Liu, 1999 Analytical Biochemistry 267 331-335]. Ki values were estimated by non-linear regression analysis (GraFit, Erithacus Software, Staines, MX, UK), using a model for competitive inhibition and a fixed value for Km (0.15 µM). A minimum of two replicates was performed for all measurements.

The following Table 1 lists compounds that were prepared according to any one of the above examples. The activities of the compounds tested are also depicted in Table 1

| Compound nr. | structure | EC$_{50}$ (µM) Replicon assay | Ki (µM) Enzymatic assay |
|---|---|---|---|
| 29 | 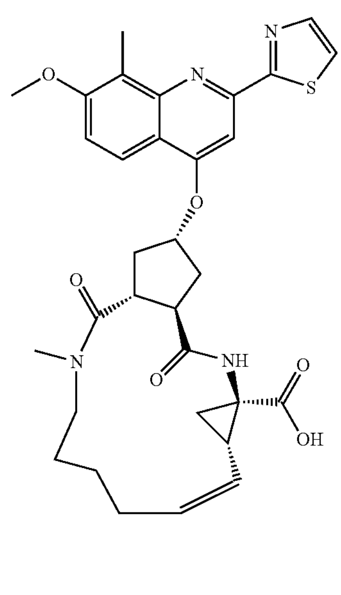 [SMILES: COc1ccc2c(O[C@@H]3C[C@H]4C(=O)N[C@]5(C(=O)O)C[C@H]5/C=C\CCCCN(C)C(=O)[C@@H]4C3)cc(-c3nccs3)nc2c1C] | 10 | — |

-continued
| Compound nr. | structure | EC$_{50}$ (μM) Replicon assay | Ki (μM) Enzymatic assay |
|---|---|---|---|
| 47 | 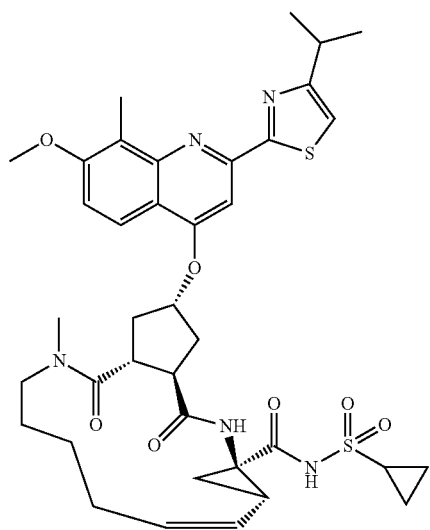 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C] | 0.00618 | 0.00050 |
| 46 | 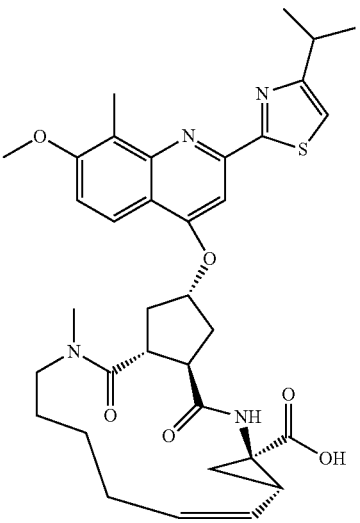 [SMILES: COc1ccc2c(O[C@@H]3C[C@H]4C(=O)N[C@]5(C(=O)O)C[C@H]5/C=C\CCCCN(C)C(=O)[C@@H]4C3)cc(-c3nc(C(C)C)cs3)nc2c1C] | 0.91 | — |

| Compound nr. | structure | EC$_{50}$ (μM) Replicon assay | Ki (μM) Enzymatic assay |
|---|---|---|---|
| 91 | 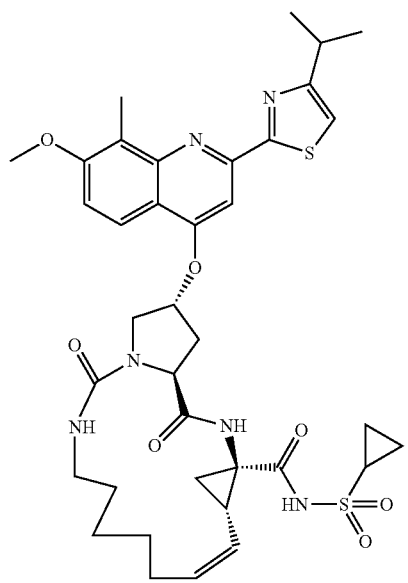 [SMILES: COc1ccc2c(O[C@@H]3C[C@H]4C(=O)N[C@]5(C(=O)NS(=O)(=O)C6CC6)C[C@H]5/C=C\CCCCCNC(=O)N4C3)cc(-c3nc(C(C)C)cs3)nc2c1C] | 8.54 × 10$^{-3}$ | 5.00 × 10$^{-5}$ |
| 55 | 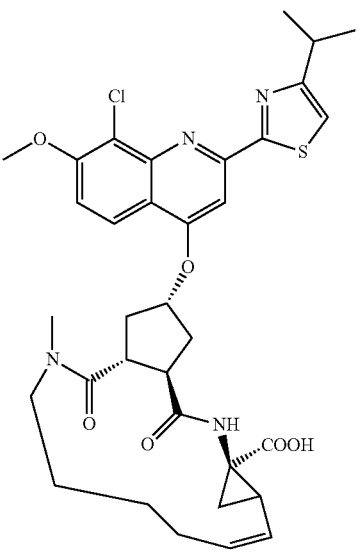 | 0.36743075 | 5.00 × 10$^{-3}$ |

-continued
| Compound nr. | structure | EC$_{50}$ (μM) Replicon assay | Ki (μM) Enzymatic assay |
|---|---|---|---|
| 81 | 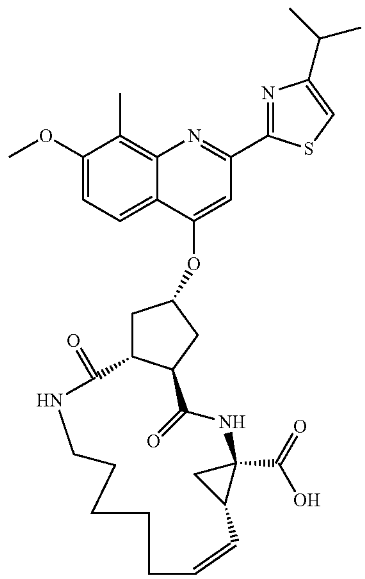 [SMILES: COc1ccc2c(O[C@H]3C[C@H]4C(=O)NCCCCC/C=C\[C@@H]5C[C@@]5(C(=O)O)NC(=O)[C@@H]4C3)cc(-c3nc(C(C)C)cs3)nc2c1C] | 10 | 1 |
| 82 | 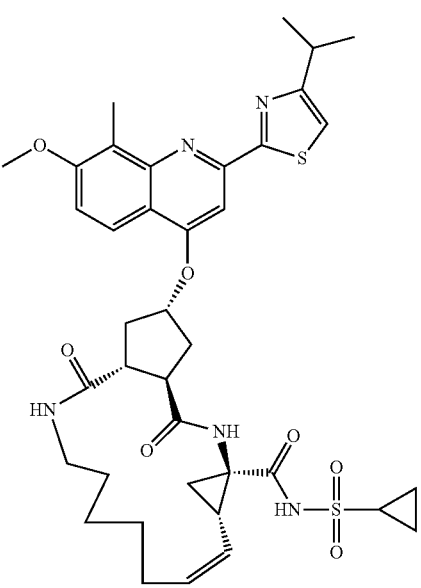 [SMILES: COc1ccc2c(O[C@H]3C[C@H]4C(=O)NCCCCC/C=C\[C@@H]5C[C@@]5(C(=O)NS(=O)(=O)C5CC5)NC(=O)[C@@H]4C3)cc(-c3nc(C(C)C)cs3)nc2c1C] | 8.321539 | 9.40 × 10$^{-3}$ |

| Compound nr. | structure | EC$_{50}$ (μM) Replicon assay | Ki (μM) Enzymatic assay |
|---|---|---|---|
| 56 | 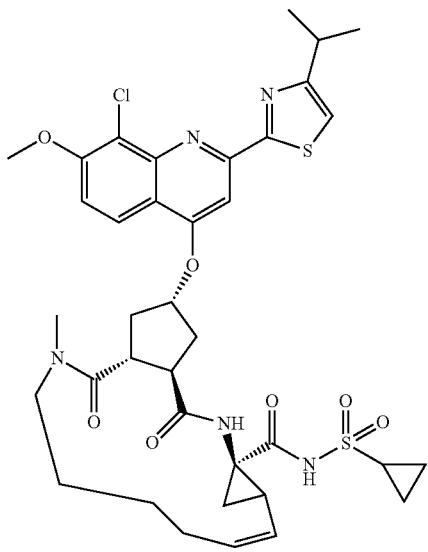 [SMILES: COc1ccc2c(O[C@@H]3C[C@H]4C(=O)N[C@]5(C(=O)NS(=O)(=O)C6CC6)CC5/C=C\CCCCN(C)C(=O)[C@@H]4C3)cc(-c3nc(C(C)C)cs3)nc2c1Cl] | $2.93 \times 10^{-3}$ | $1.00 \times 10^{-4}$ |
| 57 | 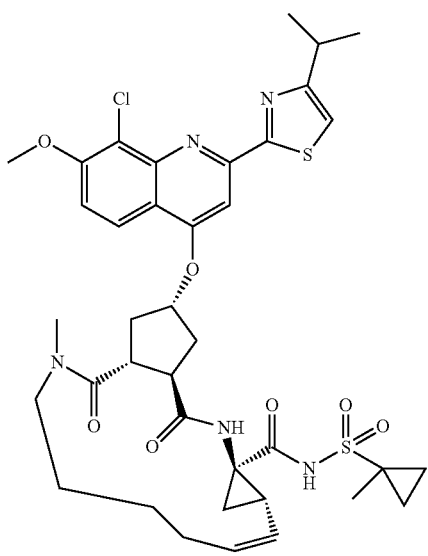 | $1.87 \times 10^{-3}$ | $3.00 \times 10^{-4}$ |

-continued
| Compound nr. | structure | EC$_{50}$ (μM) Replicon assay | Ki (μM) Enzymatic assay |
|---|---|---|---|
| 94 | 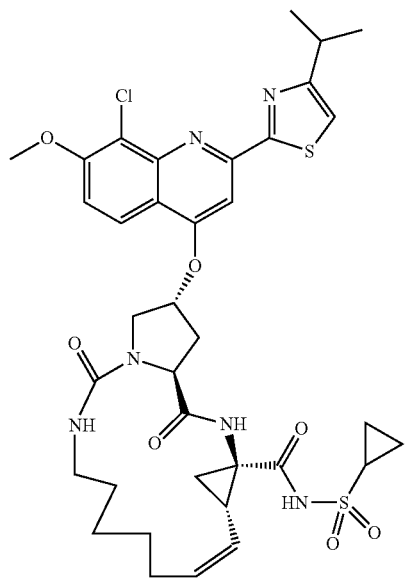 [SMILES: COc1ccc2c(O[C@@H]3C[C@H]4C(=O)N[C@]5(C(=O)NS(=O)(=O)C6CC6)C[C@H]5/C=C\CCCCCNC(=O)N4C3)cc(-c3nc(C(C)C)cs3)nc2c1Cl] | 3.26 × 10$^{-3}$ | 1.00 × 10$^{-4}$ |
| 48 | 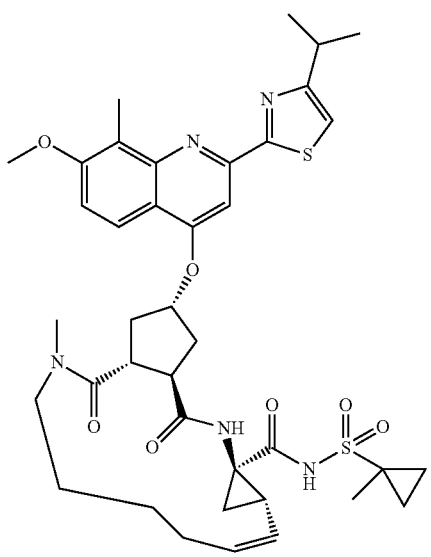 [SMILES: COc1ccc2c(O[C@@H]3C[C@H]4C(=O)N[C@]5(C(=O)NS(=O)(=O)C6(C)CC6)C[C@H]5/C=C\CCCCN(C)C(=O)[C@@H]4C3)cc(-c3nc(C(C)C)cs3)nc2c1C] | 2.33 × 10$^{-3}$ | 2.50 × 10$^{-4}$ |

| Compound nr. | structure | EC$_{50}$ (μM) Replicon assay | Ki (μM) Enzymatic assay |
|---|---|---|---|
| 95 | 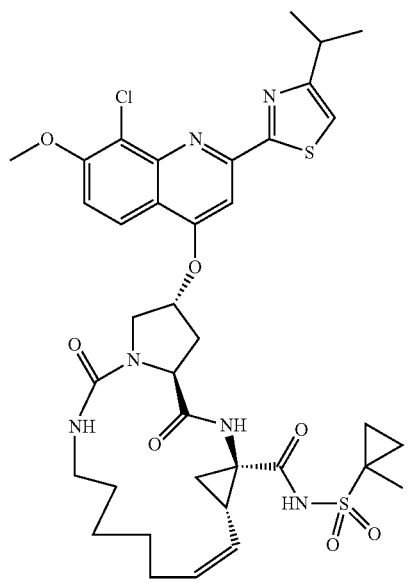 | 4.04 × 10$^{-3}$ | 1.00 × 10$^{-4}$ |
| 75 | 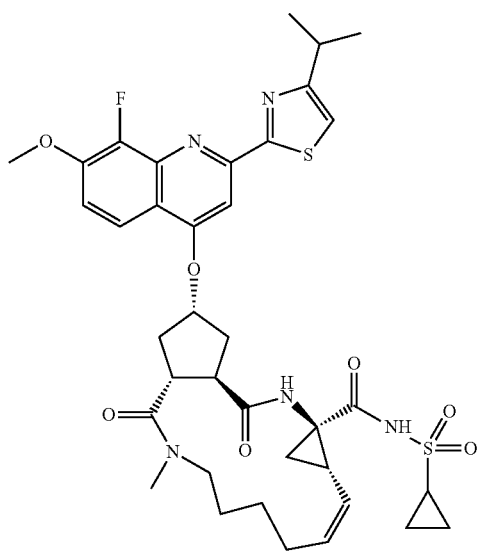 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1F] | 5.75 × 10$^{-2}$ | — |

| Compound nr. | structure | EC$_{50}$ (μM) Replicon assay | Ki (μM) Enzymatic assay |
|---|---|---|---|
| 71 | 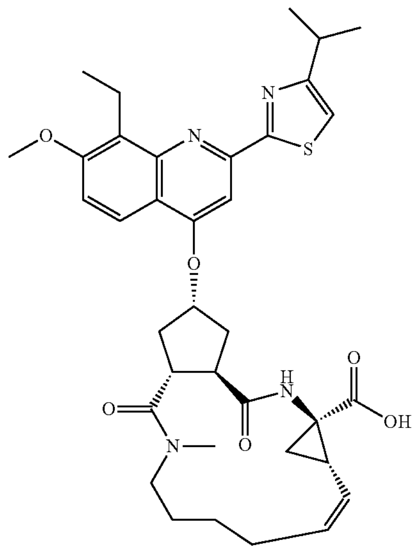 [SMILES: CCc1c(OC)ccc2c(O[C@@H]3C[C@H]4C(=O)N[C@]5(C(=O)O)C[C@H]5/C=C\CCCCN(C)C(=O)[C@@H]4C3)cc(-c3nc(C(C)C)cs3)nc12] | 10 | — |
| 103 | 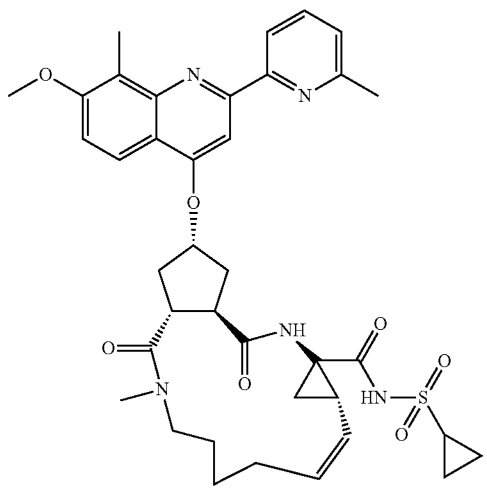 | 6.30 × 10$^{-3}$ | — |
| 72 | 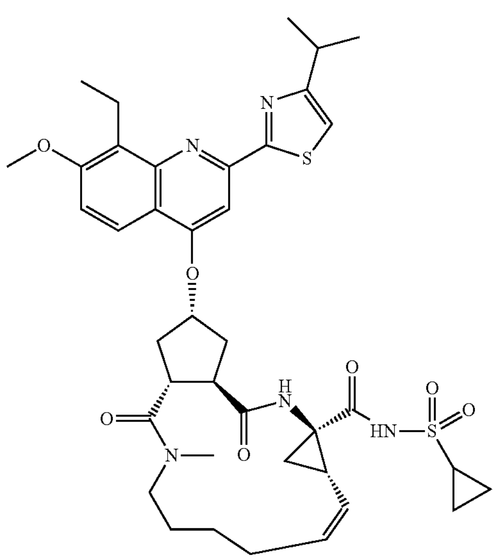 [SMILES: CCc1c(OC)ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc12] | 6.60 × 10$^{-2}$ | — |

| Compound nr. | structure | EC$_{50}$ (μM) Replicon assay | Ki (μM) Enzymatic assay |
|---|---|---|---|
| 66 | 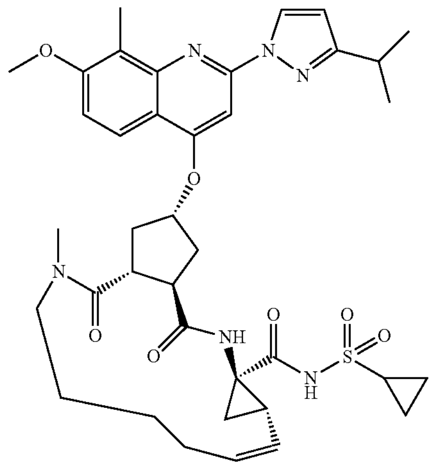 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-n3ccc(C(C)C)n3)nc2c1C] | 0.0036 | — |

Example 32

In Vivo Effects of Ritonavir on the Pharmacokinetics of Compound Nr. 47 in Rat Oral pharmacokinetics of Compound nr. 47 in male and female Sprague-Dawley rats after a single dose at 10 mg/kg, using a formulation in 50% PEG400/water and the influence of "boosting" with 10 mg/kg ritonavir were investigated.

Four male and four female Sprague-Dawley (SD)-rats (approx. body weight 200-250 g) were randomly divided into 2 groups of 2 males and females each (boosted and non-boosted) based on body weight. The weight of the individual animals did not differ too much from the group mean. The animals were fasted shortly before the trial. Drinking water remained available ad libitum.

Rats from the non-boosted group received a single oral 10 mg/kg dose of Compound nr. 47, formulated as a 3 mg/ml 50% PEG400/water at pH 8. Rats from the boosted group received a single oral dose of ritonavir, about 30 minutes before single oral dosing with 10 mg/kg of Compound nr. 47. The drug formulations were administered by oral gavage.

From each rat, a 0.5 ml blood sample was collected at 0.5 h, 1 h, 2 h, 4 h and 8 h after dosing. Plasma concentrations were determined using HPLC-MS. Results are shown in the table 2 below, expressed as fold change in pharmacokinetic parameter of the boosted group as compared to the non-boosted group.

TABLE 2

| | pharmacokinetic parameter | ritonavir |
|---|---|---|
| Compound nr. 47 | C$_{max}$ | 2.2 |
| | AUC | 2.5 |

These results demonstrate that ritonavir substantially enhances the pharmacokinetics of Compound nr. 47 in rat, with overall exposures expressed as AUC increasing over 2-fold.

The invention claimed is:
1. A combination comprising:
(a) a compound having the formula or an N-oxide, a pharmaceutically acceptable salt, or stereoisomer thereof; and
(b) another anti-HCV compound.
2. The combination according to claim 1 other than an N-oxide or pharmaceutically acceptable salt.
3. The combination according to claim 1 other than an N-oxide.
4. The combination as claimed in claim 1, wherein the other anti-HCV compound is an HCV polymerase inhibitor, an HCV protease inhibitor, an inhibitor of another target in the HCV life cycle, an immunomodulatory agent, an antiviral agent, or combinations thereof.
5. The combination as claimed in claim 4, wherein the other anti-HCV compound is an HCV polymerase inhibitor.
6. The combination as claimed in claim 4, for simultaneous, separate, or sequential use in the treatment of HCV infections.

7. The combination as claimed in claim 5, for simultaneous, separate, or sequential use in the treatment of HCV infections.

8. A method of inhibiting HCV replication comprising administering to a patient in need thereof, a compound of the formula

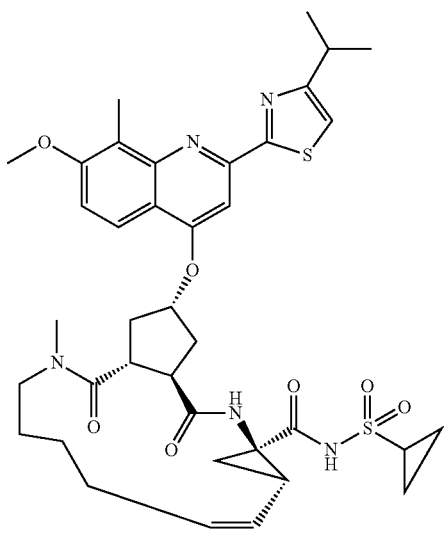 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C]

in combination with another compound.

9. The method as claimed in claim 8, wherein the other compound is another anti-HCV compound.

10. The method as claimed in claim 9, wherein the other anti-HCV compound is an HCV polymerase inhibitor, an HCV protease inhibitor, an inhibitor of another target in the HCV life cycle, an immunomodulatory agent, an antiviral agent, or combinations thereof.

11. The method as claimed in claim 9, wherein the other anti-HCV compound is an HCV polymerase inhibitor.

12. The method as claimed in claim 10, wherein the combination is administered simultaneously, separately, or sequentially in the treatment of the HCV replication inhibition.

13. The method as claimed in claim 11, wherein the combination is administered simultaneously, separately, or sequentially in the treatment of the HCV replication inhibition.

14. A pharmaceutical composition comprising a carrier, and as active ingredient an anti-virally effective amount of a combination comprising (a) a compound having the formula

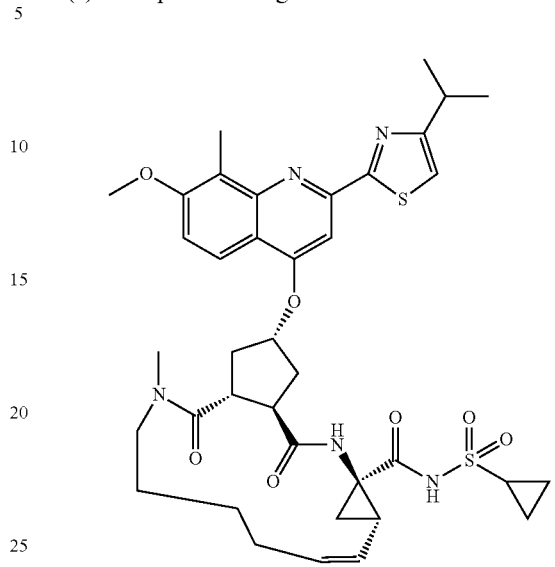

or an N-oxide, a pharmaceutically acceptable salt, or stereoisomer thereof; and (b) another anti-HCV compound.

15. The pharmaceutical composition of claim 14 wherein the other anti-HCV compound is an HCV polymerase inhibitor, an HCV protease inhibitor, an inhibitor of another target in the HCV life cycle, an immunomodulatory agent, an antiviral agent, or combinations thereof.

16. The pharmaceutical composition of claim 14 wherein the other anti-HCV compound is an HCV polymerase inhibitor.

17. The combination of claim 4, wherein the other anti-HCV compound is a protease inhibitor.

18. The method of claim 8, wherein the other compound is a protease inhibitor.

19. The pharmaceutical composition of claim 14, wherein the other anti-HCV compound is a protease inhibitor.

* * * * *